US011345713B2

(12) United States Patent
Natala et al.

(10) Patent No.: US 11,345,713 B2
(45) Date of Patent: May 31, 2022

(54) COMPOUNDS AS MODULATORS OF TLR2 SIGNALING

(71) Applicant: Neuropore Therapies, inc., San Diego, CA (US)

(72) Inventors: Srinivasa Reddy Natala, San Diego, CA (US); Wolfgang Wrasidlo, San Diego, CA (US)

(73) Assignee: Neuropore Therapies, Inc., San Diego, CA (US)

(*) Notice: Subject to any disclaimer, the term of this patent is extended or adjusted under 35 U.S.C. 154(b) by 0 days.

(21) Appl. No.: 17/042,034

(22) PCT Filed: Mar. 27, 2019

(86) PCT No.: PCT/US2019/024222
§ 371 (c)(1),
(2) Date: Sep. 25, 2020

(87) PCT Pub. No.: WO2019/191189
PCT Pub. Date: Oct. 3, 2019

(65) Prior Publication Data
US 2021/0024539 A1    Jan. 28, 2021

Related U.S. Application Data

(60) Provisional application No. 62/648,879, filed on Mar. 27, 2018.

(51) Int. Cl.
| | | |
|---|---|---|
| C07D 495/04 | (2006.01) |
| C07C 47/57 | (2006.01) |
| C07C 47/575 | (2006.01) |
| C07C 49/255 | (2006.01) |
| C07C 223/06 | (2006.01) |
| C07D 207/04 | (2006.01) |
| C07D 211/32 | (2006.01) |
| C07D 213/30 | (2006.01) |
| C07D 215/06 | (2006.01) |
| C07D 231/12 | (2006.01) |
| C07D 295/104 | (2006.01) |
| C07D 295/112 | (2006.01) |
| C07D 311/58 | (2006.01) |
| C07D 319/18 | (2006.01) |
| C07D 403/12 | (2006.01) |
| C07D 413/12 | (2006.01) |

(52) U.S. Cl.
CPC .......... *C07D 495/04* (2013.01); *C07C 47/57* (2013.01); *C07C 47/575* (2013.01); *C07C 49/255* (2013.01); *C07C 223/06* (2013.01); *C07D 207/04* (2013.01); *C07D 211/32* (2013.01); *C07D 213/30* (2013.01); *C07D 215/06* (2013.01); *C07D 231/12* (2013.01); *C07D 295/104* (2013.01); *C07D 295/112* (2013.01); *C07D 311/58* (2013.01); *C07D 319/18* (2013.01); *C07D 403/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 4,271,293 A | 6/1981 | Bremen et al. | |
| 8,193,378 B2 * | 6/2012 | Harada | A61P 1/04 549/407 |
| 2013/0096133 A1 | 4/2013 | Hergenrother | |
| 2020/0308163 A1 | 10/2020 | Srinivasa et al. | |

FOREIGN PATENT DOCUMENTS

| | | |
|---|---|---|
| CN | 101 805 338 | 8/2010 |
| EP | 0 005 465 | 11/1979 |
| EP | 1 402 887 | 3/2004 |
| WO | WO 2008/154484 | 12/2008 |
| WO | WO 2009/002790 | 12/2008 |
| WO | WO 2016/164414 | 10/2016 |
| WO | WO 2019/191189 | 10/2019 |
| WO | WO 2020/198368 | 10/2020 |

OTHER PUBLICATIONS

Khadse et al. Indian Journal of Chemistry, Section B: Organic Chemistry Including Medicinal Chemistry (1987), 268(9), 856-60.
Li, et. al., European Journal of Medicinal Chemistry (2019), 166, 178-185.
Bagshawe et al., "Antibody-directed enzyme prodrug therapy: A review," Drug Dev Res (1995) 34(2):220-230.
Beraud et al., "Misfolded α-synuclein and Toll-like receptors: therapuetic targets for Parkinson's disease," Parkinsonism Relat Disord (2012) Suppl 1(01):S17-20.
Bertolini et al., "A New Rational Hypothesis for the Pharmacophore of the Active Metabolite of Leflunomide, a Potent Immunosuppressive Drug," J Med Chem (1997) 40(13):2011-2016.
Bodor et al., "Novel Approaches to the design of safer drugs: soft drugs and site-specific chemical delivery systems," Adv Drug Res (1984) 13:255-331.
Brown et al., "Binding specificity of toll-like receptor cytoplasmic domains," Eur J Immunol (2006) 36(3):742-753.
Cario., "Toll-like receptors in inflammatory bowel diseases: A decade later," Inflamm. Bowel Dis. 2010, 16(9):1583-1597.
Casula et al., "Toll-like receptor signaling in amyotrophic lateral sclerosis spinal cord tissue," Neuroscience (2011) 179:233-243.

(Continued)

*Primary Examiner* — Samantha L Shterengarts
(74) *Attorney, Agent, or Firm* — Morrison & Foerster LLP

(57) ABSTRACT

The present disclosure relates to compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

16 Claims, No Drawings

(56) References Cited

OTHER PUBLICATIONS

Chen et al., "Engagement of Toll-like receptor 2 on CD4(+) T cells facilitates Tocal immune responses in patients with tuberculous pleurisy," J. Infect. Dis. (2009) 200(3): 399-408.

Gambuzza et al., "Toll-like receptors in Alzheimer's disease: a therapeutic perspective," CNS Neurol. Disord. Durg Targets 2014, 13(9), 1542-58.

Gangloff et al., "Toll-like receptors and immune response in allergic disease," Clin. Rev. Allergy Immunol. 2004, 26(2), 115-25.

Harding et al., "Regulation of antigen presentation by *Mycobacterium tuberculosis*: a role for Toll-like receptors," Nat Rev Microbiol (2010) 8(4):296-307.

Hong et al., "Preparation of fluoroionophores based on diamine-salicylaldehyde derivatives," Dyes and Pigments (2008) 94(3):371-379.

Howell et al., "Toll-like receptors in hepatitis C infection: implications for pathogenesis and treatment," J. Gastroenterol. Hepatol. 2013, 28(5): 766-776.

Hua et al., "Genomic profile of Toll-like receptor pathways in traumatically brain-injured mice: effect of exogenous progesterone," J. Neuroinflammation (2011) 8:42.

Huang et al., "Roll of Toll like receptors in rheumatoid arthritis," Curr. Rheumatol. Rep. 2009, 11(5):357-364.

Hussein et al. "Toll-like receptor agonists: a patent review (2011-2013)," Expert Opinion on Therapeutics Patents (2014) 24(4):453-470.

International Search Report and Written Opinion for PCT/US2020/024728, dated Jun. 2, 2020, 11 pages.

Julakanti et al., "Highly Efficient Synthesis of Chaicones from Poly Carbonyl Aromatic Compounds Using BF 3 -Et 2 0 via a Regioselective Condensation Reaction," The Pharmaceutical Society of Japan Chem Pharm Bull (2016) 570-576.

Kajava et al., "A network of hydrogen bonds on the surgace of TLR2 controls ligand positioning and cell signaling," J Bio Chem (2010) 285(9):6227-6234.

Kalathur et al., "Huntington's disease and its therapeutic target genes: a global functional profile based on the HD Research Crossroads database," BMC Neurology 2012, 12, 47.

Kim et al., "Neuron-released oligomeric a-synuclein is an endogenous agonist of TLR2 for paracrine activation of microglia," Nat Commun (2013) 4:1562.

King, S. N. et al., "Characterization of the Leukocyte Response in Acute Vocal Fold Injury," PLoS One, 2015; 10(10): e0139260.

Loudon, Organic Chemistry, Fourth Edition, New York: Oxford University Press, 2002, pp. 360-361, 1084-1085.

Miller, L.S., "Toll-like receptors in skin," Adv. Dermatol. 2008, 24, 71-87.

Miranda-Hernandez, S. et al., "Role of toll-like receptors in multiple sclerosis," Am. J. Clin. Exp. Immunol. 2013, 2(1), 75-93.

Murgueitio et al., "Balancing inflammation: Computational Design of small-molecule toll-like receptor modulators," Trends in Pharmacological Sciences (2017) 38(2):155-168.

Santegoets, K.C.M. et al., "Toll-like receptors in rheumatic diseases: are we paying a high price for our defense against bugs?" FEBS Letters 2011, 585(23), 3660-3666.

Sashidhara et al., "Synthesis of 3,6-epoxy[1,5] dioxocines from 2-hydroxyaromatic benzaldehydes",Tetragedrib Letters (2011) 52(43):5659-5663.

Sashidhara et al., "Antiplasmodial activity of novel keto-enamine chalcone-chloroquine based hybrid pharmacophores," Bioorganic & Medicinal Chemistry (2012) 20(9):2971-2981.

Schmausser, B. et al., "Toll-like receptors TLR4, TLR5 and TLR9 on gastric carcinoma cells: an implication for interaction with Helicobacter pylori," Int. J. Med. Microbiol. 2005, 295(3), 179-85.

Shan et al., "Prodrug Strategies based on intramolecular cyclization Reactions," J. Pharm. Sci. 1997, 86 (7), 765-767.

Smith, S., "Roll of Toll-like receptors in Helicobacter pylori infection and immunity," World J. Gastrointest. Pathophysiol. 2014, 5(3), 133-146.

Song, G.G. et al., "Toll-like receptor polymorphisms and vasculitis susceptibility: meta-analysis and systematic review," Mol. Biol. Rep. 2013, 40(2), 1315-23.

Tanaka et al., "Studeies on 5-aminosalicylaldehyde derivatives. II. Reduction of 5-(p-sulfophenylazo) salicylaldehyde through poly(5-nitrilosalicylidene) to a 5-aminosalicylaldehyde derivatives," Bulletin of the Chemical Society of Japan, Chemical Society of Japan (1967) 40(7):1724-1726.

Vieira, B. et al., "Neuroinflammation in multiple system atrophy: Response to and cause of a-synuclein aggregation," Front. Cell Neurosci. 2015, 9, 437.

Wang et al., "Three New Resveratrol Derivatives from the Mangrove Endophytic Fungus *Alternaria* sp," Marine Drugs (2014) 12(5):2840-2850.

Zhang, E. et al., "Toll-like receptor (TLR)-mediated innate immune responses in control of hepatitis B virus (HBV) infection," Med. Microbiol. Immunol. 2015, 204(1), 11-20.

Zhang, Q. et al., "Differential expression of Toll-like receptor pathway genes in chronic rhinosinusitis with or without nasal polyps," Acta Otolaryngol. 2013, 133(2), 165-173.

Zuo et al., "Molecular regulation of Toll-like receptors in asthma and COPD," Front Physiol (2015) 6:312.

* cited by examiner

COMPOUNDS AS MODULATORS OF TLR2 SIGNALING

CROSS-REFERENCE TO RELATED APPLICATIONS

This application is a national stage application under 35 U.S.C. § 371 of International Application No. PCT/US2019/024222, filed internationally on Mar. 27, 2019, which claims priority to U.S. Provisional Application No. 62/648,879, filed Mar. 27, 2018, entitled "COMPOUNDS AS MODULATORS OF TLR2 SIGNALING," the content of which is hereby incorporated by reference in its entirety for all purposes.

TECHNICAL FIELD

The present disclosure relates to compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

BACKGROUND

Toll-like receptors (TLRs) are sentinel receptors of the immune system. When these receptors are activated on cell surfaces, they initiate recruitment of a family of TIR-domain containing adapter proteins, which induce a signaling cascade that ultimately results in cell-type specific inflammatory responses, resulting in the elevation of pro-inflammatory mediators such as IL1, IL6, IL8 and TNFα. Of the different TLR receptors expressed on mammalian cells, TLR2 forms heterodimers with either TLR1 or TLR6 to initiate inflammatory responses with various microbial derived ligands. Among the various bacterial ligands are lipopolysaccharides (LPS), acylated lipopeptides, lipoglycans, peptidoglycans, porins, glycosylphosphatidyl-inosol anchors, and other bacterial cell wall components such as lipoteichoic acid (LTA) from *Streptococcus* pneumonia. In addition to the microbial activation of TLR2, it has also been found that abnormal aggregation of neuron released oligomeric proteins such as alpha-synuclein (aSyn) can induce similar inflammatory responses in animal models of neurodegenerative diseases, including Parkinson's disease (PD), dementia with Lewy bodies, multiple system atrophy (MSA) and Alzheimer's disease (AD). See, e.g., Kim et al., Nat. Commun. 2013, 4, 1562.

The ability of TLR2 to induce signaling via heterodimers allows discrimination between various recognition patterns, which allows for the design of ligands with specific inhibition patterns. Kajava et al., *J. Biol. Chem.* 2010, 285, 6227. Inhibitors that compete primarily with a specific pathological agonist, such as oligomeric pathogenic alpha-synuclein, but do not affect other ligands involved in pro-inflammatory signaling of bacterial or viral infections or non-competitive TIR-Myd88 inhibitors, such as compounds that function indirectly as non-competitive inhibitors of TLR2 though intracellular TIR-Myd88 inhibition, would therefore be useful as potential therapeutic agents.

The function of Toll-like receptors has been linked to various protein folding, protein dimerization, and inflammatory processes and to related diseases such as Alzheimer's disease (Gambuzza, M. et al., "Toll-like receptors in Alzheimer's disease: a therapeutic perspective," *CNS Neurol. Disord. Drug Targets* 2014, 13(9), 1542-58), Parkinson's disease and Parkinson's disease with dementia (Beraud, D. et al., "Misfolded α-synuclein and Toll-like receptors: therapeutic targets for Parkinson's disease," *Parkinsonism Relat. Disord.* 2012, 18 (Suppl. 1), S17-20), fronto-temporal dementia, dementia with Lewy bodies (Lewy body disease), multiple system atrophy (Vieira, B. et al., "Neuroinflammation in multiple system atrophy: Response to and cause of α-synuclein aggregation," *Front. Cell Neurosci.* 2015, 9, 437), amyotrophic lateral sclerosis (Casula, M. et al., "Toll-like receptor signaling in amyotrophic lateral sclerosis spinal cord tissue," *Neuroscience* 2011, 179, 233-43), Huntington's disease (Kalathur, R. K. R. et al., "Huntington's disease and its therapeutic target genes: a global functional profile based on the HD Research Crossroads database," *BMC Neurology* 2012, 12, 47), inflammatory diseases, asthma and chronic obstructive pulmonary disease (COPD) (Zuo, L. et al., "Molecular regulation of Toll-like receptors in asthma and COPD," *Front. Physiol.* 2016, 6, 312), chronic peptic ulcers (Smith, S., "Roll of Toll-like receptors in *Helicobacter pylori* infection and immunity," *World J. Gastrointest. Pathophysiol.* 2014, 5(3), 133-146), tuberculosis (Harding, C. V. et al., "Regulation of antigen presentation by *Mycobacterium tuberculosis*: a role for Toll-like receptors," *Nat. Rev. Microbiol.* 2010, 8(4), 296-307), rheumatoid arthritis (Huang, Q.-Q. et al., "Roll of Toll like receptors in rheumatoid arthritis," *Curr. Rheumatol. Rep.* 2009, 11(5), 357-364), chronic sinusitis (Zhang, Q. et al., "Differential expression of Toll-like receptor pathway genes in chronic rhinosinusitis with or without nasal polyps," *Acta Otolaryngol.* 2013, 133(2), 165-173), hepatitis (including hepatitis B and C) (Zhang, E. et al., "Toll-like receptor (TLR)-mediated innate immune responses in control of hepatitis B virus (HBV) infection," *Med. Microbiol. Immunol.* 2015, 204(1), 11-20; Howell, J. et al., "Toll-like receptors in hepatitis C infection: implications for pathogenesis and treatment," *J. Gastroenterol. Hepatol.* 2013, 28(5), 766-776), gout, lupus, psoriasis, psoriatic arthritis (Santegoets, K. C. M. et al., "Toll-like receptors in rheumatic diseases: are we paying a high price for our defense against bugs?" *FEBS Letters* 2011, 585(23), 3660-3666), vasculitis, laryngitis, pleurisy (Chen, X. et al., "Engagement of Toll-like receptor 2 on CD4(+) T cells facilitates local immune responses in patients with tuberculous pleurisy," *J. Infect. Dis.* 2009, 200(3), 399-408), eczema (Miller, L. S., "Toll-like receptors in skin," *Adv. Dermatol.* 2008, 24, 71-87), gastritis (Schmausser, B. et al., "Toll-like receptors TLR4, TLR5 and TLR9 on gastric carcinoma cells: an implication for interaction with *Helicobacter pylori*," *Int. J. Med. Microbiol.* 2005, 295(3), 179-85), vasculitis (Song, G. G. et al., "Toll-like receptor polymorphisms and vasculitis susceptibility: meta-analysis and systematic review," *Mol. Biol. Rep.* 2013, 40(2), 1315-23), laryngitis (King, S. N. et al., "Characterization of the Leukocyte Response in Acute Vocal Fold Injury," *PLoS One*, 2015; 10(10): e0139260), allergic reactions (Gangloff, S. C. et al., "Toll-like receptors and immune response in allergic disease," *Clin. Rev. Allergy Immunol.* 2004, 26(2), 115-25), multiple sclerosis (Miranda-Hernandez, S. et al., "Role of toll-like receptors in multiple sclerosis," *Am. J. Clin. Exp. Immunol.* 2013, 2(1), 75-93), Crohn's disease (Cario, E., "Toll-like receptors in inflammatory bowel diseases: A decade later," *Inflamm. Bowel Dis.* 2010, 16(9), 1583-1597), and traumatic brain injury (Hua, F. et al., "Genomic profile of Toll-like receptor pathways in traumatically brain-injured mice: effect of exogenous progesterone," *J. Neuroinflammation* 2011, 8, 42).

The signal transduction path of TLR2 can be activated either through the external domain (agonist pocket) or by mechanisms involving the cytoplasmic TIR domain, that mediates homotypic and heterotypic interactions during signaling. The proteins MyD88 and TIRAP (Mal) are involved in this type of signaling.

Importantly, a conserved proline P681 in TLR2 within the BB loop is (Brown V. et. al. (2006) European Journal of immunology 36, 742-753) is involved in the dimerization mechanism. A mutation in this loop from P681H abolishes recruitment of MyD88 and signaling. Thus compounds that bind in the vicinity of this loop and restrict its movement during the dimerization process would be useful as inhibitors of the activation of TLR2.

Described herein are compounds that serve as antagonists of TLR2 with high potency and selectivity.

SUMMARY

In one aspect, provided herein is a compound of Formula (A):

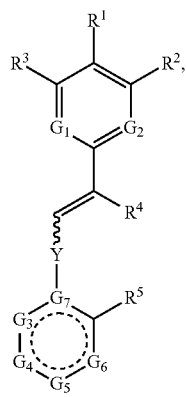

(A)

or a tautomer, or a pharmaceutically acceptable salt of any of the foregoing, wherein ◌ indicates that the ring is saturated, partially unsaturated, or fully unsaturated;

| indicates that the

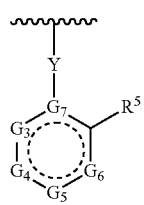

is attached in either the E or Z configuration;

$G_1$ and $G_2$ are each independently $CR^x$, or N;

$R^x$ is hydrogen or halogen;

one of $R^1$ and $R^2$ is —OH and the other is selected from the group consisting of —C(O)$R^a$, —CH=N$R^j$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocycloalkyl;

$R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl;

$R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl;

$R^f$ and $R^g$ are each independently —OH, unsubstituted heteroaryl, —N$R^m R^n$, benzoyl, or styryl;

$R^m$ and $R^n$ are each independently H, $C_1$-$C_6$alkyl, $C_2$-$C_6$alkenyl, $C_2$-$C_6$alkynyl, or unsubstituted or substituted cycloalkyl;

$R^j$ is unsubstituted or substituted heterocyclyl, unsubstituted or substituted aryl, —O$R^k$, —NH$R^k$, —NHC(O)$R^k$, —NHS(O)$_2R^k$, or —NHC(NH)NH$_2$;

$R^k$ is $C_1$-$C_6$alkyl, $C_2$-$C_6$alkenyl, $C_2$-$C_6$alkynyl, $C_3$-$C_8$cycloalkyl, or aryl;

$R^3$ is H, $C_1$-$C_6$alkyl, $C_1$-$C_6$alkoxy, or halogen, wherein the $C_1$-$C_6$alkyl and $C_1$-$C_6$alkoxy of $R^3$ are each independently unsubstituted or substituted with one or more halogen;

wherein:
when $R^1$ or $R^2$ is —$C_1$-$C_6$alkyl-OH or —$C_1$-$C_6$alkyl-N$R^m R^n$, wherein $R^m$ and $R^n$ are each $C_1$-$C_6$alkyl, $R^3$ is selected from the group consisting of $C_1$-$C_6$alkyl, $C_2$-$C_6$alkoxy, and halogen;
when $R^1$ or $R^2$ is unsubstituted or substituted $C_3$-$C_8$ cycloalkyl, —NHC(O)CH$_3$, or —S(O)$_2$—$R^c$, wherein $R^c$ is an unsubstituted or substituted heterocyclyl, $R^3$ is selected from the group consisting of $C_1$-$C_6$alkyl, $C_1$-$C_6$alkoxy, and halogen;
when $R^1$ or $R^2$ is —CHO, $R^3$ is selected from the group consisting of hydrogen, $C_2$-$C_6$alkoxy, and halogen;
when $R^1$ or $R^2$ is —C(O)CH$_3$, $R^3$ is selected from the group consisting of $C_2$-$C_6$alkoxy and halogen;
when $R^1$ or $R^2$ is —C(O)CH(Br)CH$_3$ or —C(O)CH(Br)CH$_2$CH$_3$, $G_7$ is C or CH;
when $R^3$ is hydrogen, no more than one of $R^{6a}$, $R^{6b}$, $R^{6c}$, and $R^{6d}$ is —CF$_3$, no more than one of $R^{6a}$, $R^{6b}$, $R^{6c}$, and $R^{6d}$ is —CH$_3$, and no more than one of $R^{6a}$, $R^{6b}$, $R^{6c}$, and $R^{6d}$ is —OH, Y is —C(O)— or absent and $R^4$ and $R^5$ are each H, or Y is absent and $R^4$ and $R^5$ come together to form —S—;

$G_3$ is CH($X_1$—$R^{6a}$), C($X_1$—$R^{6a}$), N,N($X_1$—$R^{6a}$), S, or O;
$G_4$ is CH($X_2$—$R^{6b}$), C($X_2$—$R^{6b}$), N,N($X_2$—$R^{6b}$), S, or O;
$G_5$ is CH($X_3$—$R^{6c}$), C($X_3$—$R^{6c}$), N,N($X_3$—$R^{6c}$), S, or O;
$G_6$ is CH($X_4$—$R^{6d}$), C($X_4$—$R^{6d}$), N,N($X_4$—$R^{6d}$), S, O, or absent;
$G_7$ is N, C, or CH;

wherein when $G_5$ is N, at least one of (i), (ii), and (iii) applies:
(i) at least one of $G_3$, $G_4$, and $G_6$ is not CH;
(ii) $R^4$ and $R^5$ come together to form —S—; and
(iii) $R^3$ is —OCH$_3$ or halo;

$X_1$, $X_2$, $X_3$, and $X_4$ are each independently absent,

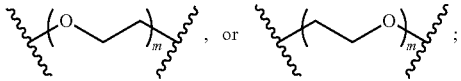

m is 1-6;

$R^{6a}$, $R^{6b}$, $R^{6c}$, and $R^{6d}$ are each independently hydrogen, $C_1$-$C_6$alkyl, $C_1$-$C_6$alkoxy, halo, —OH, —N$R^p R^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the C$_1$-C$_6$alkyl and C$_1$-C$_6$alkoxy of R$^{6a}$, R$^{6b}$, R$^{6c}$, and R$^{6d}$ are each independently unsubstituted or substituted with one or more groups selected from the group consisting of cycloalkyl and halogen; the aryl and heteroaryl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, and C$_1$-C$_6$alkyl-OH; and the heterocyclyl, —C$_1$-C$_6$alkyl-heterocyclyl, and —OC(O)-heterocyclyl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, C$_1$-C$_6$alkyl-OH, =O, and =S;

R$^h$ is selected from the group consisting of H, C$_1$-C$_6$alkyl, C$_1$-C$_6$alkoxy, and C$_3$-C$_8$cycloalkyl, and —NR$^r$R$^s$;

R$^p$ is H or C$_1$-C$_6$alkyl;

R$^q$ is C$_2$-C$_3$alkyl, —C(O)R$^t$, —C(O)OR$^u$, —C(O)NR$^v$;

R$^r$, R$^s$, R$^{w1}$, and R$^{z1}$ each independently selected from H and C$_1$-C$_6$alkyl; and R$^t$, R$^u$, R$^v$, R$^{w2}$, R$^y$, and R$^{z2}$ are each independently selected from H, C$_1$-C$_6$alkyl, unsubstituted or substituted C$_3$-C$_8$cycloalkyl, and unsubstituted or substituted heterocyclyl;

or

G$_5$ is CH(X$_3$—R$^{6c}$) or C(X$_3$—R$^{6c}$), G$_6$ is CH(X$_4$—R$^{6d}$) or C(X$_4$—R$^{6d}$), and R$^{6c}$ and R$^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted;

wherein no more than one of R$^{6a}$, R$^{6b}$, R$^{6c}$, and R$^{6d}$ is C$_1$-C$_6$alkoxy or OH; and wherein the compound is not a compound of Table 1X.

In another aspect, provided herein is a compound of Formula (A-1):

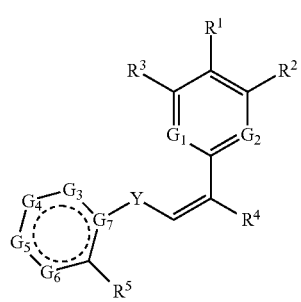

(A-1)

or a tautomer, or a pharmaceutically acceptable salt of any of the foregoing, wherein R$^1$, R$^2$, R$^3$, R$^4$, R$^5$, Y, G$_1$, G$_2$, G$_3$, G$_4$, G$_5$, G$_6$, and G$_7$ are as defined for Formula (A) or any variation or embodiment thereof, and wherein the stereochemistry with respect to the double bond shown in Formula (A-1) is as represented in the formula as drawn.

In another aspect, provided herein is a compound of Formula (A-2):

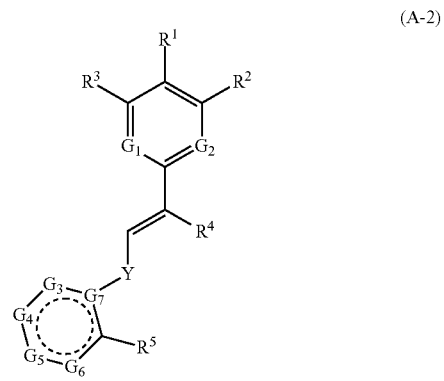

(A-2)

or a tautomer, or a pharmaceutically acceptable salt of any of the foregoing, wherein R$^1$, R$^2$, R$^3$, R$^4$, R$^5$, Y, G$_1$, G$_2$, G$_3$, G$_4$, G$_5$, G$_6$, and G$_7$ are as defined for Formula (A) or any variation or embodiment thereof, and wherein the stereochemistry with respect to the double bond shown in Formula (A-2) is as represented in the formula as drawn.

In one aspect, provided herein is a compound of Formula (I):

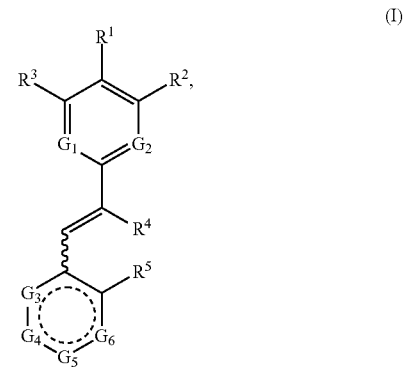

(I)

or a tautomer, or a pharmaceutically acceptable salt of any of the foregoing, wherein ◌ indicates that the ring is saturated, partially unsaturated, or fully unsaturated;

∤ indicates that the

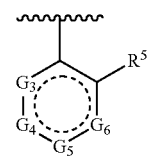

is attached in either the E or Z configuration;

G$_1$ and G$_2$ are each independently CH or N;

one of R$^1$ and R$^2$ is —OH and the other is selected from the group consisting of —C(O)R$^a$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted cycloalkyl, unsubstituted or substituted cycloalkenyl, and unsubstituted or substituted heterocycloalkyl;

$R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl;

$R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl;

$R^f$ and $R^g$ are each independently unsubstituted heteroaryl, benzoyl, or styryl;

$R^3$ is H, $C_1$-$C_6$alkyl, $C_1$-$C_6$alkoxy, or halogen; and $R^4$ and $R^5$ are each H, or $R^4$ and $R^5$ come together to form —S—;

$G_3$ is $CH(X_1-R^{6a})$, $C(X_1-R^{6a})$, $N, N(X_1-R^{6a})$, S, or O;
$G_4$ is $CH(X_2-R^{6b})$, $C(X_2-R^{6b})$, $N, N(X_2-R^{6b})$, S, or O;
$G_5$ is $CH(X_3-R^{6c})$, $C(X_3-R^{6c})$, $N, N(X_3-R^{6c})$, S, or O;
$G_6$ is $CH(X_4-R^{6d})$, $C(X_4-R^{6d})$, $N, N(X_4-R^{6d})$, S, O, or absent;

wherein when $G_5$ is N, either
(i) at least one of $G_3$, $G_4$, and $G_6$ is not CH; or
(ii) $R^4$ and $R^5$ come together to form —S—;

$X_1$, $X_2$, $X_3$, and $X_4$ are each independently absent,

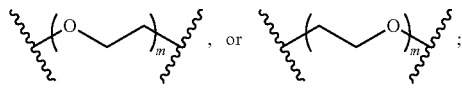

m is 1-6;

$R^{6a}$, $R^{6b}$, $R^{6c}$, and $R^{6d}$ are each independently hydrogen, $C_1$-$C_6$alkyl, $C_1$-$C_6$alkoxy, halo, or —C(O)$R^h$, wherein the $C_1$-$C_6$alkyl of $R^{6a}$, $R^{6b}$, $R^{6c}$, and $R^{6d}$ is independently unsubstituted or substituted with cycloalkyl or halogen;

$R^h$ is selected from the group consisting of H, $C_1$-$C_6$alkyl, $C_1$-$C_6$alkoxy, and $C_3$-$C_8$cycloalkyl;

wherein the compound is not a compound of Table 1X.

In another aspect, provided herein is a compound of Formula (Ia):

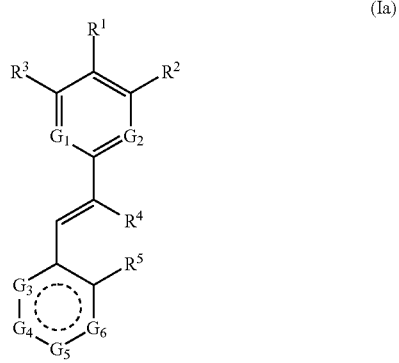

(Ia)

or a tautomer, or a pharmaceutically acceptable salt of any of the foregoing, wherein $R^1$, $R^2$, $R^3$, $R^4$, $R^5$, $G_1$, $G_2$, $G_3$, $G_4$, $G_5$, and $G_6$, are as defined for Formula (I) or any variation or embodiment thereof, and wherein the stereochemistry with respect to the double bond shown in Formula (Ia) is as represented in the formula as drawn.

In another aspect, provided herein is a compound of Formula (Ib):

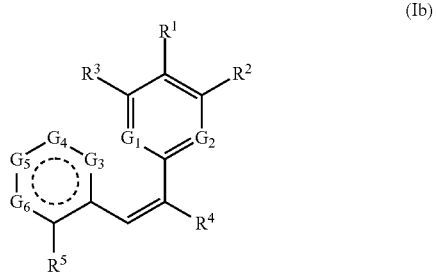

(Ib)

or a tautomer, or a pharmaceutically acceptable salt of any of the foregoing, wherein $R^1$, $R^2$, $R^3$, $R^4$, $R^5$, $G_1$, $G_2$, $G_3$, $G_4$, $G_5$, and $G_6$, are as defined for Formula (I) or any variation or embodiment thereof, and wherein the stereochemistry with respect to the double bond shown in Formula (Ib) is as represented in the formula as drawn.

In a further aspect, provided herein are pharmaceutical compositions comprising at least one compound of Formula (A), (A-1), (A-2), (I), (Ia) or (Ib), such as a compound of Table 1, or a tautomer thereof, or a pharmaceutically acceptable salt of any of the foregoing, optionally further comprising a pharmaceutically acceptable excipient.

In another aspect, provided herein is a method of treating a disease or condition associated with TLR2 heterodimerization, comprising administering to a subject in need of such treatment an effective amount of at least one compound of Formula (A), (A-1), (A-2), (I), (Ia) or (Ib), such as a compound of Table 1, or a tautomer thereof, or a pharmaceutically acceptable salt of any of the foregoing, and/or a pharmaceutical composition comprising at least one compound of Formula (A), (A-1), (A-2), (I), (Ia) or (Ib), such as a compound of Table 1. In some embodiments of any of the methods described herein, the disease or condition is selected from the group consisting of: Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, inflammatory diseases, asthma, chronic obstructive pulmonary disease (COPD), chronic peptic ulcers, tuberculosis, rheumatoid arthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), atopic dermatitis, acne vulgaris, rosacea, non-alcoholic fatty liver disease, non-alcoholic steatohepatisis, corneal wounds, corneal disorders, Stargardt disease (Juvenile macular degeneration), age-related macular degeneration, sepsis, diabetic wounds, herpes simplex virus, and anti-fungal, anti-bacterial, antiviral and antitumor diseases or conditions. In some embodiments of any of the methods described herein, the disease or condition is selected from the group consisting of: Progressive Supranuclear Palsy (PSP), Niemann-Pick disease type C, irritable bowel disease, osteoarthritis, corneal HSV, stroke, and ischemic heart disease.

In yet another aspect, provided herein is a method of interfering with the heterodimerization of TLR2 in a cell, or modulating, preventing, slowing, reversing, or inhibiting TLR2 heterodimerization in a cell, comprising contacting the cell with an effective amount of at least one compound of Formula (A), (A-1), (A-2), (I), (Ia) or (Ib), such as a compound of Table 1, or a tautomer thereof, or a pharmaceutically acceptable salt of any of the foregoing, and/or with at least one pharmaceutical composition comprising at least one compound of Formula (A), (A-1), (A-2), (I), (Ia) or (Ib), such as a compound of Table 1, wherein the contacting is in vitro, ex vivo, or in vivo.

Additional embodiments, features, and advantages of the present disclosure will be apparent from the following detailed description and through practice of the present disclosure.

For the sake of brevity, the disclosures of publications cited in this specification, including patents, are herein incorporated by reference.

DETAILED DESCRIPTION

The present disclosure relates to compounds, pharmaceutical compositions comprising such compounds, and use of such compounds in methods of treatment or in medicaments for treatment of inflammatory diseases and certain neurological disorders that are related to inflammatory signaling processes, including but not limited to misfolded proteins.

It is to be understood that this disclosure is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software, Version 14.0.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Compounds

Compounds and salts thereof (such as pharmaceutically acceptable salts) are detailed herein, including in the Summary and in the appended claims. Also provided are the use of all of the compounds described herein, including any and all stereoisomers, including geometric isomers (e.g., cis/trans isomers or E/Z isomers), enantiomers, diastereomers, and mixtures thereof in any ratio including racemic mixtures, salts and solvates of the compounds described herein, as well as methods of making such compounds. Any compound described herein may also be referred to as a drug.

In one aspect, provided are compounds of Formula (A):

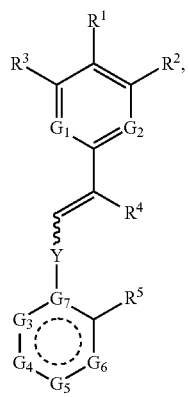
(A)

or a tautomer, or a pharmaceutically acceptable salt of any of the foregoing, wherein ◌ indicates that the ring is saturated, partially unsaturated, or fully unsaturated;

│ indicates that the

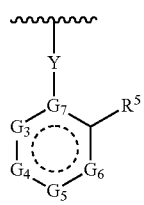

is attached in either the E or Z configuration;

$G_1$ and $G_2$ are each independently $CR^x$, or N;

$R^x$ is hydrogen or halogen;

one of $R^1$ and $R^2$ is —OH and the other is selected from the group consisting of —C(O)$R^a$, —CH=N$R^j$, —S(O)$R^b$, —S(O)$_2R^c$, —NHC(O)$R^d$, —NHS(O)$_2R^e$, —C$_1$-C$_6$alkyl-$R^f$, —C$_2$-C$_6$alkenyl-$R^g$, unsubstituted or substituted C$_3$-C$_8$ cycloalkyl, unsubstituted or substituted C$_3$-C$_8$ cycloalkenyl, and unsubstituted or substituted heterocycloalkyl;

$R^a$, $R^b$, $R^c$, and $R^e$ are each independently H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, benzoyl, or styryl;

$R^d$ is H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, or benzoyl;

$R^f$ and $R^g$ are each independently —OH, unsubstituted heteroaryl, —NR$^m$R$^n$, benzoyl, or styryl;

$R^m$ and $R^n$ are each independently H, C$_1$-C$_6$alkyl, C$_2$-C$_6$alkenyl, C$_2$-C$_6$alkynyl, or unsubstituted or substituted cycloalkyl;

$R^j$ is unsubstituted or substituted heterocyclyl, unsubstituted or substituted aryl, —OR$^k$, —NHR$^k$, —NHC(O)R$^k$, —NHS(O)$_2R^k$, or —NHC(NH)NH$_2$;

$R^k$ is C$_1$-C$_6$alkyl, C$_2$-C$_6$alkenyl, C$_2$-C$_6$alkynyl, C$_3$-C$_8$ cycloalkyl, or aryl;

$R^3$ is H, C$_1$-C$_6$alkyl, C$_1$-C$_6$alkoxy, or halogen, wherein the C$_1$-C$_6$alkyl and C$_1$-C$_6$alkoxy of $R^3$ are each independently unsubstituted or substituted with one or more halogen;

wherein:

when $R^1$ or $R^2$ is —C$_1$-C$_6$alkyl-OH or —C$_1$-C$_6$alkyl-NR$^m$R$^n$, wherein R$^m$ and R$^n$ are each C$_1$-C$_6$alkyl, $R^3$ is selected from the group consisting of C$_1$-C$_6$alkyl, C$_2$-C$_6$alkoxy, and halogen;

when $R^1$ or $R^2$ is unsubstituted or substituted C$_3$-C$_8$ cycloalkyl, —NHC(O)CH$_3$, or —S(O)$_2$—R$^c$, wherein R$^c$ is an unsubstituted or substituted heterocyclyl, $R^3$ is selected from the group consisting of C$_1$-C$_6$alkyl, C$_1$-C$_6$alkoxy, and halogen;

when $R^1$ or $R^2$ is —CHO, $R^3$ is selected from the group consisting of hydrogen, C$_2$-C$_6$alkoxy, and halogen;

when $R^1$ or $R^2$ is —C(O)CH$_3$, $R^3$ is selected from the group consisting of C$_2$-C$_6$alkoxy and halogen;

when $R^1$ or $R^2$ is —C(O)CH(Br)CH$_3$ or —C(O)CH(Br)CH$_2$CH$_3$, $G_7$ is C or CH;

when $R^3$ is hydrogen, no more than one of $R^{6a}$, $R^{6b}$, $R^{6c}$, and $R^{6d}$ is —CF$_3$, no more than one of $R^{6a}$, $R^{6b}$, $R^{6c}$, and $R^{6d}$ is —CH$_3$, and no more than one of $R^{6a}$, $R^{6b}$, $R^{6c}$, and $R^{6d}$ is —OH, Y is —C(O)— or absent and $R^4$ and $R^5$ are each H, or Y is absent and $R^4$ and $R^5$ come together to form —S—;

$G_3$ is CH(X$_1$—R$^{6a}$), C(X$_1$—R$^{6a}$), N,N(X$_1$—R$^{6a}$), S, or O;

$G_4$ is CH(X$_2$—R$^{6b}$), C(X$_2$—R$^{6b}$), N,N(X$_2$—R$^{6b}$), S, or O;

$G_5$ is CH(X$_3$—R$^{6c}$), C(X$_3$—R$^{6c}$), N,N(X$_3$—R$^{6c}$), S, or O;

$G_6$ is CH(X$_4$—R$^{6d}$), C(X$_4$—R$^{6d}$), N,N(X$_4$—R$^{6d}$), S, O, or absent;

$G_7$ is N, C, or CH;

wherein when $G_5$ is N, at least one of (i), (ii), and (iii) applies:

(i) at least one of $G_3$, $G_4$, and $G_6$ is not CH;

(ii) $R^4$ and $R^5$ come together to form —S—; and (iii) $R^3$ is —OCH$_3$ or halo;

$X_1$, $X_2$, $X_3$, and $X_4$ are each independently absent,

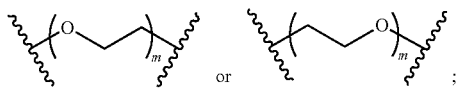

m is 1-6;

$R^{6a}$, $R^{6b}$, $R^{6c}$, and $R^{6d}$ are each independently hydrogen, C$_1$-C$_6$alkyl, C$_1$-C$_6$alkoxy, halo, —OH, —NR$^p$R$^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the C$_1$-C$_6$alkyl and C$_1$-C$_6$alkoxy of R$^{6a}$, R$^{6b}$, R$^{6c}$, and R$^{6d}$ are each independently unsubstituted or substituted with one or more groups selected from the group consisting of cycloalkyl and halogen; the aryl and heteroaryl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, and —C$_6$alkyl-OH; and the heterocyclyl, —C$_1$-C$_6$alkyl-heterocyclyl, and —OC(O)-heterocyclyl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, C$_1$-C$_6$alkyl-OH, =O, and =S;

$R^h$ is selected from the group consisting of H, C$_1$-C$_6$alkyl, C$_1$-C$_6$alkoxy, C$_3$-C$_8$cycloalkyl, and —NR$^r$R$^s$;

$R^p$ is H or C$_1$-C$_6$alkyl;

$R^q$ is C$_2$-C$_3$alkyl, —C(O)R$^t$, —C(O)OR$^u$—C(O)NR$^v$;

$R^r$, $R^s$, $R^{w1}$, and $R^{z1}$ each independently selected from H and $C_1$-$C_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl;

or $G_5$ is $CH(X_3—R^{6c})$ or $C(X_3—R^{6c})$, $G_6$ is $CH(X_4—R^{6d})$ or $C(X_4—R^{6d})$, and $R^{6c}$ and $R^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted;

wherein no more than one of $R^{6a}$, $R^{6b}$, $R^{6c}$, and $R^{6d}$ is $C_1$-$C_6$alkoxy or OH; and wherein the compound is not a compound of Table 1X.

In some embodiments, of Formula (A), ⚬ indicates that the ring is saturated, partially unsaturated, or fully unsaturated; | indicates that the

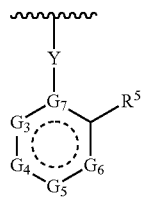

is attached in either the E or Z configuration;

$G_1$ and $G_2$ are each independently $CR^x$, or N;

$R^x$ is hydrogen or halogen;

one of $R^1$ and $R^2$ is —OH and the other is selected from the group consisting of —C(O)$R^a$, —CH=$NR^j$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted $C_3$-$C_8$ cycloalkyl, unsubstituted or substituted $C_3$-$C_8$ cycloalkenyl, and unsubstituted or substituted heterocloalkyl;

$R^a$, $R^b$, $R^c$, and $R^e$ are each independently H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, benzoyl, or styryl;

$R^d$ is H, $C_1$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl;

$R^f$ and $R^g$ are each independently —OH, unsubstituted heteroaryl, —$NR^mR^n$, benzoyl, or styryl;

$R^m$ and $R^n$ are each independently H, $C_1$-$C_6$alkyl, $C_2$-$C_6$alkenyl, $C_2$-$C_6$alkynyl, or unsubstituted or substituted cycloalkyl;

$R^j$ is unsubstituted or substituted heterocyclyl, unsubstituted or substituted aryl, —$OR^k$, —$NHR^k$, —NHC(O)$R^k$, —NHS(O)$_2R^k$, or —NHC(NH)$NH_2$;

$R^k$ is $C_1$-$C_6$alkyl, $C_2$-$C_6$alkenyl, $C_2$-$C_6$alkynyl, $C_3$-$C_8$ cycloalkyl, or aryl;

$R^3$ is H, $C_1$-$C_6$alkyl, $C_1$-$C_6$alkoxy, or halogen, wherein the $C_1$-$C_6$alkyl and $C_1$-$C_6$alkoxy of $R^3$ are each independently unsubstituted or substituted with one or more halogen;

Y is —C(O)— or absent and $R^4$ and $R^5$ are each H, or

Y is absent and $R^4$ and $R^5$ come together to form —S—;

$G_3$ is $CH(X_1—R^{6a})$, $C(X_1—R^{6a})$, N,N($X_1—R^{6a}$), S, or O;

$G_4$ is $CH(X_2—R^{6b})$, $C(X_2—R^{6b})$, N,N($X_2—R^{6b}$), S, or O;

$G_5$ is $CH(X_3—R^{6c})$, $C(X_3—R^{6c})$, N,N($X_3—R^{6c}$), S, or O;

$G_6$ is $CH(X_4—R^{6d})$, $C(X_4—R^{6d})$, N,N($X_4—R^{6d}$), S, O, or absent;

$G_7$ is N, C, or CH;

wherein when $G_5$ is N, either at least one of (i), (ii), and (iii) applies:
(i) at least one of $G_3$, $G_4$, and $G_6$ is not CH;
(ii) $R^4$ and $R^5$ come together to form —S—; and
(iii) $R^3$ is —$OCH_3$ or halo;

$X_1$, $X_2$, $X_3$, and $X_4$ are each independently absent,

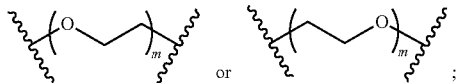

m is 1-6;

$R^{6a}$, $R^{6b}$, $R^{6c}$, and $R^{6d}$ are each independently hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —S(O)$_2NR^{w1}R^{w2}$, —S(O)$_2R^y$, or —$NR^{z1}S(O)_2R^{z2}$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with one or more groups selected from the group consisting of cycloalkyl and halogen; the aryl and heteroaryl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S;

$R^h$ is selected from the group consisting of H, $C_1$-$C_6$alkyl, $C_1$-$C_6$alkoxy, and $C_3$-$C_8$cycloalkyl, and —$NR'R^s$;

$R^p$ is H or $C_1$-$C_6$alkyl;

$R^q$ is $C_2$-$C_3$alkyl, —C(O)$R^t$, —C(O)$OR^u$, —C(O)$NR^v$;

$R^r$, $R^s$, $R^{w1}$, and $R^{z1}$ each independently selected from H and $C_1$-$C_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl;

or $G_5$ is $CH(X_3—R^{6c})$ or $C(X_3—R^{6c})$, $G_6$ is $CH(X_4—R^{6d})$ or $C(X_4—R^{6d})$, and $R^{6c}$ and $R^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted;

wherein no more than one of $R^{6a}$, $R^{6b}$, $R^{6c}$, and $R^{6d}$ is $C_1$-$C_6$alkoxy or —OH; and wherein the compound is not a compound of Table 1X.

In some embodiments of Formula (A), one or more of the following applies:

(1) when $R^1$ or $R^2$ is —$C_1$-$C_6$alkyl-OH or —$C_1$-$C_6$alkyl-$NR^mR^n$, wherein $R^m$ and $R^n$ are each $C_1$-$C_6$alkyl, $R^3$ is selected from the group consisting of $C_1$-$C_6$alkyl, $C_2$-$C_6$alkoxy, and halogen;

(2) when $R^1$ or $R^2$ is unsubstituted or substituted $C_3$-$C_8$ cycloalkyl, —NHC(O)CH$_3$, or —S(O)$_2$—R$^c$, wherein R$^c$ is an unsubstituted or substituted heterocyclyl, $R^3$ is selected from the group consisting of $C_1$-$C_6$alkyl, $C_1$-$C_6$alkoxy, and halogen;

(3) when $R^1$ or $R^2$ is —CHO, $R^3$ is selected from the group consisting of hydrogen, $C_2$-$C_6$alkoxy, and halogen;

(4) when $R^1$ or $R^2$ is —C(O)CH$_3$, $R^3$ is selected from the group consisting of $C_2$-$C_6$alkoxy and halogen;

(5) when $R^1$ or $R^2$ is —C(O)CH(Br)CH$_3$ or —C(O)CH(Br)CH$_2$CH$_3$, $G_7$ is C or CH; and (6) when $R^3$ is hydrogen, no more than one of $R^{6a}$, $R^{6b}$, $R^{6c}$, and $R^{6d}$ is —CF$_3$, no more than one of $R^{6a}$, $R^{6b}$, $R^{6c}$, and $R^{6d}$ is —CH$_3$, and no more than one of $R^{6a}$, $R^{6b}$, $R^{6c}$, and $R^{6d}$ is —OH.

In some embodiments of Formula (A), Y is —C(O)— and $R^4$ and $R^5$ are each H. In some embodiments, Y is absent and $R^4$ and $R^5$ are each H. In other embodiments, Y is absent and $R^4$ and $R^5$ come together to form —S—.

In some embodiments of Formula (A), $G_1$ and $G_2$ are each independently CR$^x$, wherein R$^x$ is H or halogen. In some embodiments, $G_1$ and $G_2$ are each independently CH, CF, CCl, or CBr. In some embodiments, $G_1$ and $G_2$ are each CH. In a particular embodiment, $G_1$ is CF and $G_2$ is CH. In another embodiment, $G_1$ is CH and $G_2$ is CF. In some embodiments, $G_1$ is CR$^x$ and $G_2$ is N. For instance, in some embodiments, $G_1$ is CH, CF, CCl, or CBr, and $G_2$ is N. In some embodiments, $G_1$ is N and $G_2$ is CR$^x$. For instance, in some embodiments, $G_1$ is N and $G_2$ is CH, CF, CCl, or CBr. In other embodiments, $G_1$ and $G_2$ are each N.

In some embodiments, when any particular group is substituted, the indicated group is substituted by one or more substituents selected from the group consisting of oxo, $C_1$-$C_6$ alkyl, $C_2$-$C_6$ alkenyl, $C_2$-$C_6$ alkynyl, halogen, —CN, —OR$^{A1}$, —SR$^{A1}$, —NR$^{A2}$R$^{A3}$, —NO$_2$, —C=NH(OR$^{A1}$), —C(O)R$^{A1}$, —OC(O)R$^{A1}$, —C(O)OR$^{A1}$, —C(O)NR$^{A2}$R$^{A3}$, —OC(O)NR$^{A2}$R$^{A3}$, —NR$^{A1}$C(O)R$^{A2}$, —NR$^{A1}$C(O)OR$^{A2}$, —NR$^{A1}$C(O)NR$^{A2}$R$^{A3}$, —S(O)R$^{A1}$, —S(O)$_2$R$^{A1}$, —NR$^{A1}$S(O)R$^{A2}$, —C(O)NR$^{A1}$S(O)R$^{A2}$, —NR$^{A1}$S(O)$_2$R$^{A2}$, —C(O)NR$^{A1}$S(O)$_2$R$^{A2}$, —S(O)NR$^{A2}$R$^{A3}$, —S(O)$_2$NR$^{A2}$R$^{A3}$, —P(O)(OR$^{A2}$)(OR$^{A3}$), $C_3$-$C_8$ cycloalkyl, 3-12-membered heterocyclyl, 5- to 10-membered heteroaryl, $C_6$-$C_{14}$ aryl, —(C$_1$-$C_3$ alkylene)CN, —(C$_1$-$C_3$ alkylene)OR$^{A1}$, —(C$_1$-$C_3$ alkylene)SR$^{A1}$, —(C$_1$-$C_3$ alkylene)NR$^{A2}$R$^{A3}$, —(C$_1$-$C_3$ alkylene)CF$_3$, —(C$_1$-$C_3$ alkylene)NO$_2$, —C=NH(OR$^{A1}$), —(C$_1$-$C_3$ alkylene)C(O)R$^{A1}$, —(C$_1$-$C_3$ alkylene)OC(O)R$^{A1}$, —(C$_1$-$C_3$ alkylene)C(O)OR$^{A1}$, —(C$_1$-$C_3$ alkylene)C(O)NR$^{A2}$R$^{A3}$, —(C$_1$-$C_3$ alkylene)OC(O)NR$^{A2}$R$^{A3}$, —(C$_1$-$C_3$ alkylene)NR$^{A1}$C(O)R$^{A2}$, —(C$_1$-$C_3$ alkylene)NR$^{A1}$C(O)OR$^{A2}$, —(C$_1$-$C_3$ alkylene)NR$^{A1}$C(O)NR$^{A2}$R$^{A3}$, —(C$_1$-$C_3$ alkylene)S(O)R$^{A1}$, —(C$_1$-$C_3$ alkylene)S(O)$_2$R$^{A1}$, —(C$_1$-$C_3$ alkylene)NR$^{A1}$S(O)R$^{A2}$, —C(O)(C$_1$-$C_3$ alkylene)NR$^{A1}$S(O)R$^{A2}$, —(C$_1$-$C_3$ alkylene)NR$^{A1}$S(O)$_2$R$^{A2}$, —C$_1$-$C_3$ alkylene)C(O)NR$^{A1}$S(O)$_2$R$^{A2}$, —(C$_1$-$C_3$ alkylene)S(O)NR$^{A2}$R$^{A3}$, —(C$_1$-$C_3$ alkylene)S(O)$_2$NR$^{A2}$R$^{A3}$, —(C$_1$-$C_3$ alkylene)P(O)(OR$^{A2}$)(OR$^{A3}$), —(C$_1$-$C_3$ alkylene)(C$_3$-$C_8$ cycloalkyl), —(C$_1$-$C_3$ alkylene) (3-12-membered heterocyclyl), —(C$_1$-$C_3$ alkylene) (5-10-membered heteroaryl) and —(C$_1$-$C_3$ alkylene) (C$_6$-$C_{14}$ aryl), wherein the one or more substituents are each independently unsubstituted or substituted with one or more further substituents selected from the group consisting of halogen, oxo, —OR$^{A4}$, —NR$^{A4}$R$^{A5}$, —C(O)R$^{A4}$, —CN, —S(O)R$^{A4}$, —S(O)$_2$R$^{A4}$, —P(O)(OR$^{A4}$)(OR$^{A5}$), —(C$_1$-$C_3$ alkylene)OR$^{A4}$, —(C$_1$-$C_3$ alkylene)NR$^{A4}$R$^{A5}$, —(C$_1$-$C_3$ alkylene)C(O)R$^{A4}$, —(C$_1$-$C_3$ alkylene)S(O)R$^{A4}$, —(C$_1$-$C_3$ alkylene)S(O)$_2$R$^{A4}$, —(C$_1$-$C_3$ alkylene) P(O)(OR$^{A4}$)(OR$^{A5}$), $C_3$-$C_8$ cycloalkyl, $C_1$-$C_6$ alkyl, and $C_1$-$C_6$ alkyl substituted by oxo, —OH or halogen; wherein each R$^{A1}$ is independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl or 3-6-membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl and 3-6-membered heterocyclyl are independently unsubstituted or substituted by halogen, oxo, —CN, —OR$^{A6}$, —NR$^{A6}$R$^{A7}$, —P(O)(OR$^{A6}$)(OR$^{A6}$), phenyl, phenyl substituted by halogen, $C_1$-$C_6$ alkyl, or $C_1$-$C_6$ alkyl substituted by halogen, —OH or oxo; R$^{A2}$ and R$^{A3}$ are each independently hydrogen, $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl or 3-6 membered heterocyclyl, wherein the $C_1$-$C_6$ alkyl, $C_2$-$C_6$ alkenyl, $C_2$-$C_6$ alkynyl, $C_3$-$C_8$ cycloalkyl, $C_6$-$C_{14}$ aryl, 5-6-membered heteroaryl and 3-6 membered heterocyclyl are each independently unsubstituted or substituted by halogen, oxo, —CN, —OR$^{A6}$, —NR$^{A6}$R$^{A7}$, $C_1$-$C_6$ alkyl, or $C_1$-$C_6$ alkyl substituted by halogen, —OH or oxo; and R$^{A4}$, R$^{A5}$, R$^{A6}$ and R$^{A7}$ are each independently hydrogen, $C_1$-$C_6$ alkyl, $C_2$-$C_6$ alkenyl, $C_2$-$C_6$ alkynyl, $C_1$-$C_6$ alkyl substituted by one or more halogen, $C_2$-$C_6$ alkenyl substituted by one or more halogen, or $C_2$-$C_6$ alkynyl substituted by one or more halogen.

In some embodiments, $R^3$ is $C_2$-$C_6$alkoxy or halogen, and $R^1$, $R^2$, $R^4$, $R^5$, Y, $G_1$, $G_2$, $G_3$, $G_4$, $G_5$, $G_6$, and $G_7$ are as defined for Formula (A) or any variation or embodiment thereof. In some embodiments, one of $R^1$ and $R^2$ is —OH and the other is selected from the group consisting of —CH=NR$^j$, —S(O)R$^b$, —NHS(O)$_2$R$^e$, —C$_2$-$C_6$alkenyl-R$^g$, unsubstituted or substituted $C_3$-$C_8$ cycloalkenyl, and unsubstituted or substituted heterocycloalkyl, and $R^1$, $R^3$, $R^4$, $R^5$, Y, $G_1$, $G_2$, $G_3$, $G_4$, $G_5$, $G_6$, and $G_7$ are as defined for Formula (A) or any variation or embodiment thereof. In some embodiments, one of $R^1$ and $R^2$ is —OH and the other is selected from the group consisting of —C(O)R$^a$, —CH=NR$^j$, —S(O)R$^b$, —S(O)$_2$R$^c$, —NHC(O)R$^d$, —NHS(O)$_2$R$^e$, —C$_1$-$C_6$alkyl-R$^f$, —C$_2$-$C_6$alkenyl-R$^g$, unsubstituted or substituted $C_3$-$C_8$ cycloalkenyl, and unsubstituted or substituted heterocycloalkyl; R$^a$ is $C_2$-$C_6$alkyl, $C_2$-$C_6$alkenyl, $C_2$-$C_6$alkynyl, unsubstituted or substituted heterocyclyl, unsubstituted or substituted heteroaryl, benzoyl, or styryl; R$^c$ is H, $C_1$-$C_6$alkyl, $C_2$-$C_6$alkenyl, $C_2$-$C_6$alkynyl, $C_1$-$C_6$haloalkyl, unsubstituted or substituted heteroaryl, benzoyl, or styryl; R$^d$ is H, $C_2$-$C_6$alkyl, $C_2$-$C_6$alkenyl, $C_2$-$C_6$alkynyl, $C_1$-$C_6$haloalkyl, unsubstituted or substituted heterocyclyl, unsubstituted or substituted heteroaryl, or benzoyl; R$^f$ is unsubstituted heteroaryl, benzoyl, or styryl; and $R^3$, $R^4$, $R^5$, Y, $G_1$, $G_2$, $G_3$, $G_4$, $G_5$, $G_6$, and $G_7$ are as defined for Formula (A) or any variation or embodiment thereof. In some embodiments, $R^3$ is $C_2$-$C_6$alkoxy or halogen; $G_5$ is CH(X$_3$—R$^{6c}$), C(X$_3$—R$^{6c}$), S, or O; R$^{6a}$, R$^{6b}$, R$^{6c}$, and R$^{6d}$ are each independently hydrogen, $C_1$-$C_6$alkyl, halo, —NR$^p$R$^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$; and $R^1$, $R^2$, $R^4$, $R^5$, R$^p$, R$^q$, R$^h$, R$^{w1}$, R$^{w2}$, R$^y$, R$^{z1}$, R$^{z2}$, Y, $G_1$, $G_2$, $G_3$, $G_4$, $G_6$, and $G_7$ are as defined for Formula (A) or any variation or embodiment thereof. In some embodiments, one of $R^1$ and $R^2$ is —OH and the other is selected from the group consisting of —CH=NR$^j$, —S(O)R$^b$, —NHS(O)$_2$R$^e$, —C$_2$-$C_6$alkenyl-R$^g$, unsubstituted or substituted $C_3$-$C_8$ cycloalkenyl, and unsubstituted or substituted heterocycloalkyl; $G_5$ is CH(X$_3$—R$^{6c}$), C(X$_3$—R$^{6c}$), S, or O; R$^{6a}$, R$^{6b}$, R$^{6c}$, and R$^{6d}$ are each independently hydrogen, $C_1$-$C_6$alkyl, halo, —NR$^p$R$^q$, aryl, heterocyclyl, heteroaryl, —C$_1$-

$C_6$alkyl-heterocyclyl, —OC(O)-heterocyclyl, —C(O)$R^h$, —S(O)$_2$NR$^{w1}$R$^{w2}$, —S(O)$_2$R$^y$, or —NR$^{z1}$S(O)$_2$R$^{z2}$; and R$^1$, R$^3$, R$^4$, R$^5$, R$^p$, R$^q$, R$^h$, R$^{w1}$, R$^{w2}$, R$^y$, R$^{z1}$, R$^{z2}$, Y, G$_1$, G$_2$, G$_3$, G$_4$, G$_6$, and G$_7$ are as defined for Formula (A) or any variation or embodiment thereof. In some embodiments, one of R$^1$ and R$^2$ is —OH and the other is selected from the group consisting of —C(O)R$^a$, —CH═NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted C$_3$-C$_8$ cycloalkenyl, and unsubstituted or substituted heterocycloalkyl; R$^a$ is C$_2$-C$_6$alkyl, C$_2$-C$_6$alkenyl, C$_2$-C$_6$alkynyl, unsubstituted or substituted heterocyclyl, unsubstituted or substituted heteroaryl, benzoyl, or styryl; R$^e$ is H, C$_1$-C$_6$alkyl, C$_2$-C$_6$alkenyl, C$_2$-C$_6$alkynyl, C$_1$-C$_6$haloalkyl, unsubstituted or substituted heteroaryl, benzoyl, or styryl; R$^d$ is H, C$_2$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, or benzoyl; R$^f$ is unsubstituted heteroaryl, benzoyl, or styryl; G$_5$ is CH(X$_3$—R$^{6c}$), C(X$_3$—R$^{6c}$), S, or O; R$^{6a}$, R$^{6b}$, R$^{6c}$, and R$^{6d}$ are each independently hydrogen, C$_1$-C$_6$alkyl, halo, —NR$^p$R$^q$, aryl, heterocyclyl, heteroaryl, —C$_1$-C$_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$; and R$^3$, R$^4$, R$^5$, R$^p$, R$^q$, R$^h$, R$^{w1}$, R$^{w2}$, R$^y$, R$^{z1}$, R$^{z2}$, Y, G$_1$, G$_2$, G$_3$, G$_4$, G$_6$, and G$_7$ are as defined for Formula (A) or any variation or embodiment thereof.

In some embodiments, one of R$^1$ and R$^2$ is —OH and the other is selected from the group consisting of —C(O)R$^a$, —CH═NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, C$_3$-C$_8$ cycloalkyl, C$_3$-C$_8$ cycloalkenyl, and 5- or 6-membered heterocycloalkyl, wherein the C$_3$-C$_8$ cycloalkyl and C$_3$-C$_8$ cycloalkenyl are each independently unsubstituted or substituted with one or more ═O, and the 5- or 6-membered heterocycloalkyl is unsubstituted or substituted with one or more substituents selected from the group consisting of C$_1$-C$_6$alkyl, C$_3$-C$_8$cycloalkyl, ═O, and —C(O)O—C$_1$-C$_6$alkyl;

R$^a$, R$^b$, R$^c$, and R$^e$ are each independently H, C$_1$-C$_6$alkyl, C$_2$-C$_6$alkenyl, C$_2$-C$_6$alkynyl, C$_1$-C$_6$haloalkyl, 3- to 10-membered heterocyclyl, 5- to 10-membered heteroaryl, benzoyl, or styryl, wherein the 3- to 10-membered heterocyclyl of R$^a$, R$^b$, R$^c$, and R$^e$ are each independently selected from the group consisting of C$_1$-C$_6$alkyl, C$_3$-C$_8$cycloalkyl, ═O, and —C(O)O—C$_1$-C$_6$alkyl, and the 5- to 10-membered heteroaryl of R$^a$, R$^b$, R$^c$, and R$^e$ are each independently selected from the group consisting of C$_1$-C$_6$alkyl, C$_3$-C$_8$cycloalkyl, and —C(O)O—C$_1$-C$_6$alkyl;

R$^d$ is H, C$_1$-C$_6$alkyl, C$_2$-C$_6$alkenyl, C$_2$-C$_6$alkynyl, C$_1$-C$_6$haloalkyl, 3- to 10-membered heterocyclyl, 5- to 10-membered heteroaryl, or benzoyl, wherein the 3- to 10-membered heterocyclyl of R$^d$ is selected from the group consisting of C$_1$-C$_6$alkyl, C$_3$-C$_8$cycloalkyl, ═O, and —C(O)O—C$_1$-C$_6$alkyl, and the 5- to 10-membered heteroaryl of R$^d$ is selected from the group consisting of C$_1$-C$_6$alkyl, C$_3$-C$_8$cycloalkyl, and —C(O)O—C$_1$-C$_6$alkyl;

R$^f$ and R$^g$ are each independently —OH, unsubstituted 5- to 6-membered heteroaryl, —NR$^m$R$^n$, benzoyl, or styryl;

R$^m$ and R$^n$ are each independently H, C$_1$-C$_6$alkyl, C$_2$-C$_6$alkenyl, C$_2$-C$_6$alkynyl, or C$_3$-C$_8$ cycloalkyl, wherein the C$_3$-C$_8$ cycloalkyl is unsubstituted or substituted with one or more groups selected from C$_1$-C$_6$alkyl and halo;

R$^j$ is 5- to 6-membered heterocyclyl, 5- to 6-membered heteroaryl, 6- to 12-membered aryl, —OR$^k$, —NHR$^k$, —NHC(O)R$^k$, —NHS(O)$_2$R$^k$, or —NHC(NH)NH$_2$, wherein the 5- to 6-membered heterocyclyl of R$^j$ is unsubstituted or substituted with one or more substituents selected from the group consisting of C$_1$-C$_6$alkyl, C$_3$-C$_8$cycloalkyl, ═O, and —C(O)O—C$_1$-C$_6$alkyl, and the 5- to 6-membered heteroaryl and 6- to 12-membered aryl of R$^j$ are each independently unsubstituted or substituted with one or more substituents selected from the group consisting of C$_1$-C$_6$alkyl, C$_3$-C$_8$cycloalkyl, and —C(O)O—C$_1$-C$_6$alkyl; and R$^k$ is C$_1$-C$_6$alkyl, C$_2$-C$_6$alkenyl, C$_2$-C$_6$alkynyl, C$_3$-C$_8$cycloalkyl, or 6- to 12-membered aryl, wherein the C$_1$-C$_6$alkyl is unsubstituted or substituted with 5- to 6-membered heterocyclyl or 5- to 6-membered heteroaryl.

In some embodiments, R$^{6a}$, R$^{6b}$, R$^{6c}$, and R$^{6d}$ are each independently hydrogen, C$_1$-C$_6$alkyl, C$_1$-C$_6$alkoxy, halo, —OH, —NR$^p$R$^q$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the C$_1$-C$_6$alkyl and C$_1$-C$_6$alkoxy of R$^{6a}$, R$^{6b}$, R$^{6c}$, and R$^{6d}$ are each independently unsubstituted or substituted with one or more groups selected from the group consisting of C$_3$-C$_8$ cycloalkyl and halogen; the C$_6$-C$_{12}$ aryl and 5- to 10-membered heteroaryl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, and C$_1$-C$_6$alkyl-OH; and the 3- to 10-membered heterocyclyl, —C$_1$-C$_6$alkyl-5- to 6-membered heterocyclyl, and —OC(O)-5- to 6-membered heterocyclyl of R$^{6a}$, R$^{6b}$, R$^{6c}$, and R$^{6d}$ are each independently unsubstituted or substituted with one or more groups selected from the group consisting of C$_1$-C$_6$alkyl, C$_1$-C$_6$alkoxy, —OH, C$_1$-C$_6$alkyl-OH, ═O, and ═S;

R$^h$ is selected from the group consisting of H, C$_1$-C$_6$alkyl, C$_1$-C$_6$alkoxy, C$_3$-C$_8$cycloalkyl, and —NR$^r$R$^s$;

R$^p$ is H or C$_1$-C$_6$alkyl; —R$^q$ is C$_2$-C$_3$alkyl, —C(O)R$^t$, —C(O)OR$^u$, —C(O)NR$^v$; —R$^r$, R$^s$, R$^{w1}$, and R$^{z1}$ each independently selected from H and C$_1$-C$_6$alkyl; and —R$^t$, R$^u$, R$^v$, R$^{w2}$, R$^y$, and R$^{z2}$ are each independently selected from H, C$_1$-C$_6$alkyl, unsubstituted or substituted C$_3$-C$_8$cycloalkyl, and unsubstituted or substituted heterocyclyl;

or

G$_5$ is CH(X$_3$—R$^{6c}$) or C(X$_3$—R$^{6c}$), G$_6$ is CH(X$_4$—R$^{6d}$) or C(X$_4$—R$^{6d}$), and R$^{6c}$ and R$^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of C$_1$-C$_6$alkyl and —C(O)O—C$_1$-C$_6$alkyl; and wherein no more than one of R$^{6a}$, R$^{6b}$, R$^{6c}$, and R$^{6d}$ is C$_1$-C$_6$alkoxy or —OH.

In some embodiments, one of R$^1$ and R$^2$ is —OH and the other is selected from the group consisting of —C(O)R$^a$, —CH═NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted C$_3$-C$_8$ cycloalkyl, unsubstituted or substituted C$_3$-C$_8$ cycloalkenyl, and unsubstituted or substituted heterocycloalkyl. In some embodiments, one of R$^1$ and R$^2$ is —OH and the other is selected from the group consisting of —C(O)R$^a$, —CH═NR$^j$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, C$_3$-C$_8$ cycloalkyl, C$_3$-C$_8$ cycloalkenyl, and heterocycloalkyl, wherein the C$_3$-C$_8$ cycloalkyl, C$_3$-C$_8$ cycloalkenyl, and heterocycloalkyl are optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl. In some embodiments, R$^a$, R$^b$, R$^c$, and R$^e$ are each independently H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, benzoyl, or styryl. In some embodiments R$^a$, R$^b$, R$^c$, and R$^e$ are each independently H, C$_1$-C$_6$alkyl, C$_2$-C$_6$alkenyl, C$_2$-C$_6$alkynyl, C$_1$-C$_6$haloalkyl, heterocyclyl, heteroaryl, benzoyl, or styryl, wherein the heterocyclyl and heteroaryl are optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl. In some embodiments, R$^d$ is H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, or benzoyl. In some embodiments, R$^d$ is H, C$_1$-C$_6$alkyl, C$_2$-C$_6$alkenyl, C$_2$-C$_6$alkynyl, C$_1$-C$_6$haloalkyl, heterocyclyl, heteroaryl, or benzoyl, wherein the heterocyclyl and heteroaryl are optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl. In some embodiments, R$^f$ and R$^g$ are each independently OH, unsubstituted heteroaryl, —NR$^m$R$^n$, benzoyl, or styryl, wherein R$^m$ and R$^n$ are each independently H, C$_1$-C$_6$alkyl, C$_2$-C$_6$alkenyl, C$_2$-C$_6$alkynyl, or C$_3$-C$_8$ cycloalkyl, wherein the C$_3$-C$_8$ cycloalkyl is optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl. In some embodiments, R$^j$ is heterocyclyl, aryl, —OR$^k$, —NHR$^k$, —NHC(O)R$^k$, —NHS(O)$_2$R$^k$, or —NHC(NH)NH$_2$, wherein the heterocyclyl and aryl are optionally substituted with one or more substituents selected from the group consisting of C$_1$-C$_6$ alkyl, C$_1$-C$_6$ haloalkyl, halo, —OH, —C(O)H, —C(O)OH, —C(O)OC$_1$-C$_6$ alkyl, —OC$_1$-C$_6$ alkyl, and C$_3$-C$_8$ cycloalkyl.

In some embodiments, one of R$^1$ and R$^2$ is —OH and the other is —C(O)R$^a$, wherein R$^a$ is a 3- to 18-membered heterocyclyl. In some embodiments, R$^a$ is a 3- to 10-membered heterocyclyl, unsubstituted or substituted with one or more substituents selected from the group consisting of C$_1$-C$_6$alkyl, C$_3$-C$_8$ cycloalkyl, =O, and C(O)O—C$_1$-C$_6$alkyl. In some embodiments, one of R$^1$ and R$^2$ is —OH and the other is —C(O)R$^a$, wherein R$^a$ is a 5- to 18-membered heteroaryl. In some embodiments, R$^a$ is a 5- to 10-membered heteroaryl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, one of R$^1$ and R$^2$ is —OH and the other is —CH=NR$^j$, wherein R$^j$ is a 3- to 18-membered heterocyclyl. In some embodiments, R$^j$ is a 5- to 6-membered heterocyclyl, unsubstituted or substituted with one or more substituents selected from the group consisting of C$_1$-C$_6$alkyl, C$_3$-C$_8$cycloalkyl, =O, and —C(O)O—C$_1$-C$_6$alkyl. In some embodiments, one of R$^1$ and R$^2$ is —OH and the other is —CH=NR$^j$, wherein is a 5- to 18-membered heteroaryl. In some embodiments, R$^j$ is a 5- to 10-membered heteroaryl, unsubstituted or substituted with one or more substituents selected from the group consisting of C$_3$-C$_8$cycloalkyl, and —C(O)O—C$_1$-C$_6$alkyl. In some embodiments, one of R$^1$ and R$^2$ is —OH and the other is —CH=NR$^j$, wherein R$^j$ is a 6- to 14-membered aryl. In some embodiments, R$^j$ is a phenyl or naphthyl, unsubstituted or substituted with one or more substituents selected from the group consisting of C$_1$-C$_6$alkyl, C$_3$-C$_8$cycloalkyl, and —C(O)O—C$_1$-C$_6$alkyl. In some embodiments, R$^j$ is phenyl. In some embodiments, one of R$^1$ and R$^2$ is —OH and the other is —CH=NR$^j$, wherein —CH=NR$^j$ is selected from the group consisting of

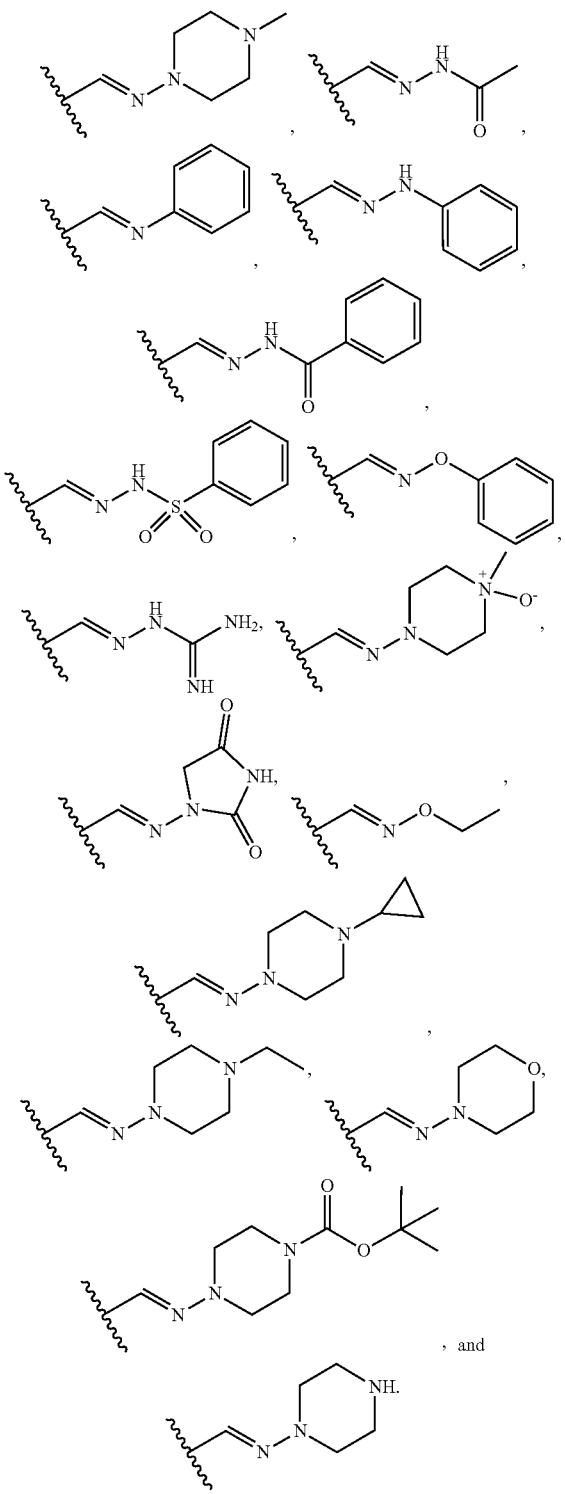

In some embodiments, one of R$^1$ and R$^2$ is —OH and the other is —CH=NR$^j$, wherein —CH=NR$^j$ is selected from the group consisting of

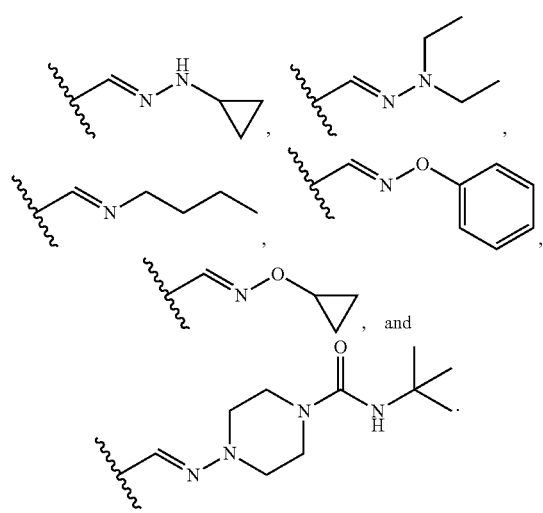

In some embodiments, one of $R^1$ and $R^2$ is —OH and the other is —S(O)$R^b$, —S(O)$_2R^c$, —NHC(O)$R^d$, or —NHS(O)$_2R^e$, wherein $R^b$, $R^c$, $R^d$, and $R^e$ are each independently an unsubstituted 3- to 18-membered heterocyclyl or an unsubstituted 5- to 18-membered heterocyclyl. In some embodiments, $R^b$, $R^c$, $R^d$, and $R^e$ are each independently a 3- to 18-membered heterocyclyl or a 5- to 18-membered heterocyclyl, each independently substituted with one or more substituents selected from the group consisting of $C_1$-$C_6$alkyl, $C_3$-$C_8$cycloalkyl, and —C(O)O—$C_1$-$C_6$alkyl. In some embodiments, one of $R^1$ and $R^2$ is —OH and the other is —$C_1$-$C_6$alkyl-$R^f$, wherein $R^f$ is —OH or NR$^m$R$^n$, wherein $R^m$ and $R^n$ are each independently H, $C_1$-$C_6$alkyl, $C_2$-$C_6$alkenyl, $C_2$-$C_6$alkynyl, or unsubstituted or substituted $C_3$-$C_6$cycloalkyl. In some embodiments, $R^f$ is NR$^m$R$^n$, wherein $R^m$ is H and $R^n$ is $C_3$-$C_6$cycloalkyl, wherein the $C_3$-$C_6$cycloalkyl is unsubstituted or substituted with one or more groups selected from $C_1$-$C_6$alkyl and halo. In some embodiments, one of $R^1$ and $R^2$ is —OH and the other is —$C_2$-$C_6$alkenyl-$R^g$, wherein $R^g$ is benzoyl. In some embodiments, one of $R^1$ and $R^2$ is —OH and the other is —$C_1$-$C_6$alkenyl-$R^g$, wherein $R^g$ is —OH or —NR$^m$R$^n$, wherein $R^m$ and $R^n$ are each independently H, $C_1$-$C_6$alkyl, $C_2$-$C_6$alkenyl, $C_2$-$C_6$alkynyl, or unsubstituted or substituted $C_3$-$C_6$cycloalkyl. In some embodiments, $R^g$ is NR$^m$R$^n$, wherein $R^m$ is H and $R^n$ is $C_3$-$C_6$cycloalkyl, wherein the $C_3$-$C_6$cycloalkyl is unsubstituted or substituted with one or more groups selected from $C_1$-$C_6$alkyl and halo. In some embodiments, $R^m$ is unsubstituted or substituted $C_3$-$C_8$ cycloalkyl, and $R^n$ is H, $C_1$-$C_6$alkyl, $C_2$-$C_6$alkenyl, or $C_2$-$C_6$alkynyl. In some embodiments, $R^m$ is $C_3$-$C_8$ cycloalkyl, and $R^n$ is H.

In some embodiments, one of $R^1$ and $R^2$ is —OH and the other is —CH=NR$^j$, wherein NR$^j$ is unsubstituted or substituted heterocyclyl, unsubstituted or substituted aryl, —OR$^k$, —NHR$^k$, —NHC(O)R$^k$, —NHS(O)$_2$R$^k$, or —NHC(NH)NH$_2$. In some embodiments, one of $R^1$ and $R^2$ is —OH and the other is —CH=NR$^j$, wherein NR$^j$ is unsubstituted or substituted 4- to 12-membered heterocyclyl. In some embodiments, one of $R^1$ and $R^2$ is —OH and the other is —CH=NR$^j$, wherein NR$^j$ is an unsubstituted 4- to 12-membered heterocyclyl. In some embodiments, one of $R^1$ and $R^2$ is —OH and the other is —CH=NR$^j$, wherein NR$^j$ is a 4- to 12-membered heterocyclyl substituted with one or more groups selected from the group consisting of $C_1$-$C_6$ alkyl, $C_3$-$C_8$ cycloalkyl, and oxo. In some embodiments, one of $R^1$ and $R^2$ is —OH and the other is —CH=NR$^j$, wherein NR$^j$ is unsubstituted or substituted 5- to 6-membered heterocyclyl. In certain embodiments, one of $R^1$ and $R^2$ is —OH and the other is —CH=NR$^j$, wherein NR$^j$ is an unsubstituted heterocyclyl. In some embodiments, one of $R^1$ and $R^2$ is —OH and the other is —CH=NR$^j$, wherein NR$^j$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In other embodiments, one of $R^1$ and $R^2$ is —OH and the other is —CH=NR$^j$, wherein NR$^j$ is a heterocyclyl substituted with one or more substituents selected from the group consisting of $C_1$-$C_6$alkyl, $C_3$-$C_8$cycloalkyl, and oxo. In some embodiments, R$^j$ is a heterocyclyl, wherein the nitrogen and/or sulfur atom(s) of the heterocyclyl are optionally oxidized to provide for N-oxide, —S(O)—, or —SO$_2$— moieties. In some embodiments, one of $R^1$ and $R^2$ is OH and the other is $C_3$-$C_8$ cycloalkyl or $C_3$-$C_8$ cycloalkenyl, each unsubstituted or substituted with one or more groups selected from the group consisting of halo, $C_1$-$C_6$alkyl, $C_1$-$C_6$alkoxy, —C(O)O—$C_1$-$C_6$alkyl, and oxo. In some embodiments, one of $R^1$ and $R^2$ is —OH and the other is $C_3$-$C_8$ cycloalkenyl, substituted with one or more oxo. In some embodiments, one of $R^1$ and $R^2$ is —OH and the other is an unsubstituted or substituted 3- to 18-membered heterocycloalkyl. In some embodiments, one of $R^1$ and $R^2$ is —OH and the other is an unsubstituted or substituted 5- to 6-membered heterocycloalkyl. In some embodiments, one of $R^1$ and $R^2$ is —OH and the other is a 5- to 6-membered heterocycloalkyl, unsubstituted or substituted with one or more groups selected from $C_1$-$C_6$alkyl, $C_3$-$C_8$cycloalkyl, =O, and —C(O)O—$C_1$-$C_6$alkyl.

In some embodiments, one of $R^1$ and $R^2$ is —OH and the other is —CH=NR$^j$, wherein NR$^j$ is unsubstituted or substituted aryl. In some embodiments, one of $R^1$ and $R^2$ is —OH and the other is —CH=NR$^j$, wherein NR$^j$ is unsubstituted or substituted 6- to 14-membered aryl. In some embodiments, one of $R^1$ and $R^2$ is —OH and the other is —CH=NR$^j$, wherein NR$^j$ is unsubstituted phenyl or naphthyl. In other embodiments, one of $R^1$ and $R^2$ is —OH and the other is —CH=NR$^j$, wherein NR$^j$ is a phenyl or naphthyl substituted with one or more substituents selected from the group consisting of $C_1$-$C_6$alkyl, $C_3$-$C_8$cycloalkyl, and oxo.

In some embodiments, one of $R^1$ and $R^2$ is —OH and the other is —CH=NR$^j$, wherein R$^j$ is —OR$^k$. In some embodiments, one of $R^1$ and $R^2$ is —OH and the other is —CH=NR$^j$, wherein R$^j$ is —OC$_1$-$C_6$alkyl. In some embodiments, one of $R^1$ and $R^2$ is —OH and the other is —CH=NR$^j$, wherein R$^j$ is —OC$_1$-$C_6$alkenyl or —OC$_1$-$C_6$alkynyl. In some embodiments, one of $R^1$ and $R^2$ is —OH and the other is —CH=NR$^j$, wherein R$^j$ is —OC$_3$-$C_8$cycloalkyl. In other embodiments, one of $R^1$ and $R^2$ is —OH and the other is —CH=NR$^j$, wherein R$^j$ is —O-aryl. In some embodiments, one of $R^1$ and $R^2$ is —OH and the other is —CH=NR$^j$, wherein R$^j$ is —NHR$^k$. In some embodiments, one of $R^1$ and $R^2$ is —OH and the other is —CH=NR$^j$, wherein is —NHC$_1$-$C_6$alkyl. In some embodiments, one of $R^1$ and $R^2$ is —OH and the other is —CH=NR$^j$, wherein R$^j$ is —NHC$_1$-$C_6$alkenyl or —NHC$_1$-$C_6$alkynyl. In some embodiments, one of $R^1$ and $R^2$ is —OH and the other is —CH=NR$^j$, wherein R$^j$ is —NHC$_3$-$C_8$cycloalkyl. In other embodiments, one of $R^1$ and $R^2$ is —OH and the other is —CH=NR$^j$, wherein R$^j$ is —NH-aryl. In some embodiments, one of $R^1$ and $R^2$ is —OH and the other is —CH=NR$^j$, wherein R$^j$ is —NHC(O)R$^k$. In some embodiments, one of R$^1$ and R$^2$ is —OH and the other is —CH=NR$^j$, wherein is —NHC(O)C$_1$-C$_6$alkyl. In some embodiments, one of R$^1$ and R$^2$ is —OH and the other is —CH=NR$^j$, wherein R$^j$ is —NHC(O)C$_1$-C$_6$alkenyl or —NHC(O)C$_1$-C$_6$alkynyl. In some embodiments, one of R$^1$ and R$^2$ is —OH and the other is —CH=NR$^j$, wherein R$^j$ is —NHC(O)C$_3$-C$_8$cycloalkyl. In other embodiments, one of R$^1$ and R$^2$ is —OH and the other is —CH=NR$^j$, wherein R$^j$ is —NHC(O)-aryl. In some embodiments, one of R$^1$ and R$^2$ is —OH and the other is —CH=NR$^j$, wherein R$^j$ is —NHS(O)$_2$R$^k$. In some embodiments, one of R$^1$ and R$^2$ is —OH and the other is —CH=NR$^j$, wherein R$^j$ is —NHS(O)$_2$C$_1$-C$_6$alkyl. In some embodiments, one of R$^1$ and R$^2$ is —OH and the other is —CH=NR$^j$, wherein R$^j$ is —NHS(O)$_2$C$_1$-C$_6$alkenyl or —NHS(O)$_2$C$_1$-C$_6$alkynyl. In some embodiments, one of R$^1$ and R$^2$ is —OH and the other is —CH=NR$^j$, wherein R$^j$ is —NHS(O)$_2$C$_3$-C$_8$cycloalkyl. In other embodiments, one of R$^1$ and R$^2$ is —OH and the other is —CH=NR$^j$, wherein R$^j$ is —NHS(O)$_2$-aryl. In some embodiments, one of R$^1$ and R$^2$ is —OH and the other is —CH=NR$^j$, wherein is —NHC(NH)NH$_2$.

In some embodiments, one of R$^1$ and R$^2$ is —OH and the other is —C$_1$-C$_6$alkyl-R$^f$, wherein R$^f$ is selected from the group consisting of —OH, unsubstituted heteroaryl, benzoyl, or styryl, and R$^m$ and R$^n$ are each independently H, C$_1$-C$_6$alkyl, C$_2$-C$_6$alkenyl, C$_2$-C$_6$alkynyl, or unsubstituted or substituted C$_3$-C$_8$ cycloalkyl. In some embodiments, one of R$^1$ and R$^2$ is —OH and the other is —C$_2$-C$_6$alkenyl-R$^g$, wherein R$^g$ is selected from the group consisting of —OH, unsubstituted heteroaryl, —NR$^m$R$^n$, benzoyl, or styryl, and R$^m$ and R$^n$ are each independently H, C$_1$-C$_6$alkyl, C$_2$-C$_6$alkenyl, C$_2$-C$_6$alkynyl, or unsubstituted or substituted C$_3$-C$_8$ cycloalkyl. In some embodiments, R$^m$ and R$^n$ are each independently H, C$_1$-C$_6$alkyl, C$_2$-C$_6$alkenyl, C$_2$-C$_6$alkynyl, or unsubstituted C$_3$-C$_8$cycloalkyl, or C$_3$-C$_8$cycloalkyl substituted with one or more substituents selected from the group consisting of C$_1$-C$_6$alkyl, C$_2$-C$_6$alkenyl, C$_2$-C$_6$alkynyl, C$_1$-C$_6$alkoxy, C$_1$-C$_6$haloalkyl, —OH, and halo.

In some embodiments, one of R$^1$ and R$^2$ is —OH and the other is unsubstituted C$_3$-C$_8$ cycloalkyl. In other embodiments, one of R$^1$ and R$^2$ is —OH and the other is substituted C$_3$-C$_8$ cycloalkyl. In some embodiments, one of R$^1$ and R$^2$ is —OH and the other is unsubstituted C$_3$-C$_8$ cycloalkenyl. In other embodiments, one of R$^1$ and R$^2$ is —OH and the other is substituted C$_3$-C$_8$ cycloalkenyl.

In some embodiments, R$^3$ is H. In some embodiments, R$^3$ is unsubstituted C$_1$-C$_6$alkyl. In some embodiments, R$^3$ is C$_1$-C$_6$alkyl substituted with one or more halogen. In some embodiments, R$^3$ is unsubstituted C$_1$-C$_6$alkoxy. In some embodiments, R$^3$ is C$_1$-C$_6$alkoxy substituted with one or more halogen. In other embodiments, R$^3$ is halogen.

In some embodiments, one of R$^1$ and R$^2$ is —OH and the other is —C(O)H. In some embodiments, R$^1$ is —OH, R$^2$ is —C(O)H, and R$^3$ is H. In some embodiments, R$^1$ is —OH, R$^2$ is —C(O)H, and R$^3$ is unsubstituted C$_1$-C$_6$alkyl. In some embodiments, R$^1$ is —OH, R$^2$ is —C(O)H, and R$^3$ is C$_1$-C$_6$haloalkyl. In some embodiments, R$^1$ is —OH, R$^2$ is —C(O)H, and R$^3$ is unsubstituted C$_1$-C$_6$alkoxy. In some embodiments, R$^1$ is —OH, R$^2$ is —C(O)H, and R$^3$ is C$_1$-C$_6$alkoxy substituted with one or more halogen. In other embodiments, R$^1$ is —OH, R$^2$ is —C(O)H, and R$^3$ is halogen. In certain embodiments, R$^1$ is —OH, R$^2$ is —C(O)H, and R$^3$ is fluoro. In certain embodiments, R$^1$ is —OH, R$^2$ is —C(O)H, and R$^3$ is methyl. In some embodiments, R$^1$ is —OH, R$^2$ is —C(O)H, and R$^3$ is methoxy. In some embodiments, R$^2$ is —OH, R$^1$ is —C(O)H, and R$^3$ is H. In some embodiments, R$^2$ is —OH, R$^1$ is —C(O)H, and R$^3$ is unsubstituted C$_1$-C$_6$alkyl. In some embodiments, R$^2$ is —OH, R$^1$ is —C(O)H, and R$^3$ is C$_1$-C$_6$haloalkyl. In some embodiments, R$^2$ is —OH, R$^1$ is —C(O)H, and R$^3$ is unsubstituted C$_1$-C$_6$alkoxy. In some embodiments, R$^2$ is —OH, R$^1$ is —C(O)H, and R$^3$ is C$_1$-C$_6$alkoxy substituted with one or more halogen. In other embodiments, R$^2$ is —OH, R$^1$ is —C(O)H, and R$^3$ is halogen. In certain embodiments, R$^2$ is —OH, R$^1$ is —C(O)H, and R$^3$ is fluoro. In certain embodiments, R$^2$ is —OH, R$^1$ is —C(O)H, and R$^3$ is methyl. In some embodiments, R$^2$ is —OH, R$^1$ is —C(O)H, and R$^3$ is methoxy.

In some embodiments, G$_3$ is CH(X$_1$—R$^{6a}$), C(X$_1$—R$^{6a}$), N,N(X$_1$—R$^{6a}$), S, or O; G$_4$ is CH(X$_2$—R$^{6b}$), C(X$_2$—R$^{6b}$), N,N(X$_2$—R$^{6b}$), S, or O; G$_5$ is CH(X$_3$—R$^{6c}$), C(X$_3$—R$^{6c}$), N,N(X$_3$—R$^{6c}$), S, or O; G$_6$ is CH(X$_4$—R$^{6d}$), C(X$_4$—R$^{6d}$), N,N(X$_4$—R$^{6d}$), S, O, or absent; and G$_7$ is N, C, or CH, wherein G$_1$, G$_2$, G$_3$, G$_4$, G$_5$, G$_6$, and G$_7$ each have a charge of zero (e.g., the nitrogen of G$_1$, G$_2$, G$_3$, G$_4$, G$_5$, G$_6$, and G$_7$ is not cationic).

In some embodiments,

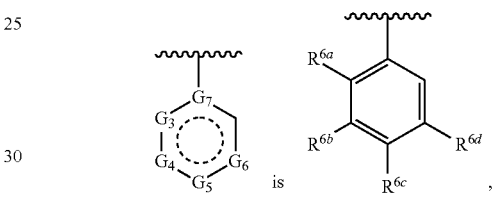

wherein one or more of R$^{6a}$, R$^{6b}$, R$^{6c}$, and R$^{6d}$ is selected from the group consisting of C$_1$-C$_6$alkyl, C$_1$-C$_6$alkoxy, halo, —OH, —NR$^p$R$^q$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^h$, —S(O)$_2$NR$^{w1}$R$^{w2}$, —S(O)$_2$R$^y$, and —NR$^{z1}$S(O)$_2$R$^{z2}$.

In some embodiments,

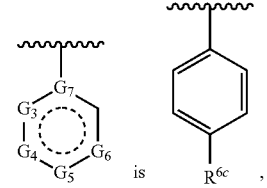

wherein R$^{6c}$ is selected from the group consisting of C$_1$-C$_6$alkyl, C$_1$-C$_6$alkoxy, halo, —OH, —NR$^p$R$^q$, C$_6$-C$_{12}$ aryl, 3- to 10-membered heterocyclyl, 5- to 10-membered heteroaryl, —C$_1$-C$_6$alkyl-5- to 6-membered heterocyclyl, —OC(O)-5- to 6-membered heterocyclyl, —C(O)R$^h$, —S(O)$_2$NR$^{w1}$R$^{w2}$, —S(O)$_2$R$^y$, or —NR$^{z1}$S(O)$_2$R$^{z2}$. In some embodiments, R$^{6c}$ is unsubstituted C$_1$-C$_6$alkyl. For instance, in some embodiments, R$^{6c}$ is methyl, ethyl, propyl, isopropyl, butyl, isobutyl, secbutyl, and tertbutyl. In some embodiments, R$^{6c}$ is C$_1$-C$_6$alkyl substituted with one or more groups selected from the group consisting of C$_3$-C$_8$ cycloalkyl and halogen. In some embodiments, R$^{6c}$ is C$_1$-C$_6$alkoxy. For instance, in some embodiments, R$^{6c}$ is methoxy, ethoxy, propoxy, isopropoxy, butoxy, isobutoxy, secbutoxy, and tertbutoxy. In some embodiments, R$^{6c}$ is C$_1$-C$_6$alkoxy substituted with one or more groups selected from the group consisting of $C_3$-$C_8$ cycloalkyl and halogen. In some embodiments, $R^{6c}$ is halo. For instance, in some embodiments, $R^{6c}$ is fluoro, chloro, or bromo. In other embodiments, $R^{6c}$ is $C_1$-$C_6$haloalkyl. For instance, in some embodiments, $R^{6c}$ is fluoroethyl, trifluoromethyl, difluoromethyl, trifluoroethyl, and trichloromethyl. In some embodiments, $R^{6c}$ is —C(O)$R^h$, wherein $R^h$ is H, $C_1$-$C_6$alkyl, $C_1$-$C_6$alkoxy, $C_3$-$C_8$cycloalkyl, or —NR'$R^s$. For instance, in some embodiments, $R^{6c}$ is —C(O)H, —C(O)$CH_3$, —C(O)OC($CH_3$)$_3$, or —C(O)-cyclopropyl. In some embodiments, $R^{6c}$ is an unsubstituted 5- to 6-membered heterocycle. In some embodiments, $R^{6c}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6c}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6c}$ is pyrrolidinyl. In certain embodiments, $R^{6c}$ is 4-pyrrolidin-1-yl. In some embodiments, $R^{6c}$ is an unsubstituted 5- to 10-membered heteroaryl. In some embodiments, $R^{6c}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6c}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments,

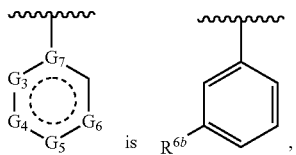

is wherein $R^{6b}$ is selected from the group consisting of $C_1$-$C_6$alkyl, $C_1$-$C_6$alkoxy, halo, —OH, —NR$^p$R$^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$NR$^{w1}$R$^{w2}$, —S(O)$_2$R$^y$, or —NR$^{z1}$S(O)$_2$R$^{z2}$. In some embodiments, $R^{6b}$ is unsubstituted $C_1$-$C_6$alkyl. For instance, in some embodiments, $R^{6b}$ is methyl, ethyl, propyl, isopropyl, butyl, isobutyl, secbutyl, and tertbutyl. In some embodiments, $R^{6b}$ is $C_1$-$C_6$alkyl substituted with one or more groups selected from the group consisting of $C_3$-$C_8$ cycloalkyl and halogen. In some embodiments, $R^{6b}$ is $C_1$-$C_6$alkoxy. For instance, in some embodiments, $R^{6b}$ is methoxy, ethoxy, propoxy, isopropoxy, butoxy, isobutoxy, secbutoxy, and tertbutoxy. In some embodiments, $R^{6b}$ is $C_1$-$C_6$alkoxy substituted with one or more groups selected from the group consisting of $C_3$-$C_8$ cycloalkyl and halogen. In some embodiments, $R^{6b}$ is halo. For instance, in some embodiments, $R^{6b}$ is fluoro, chloro, or bromo. In other embodiments, $R^{6b}$ is $C_1$-$C_6$haloalkyl. For instance, in some embodiments, $R^{6b}$ is fluoroethyl, trifluoromethyl, difluoromethyl, trifluoroethyl, and trichloromethyl. In some embodiments, $R^{6b}$ is —C(O)$R^h$, wherein $R^h$ is H, $C_1$-$C_6$alkyl, $C_1$-$C_6$alkoxy, $C_3$-$C_8$cycloalkyl, or —NR'$R^s$. For instance, in some embodiments, $R^{6b}$ is —C(O)H, —C(O)$CH_3$, —C(O)OC($CH_3$)$_3$, or —C(O)-cyclopropyl. In some embodiments, $R^{6b}$ is an unsubstituted 5- to 6-membered heterocycle. In some embodiments, $R^{6b}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6b}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6b}$ is an unsubstituted 5- to 10-membered heteroaryl. In some embodiments, $R^{6b}$ is a 5- to 10-membered heteroaryl, substituted with one or more groups selected from the group consisting of $C_1$-$C_6$alkyl, $C_1$-$C_6$alkoxy, —OH, and $C_1$-$C_6$alkyl-OH. In some embodiments, $R^{6b}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments,

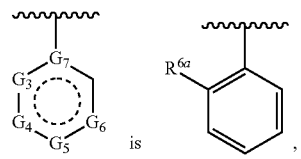

is wherein $R^{6a}$ is selected from the group consisting of $C_1$-$C_6$alkyl, $C_1$-$C_6$alkoxy, halo, —OH, —NR$^p$R$^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$^2$NR$^{w1}$R$^{w2}$, —S(O)$_2$R$^y$, or —NR$^{z1}$S(O)$_2$R$^{z2}$. In some embodiments, $R^{6a}$ is unsubstituted $C_1$-$C_6$alkyl. For instance, in some embodiments, $R^{6a}$ is methyl, ethyl, propyl, isopropyl, butyl, isobutyl, secbutyl, and tertbutyl. In some embodiments, $R^{6a}$ is $C_1$-$C_6$alkyl substituted with one or more groups selected from the group consisting of $C_3$-$C_8$ cycloalkyl and halogen. In some embodiments, $R^{6a}$ is $C_1$-$C_6$alkoxy. For instance, in some embodiments, $R^{6a}$ is methoxy, ethoxy, propoxy, isopropoxy, butoxy, isobutoxy, secbutoxy, and tertbutoxy. In some embodiments, $R^{6a}$ is $C_1$-$C_6$alkoxy substituted with one or more groups selected from the group consisting of $C_3$-$C_8$ cycloalkyl and halogen. In some embodiments, $R^{6a}$ is halo. For instance, in some embodiments, $R^{6a}$ is fluoro, chloro, or bromo. In other embodiments, $R^{6a}$ is $C_1$-$C_6$haloalkyl. For instance, in some embodiments, $R^{6a}$ is fluoroethyl, trifluoromethyl, difluoromethyl, trifluoroethyl, and trichloromethyl. In some embodiments, $R^{6a}$ is —C(O)$R^h$, wherein $R^h$ is H, $C_1$-$C_6$alkyl, $C_1$-$C_6$alkoxy, $C_3$-$C_8$cycloalkyl, or —NR'$R^s$. For instance, in some embodiments, $R^{6a}$ is —C(O)H, —C(O)$CH_3$, —C(O)OC($CH_3$)$_3$, or —C(O)-cyclopropyl. In some embodiments, $R^{6a}$ is an unsubstituted 5- to 6-membered heterocycle. In some embodiments, $R^{6a}$ is a 5- to 6-membered heterocycle, substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, $R^{6a}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some embodiments, $R^{6a}$ is an unsubstituted 5- to 10-membered heteroaryl. In some embodiments, $R^{6a}$ is a 5- to 10-membered heteroaryl, substituted with one or more groups selected from the group consisting of C₁-C₆alkyl, C₁-C₆alkoxy, —OH, and C₁-C₆alkyl-OH. In some embodiments, R⁶ᵃ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl.

In some embodiments,

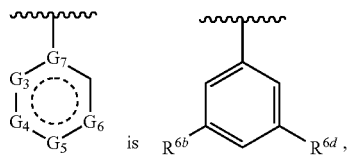

wherein $R^{6b}$ and $R^{6d}$ are each independently selected from the group consisting of C₁-C₆alkyl, C₁-C₆alkoxy, halo, —OH, —NR$^p$R$^q$, C₆-C₁₂ aryl, 3- to 10-membered heterocyclyl, 5- to 10-membered heteroaryl, —C₁-C₆alkyl-5- to 6-membered heterocyclyl, —OC(O)-5- to 6-membered heterocyclyl, —C(O)R$^h$, —S(O)₂NR$^{w1}$R$^{w2}$, —S(O)₂R$^y$, or —NR$^{z1}$S(O)₂R$^{z2}$. In some embodiments,

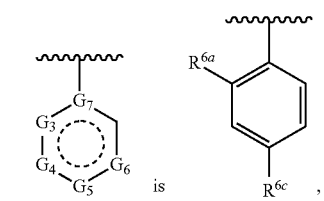

wherein $R^{6a}$ and $R^{6c}$ are each independently selected from the group consisting of C₁-C₆alkyl, C₁-C₆alkoxy, halo, —OH, —NR$^p$R$^q$, C₆-C₁₂ aryl, 3- to 10-membered heterocyclyl, 5- to 10-membered heteroaryl, —C₁-C₆alkyl-5- to 6-membered heterocyclyl, —OC(O)-5- to 6-membered heterocyclyl, —C(O)R$^h$, —S(O)₂NR$^{w1}$R$^{w2}$, —S(O)₂R$^y$, or —NR$^{z1}$S(O)₂R$^{z2}$. In some embodiments,

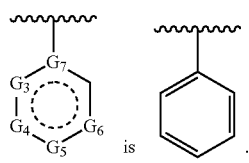

In some embodiments,

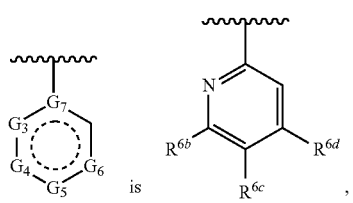

wherein one or more of $R^{6b}$, $R^{6c}$, and $R^{6d}$ is selected from the group consisting of C₁-C₆alkyl, C₁-C₆haloalkyl, halo, C₆-C₁₂ aryl, 3- to 10-membered heterocyclyl, and 5- to 10-membered heteroaryl. In some embodiments,

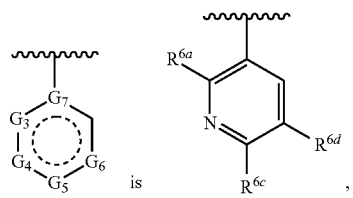

wherein one or more of $R^{6a}$, $R^{6c}$, and $R^{6d}$ is selected from the group consisting of C₁-C₆alkyl, C₁-C₆haloalkyl, halo, C₆-C₁₂ aryl, 3- to 10-membered heterocyclyl, and 5- to 10-membered heteroaryl. In some embodiments,

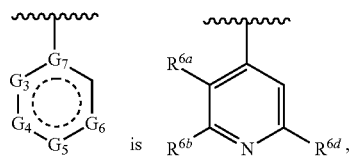

wherein one or more of $R^{6a}$, $R^{6b}$, and $R^{6d}$ is selected from the group consisting of C₁-C₆alkyl, C₁-C₆haloalkyl, halo, C₆-C₁₂ aryl, 3- to 10-membered heterocyclyl, and 5- to 10-membered heteroaryl. In some embodiments,

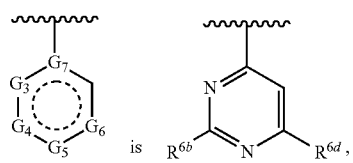

wherein one or both of $R^{6b}$ and $R^{6d}$ is selected from the group consisting of C₁-C₆alkyl, C₁-C₆haloalkyl, halo, C₆-C₁₂ aryl, 3- to 10-membered heterocyclyl, and 5- to 10-membered heteroaryl. In some embodiments,

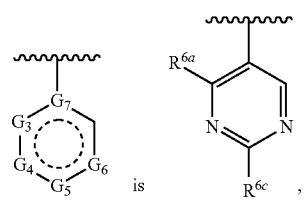

wherein one or both of $R^{6a}$ and $R^{6c}$ is selected from the group consisting of C₁-C₆alkyl, C₁-C₆haloalkyl, halo, C₆-C₁₂ aryl, 3- to 10-membered heterocyclyl, and 5- to 10-membered membered heteroaryl. In some embodiments,

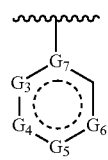

is selected from the group consisting of

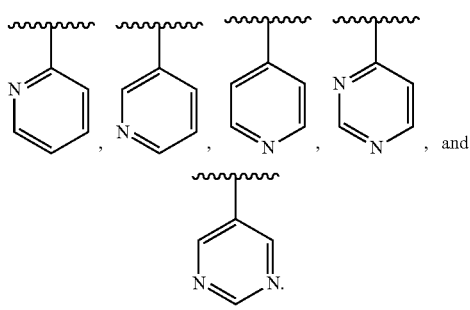

In some embodiments,

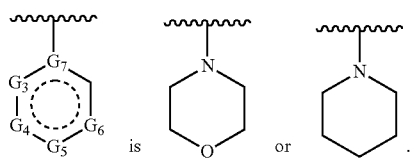

In some embodiments,

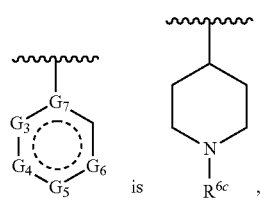

wherein $R^{6c}$ is selected from the group consisting of hydrogen, $C_1$-$C_6$alkyl, $C_1$-$C_6$alkoxy, halo, —OH, —$NR^pR^q$, $C_6$-$C_{12}$ aryl, 3- to 10-membered heterocyclyl, 5- to 10-membered heteroaryl, —$C_1$-$C_6$alkyl-5- to 6-membered heterocyclyl, —OC(O)-5- to 6-membered heterocyclyl, —C(O)$R^h$, —S(O)$_2$$NR^{w1}R^{w2}$, —S(O)$_2$$R^y$, and —$NR^{z1}$S(O)$_2$$R^{z2}$. In certain embodiments, $R^{6c}$ is —C(O)OC(CH$_3$)$_3$.

In some embodiments,

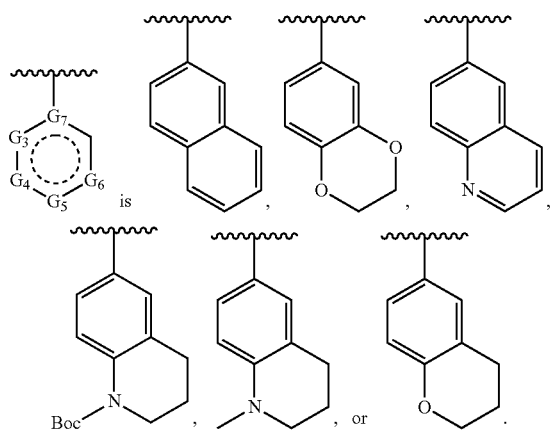

In some embodiments,

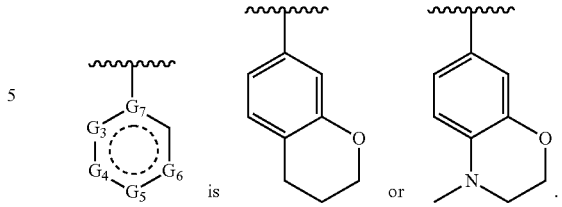

In any of the foregoing embodiments, one or more of $R^{6a}$, $R^{6b}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In some embodiments, one or more of $R^{6a}$, $R^{6b}$, $R^{6c}$, and $R^{6d}$ is $C_6$-$C_{12}$ aryl, unsubstituted or substituted with one or more groups selected from the group consisting of $C_1$-$C_6$alkyl, $C_1$-$C_6$alkoxy, —OH, and $C_1$-$C_6$alkyl-OH. For instance, in some embodiments, one of $R^{6a}$, $R^{6b}$, $R^{6c}$, and $R^{6d}$ is phenyl or naphthyl. In some embodiments, one or more of $R^{6a}$, $R^{6b}$, $R^{6c}$, and $R^{6d}$ is 3- to 10-membered heterocyclyl, unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S. For instance, in some embodiments, one of $R^{6a}$, $R^{6b}$, $R^{6c}$, and $R^{6d}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, thiomorpholinyl, tetrahydroquinolinyl, tetrahydroisoquinolinyl, decahydroquinolinyl, decahydroisoquinolinyl, indolinyl, isoindolinyl, tetrahydronaphthyridinyl or hexahydrobenzoimidazolyl, each independently unsubstituted or substituted with one or more groups selected from the group consisting of $C_1$-$C_6$alkyl, $C_1$-$C_6$alkoxy, halo, —OH, $C_1$-$C_6$alkyl-OH, =O, and =S.

In some embodiments, one of $R^{6a}$, $R^{6b}$, $R^{6c}$, and $R^{6d}$ is selected from the group consisting of $C_1$-$C_6$alkyl, $C_1$-$C_6$haloalkyl, halo, $C_6$-$C_{12}$ aryl, 3- to 10-membered heterocyclyl, and 5- to 10-membered heteroaryl. In certain embodiments, one of $R^{6a}$, $R^{6b}$, $R^{6c}$, and $R^{6d}$ is selected from the group consisting of methyl, ethyl, F, Cl, —CF$_3$, pyrrolidinyl, piperidinyl, morpholinyl, piperazinyl, pyrazolyl, and triazolyl. In certain embodiments, one of $R^{6a}$, $R^{6b}$, $R^{6c}$, and $R^{6d}$ is selected from the group consisting of pyrrolidinyl, piperidinyl, morpholinyl, piperazinyl, pyrazolyl, and triazolyl, each optionally substituted with one or more groups selected from the group consisting of $C_1$-$C_6$alkyl, $C_1$-$C_6$alkoxy, halo, —OH, $C_1$-$C_6$alkyl-OH, =O, and =S. In some embodiments, two or three of $R^{6a}$, $R^{6b}$, $R^{6c}$, and $R^{6d}$ is selected from the group consisting of methyl, ethyl, F, Cl, —CF$_3$, pyrrolidinyl, piperidinyl, morpholinyl, piperazinyl, pyrazolyl, and triazolyl. In some embodiments, one of $R^{6a}$, $R^{6b}$, $R^{6c}$, and $R^{6d}$ is selected from the group consisting of methyl, ethyl, methoxy, F, Cl, —CF$_3$,

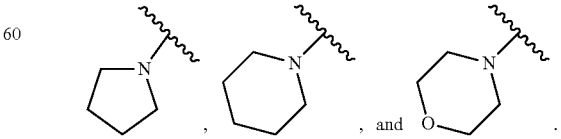

In some embodiments, one of $R^{6a}$, $R^{6b}$, $R^{6c}$, and $R^{6d}$ is selected from the group consisting of

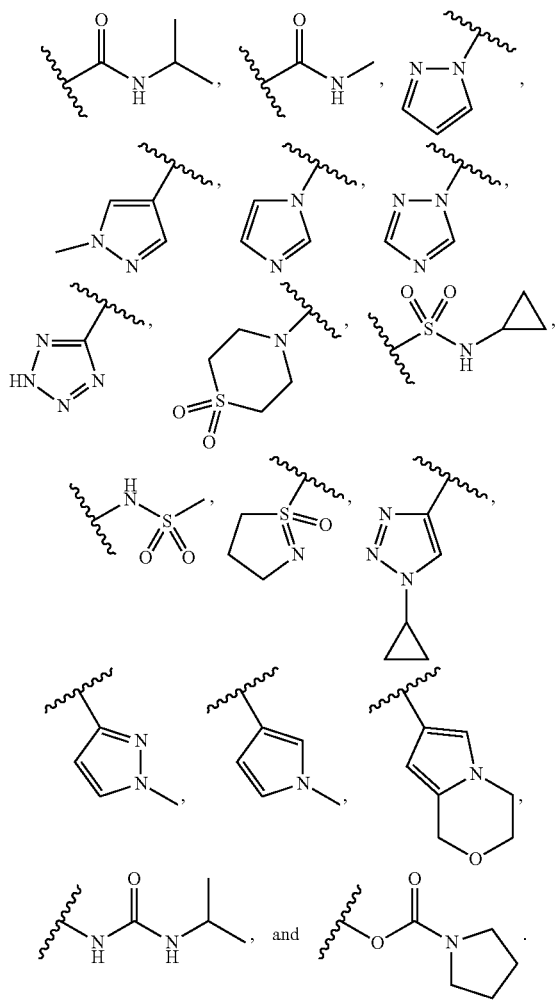

In other embodiments, $R^{6a}$, $R^{6b}$, $R^{6c}$, and $R^{6d}$ are each H.

In some embodiments, $G_3$ is $CH(X_1-R^{6a})$, $C(X_1-R^{6a})$, or $N(X_1-R^{6a})$, $X_1$ is absent,

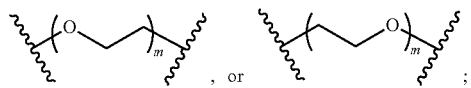

and $R^{6a}$ is hydrogen, $C_1$-$C_6$alkyl, $C_1$-$C_6$alkoxy, halo, —OH, —$NR^pR^q$, aryl, heterocyclyl, heteroaryl, —$C_1$-$C_6$alkyl-heterocyclyl, —OC(O)-heterocyclyl, —C(O)$R^h$, —S(O)$_2NR^{w1}R^{w2}$, —S(O)$_2R^y$, or —$NR^{z1}S(O)_2R^{z2}$, wherein the $C_1$-$C_6$alkyl and $C_1$-$C_6$alkoxy of $R^{6a}$ are each independently unsubstituted or substituted with one or more groups selected from the group consisting of cycloalkyl and halogen; the aryl and heteroaryl of $R^{6a}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of $R^{6a}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S; $R^h$ is selected from the group consisting of H, $C_1$-$C_6$alkoxy, $C_3$-$C_8$cycloalkyl, and —$NR^rR^s$, $R^p$ is H or $C_1$-$C_6$alkyl; $R^q$ is $C_2$-$C_3$alkyl, —C(O)$R^t$, —C(O)O$R^u$, —C(O)$NR^v$; $R^r$, $R^s$, $R^{w1}$, and $R^{z1}$ each independently selected from H and $C_1$-$C_6$alkyl; and $R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl.

In some embodiments, $G_3$ is $CH(X_1-R^{6a})$ or $C(X_1-R^{6a})$, wherein $X_1$ is absent; $R^{6a}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, and $C_3$-$C_8$ cycloalkyl. In some embodiments, $G_3$ is $CH(X_1-R^{6a})$ or $C(X_1-R^{6a})$, wherein $X_1$ is

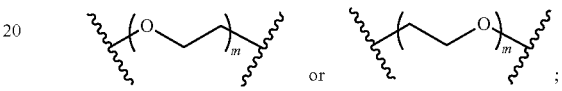

m is 1-6; $R^{6a}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, and $C_3$-$C_8$ cycloalkyl. In some embodiments, $G_3$ is N or $N(X_1-R^{6a})$, wherein $X_1$ is absent; $R^{6a}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, and $C_3$-$C_8$ cycloalkyl. In some embodiments, $G_3$ is N or $N(X_1-R^{6a})$, wherein $X_1$ is

m is 1-6; $R^{6a}$ is hydrogen, $C_1$-$C_6$alkyl, $C_1$-$C_6$alkoxy, halo, —OH, —$NR^pR^q$, aryl, heterocyclyl, heteroaryl, or —C(O)$R^h$, wherein $C_1$-$C_6$alkyl and $C_1$-$C_6$alkoxy are unsubstituted or substituted with $C_3$-$C_8$ cycloalkyl or halogen; $R^p$ is H or $C_1$-$C_6$alkyl; $R^q$ is $C_2$-$C_3$alkyl; and $R^h$ is selected from the group consisting of H, $C_1$-$C_6$alkyl, $C_1$-$C_6$alkoxy, and $C_3$-$C_8$ cycloalkyl. In some of any of the preceding embodiments, $R^{6a}$ is methyl, ethyl, n-propyl, isopropyl, n-butyl, isobutyl, secbutyl, or tertbutyl. In some of any of the preceding embodiments, $R^{6a}$ is $C_1$-$C_6$ alkyl substituted with $C_3$-$C_8$ cycloalkyl or halogen. In some of any of the preceding embodiments, $R^{6a}$ is methoxy, ethoxy, n-propoxy, isopropoxy, n-butoxy, isobutoxy, secbutoxy, or tertbutoxy. In some of any of the preceding embodiments, $R^{6a}$ is $C_1$-$C_6$alkoxy substituted with $C_3$-$C_8$ cycloalkyl or halogen. In some of any of the preceding embodiments, $R^{6a}$ is fluoro, chloro, bromo, or iodo. In some of any of the preceding embodiments, $R^{6a}$ is —$N(CH_2CH_3)_2$, —$N(CH_2CH_2CH_3)_2$, or —$N(CH_2CH_3)(CH_2CH_2CH_3)$. In some of any of the preceding embodiments, $R^{6a}$ is phenyl or naphthyl. In some of any of the preceding embodiments, $R^{6a}$ is a 5- to 14-membered heterocyclyl. In some embodiments, $R^{6a}$ is a 5- to 6-membered heterocyclyl. In some of any of the preceding embodiments, $R^{6a}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, $R^{6a}$ is a 5- to 14-membered heteroaryl. In some embodiments, $R^{6a}$ is a 5- to 6-membered heteroaryl. In some of any of the preceding embodiments, $R^{6a}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, $R^{6a}$ is aryl, heterocyclyl, or heteroaryl, each substituted with $C_1$-$C_6$alkyl. In some of any of the preceding embodiments, $R^{6a}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, $R^{6a}$ is —OH, —NR$^p$R$^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, $R^{6a}$ is hydrogen, —CH$_3$, —OH, —OCH$_3$, —C(O)OC(CH$_3$)$_3$, —N(CH$_2$CH$_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_3$ is S. In other embodiments, $G_3$ is O.

In some embodiments, $G_4$ is CH(X$_2$—R$^{6b}$), C(X$_2$—R$^{6b}$), or N(X$_2$—R$^{6b}$), wherein X$_2$ is absent,

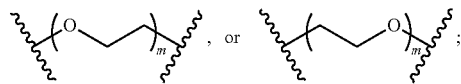

$R^{6b}$ is hydrogen, $C_1$-$C_6$alkyl, $C_1$-$C_6$alkoxy, halo, —OH, —NR$^p$R$^q$, aryl, heterocyclyl, heteroaryl, —$C_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of R$^{6b}$ are each independently unsubstituted or substituted with one or more groups selected from the group consisting of cycloalkyl and halogen; the aryl and heteroaryl of R$^{6b}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of R$^{6b}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S; R$^h$ is selected from the group consisting of H, $C_1$-$C_6$alkyl, $C_1$-$C_6$alkoxy, $C_3$-$C_8$cycloalkyl, and —NR$^r$R$^s$; R$^p$ is H or $C_1$-$C_6$alkyl; R$^q$ is $C_2$-$C_3$alkyl, —C(O)R$^t$, —C(O)OR$^u$, —C(O)NR$^v$; R$^r$, R$^s$, R$^{w1}$, and R$^{z1}$ each independently selected from H and $C_1$-$C_6$alkyl; and R$^t$, R$^u$, R$^v$, R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted heterocyclyl.

In some embodiments, $G_4$ is CH(X$_2$—R$^{6b}$) or C(X$_2$—R$^{6b}$), wherein X$_2$ is absent; R$^{6b}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$ cycloalkyl. In some embodiments, $G_4$ is CH(X$_2$—R$^{6b}$) or C(X$_2$—R$^{6b}$), wherein X$_2$ is

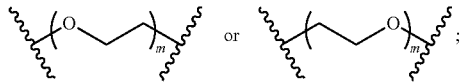

m is 1-6; R$^{6b}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some embodiments, $G_4$ is N or N(X$_2$—R$^{6b}$), wherein X$_2$ is absent; R$^{6b}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$ cycloalkyl. In some embodiments, $G_4$ is N or N(X$_2$—R$^{6b}$), wherein X$_2$

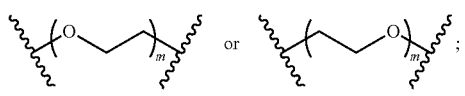

m is 1-6; R$^{6b}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$ cycloalkyl. In some of any of the preceding embodiments, R$^{6b}$ is methyl, ethyl, n-propyl, isopropyl, n-butyl, isobutyl, secbutyl, or tertbutyl. In some of any of the preceding embodiments, R$^{6b}$ is $C_1$-$C_6$alkyl substituted with $C_3$-$C_8$ cycloalkyl or halogen. In some of any of the preceding embodiments, R$^{6b}$ is methoxy, ethoxy, n-propoxy, isopropoxy, n-butoxy, isobutoxy, secbutoxy, or tertbutoxy. In some of any of the preceding embodiments, R$^{6b}$ is $C_1$-$C_6$alkoxy substituted with $C_3$-$C_8$ cycloalkyl or halogen. In some of any of the preceding embodiments, R$^{6b}$ is fluoro, chloro, bromo, or iodo. In some of any of the preceding embodiments, R$^{6b}$ is —N(CH$_2$CH$_3$)$_2$, —N(CH$_2$CH$_2$CH$_3$)$_2$, or —N(CH$_2$CH$_3$)(CH$_2$CH$_2$CH$_3$). In some of any of the preceding embodiments, R$^{6b}$ is phenyl or naphthyl. In some of any of the preceding embodiments, R$^{6b}$ is a 5- to 14-membered heterocyclyl. In some embodiments, R$^{6b}$ is a 5- to 6-membered heterocyclyl. In some of any of the preceding embodiments, R$^{6b}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, R$^{6b}$ is a 5- to 14-membered heteroaryl. In some embodiments, R$^{6b}$ is a 5- to 6-membered heteroaryl. In some of any of the preceding embodiments, R$^{6b}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, R$^{6b}$ is aryl, heterocyclyl, or heteroaryl, each substituted with $C_1$-$C_6$alkyl. In some of any of the preceding embodiments, $R^{6b}$ is —C(O)H, —C(O) $C_1$-$C_6$alkyl, —C(O)$C_1$-$C_6$alkoxy, or —C(O)$C_3$-$C_8$cycloalkyl. In some of any of the preceding embodiments, $R^{6b}$ is —OH, —NR$^p$R$^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, $R^{6b}$ is hydrogen, —CH$_3$, —OH, —OCH$_3$, —C(O)OC(CH$_3$)$_3$, —N(CH$_2$CH$_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_4$ is S. In other embodiments, $G_4$ is O.

In some embodiments, $G_5$ is CH(X$_3$—R$^{6c}$), C(X$_3$—R$^{6c}$), or N(X$_3$—R$^{6c}$), wherein X$_3$ is absent,

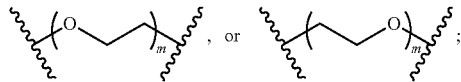

$R^{6c}$ is hydrogen, $C_1$-$C_6$alkyl, $C_1$-$C_6$alkoxy, halo, —OH, —NR$^p$R$^q$, aryl, heterocyclyl, heteroaryl, —$C_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of R$^{6c}$ are each independently unsubstituted or substituted with one or more groups selected from the group consisting of cycloalkyl and halogen; the aryl and heteroaryl of R$^{6c}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of R$^{6c}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S; R$^h$ is selected from the group consisting of H, $C_1$-$C_6$alkyl, $C_1$-$C_6$alkoxy, $C_3$-$C_8$cycloalkyl, and —NR$^r$R$^s$; R$^p$ is H or $C_1$-$C_6$alkyl; R$^q$ is $C_2$-$C_3$alkyl, —C(O)R$^t$, —C(O)OR$^u$, —C(O)NR$^v$; R$^r$, R$^s$, R$^{w1}$, and R$^{z1}$ each independently selected from H and $C_1$-$C_6$alkyl; and R$^t$, R$^u$, R$^v$, R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted heterocyclyl.

In some embodiments, $G_5$ is CH(X$_3$—R$^{6c}$) or C(X$_3$—R$^{6c}$), wherein X$_3$ is absent; R$^{6c}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$ cycloalkyl. In some embodiments, $G_5$ is CH(X$_3$—R$^{6c}$) or C(X$_3$—R$^{6c}$), wherein X$_3$ is

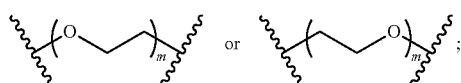

m is 1-6; R$^{6c}$ is hydrogen, $C_1$-$C_6$alkyl, $C_1$-$C_6$alkoxy, halo, —OH, —NR$^p$R$^q$, aryl, heterocyclyl, heteroaryl, or —C(O) R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$cycloalkyl. In some embodiments, $G_5$ is N or N(X$_3$—R$^{6c}$), wherein X$_3$ is absent; R$^{6c}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some embodiments, $G_5$ is N or N(X$_3$—R$^{6c}$), wherein X$_3$ is

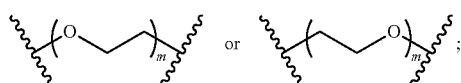

m is 1-6; R$^{6c}$ is hydrogen, $C_1$-$C_6$alkyl, $C_1$-$C_6$alkoxy, halo, —OH, —NR$^p$R$^q$, aryl, heterocyclyl, heteroaryl, or —C(O) R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some of any of the preceding embodiments, R$^{6c}$ is methyl, ethyl, n-propyl, isopropyl, n-butyl, isobutyl, secbutyl, or tertbutyl. In some of any of the preceding embodiments, R$^{6c}$ is $C_1$-$C_6$alkyl substituted with $C_3$-$C_8$ cycloalkyl or halogen. In some of any of the preceding embodiments, R$^{6c}$ is methoxy, ethoxy, n-propoxy, isopropoxy, n-butoxy, isobutoxy, secbutoxy, or tertbutoxy. In some of any of the preceding embodiments, R$^{6c}$ is $C_1$-$C_6$alkoxy substituted with $C_3$-$C_8$ cycloalkyl or halogen. In some of any of the preceding embodiments, R$^{6c}$ is fluoro, chloro, bromo, or iodo. In some of any of the preceding embodiments, R$^{6c}$ is —N(CH$_2$CH$_3$)$_2$, —N(CH$_2$CH$_2$CH$_3$)$_2$, or —N(CH$_2$CH$_3$)(CH$_2$CH$_2$CH$_3$). In some of any of the preceding embodiments, R$^{6c}$ is phenyl or naphthyl. In some of any of the preceding embodiments, R$^{6c}$ is a 5- to 14-membered heterocyclyl. In some embodiments, R$^{6c}$ is a 5- to 6-membered heterocyclyl. In some of any of the preceding embodiments, R$^{6c}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, R$^{6c}$ is a 5- to 14-membered heteroaryl. In some embodiments, R$^{6c}$ is a 5- to 6-membered heteroaryl. In some of any of the preceding embodiments, R$^{6c}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, R$^{6c}$ is aryl, heterocyclyl, or heteroaryl, each substituted with $C_1$-$C_6$alkyl. In some of any of the preceding embodiments, R$^{6c}$ is —C(O)H, —C(O) $C_1$-$C_6$alkyl, —C(O)$C_1$-$C_6$alkoxy, or —C(O)$C_3$-$C_8$cycloalkyl. In some of any of the preceding embodiments, R$^{6c}$ is —OH, —NR$^p$R$^q$, aryl, heterocyclyl, heteroaryl, unsubstituted $C_1$-$C_6$alkoxy, or $C_1$-$C_6$alkoxy substituted with $C_3$-$C_8$ $C_3$-$C_8$ cycloalkyl or halogen. In some of any of the preceding embodiments, R$^{6c}$ is hydrogen, —CH$_3$, —OH, —OCH$_3$, —C(O)OC(CH$_3$)$_3$, —N(CH$_2$CH$_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_5$ is S. In other embodiments, $G_5$ is O.

In some embodiments, $G_6$ is CH(X$_4$—R$^{6d}$), C(X$_4$—R$^{6d}$), or N(X$_4$—R$^{6d}$), wherein X$_4$ is absent,

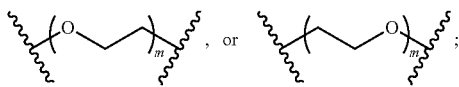, or $R^{6d}$ is hydrogen, $C_1$-$C_6$alkyl, $C_1$-$C_6$alkoxy, halo, —OH, —NR$^p$R$^q$, aryl, heterocyclyl, heteroaryl, —$C_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of $R^{6d}$ are each independently unsubstituted or substituted with one or more groups selected from the group consisting of cycloalkyl and halogen; the aryl and heteroaryl of $R^{6d}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of $R^{6d}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S; R$^h$ is selected from the group consisting of H, $C_1$-$C_6$alkyl, $C_1$-$C_6$alkoxy, $C_3$-$C_8$cycloalkyl, and —NR$^r$R$^s$; R$^p$ is H or $C_1$-$C_6$alkyl; R$^q$ is $C_2$-$C_3$alkyl, —C(O)R$^t$, —C(O)OR$^u$, —C(O)NR$^v$; R$^r$, R$^s$, R$^{w1}$, and R$^{z1}$ each independently selected from H and $C_1$-$C_6$alkyl; and R$^t$, R$^u$, R$^v$, R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted heterocyclyl.

In some embodiments, $G_6$ is CH(X$_4$—R$^{6d}$) or C(X$_4$—R$^{6d}$), wherein X$_4$ is absent; R$^{6d}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, or $C_3$-$C_8$cycloalkyl. In some embodiments, $G_6$ is CH(X$_4$—R$^{6d}$) or C(X$_4$—R$^{6d}$), wherein X$_4$ is

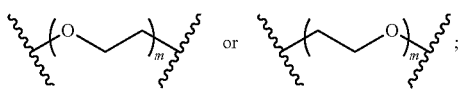

m is 1-6; R$^{6d}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some embodiments, $G_6$ is N or N(X$_4$—R$^{6d}$), wherein X$_4$ is absent; R$^{6d}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some embodiments, $G_6$ is N or N(X$_4$—R$^{6d}$), wherein X$_4$ is

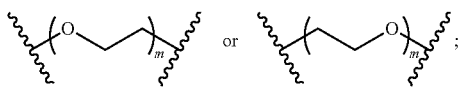

m is 1-6; R$^{6d}$ is hydrogen, $C_1$-$C_6$alkyl, $C_1$-$C_6$alkoxy, halo, —OH, —NR$^p$R$^q$, aryl, heterocyclyl, heteroaryl, or —C(O)R$^h$, wherein $C_1$-$C_6$alkyl and $C_1$-$C_6$alkoxy are unsubstituted or substituted with $C_3$-$C_8$ cycloalkyl or halogen; R$^p$ is H or $C_1$-$C_6$alkyl; R$^q$ is $C_2$-$C_3$alkyl; and R$^h$ is selected from the group consisting of H, $C_1$-$C_6$alkyl, $C_1$-$C_6$alkoxy, and $C_3$-$C_8$cycloalkyl. In some of any of the preceding embodiments, R$^{6d}$ is methyl, ethyl, n-propyl, isopropyl, n-butyl, isobutyl, secbutyl, or tertbutyl. In some of any of the preceding embodiments, R$^{6d}$ is $C_1$-$C_6$alkyl substituted with $C_3$-$C_8$ cycloalkyl or halogen. In some of any of the preceding embodiments, R$^{6d}$ is methoxy, ethoxy, n-propoxy, isopropoxy, n-butoxy, isobutoxy, secbutoxy, or tertbutoxy. In some of any of the preceding embodiments, R$^{6d}$ is $C_1$-$C_6$alkoxy substituted with $C_3$-$C_8$ cycloalkyl or halogen. In some of any of the preceding embodiments, R$^{6d}$ is fluoro, chloro, bromo, or iodo. In some of any of the preceding embodiments, R$^{6d}$ is —N(CH$_2$CH$_3$)$_2$, —N(CH$_2$CH$_2$CH$_3$)$_2$, or —N(CH$_2$CH$_3$)(CH$_2$CH$_2$CH$_3$). In some of any of the preceding embodiments, R$^{6d}$ is phenyl or naphthyl. In some of any of the preceding embodiments, R$^{6d}$ is a 5- to 14-membered heterocyclyl. In some embodiments, R$^{6d}$ is a 5- to 6-membered heterocyclyl. In some of any of the preceding embodiments, R$^{6d}$ is pyrrolidinyl, pyrazolidinyl, imidazolidinyl, tetrahydrofuranyl, 1,3-dioxolanyl, tetrahydrothiophenyl, oxathiolanyl, sulfolanyl, piperidinyl, piperazinyl, tetrahydropyranyl, dioxanyl, thianyl, dithianyl, trithianyl, morpholinyl, or thiomorpholinyl. In some of any of the preceding embodiments, R$^{6d}$ is a 5- to 14-membered heteroaryl. In some embodiments, R$^{6d}$ is a 5- to 6-membered heteroaryl. In some of any of the preceding embodiments, R$^{6d}$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl. In some of any of the preceding embodiments, R$^{6d}$ is aryl, heterocyclyl, or heteroaryl, each substituted with $C_1$-$C_6$alkyl. In some of any of the preceding embodiments, R$^{6d}$ is —C(O)H, —C(O)$C_1$-$C_6$alkyl, —C(O)$C_1$-$C_6$alkoxy, or —C(O)$C_3$-$C_8$cycloalkyl. In some of any of the preceding embodiments, R$^{6d}$ is —OH, —NR$^p$R$^q$, aryl, heterocyclyl, heteroaryl, unsubstituted $C_1$-$C_6$alkoxy, or $C_1$-$C_6$alkoxy substituted with $C_3$-$C_8$ cycloalkyl or halogen. In some of any of the preceding embodiments, R$^{6d}$ is hydrogen, —CH$_3$, —OH, —OCH$_3$, —C(O)OC(CH$_3$)$_3$, —N(CH$_2$CH$_3$)$_2$, phenyl, morpholinyl, piperidinyl, piperazinyl, 4-ethylpiperazinyl, pyrrolidinyl, pyrazolyl, cyclopropylmethoxy, or cyclopropanecarbonyl. In some embodiments, $G_6$ is S. In other embodiments, $G_6$ is O. In some embodiments, $G_6$ is absent.

In some embodiments, $G_5$ is CH(X$_3$—R$^{6c}$), $G_6$ is CH(X$_4$—R$^{6d}$), ring ⌒ is saturated, and R$^{6c}$ and R$^{6d}$ are taken together with the carbons to which they are attached to form a 6-membered heterocyclyl ring; wherein the heterocyclyl ring is unsubstituted or substituted with one or more groups selected from the group consisting of $C_1$-$C_6$alkyl and C(O)O—$C_1$-$C_6$alkyl. In some embodiments, $G_5$ is C(X$_3$—R$^{6c}$), $G_6$ is C(X$_4$—R$^{6d}$), ⌒ is partially unsaturated or fully unsaturated, and R$^{6c}$ and R$^{6d}$ are taken together with the carbons to which they are attached to form a 6-membered aryl, 6-membered heterocyclyl, or 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl. In some embodiments, $G_5$ is C(X$_3$—R$^{6c}$), $G_6$ is C(X$_4$—R$^{6d}$), ⌒ is fully unsaturated, and R$^{6c}$ and R$^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted with one or more groups selected from the group consisting of $C_1$-$C_6$alkyl and —C(O)O—$C_1$-$C_6$alkyl. In some embodiments, $R^{6c}$ and $R^{6d}$ come together with the carbons to which they are attached to form a phenyl ring. In some embodiments, $R^{6c}$ and $R^{6d}$ are taken together with the carbons to which they are attached to form a 6-membered heterocyclyl or 6-membered heteroaryl ring, wherein the 6-membered heterocyclyl or 6-membered heteroaryl ring each contains one, two, or three heteroatoms independently selected from the group consisting of N, S, and O. In some embodiments, $R^{6c}$ and $R^{6d}$ are taken together with the carbons to which they are attached to form an unsubstituted 6-membered aryl, 6-membered heterocyclyl, or 6-membered heteroaryl ring. In some embodiments, $R^{6c}$ and $R^{6d}$ are taken together with the carbons to which they are attached to form a 6-membered aryl, 6-membered heterocyclyl, or 6-membered heteroaryl ring, wherein the 6-membered aryl, 6-membered heterocyclyl, or 6-membered heteroaryl ring are each independently substituted with one or more substituents selected from the group consisting of $C_1$-$C_6$ alkyl, $C_1$-$C_6$ haloalkyl, halo, —OH, —C(O)H, —C(O)OH, —C(O)OC$_1$-$C_6$ alkyl, —OC$_1$-$C_6$ alkyl, and $C_3$-$C_8$ cycloalkyl.

In some embodiments, $G_7$ is N. In some embodiments, $G_7$ is C. In other embodiments, $G_7$ is CH.

In some embodiments, $R^{6a}$, $R^{6b}$, $R^{6c}$, and $R^{6d}$ are each independently hydrogen, $C_1$-$C_6$alkyl, $C_1$-$C_6$alkoxy, halo, —OH, —NR$^p$R$^q$, aryl, heterocyclyl, heteroaryl, —C$_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with one or more groups selected from the group consisting of cycloalkyl and halogen; the aryl and heteroaryl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the aryl, heterocyclyl, heteroaryl, —C$_1$-$C_6$alkyl-heterocyclyl, and —OC(O)-heterocyclyl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S; wherein each aryl of $R^{6a}$, $R^{6b}$, $R^{6c}$, and $R^{6d}$ is 6- to 12-membered, each heterocyclyl of $R^{6a}$, $R^{6b}$, $R^{6c}$, and $R^{6d}$ is 3- to 18-membered, and each heteroaryl of $R^{6a}$, $R^{6b}$, $R^{6c}$, and $R^{6d}$ is 5- to 18-membered.

In some embodiments, one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —NR$^p$R$^q$, aryl, heterocyclyl, heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —NR$^p$R$^q$, 6- to 12-membered aryl, 3- to 12-membered heterocyclyl, 5- to 12-membered heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, two of $R^{6a}$, $R^{6b}$, $R^{6c}$, and $R^{6d}$ are selected from the group consisting of $C_1$-$C_6$alkyl, $C_1$-$C_6$alkoxy, halo, —OH, —NR$^p$R$^q$, aryl, heterocyclyl, heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, two of $R^{6a}$, $R^{6b}$, $R^{6c}$, and $R^{6d}$ is selected from the group consisting of $C_1$-$C_6$alkyl, $C_1$-$C_6$alkoxy, halo, —OH, —NR$^p$R$^q$, 6- to 12-membered aryl, 3- to 12-membered heterocyclyl, 5- to 12-membered heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H.

In some embodiments, one of $R^{6a}$, $R^{6b}$, $R^{6c}$, and $R^{6d}$ is selected from the group consisting of $C_1$-$C_6$alkyl, $C_1$-$C_6$alkoxy, halo, —OH, —NR$^p$R$^q$, aryl, heterocyclyl, heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$, and $R^{6d}$ are each H. In some embodiments, one of $R^{6a}$, $R^{6b}$, $R^{6c}$, and $R^{6d}$ is selected from the group consisting of —C$_1$-$C_6$alkyl-heterocyclyl, —OC(O)-heterocyclyl, —S(O)$_2$NR$^{w1}$R$^{w2}$, —S(O)$_2$R$^y$, and —NR$^{z1}$S(O)$_2$R$^{z2}$; wherein R$^{w1}$ and R$^{z1}$ each independently selected from H and $C_1$-$C_6$alkyl, and R$^{w2}$, R$^y$, and R$^{z2}$ are each independently selected from H, $C_1$-$C_6$alkyl, unsubstituted or substituted $C_3$-$C_8$cycloalkyl, and unsubstituted or substituted 3- to 12-membered heterocyclyl.

In some embodiments, two of $R^{6a}$, $R^{6b}$, $R^{6c}$, and $R^{6d}$ is selected from the group consisting of $C_1$-$C_6$alkyl, $C_1$-$C_6$alkoxy, halo, —OH, —NR$^p$R$^q$, aryl, heterocyclyl, heteroaryl, and —C(O)R$^h$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with $C_3$-$C_8$ cycloalkyl or halogen; and the rest of $R^{6a}$, $R^{6b}$, $R^{6c}$ and $R^{6d}$ are each H.

In some embodiments, one, two, or three of $R^{6a}$, $R^{6b}$, $R^{6c}$, and $R^{6d}$ is a 5- to 10-membered heterocyclyl, unsubstituted or substituted with one or more groups selected from the group consisting of $C_1$-$C_6$alkyl, —OH, $C_1$-$C_6$alkyl-OH, =O, =S. In some embodiments, one, two, or three of $R^{6a}$, $R^{6b}$, $R^{6c}$, and $R^{6d}$ is a monocyclic heterocyclyl, bicyclic heterocyclyl, or a spirocyclic heterocyclyl, each unsubstituted or substituted with one or more groups selected from the group consisting of $C_1$-$C_6$alkyl, —OH, $C_1$-$C_6$alkyl-OH, =O, =S. In some embodiments, one, two, or three of $R^{6a}$, $R^{6b}$, $R^{6c}$, and $R^{6d}$ is a 5- to 10-membered heteroaryl, unsubstituted or substituted with one or more groups selected from the group consisting of $C_1$-$C_6$alkyl, —OH, $C_1$-$C_6$alkyl-OH, =O, =S.

In some embodiments,

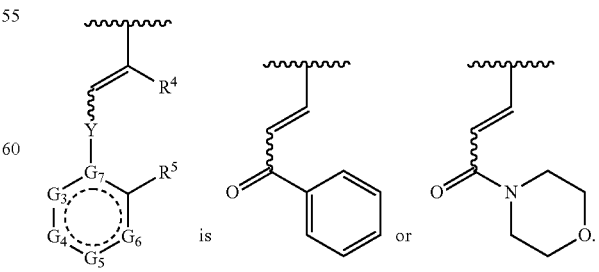

In some embodiments,

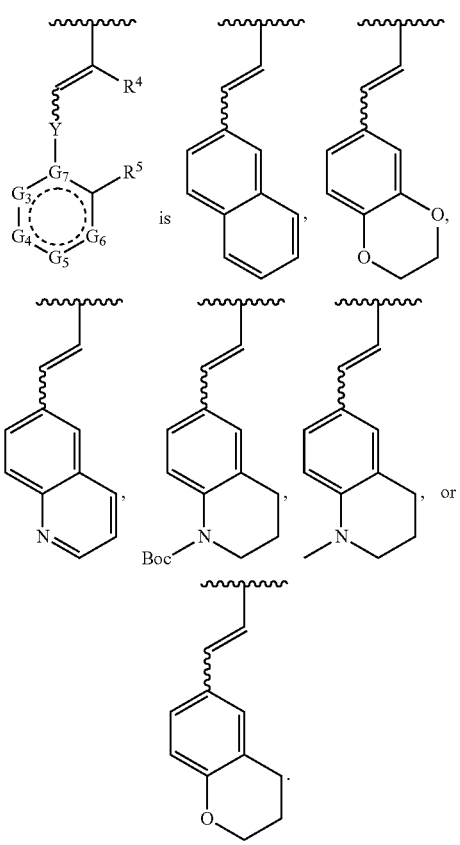
In some embodiments,
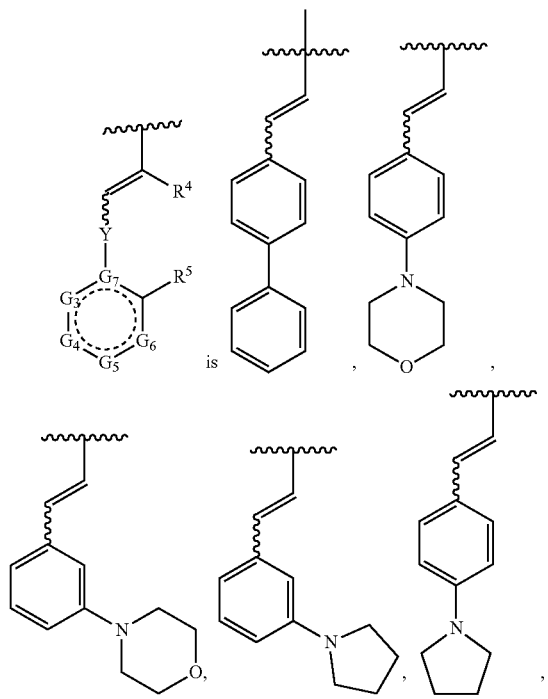
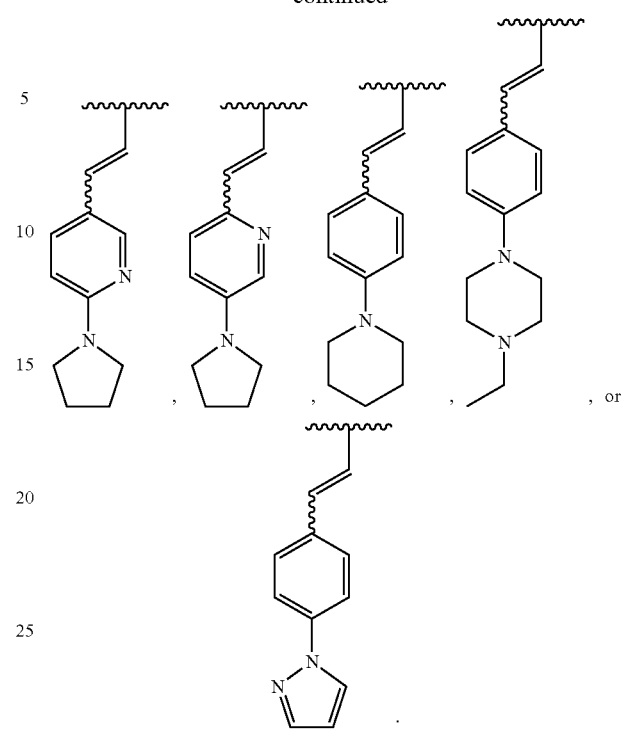
In some embodiments,
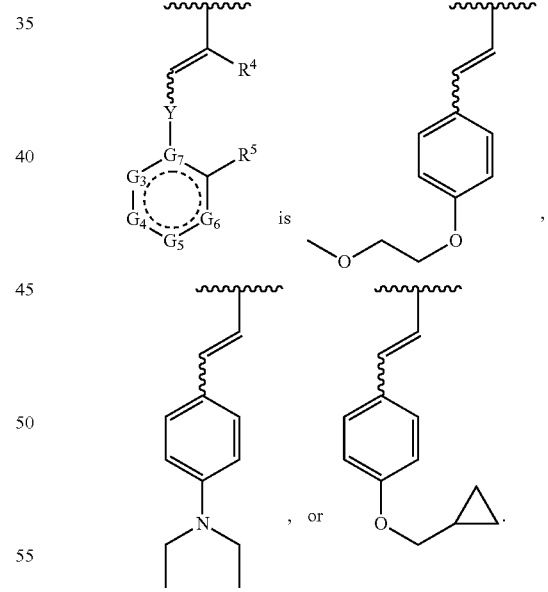
In one aspect, provided are compounds of Formula (I):

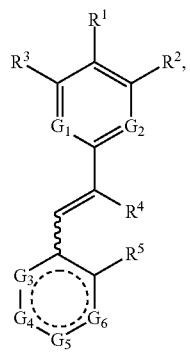

(I)

or a tautomer thereof, or a pharmaceutically acceptable salt of any of the foregoing, wherein
◌ indicates that the ring is saturated, partially unsaturated, or fully unsaturated;
| indicates that the

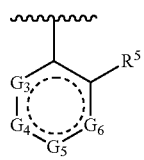

is attached in either the E or Z configuration;
$G_1$ and $G_2$ are each independently CH or N;
one of $R^1$ and $R^2$ is —OH and the other is selected from the group consisting of —C(O)$R^a$, —S(O)$R^b$, —S(O)$_2R^c$, —NHC(O)$R^d$, —NHS(O)$_2R^e$, —C$_1$-C$_6$alkyl-$R^f$, —C$_2$-C$_6$alkenyl-$R^g$, unsubstituted or substituted cycloalkyl, unsubstituted or substituted cycloalkenyl, and unsubstituted or substituted heterocycloalkyl;
$R^a$, $R^b$, $R^c$, and $R^e$ are each independently H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, benzoyl, or styryl;
$R^d$ is H, C$_1$-C$_6$alkyl, C$_2$-C$_6$alkenyl, C$_2$-C$_6$alkynyl, C$_1$-C$_6$haloalkyl, unsubstituted or substituted heterocyclyl, unsubstituted or substituted heteroaryl, or benzoyl;
$R^f$ and $R^g$ are each independently unsubstituted heteroaryl, benzoyl, or styryl;
$R^3$ is H, C$_1$-C$_6$alkyl, C$_1$-C$_6$alkoxy, or halogen; and
$R^4$ and $R^5$ are each H,
or
$R^4$ and $R^5$ come together to form —S—;
$G_3$ is CH($X_1$—$R^{6a}$), C($X_1$—$R^{6a}$), N,N($X_1$—$R^{6a}$), S, or O;
$G_4$ is CH($X_2$—$R^{6b}$), C($X_2$—$R^{6b}$), N,N($X_2$—$R^{6b}$), S, or O;
$G_5$ is CH($X_3$—$R^{6c}$), C($X_3$—$R^{6c}$), N,N($X_3$—$R^{6c}$), S, or O;
$G_6$ is CH($X_4$—$R^{6d}$), C($X_4$—$R^{6d}$), N,N($X_4$—$R^{6d}$), S, O, or absent;
wherein when $G_5$ is N, either
(i) at least one of $G_3$, $G_4$, and $G_6$ is not CH; or
(ii) $R^4$ and $R^5$ come together to form —S—;
$X_1$, $X_2$, $X_3$, and $X_4$ are each independently absent,

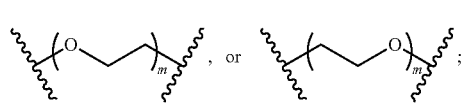

m is 1-6;
$R^{6a}$, $R^{6b}$, $R^{6c}$, and $R^{6d}$ are each independently hydrogen, C$_1$-C$_6$alkyl, C$_1$-C$_6$alkoxy, halo, or —C(O)$R^h$, wherein C$_1$-C$_6$alkyl is unsubstituted or substituted with cycloalkyl or halogen;
$R^h$ is selected from the group consisting of H, C$_1$-C$_6$alkyl, C$_1$-C$_6$alkoxy, and C$_3$-C$_8$cycloalkyl;
wherein the compound is not a compound of Table 1X.

In some embodiments of Formula (I), $G_1$ and $G_2$ are each CH. In some embodiments, $G_1$ is CH and $G_2$ is N. In some embodiments, $G_1$ is N and $G_2$ is CH. In other embodiments, $G_1$ and $G_2$ are each N.

In some embodiments, $R^1$ is —OH and $R^2$ is selected from the group consisting of —C(O)$R^a$, —S(O)$R^b$, —S(O)$_2R^c$, —NHC(O)$R^d$, —NHS(O)$_2R^e$, —C$_2$-C$_6$alkyl-$R^f$, —C$_2$-C$_6$alkenyl-$R^g$, unsubstituted or substituted cycloalkyl, unsubstituted or substituted cycloalkenyl, and unsubstituted or substituted heterocycloalkyl. In some embodiments, $R^1$ is —OH and $R^2$ is selected from the group consisting of —C(O)$R^a$, —S(O)$_2R^c$, —NHC(O)$R^d$, —NHS(O)$_2R^e$, —C$_2$-C$_6$alkenyl-$R^g$, and unsubstituted or substituted cycloalkenyl. In some embodiments, $R^1$ is —OH and $R^2$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

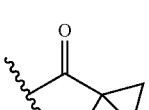

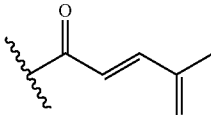

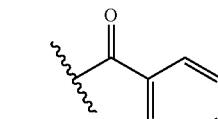

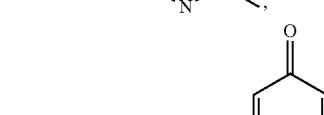

, and

In some embodiments, $R^1$ is —OH and $R^2$ is selected from the group consisting of

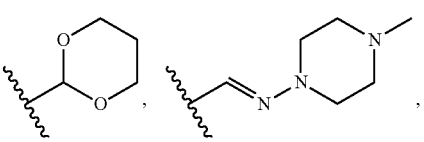

-continued

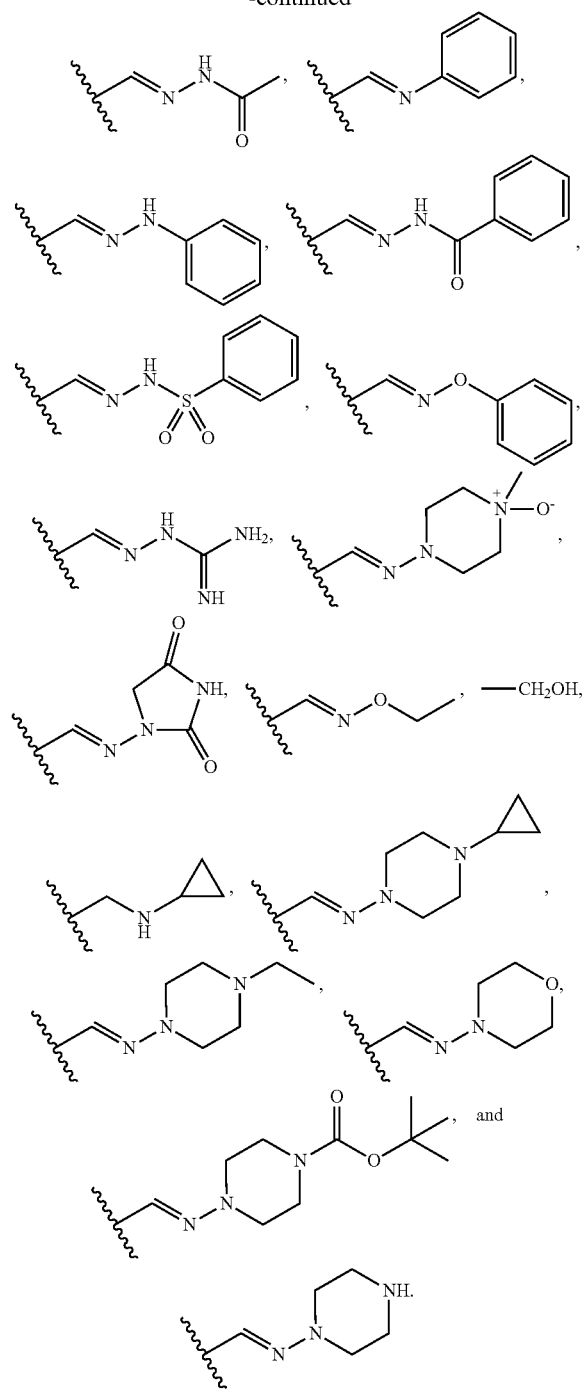

In some embodiments, R² is —OH and R¹ is selected from the group consisting of —C(O)Rᵃ, —S(O)Rᵇ, —S(O)₂Rᶜ, —NHC(O)Rᵈ, —NHS(O)₂Rᵉ, —C₁-C₆alkyl-Rᶠ, —C₂-C₆alkenyl-Rᵍ, unsubstituted or substituted cycloalkyl, unsubstituted or substituted cycloalkenyl, and unsubstituted or substituted heterocycloalkyl. In some embodiments, R² is —OH and R¹ is selected from the group consisting of —C(O)Rᵃ, —S(O)₂Rᶜ, —NHC(O)Rᵈ, —NHS(O)₂Rᵉ, —C₂-C₆alkenyl-Rᵍ, and unsubstituted or substituted cycloalkenyl. In some embodiments, R² is —OH and R¹ is selected from the group consisting of —CHO, —C(O)CH₃, —C(O)CH₂F, —C(O)CH=CH₂, —S(O)₂CH=CH₂, —C(O)C≡CH, —C(O)C≡CCH₃, —NHS(O)₂CH=CH₂, —NHC(O)CH=CH₂, —C(O)C(=CH₂)CH₃,

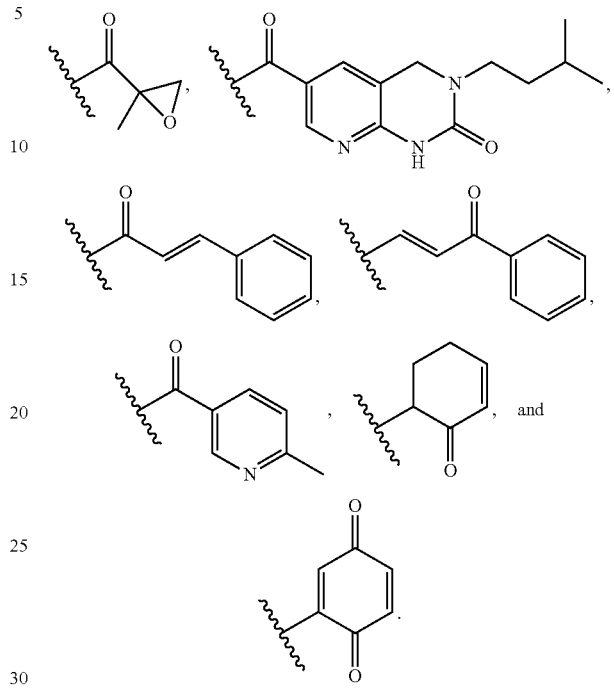

In some embodiments, R² is —OH and R¹ is selected from the group consisting of

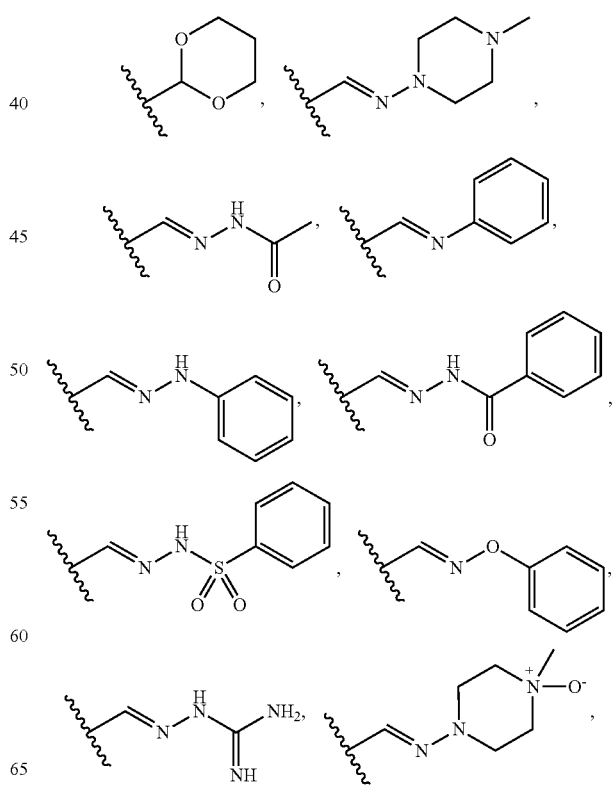

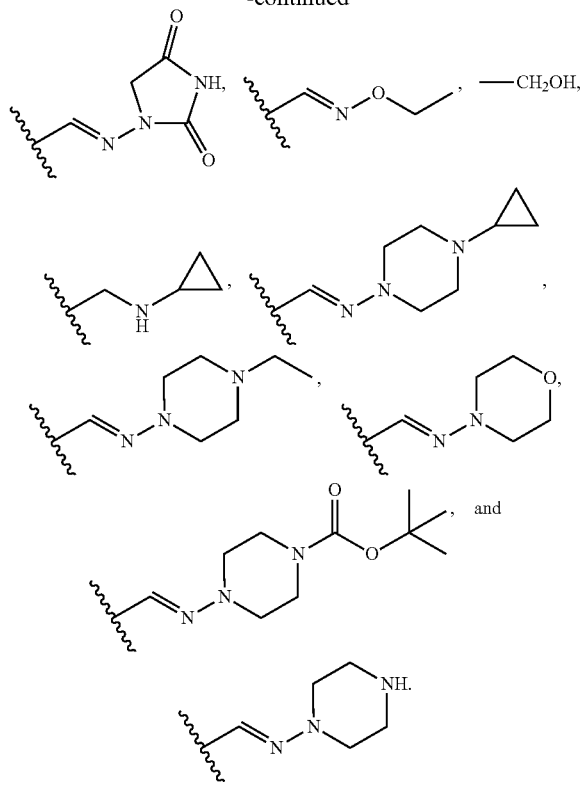

In some embodiments, one of R¹ and R² is —OH and the other is —C(O)Rᵃ, wherein Rᵃ is H, C₁-C₆alkyl, C₂-C₆alkenyl, C₂-C₆alkynyl, C₁-C₆haloalkyl, unsubstituted or substituted heterocyclyl, unsubstituted or substituted heteroaryl, benzoyl, or styryl. In some embodiments, one of R¹ and R² is —OH and the other is —C(O)Rᵃ, wherein Rᵃ is substituted heterocyclyl or substituted heteroaryl. It is to be understood that in any of the embodiments described herein, the substituent of a substituted cyclic group (e.g., a substituted heterocyclyl or substituted heteroaryl group) may be attached to the same atom of the cyclic group that is joined to the remainder of the compound. For instance,

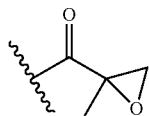

is a particular embodiment of —C(O)Rᵃ when Rᵃ is an epoxyl group substituted with methyl. In some embodiments, one of R¹ and R² is —OH and the other is —S(O)Rᵇ, wherein Rᵇ is H, C₁-C₆alkyl, C₂-C₆alkenyl, C₂-C₆alkynyl, C₁-C₆haloalkyl, unsubstituted or substituted heterocyclyl, unsubstituted or substituted heteroaryl, benzoyl, or styryl. In some embodiments, one of R¹ and R² is —OH and the other is —S(O)₂Rᶜ, wherein Rᶜ is H, C₁-C₆alkyl, C₂-C₆alkenyl, C₂-C₆alkynyl, C₁-C₆haloalkyl, unsubstituted or substituted heterocyclyl, unsubstituted or substituted heteroaryl, benzoyl, or styryl. In some embodiments, one of R¹ and R² is —OH and the other is —NHC(O)Rᵈ, wherein Rᵈ is H, C₁-C₆alkyl, C₂-C₆alkenyl, C₂-C₆alkynyl, C₁-C₆haloalkyl, unsubstituted or substituted heterocyclyl, unsubstituted or substituted heteroaryl, or benzoyl. In some embodiments, one of R¹ and R² is —OH and the other is —NHS(O)₂Rᵉ, wherein Rᵉ is H, C₁-C₆alkyl, C₂-C₆alkenyl, C₂-C₆alkynyl, C₁-C₆haloalkyl, unsubstituted or substituted heterocyclyl, unsubstituted or substituted heteroaryl, benzoyl, or styryl. In some embodiments, one of R¹ and R² is —OH and the other is —C₁-C₆alkyl-Rᶠ, wherein Rᶠ is unsubstituted heteroaryl, benzoyl, or styryl. In some embodiments, one of R¹ and R² is —OH and the other is —C₂-C₆alkenyl-Rᵍ, wherein Rᵍ is unsubstituted heteroaryl, benzoyl, or styryl. In some embodiments, one of R¹ and R² is —OH and the other is unsubstituted or substituted cycloalkyl. In some embodiments, one of R¹ and R² is —OH and the other is unsubstituted or substituted cycloalkenyl. In other embodiments, one of R¹ and R² is —OH and the other is unsubstituted or substituted heterocycloalkyl.

In some embodiments, R¹ is —OH and R² is C(O)Rᵃ. In other embodiments, R¹ is C(O)Rᵃ and R² is —OH. In some embodiments, R¹ is —OH and R² is —CHO. In other embodiments, R¹ is —CHO and R² is —OH.

In some embodiments, R³ is selected from the group consisting of C₁-C₆alkyl, C₁-C₆alkoxy, and halogen. In some embodiments, R³ is methyl, ethyl, n-propyl, isopropyl, n-butyl, isobutyl, secbutyl, or tertbutyl. In some embodiments, R³ is methyl, ethyl, isopropyl, or tertbutyl. In some embodiments, R³ is methoxy, ethoxy, propoxy, isoproxy, butoxy, or tertbutoxy. In some embodiments, R³ is F, Cl, Br, or I. In some embodiments, R³ is —OCH₃. In some embodiments, R³ is F. In other embodiments, R³ is H. In some embodiments, R¹ is —OH; R² is selected from the group consisting of —C(O)Rᵃ, —S(O)Rᵇ, —S(O)₂Rᶜ, —NHC(O)Rᵈ, —NHS(O)₂Rᵉ, —C₁-C₆alkyl-Rᶠ, —C₂-C₆alkenyl-Rᵍ, unsubstituted or substituted cycloalkyl, unsubstituted or substituted cycloalkenyl, and unsubstituted or substituted heterocycloalkyl; and R³ is hydrogen, C₁-C₆alkoxy, or halogen. In some embodiments, R¹ is —OH and R² is selected from the group consisting of —C(O)Rᵃ, —S(O)₂Rᶜ, —NHC(O)Rᵈ, —NHS(O)₂Rᵉ, —C₂-C₆alkenyl-Rᵍ, and unsubstituted or substituted cycloalkenyl; and R³ is hydrogen, —OCH₃, or F. In some embodiments, R¹ is —OH; R² is selected from the group consisting of —CHO, —C(O)CH₃, —C(O)CH₂F, —C(O)CH=CH₂, —S(O)₂CH=CH₂, —C(O)C≡CH, —C(O)C≡CCH₃, —NHS(O)₂CH=CH₂, —NHC(O)CH=CH₂, —C(O)C(=CH₂)CH₃,

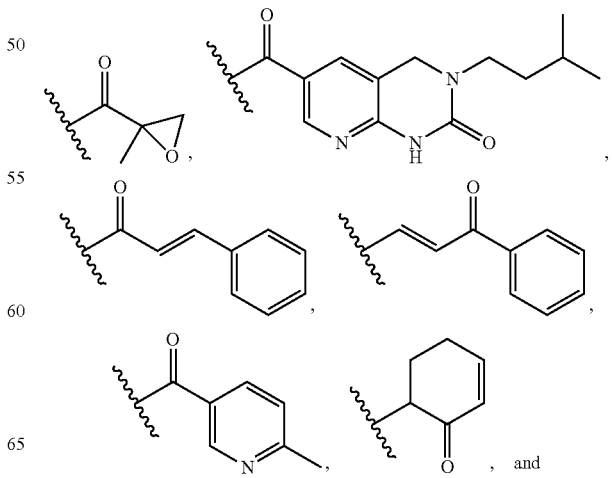

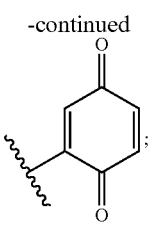

and $R^3$ is hydrogen, —OCH$_3$, or F. In some embodiments, $R^2$ is —OH; $R^1$ is selected from the group consisting of —C(O)R$^a$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted cycloalkyl, unsubstituted or substituted cycloalkenyl, and unsubstituted or substituted heterocycloalkyl; and $R^3$ is hydrogen, C$_1$-C$_6$alkoxy, or halogen. In some embodiments, $R^2$ is —OH; $R^1$ is selected from the group consisting of —C(O)R$^a$, —S(O)$_2$R$^c$, —NHC(O)R$^d$, —NHS(O)$_2$R$^e$, —C$_2$-C$_6$alkenyl-R$^g$, and unsubstituted or substituted cycloalkenyl; and $R^3$ is hydrogen, —OCH$_3$, or F. In some embodiments, $R^2$ is —OH and $R^1$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

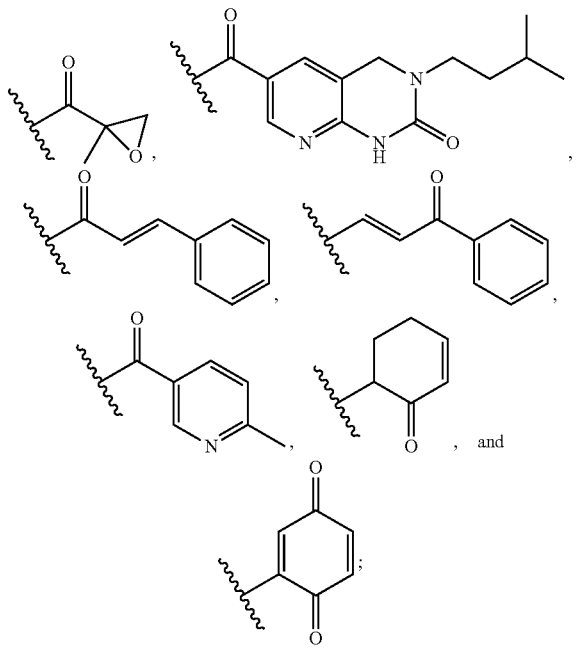

and $R^3$ is hydrogen, —OCH$_3$, or F.

In some embodiments, $R^1$ is —OH, $R^2$ is —CHO, and $R^3$ is H. In some embodiments, $R^1$ is —CHO, $R^2$ is —OH, and $R^3$ is H. In some embodiments, $R^1$ is —OH, $R^2$ is —CHO, and $R^3$ is —OCH$_3$. In other embodiments, $R^1$ is —CHO, $R^2$ is —OH, and $R^3$ is —OCH$_3$. In some embodiments, $R^1$ is —OH, $R^2$ is —CHO, and $R^3$ is F. In other embodiments, $R^1$ is —CHO, $R^2$ is —OH, and $R^3$ is F.

In some embodiments, $R^4$ and $R^5$ are each H. In some embodiments, $R^4$ and $R^5$ come together to form —S—, such that $R^4$ is taken together with $R^5$ and the atoms to which they are attached to form a thiophene ring.

In some embodiments, G$_3$ is CH(X$_1$—R$^{6a}$) or C(X$_1$—R$^{6a}$), wherein X$_1$ is absent; R$^{6a}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkyl, C$_1$-C$_6$alkoxy, and C$_3$-C$_8$cycloalkyl. In some embodiments, G$_3$ is CH(X$_1$—R$^{6a}$) or C(X$_1$—R$^{6a}$), wherein X$_1$ is

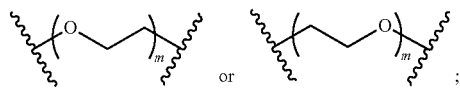

m is 1-6; R$^{6a}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkyl, C$_1$-C$_6$alkoxy, and C$_3$-C$_8$cycloalkyl. In some embodiments, G$_3$ is N or N(X$_1$—R$^{6a}$), wherein X$_1$ is absent; R$^{6a}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkoxy, C$_1$-C$_6$alkoxy, or C$_3$-C$_8$cycloalkyl. In some embodiments, G$_3$ is N or N(X$_1$—R$^{6a}$), wherein X$_1$ is

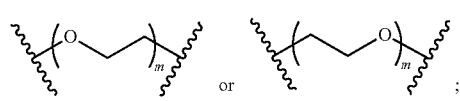

m is 1-6; R$^{6a}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkyl, C$_1$-C$_6$alkoxy, and C$_3$-C$_8$cycloalkyl. In some embodiments, G$_3$ is S. In other embodiments, G$_3$ is O.

In some embodiments, G$_4$ is CH(X$_2$—R$^{6b}$) or C(X$_2$—R$^{6b}$), wherein X$_2$ is absent; R$^{6b}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkyl, C$_1$-C$_6$alkoxy, and C$_3$-C$_8$cycloalkyl. In some embodiments, G$_4$ is CH(X$_2$—R$^{6b}$) or C(X$_2$—R$^{6b}$), wherein X$_2$ is

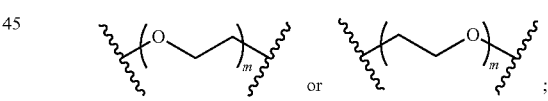

m is 1-6; R$^{6b}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkoxy, and C$_3$-C$_8$cycloalkyl. In some embodiments, G$_4$ is N or N(X$_2$—R$^{6b}$), wherein X$_2$ is absent; R$^{6b}$ is hydrogen, C$_1$-C$_6$alkyl, C$_1$-C$_6$alkoxy, halo, or —C(O)R$^h$, wherein C$_1$-C$_6$alkyl is unsubstituted or substituted with cycloalkyl or halogen; and R$^h$ is selected from the group consisting of H, C$_1$-C$_6$alkyl, C$_1$-C$_6$alkoxy, or C$_3$-C$_8$cycloalkyl. In some embodiments, G$_4$ is N or N(X$_2$—R$^{6b}$), wherein X$_2$

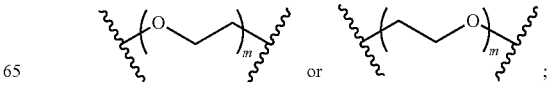

m is 1-6; $R^{6b}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkoxy, and $C_3$-$C_8$cycloalkyl. In some embodiments, $G_4$ is S. In other embodiments, $G_4$ is O.

In some embodiments, $G_5$ is CH($X_3$—$R^{6c}$) or C($X_3$—$R^{6c}$), wherein $X_3$ is absent; $R^{6c}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl. In some embodiments, $G_5$ is CH($X_3$—$R^{6c}$) or C($X_3$—$R^{6c}$), wherein $X_3$ is

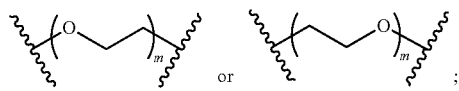

m is 1-6; $R^{6c}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl. In some embodiments, $G_5$ is N or N($X_3$—$R^{6c}$), wherein $X_3$ is absent; $R^{6c}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, or $C_3$-$C_8$cycloalkyl. In some embodiments, $G_5$ is N or N($X_3$—$R^{6c}$), wherein $X_3$ is

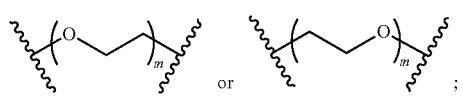

m is 1-6; $R^{6c}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl. In some embodiments, $G_5$ is S. In other embodiments, $G_5$ is O.

In some embodiments, $G_6$ is CH($X_4$—$R^{6d}$) or C($X_4$—$R^{6d}$), wherein $X_4$ is absent; $R^{6d}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl. In some embodiments, $G_6$ is CH($X_4$—$R^{6d}$) or C($X_4$—$R^{6d}$), wherein $X_4$ is

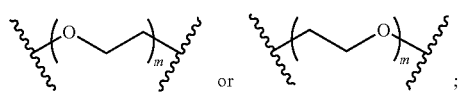

m is 1-6; $R^{6d}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, or $C_3$-$C_8$cycloalkyl. In some embodiments, $G_6$ is N or N($X_4$—$R^{6d}$), wherein $X_4$ is absent; $R^{6d}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkoxy, or $C_3$-$C_8$cycloalkyl. In some embodiments, $G_6$ is N or N($X_4$—$R^{6d}$), wherein $X_4$ is

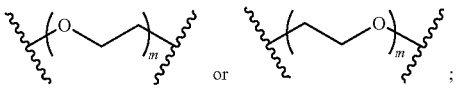

m is 1-6; $R^{6d}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl. In some embodiments, $G_6$ is S. In other embodiments, $G_6$ is O. In some embodiments, $G_6$ is absent.

In some embodiments, the ring bearing ⓘ is saturated, such that the ring consists entirely of single bonds. Examples of saturated rings include, but are not limited to,

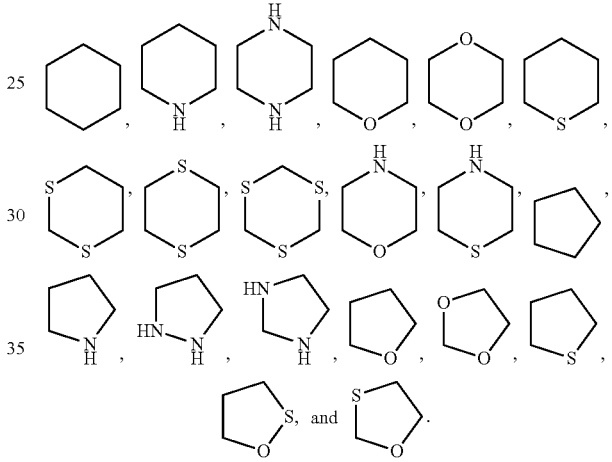

In some embodiments, the ring bearing ⓘ is partially unsaturated, such that the ring is nonaromatic and comprises at least one double bond, such as one or two double bonds. Examples of partially unsaturated rings include, but are not limited to,

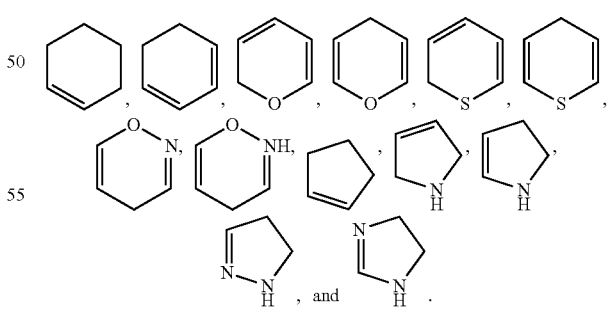

In other embodiments, the ring bearing ⓘ is fully unsaturated and comprises two or three double bonds. In certain embodiments, the ring bearing ⓘ is fully unsaturated. In certain embodiments, the ring bearing ⓘ is fully unsaturated and aromatic. Examples of fully unsaturated rings include, but are not limited to

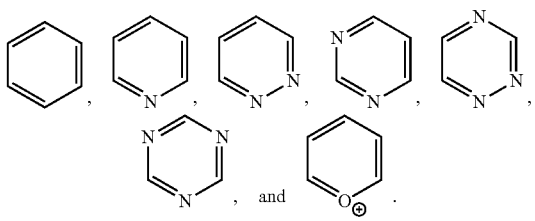

In some embodiments, $G_3$ is $CH(X_1—R^{6a})$ or $C(X_1—R^{6a})$, $G_4$ is $CH(X_2—R^{6b})$ or $C(X_2—R^{6b})$, $G_5$ is $CH(X_3—R^{6c})$ or $C(X_3—R^{6c})$, $G_6$ is $CH(X_4—R^{6d})$ or $C(X_4—R^{6d})$, and the ring bearing ◌ is partially unsaturated. In some embodiments, $G_3$ is $C(X_1—R^{6a})$, $G_4$ is $C(X_2—R^{6b})$, $G_5$ is $C(X_3—R^{6c})$, $G_6$ is $C(X_4—R^{6d})$, and the ring bearing ◌ is fully unsaturated. In some embodiments, $G_3$ is $CH(X_1—R^{6a})$, $G_4$ is $CH(X_2—R^{6b})$, $G_5$ is $CH(X_3—R^{6c})$, $G_6$ is $CH(X_4—R^{6d})$, and the ring bearing ◌ is saturated. In other embodiments, $G_3$ is $CH(X_1—R^{6a})$ or $C(X_1—R^{6a})$, $G_4$ is $CH(X_2—R^{6b})$ or $C(X_2—R^{6b})$, $G_5$ is $CH(X_3—R^{6c})$ or $C(X_3—R^{6c})$, and $G_6$ is absent.

In some embodiments, $G_3$ is $CH(X_1—R^{6a})$ or $C(X_1—R^{6a})$, $G_4$ is N or $N(X_2—R^{6b})$, $G_5$ is $CH(X_3—R^{6c})$ or $C(X_3—R^{6c})$, $G_6$ is $CH(X_4—R^{6d})$ or $C(X_4—R^{6d})$, and the ring bearing ◌ is partially unsaturated. In some embodiments, $G_3$ is $C(X_1—R^{6a})$, $G_4$ is N, $G_5$ is $C(X_3—R^{6c})$, $G_6$ is $C(X_4—R^{6d})$, and the ring bearing ◌ is fully unsaturated. In some embodiments, $G_3$ is $CH(X_1—R^{6a})$, $G_4$ is $N(X_2—R^{6b})$, $G_5$ is $CH(X_3—R^{6c})$, $G_6$ is $CH(X_4—R^{6d})$, and the ring bearing ◌ is saturated. In other embodiments, $G_3$ is $CH(X_1—R^{6a})$ or $C(X_1—R^{6a})$, $G_4$ is N or $N(X_2—R^{6b})$, $G_5$ is $CH(X_3—R^{6c})$ or $C(X_3—R^{6c})$, and $G_6$ is absent.

In some embodiments, $G_3$ is N or $N(X_1—R^{6a})$, $G_4$ is $CH(X_2—R^{6b})$ or $C(X_2—R^{6b})$, $G_5$ is $CH(X_3—R^{6c})$ or $C(X_3—R^{6c})$, $G_6$ is $CH(X_4—R^{6d})$ or $C(X_4—R^{6d})$, and the ring bearing ◌ is partially unsaturated. In some embodiments, $G_3$ is N, $G_4$ is $C(X_2—R^{6b})$, $G_5$ is $C(X_3—R^{6c})$, $G_6$ is $C(X_4—R^{6d})$, and the ring bearing ◌ is fully unsaturated. In some embodiments, $G_3$ is $N(X_1—R^{6a})$, $G_4$ is $CH(X_2—R^{6b})$, $G_5$ is $CH(X_3—R^{6c})$, $G_6$ is $CH(X_4—R^{6d})$, and the ring bearing ◌ is saturated. In other embodiments, $G_3$ is N or $N(X_1—R^{6a})$, $G_4$ is $CH(X_2—R^{6b})$ or $C(X_2—R^{6b})$, $G_5$ is $CH(X_3—R^{6c})$ or $C(X_3—R^{6c})$, and $G_6$ is absent.

In some embodiments, $G_3$ is $CH(X_1—R^{6a})$ or $C(X_1—R^{6a})$, $G_4$ is $CH(X_2—R^{6b})$ or $C(X_2—R^{6b})$, $G_5$ is N or $N(X_3—R^{6c})$, $G_6$ is $CH(X_4—R^{6d})$ or $C(X_4—R^{6d})$, and the ring bearing ◌ is partially unsaturated. In some embodiments, $G_3$ is $C(X_1—R^{6a})$, $G_4$ is $C(X_2—R^{6b})$, $G_5$ is N, $G_6$ is $C(X_4—R^{6d})$, and the ring bearing ◌ is fully unsaturated. In some embodiments, $G_3$ is $CH(X_1—R^{6a})$, $G_4$ is $CH(X_2—R^{6b})$, $G_5$ is $N(X_3—R^{6c})$, $G_6$ is $CH(X_4—R^{6d})$, and the ring bearing ◌ is saturated. In other embodiments, $G_3$ is $CH(X_1—R^{6a})$ or $C(X_1—R^{6a})$, $G_4$ is $CH(X_2—R^{6b})$ or $C(X_2—R^{6b})$, $G_5$ is N or $N(X_3—R^{6c})$, and $G_6$ is absent.

In other embodiments, $G_3$ is N or $N(X_1—R^{6a})$, $G_4$ is $CH(X_2—R^{6b})$ or $C(X_2—R^{6b})$, $G_5$ is N or $N(X_1—R^{6c})$, $G_6$ is $CH(X_4—R^{6d})$ or $C(X_4—R^{6d})$, and the ring bearing ◌ is partially unsaturated. In some embodiments, $G_3$ is N, $G_4$ is $C(X_2—R^{6b})$, $G_5$ is N, $G_6$ is $C(X_4—R^{6d})$, and the ring bearing ◌ is fully unsaturated. In some embodiments, $G_3$ is $N(X_1—R^{6a})$, $G_4$ is $CH(X_2—R^{6b})$, $G_5$ is $N(X_1—R^{6c})$, $G_6$ is $CH(X_4—R^{6d})$, and the ring bearing ◌ is saturated. In other embodiments, $G_3$ is N or $N(X_1—R^{6a})$, $G_4$ is $CH(X_2—R^{6b})$ or $C(X_2—R^{6b})$, $G_5$ is N or $N(X_1—R^{6c})$, and $G_6$ is absent.

In certain embodiments, $R^4$ and $R^5$ come together to form —S—, $G_3$ is $CH(X_1—R^{6a})$, $G_4$ is $N(X_2—R^{6b})$, $G_5$ is $CH(X_1—R^{6a})$, $G_6$ is $CH(X_1—R^{6a})$, and the ring bearing ◌ is a saturated ring. In certain embodiments, $R^4$ and $R^5$ come together to form —S—, $G_3$, $G_5$, and $G_6$ are each $CH_2$, $G_4$ is $N(X_2—R^{6b})$, and the ring bearing ◌ is a saturated ring.

In some of any of the foregoing embodiments, $R^{6a}$, $R^{6b}$, $R^{6c}$, and $R^{6d}$ are each independently hydrogen, $C_1$-$C_6$alkyl, $C_1$-$C_6$alkoxy, halo, or —$C(O)R^h$, wherein $C_1$-$C_6$alkyl is unsubstituted or substituted with cycloalkyl or halogen; $R^h$ is selected from the group consisting of H, $C_1$-$C_6$alkyl, $C_1$-$C_6$alkoxy, and $C_3$-$C_8$cycloalkyl. In some embodiments, $R^{6a}$, $R^{6b}$, $R^{6c}$, and $R^{6d}$ are each independently hydrogen, $C_1$-$C_6$alkyl, $C_1$-$C_6$alkoxy, or halo. In some embodiments, each $R^6$ is independently selected from the group consisting of Cl, F, —$CH_3$, —$OCH_3$, —$CF_3$, —$CH_2CH_2F$, —$CH(CH_3)_2$, —$C(O)OC(CH_3)_3$, —$C(O)CH_3$,

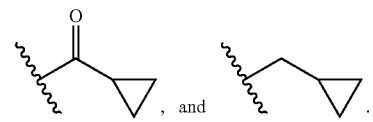 [SMILES: *C(=O)C1CC1 ; *CC1CC1]

In some embodiments, $R^{6a}$, $R^{6b}$, $R^{6c}$, and $R^{6d}$ are each independently selected from the group consisting of H, Cl, F, —$CH_3$, —$OCH_3$, —$CF_3$, —$CH_2CH_2F$, —$CH(CH_3)_2$, —$C(O)OC(CH_3)_3$, —$C(O)CH_3$,

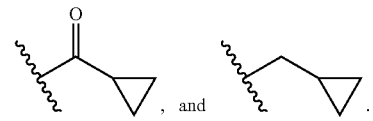 [SMILES: *C(=O)C1CC1 ; *CC1CC1]

In some embodiments, $R^{6a}$, $R^{6b}$, $R^{6c}$, and $R^{6d}$ are each independently selected from the group consisting of H, —OH,

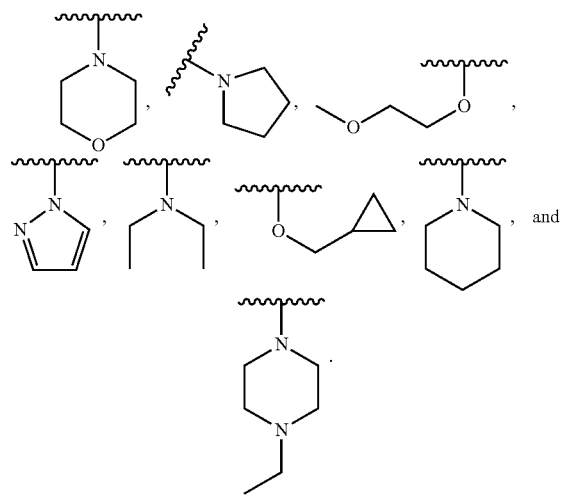

In some embodiments, $R^{6a}$, $R^{6b}$, $R^{6c}$, and $R^{6d}$ are each independently selected from the group consisting of H,

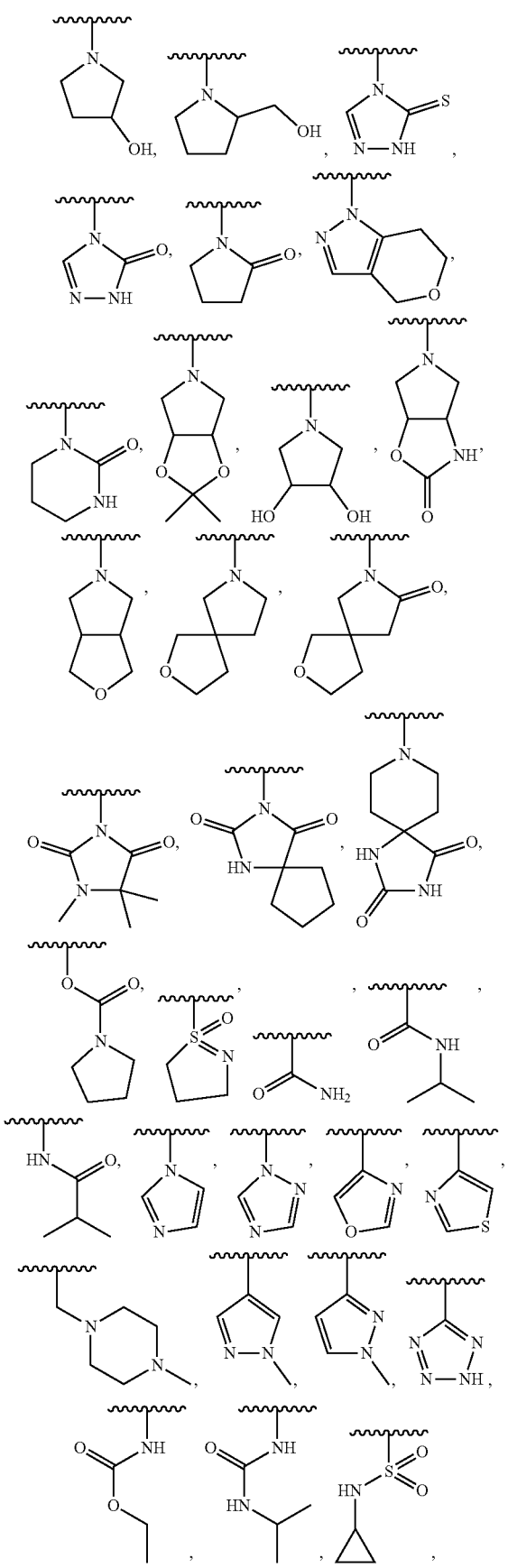

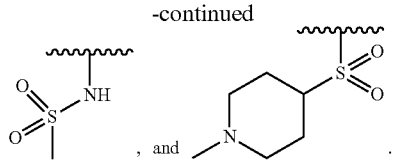

In some of any of the foregoing embodiments, one of $R^{6a}$, $R^{6b}$, $R^{6c}$, and $R^{6d}$ is selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen, and the other three of $R^{6a}$, $R^{6b}$, $R^{6c}$, and $R^{6d}$ are each hydrogen. In some embodiments, one of $R^{6a}$, $R^{6b}$, $R^{6c}$, and $R^{6d}$ is selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

and the other three of $R^{6a}$, $R^{6b}$, $R^{6c}$, and $R^{6d}$ are each hydrogen.

In some embodiments, $R^{6a}$, $R^{6b}$, and $R^{6d}$ are each H, and $R^{6c}$ is selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$, $R^{6b}$, and $R^{6d}$ are each H, and $R^{6c}$ is selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

In some embodiments, $R^{6b}$, $R^{6c}$, and $R^{6d}$ are each H, and $R^{6a}$ is selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6b}$, $R^{6c}$, and $R^{6d}$ are each H, and $R^{6a}$ is selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

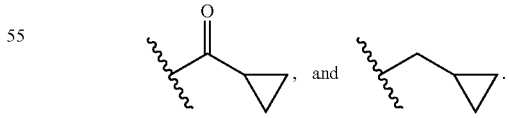

In some embodiments, $R^{6a}$, $R^{6c}$, and $R^{6d}$ are each H, and $R^{6b}$ is selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$, $R^{6c}$, and $R^{6d}$ are each H, and $R^{6b}$ is selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

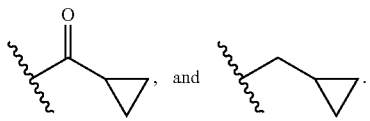, and 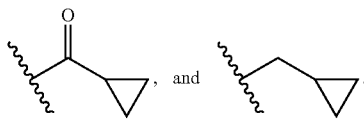.

In some embodiments, $R^{6a}$, $R^{6b}$, and $R^{6c}$ are each H, and $R^{6d}$ is selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$, $R^{6b}$, and $R^6$ are each H, and $R^{6d}$ is selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

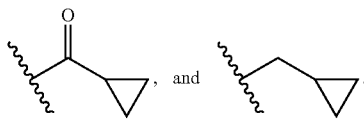, and 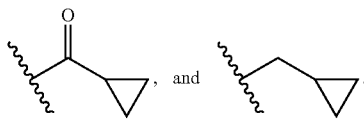.

In some of any of the foregoing embodiments, two of $R^{6a}$, $R^{6b}$, $R^{6c}$, and $R^{6d}$ are selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen, and the other two of $R^{6a}$, $R^{6b}$, $R^{6c}$, and $R^{6d}$ are each hydrogen. In some embodiments, two of $R^{6a}$, $R^{6b}$, $R^{6c}$, and $R^{6d}$ are selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

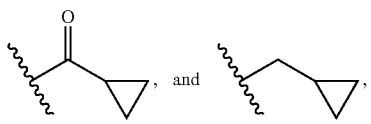 [SMILES: *C(=O)C1CC1 ; *CC1CC1], and 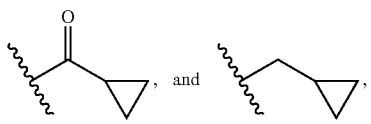 [SMILES: *C(=O)C1CC1 ; *CC1CC1], and the other two of $R^{6a}$, $R^{6b}$, $R^{6c}$, and $R^{6d}$ are each hydrogen.

In some embodiments, $R^{6a}$ and $R^{6b}$ are each H, and $R^{6c}$ and $R^{6d}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$ and $R^{6b}$ are each H, and $R^{6c}$ and $R^{6d}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

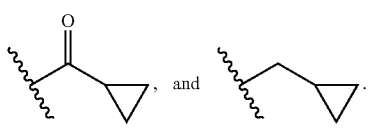, and 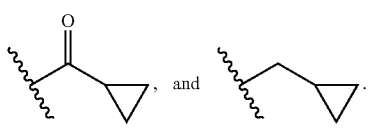.

In some embodiments, $R^{6a}$ and $R^{6c}$ are each H, and $R^{6b}$ and $R^{6d}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$ and $R^{6c}$ are each H, and $R^{6b}$ and $R^{6d}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

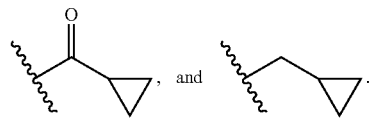, and 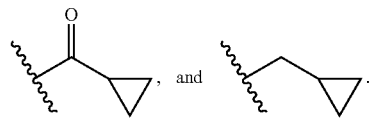.

In some embodiments, $R^{6a}$ and $R^{6d}$ are each H, and $R^{6b}$ and $R^{6c}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6a}$ and $R^{6d}$ are each H, and $R^{6b}$ and $R^{6c}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

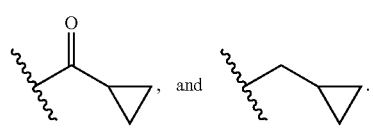 [SMILES: *C(=O)C1CC1 ; *CC1CC1], and 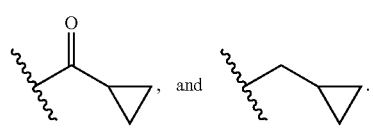 [SMILES: *C(=O)C1CC1 ; *CC1CC1].

In some embodiments, $R^{6b}$ and $R^{6c}$ are each H, and $R^{6a}$ and $R^{6d}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6b}$ and $R^{6c}$ are each H, and $R^{6a}$ and $R^{6d}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

, and .

In some embodiments, $R^{6b}$ and $R^{6d}$ are each H, and $R^{6a}$ and $R^{6c}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6b}$ and $R^{6d}$ are each H, and $R^{6a}$ and $R^{6c}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

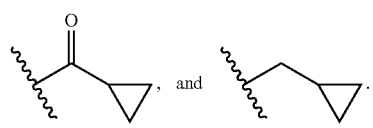, and 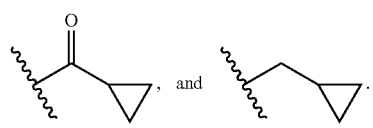.

In some embodiments, $R^{6c}$ and $R^{6d}$ are each H, and $R^{6a}$ and $R^{6b}$ are independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, $R^{6c}$ and $R^{6d}$ are each H, and $R^{6a}$ and $R^{6b}$ are independently selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

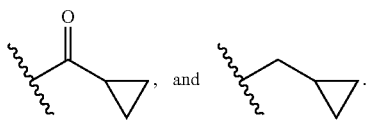, and

In some of any of the foregoing embodiments, three of $R^{6a}$, $R^{6b}$, $R^{6c}$, and $R^{6d}$ are selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments, three of $R^{6a}$, $R^{6b}$, $R^{6c}$, and $R^{6d}$ are selected from the group consisting of Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

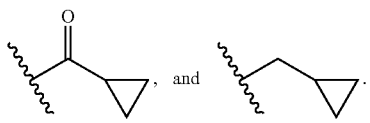, and

In some embodiments, $R^{6a}$, $R^{6b}$, $R^{6c}$, and $R^{6d}$ are each selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments $R^{6a}$, $R^{6b}$, $R^{6c}$, and $R^{6d}$ are each hydrogen.

In some embodiments,

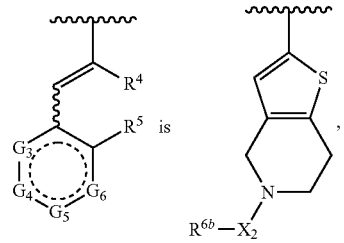

$X_2$ is absent,

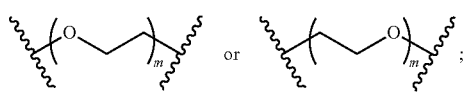;

m is 1-6; $R^{6b}$ is hydrogen, $C_1$-$C_6$alkyl, $C_1$-$C_6$alkoxy, halo, or —C(O)$R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, or $C_3$-$C_8$cycloalkyl. In some embodiments,

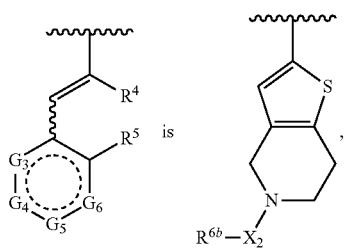

$X_2$ is absent, and $R^{6b}$ is selected from hydrogen Cl, F, —CH$_3$, —OCH$_3$, —CF$_3$, —CH$_2$CH$_2$F, —CH(CH$_3$)$_2$, —C(O)OC(CH$_3$)$_3$, —C(O)CH$_3$,

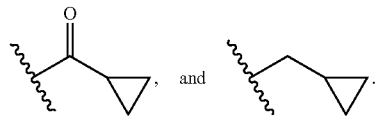 [SMILES: *C(=O)C1CC1 ; *CC1CC1], and

In some embodiments,

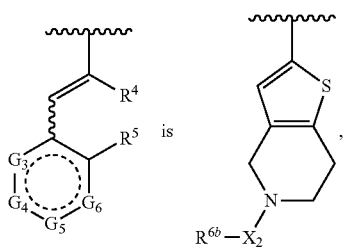

$X_2$ is absent, and $R^{6b}$ is selected from hydrogen —CH$_3$, —CH$_2$CH$_2$F, —CH(CH$_3$)$_2$, —C(O)OC(CH$_3$)$_3$, —C(O)CH$_3$,

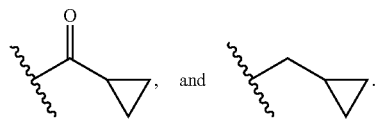 [SMILES: *C(=O)C1CC1 ; *CC1CC1], and

In some embodiments,

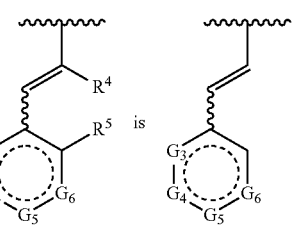

In some embodiments,

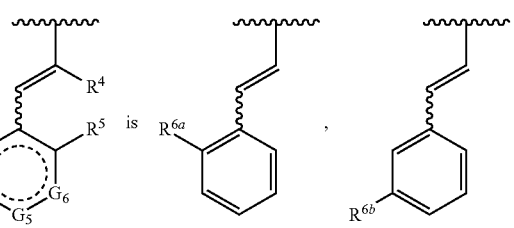

-continued

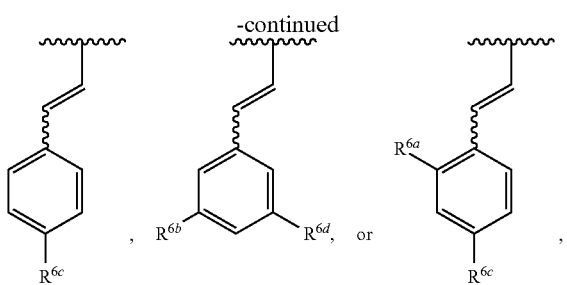

wherein $R^{6a}$, $R^{6b}$, $R^{6c}$, and $R^{6d}$ are each independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments,

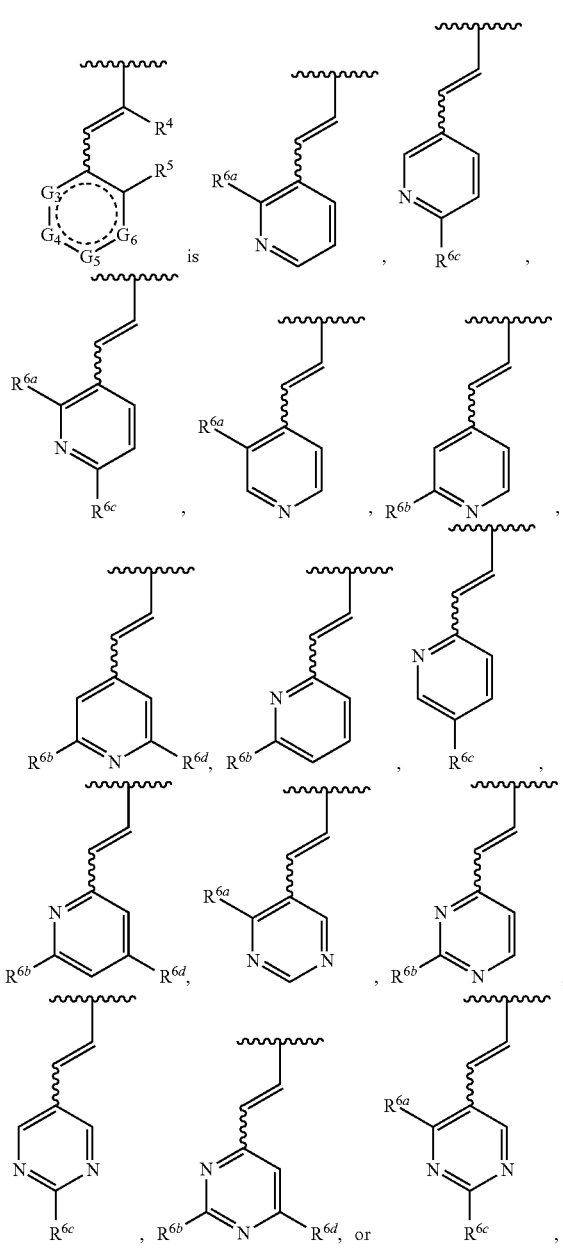

wherein $R^{6a}$, $R^{6b}$, $R^{6c}$, and $R^{6d}$ are each independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen. In some embodiments,

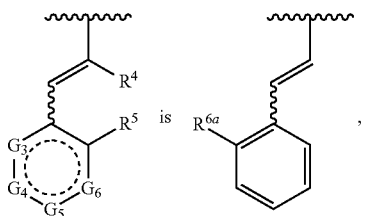

wherein $R^{6a}$ is selected from the group consisting of —CH$_3$, —CH$_2$CH$_2$F, —CH(CH$_3$)$_2$, —C(O)OC(CH$_3$)$_3$, —C(O)CH$_3$,

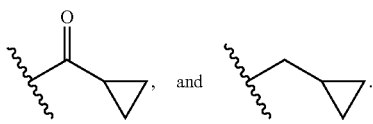 [SMILES: *C(=O)C1CC1 ; *CC1CC1]

In some embodiments,

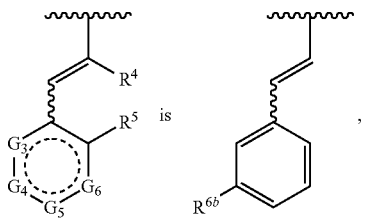

wherein $R^{6a}$ is selected from the group consisting of —CH$_3$, —CH$_2$CH$_2$F, —CH(CH$_3$)$_2$, —C(O)OC(CH$_3$)$_3$, —C(O)CH$_3$,

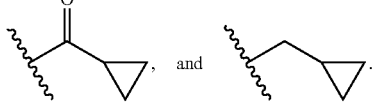

In some embodiments,

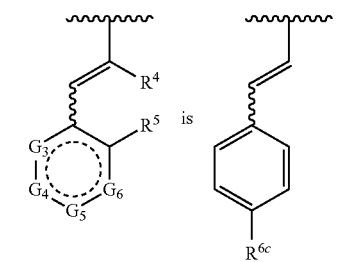

wherein $R^{6c}$ is selected from the group consisting of —CH$_3$, —CH$_2$CH$_2$F, —CH(CH$_3$)$_2$, —C(O)OC(CH$_3$)$_3$, —C(O)CH$_3$,

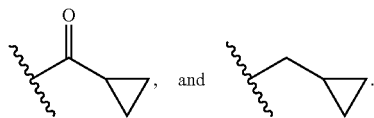 [SMILES: *C(=O)C1CC1 ; *CC1CC1]

In some embodiments,

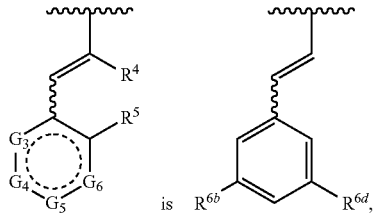

wherein $R^{6b}$ and $R^{6d}$ are each independently selected from the group consisting of —CH$_3$, —CH$_2$CH$_2$F, —CH(CH$_3$)$_2$, —C(O)OC(CH$_3$)$_3$, —C(O)CH$_3$,

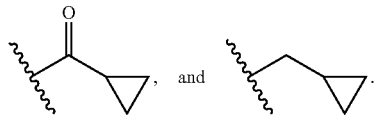 [SMILES: *C(=O)C1CC1 ; *CC1CC1]

In some embodiments,

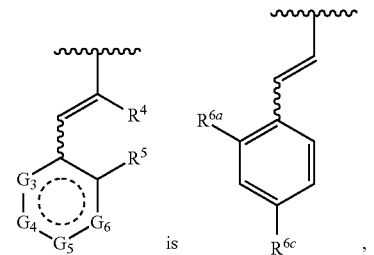

wherein $R^{6a}$ and $R^{6d}$ are each independently selected from the group consisting of —CH$_3$, —CH$_2$CH$_2$F, —CH(CH$_3$)$_2$, —C(O)OC(CH$_3$)$_3$, —C(O)CH$_3$,

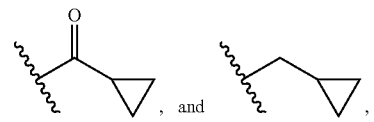 [SMILES: *C(=O)C1CC1 ; *CC1CC1]

In some embodiments,

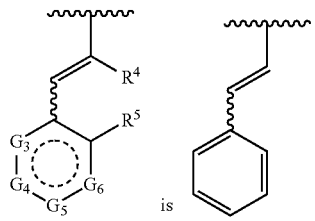

In other embodiments,

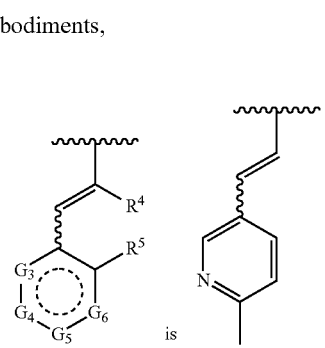

In some embodiments, $G_1$ and $G_2$ are each CH; $R^1$ is —OH; $R^2$ is selected from the group consisting of —C(O)R$^a$, —S(O)R$^b$, —S(O)$_2$R$^c$, —NHC(O)R$^d$, —NHS(O)$_2$R$^e$, —C$_1$-C$_6$alkyl-R$^f$, —C$_2$-C$_6$alkenyl-R$^g$, unsubstituted or substituted cycloalkyl, unsubstituted or substituted cycloalkenyl, and unsubstituted or substituted heterocycloalkyl; $R^3$ is hydrogen, C$_1$-C$_6$alkoxy, or halogen; and $R^4$ and $R^5$ are each H. In some embodiments, $G_1$ and $G_2$ are each CH; $R^1$ is —OH and $R^2$ is selected from the group consisting of —C(O)R$^a$, —S(O)$_2$R$^c$, —NHC(O)R$^d$, —NHS(O)$_2$R$^e$, —C$_2$-C$_6$alkenyl-R$^g$, and unsubstituted or substituted cycloalkenyl; $R^3$ is hydrogen, —OCH$_3$, or F; and $R^4$ and $R^5$ are each H. In some embodiments, $G_1$ and $G_2$ are each CH; $R^1$ is —OH; $R^2$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

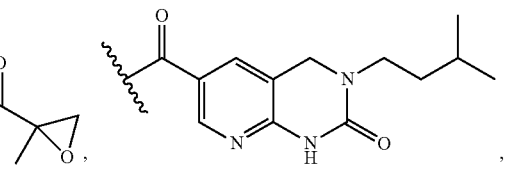

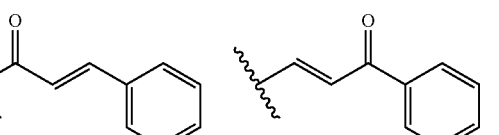

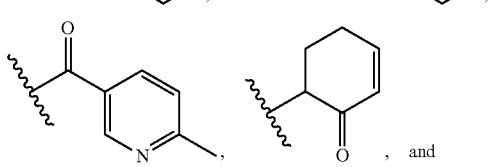

, and

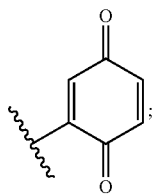

$R^3$ is hydrogen, —OCH$_3$, or F; and $R^4$ and $R^5$ are each H. In some embodiments, G$_1$ and G$_2$ are each CH; $R^2$ is —OH; $R^1$ is selected from the group consisting of —C(O)R$^a$, —S(O)R$^b$, —S(O)$_2$R$^c$, —NHC(O)R$^d$, —NHS(O)$_2$R$^e$, —C$_2$-C$_6$alkenyl-R$^g$, unsubstituted or substituted cycloalkyl, unsubstituted or substituted cycloalkenyl, and unsubstituted or substituted heterocycloalkyl; $R^3$ is hydrogen, C$_1$-C$_6$alkoxy, or halogen; and $R^4$ and $R^5$ are each H. In some embodiments, G$_1$ and G$_2$ are each CH; $R^2$ is —OH; $R^1$ is selected from the group consisting of —C(O)R$^a$, —S(O)$_2$R$^c$, —NHC(O)R$^d$, —NHS(O)$_2$R$^e$, —C$_2$-C$_6$alkenyl-R$^g$, and unsubstituted or substituted cycloalkenyl; $R^3$ is hydrogen, —OCH$_3$, or F; and $R^4$ and $R^5$ are each H. In some embodiments, G$_1$ and G$_2$ are each CH; $R^2$ is —OH and $R^1$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

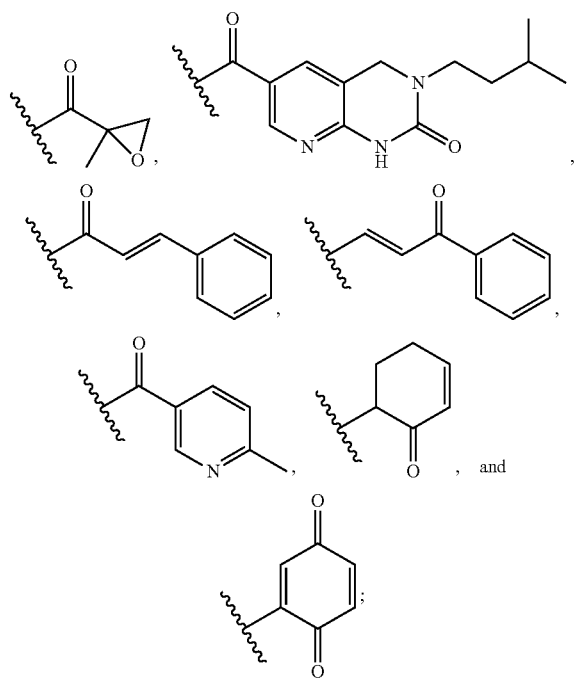

$R^3$ is hydrogen, —OCH$_3$, or F; and $R^4$ and $R^5$ are each H. In any of the foregoing embodiments,

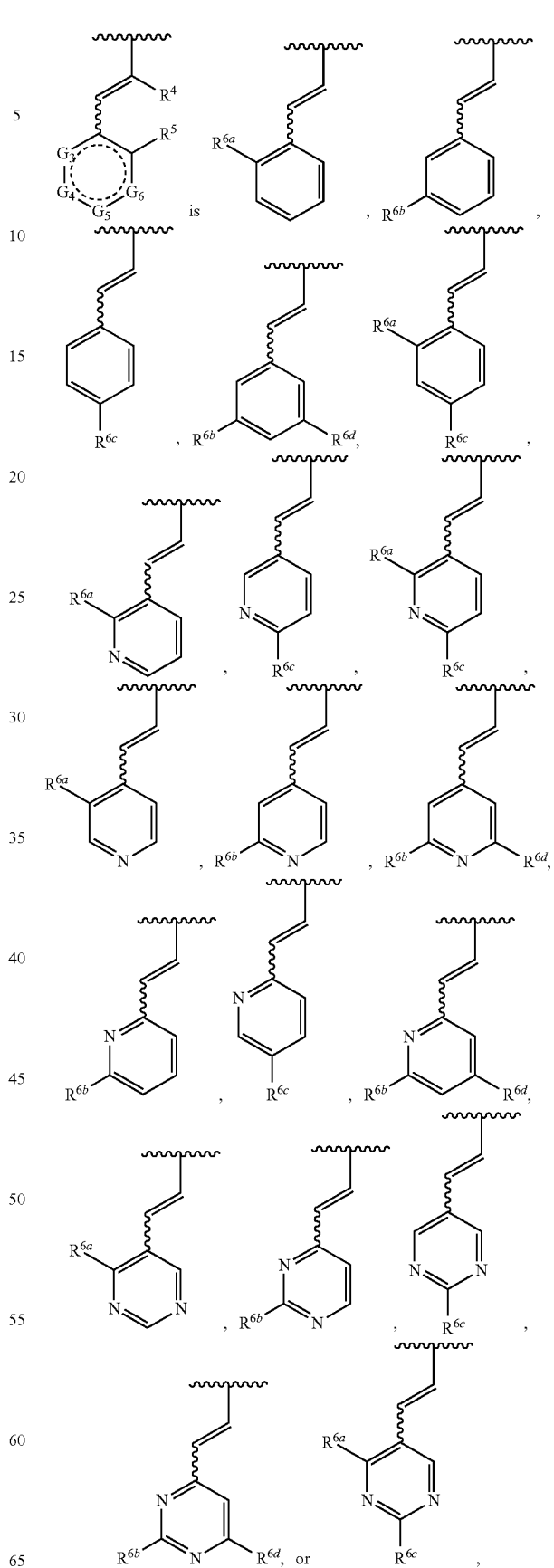

wherein $R^{6a}$, $R^{6b}$, $R^{6c}$, and $R^{6d}$ are each independently selected from the group consisting of $C_1$-$C_6$alkyl, $C_1$-$C_6$alkoxy, halo, or —C(O)$R^h$, wherein $C_1$-$C_6$alkyl is unsubstituted or substituted with cycloalkyl or halogen.

In some embodiments, $G_1$ and $G_2$ are each CH; $R^1$ is —OH; $R^2$ is selected from the group consisting of —C(O)$R^a$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted cycloalkyl, unsubstituted or substituted cycloalkenyl, and unsubstituted or substituted heterocycloalkyl; $R^3$ is hydrogen, $C_1$-$C_6$alkoxy, or halogen; and $R^4$ and $R^5$ come together to form —S—. In some embodiments, $G_1$ and $G_2$ are each CH; $R^1$ is —OH and $R^2$ is selected from the group consisting of —C(O)$R^a$, —S(O)$_2R^c$, —NHC(O)$R^d$, —NHS(O)$_2R^e$, —$C_2$-$C_6$alkenyl-$R^g$, and unsubstituted or substituted cycloalkenyl; $R^3$ is hydrogen, —OCH$_3$, or F; and $R^4$ and $R^5$ come together to form —S—. In some embodiments, $G_1$ and $G_2$ are each CH; $R^1$ is —OH; $R^2$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

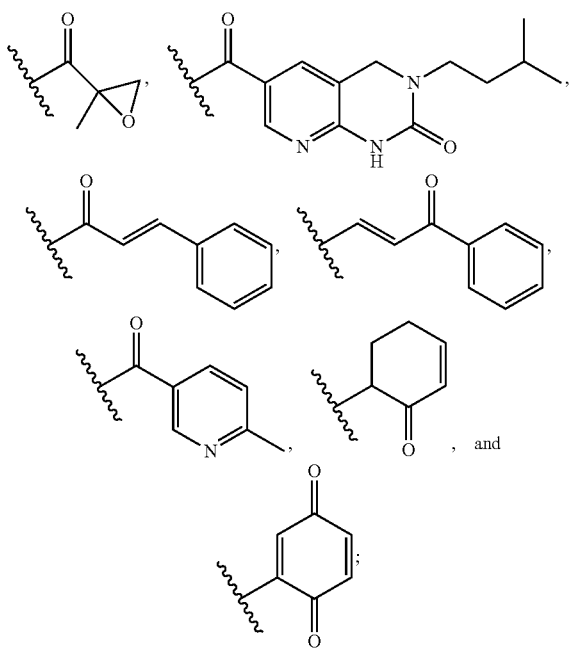

$R^3$ is hydrogen, —OCH$_3$, or F; and $R^4$ and $R^5$ come together to form —S—. In some embodiments, $G_1$ and $G_2$ are each CH; $R^2$ is —OH; $R^1$ is selected from the group consisting of —C(O)$R^a$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted cycloalkyl, unsubstituted or substituted cycloalkenyl, and unsubstituted or substituted heterocycloalkyl; $R^3$ is hydrogen, $C_1$-$C_6$alkoxy, or halogen; and $R^4$ and $R^5$ come together to form —S—. In some embodiments, $G_1$ and $G_2$ are each CH; $R^2$ is —OH; $R^1$ is selected from the group consisting of —C(O)$R^a$, —S(O)$_2R^c$, —NHC(O)$R^d$, —NHS(O)$_2R^e$, —$C_2$-$C_6$alkenyl-$R^g$, and unsubstituted or substituted cycloalkenyl; $R^3$ is hydrogen, —OCH$_3$, or F; and $R^4$ and $R^5$ come together to form —S—. In some embodiments, $G_1$ and $G_2$ are each CH; $R^2$ is —OH and $R^1$ is selected from the group consisting of —CHO, —C(O)CH$_3$, —C(O)CH$_2$F, —C(O)CH=CH$_2$, —S(O)$_2$CH=CH$_2$, —C(O)C≡CH, —C(O)C≡CCH$_3$, —NHS(O)$_2$CH=CH$_2$, —NHC(O)CH=CH$_2$, —C(O)C(=CH$_2$)CH$_3$,

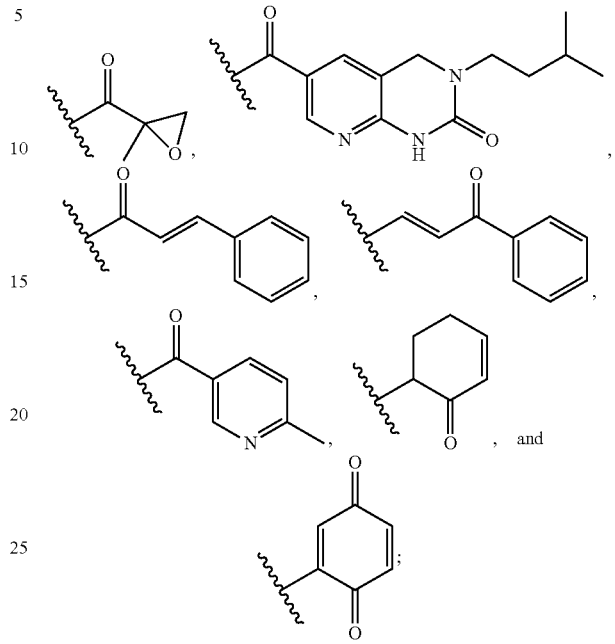

$R^3$ is hydrogen, —OCH$_3$, or F; and $R^4$ and $R^5$ come together to form —S—. In any of the foregoing embodiments,

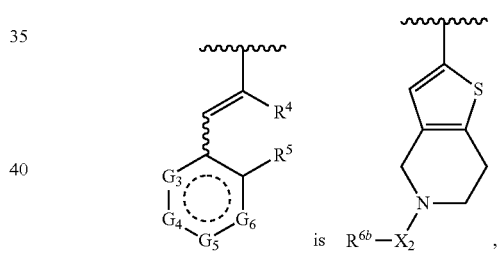

$X_2$ is absent, and $R^{6b}$ is selected from hydrogen —CH$_3$, —CH$_2$CH$_2$F, —CH(CH$_3$)$_2$, —C(O)OC(CH$_3$)$_3$, —C(O)CH$_3$,

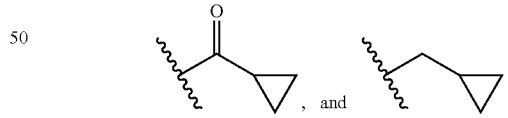

In some embodiments, one of $G_1$ and $G_2$ is N, and the other is CH; $R^1$ is —OH; $R^2$ is selected from the group consisting of —C(O)$R^a$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted cycloalkyl, unsubstituted or substituted cycloalkenyl, and unsubstituted or substituted heterocycloalkyl; $R^3$ is hydrogen, $C_1$-$C_6$alkoxy, or halogen; and $R^4$ and $R^5$ are each H. In some embodiments, one of $G_1$ and $G_2$ is N, and the other is CH; $R^2$ is —OH; $R^1$ is selected from the group consisting of —C(O)$R^a$, —S(O)$R^b$, —S(O)$_2R^c$, —NHC(O)$R^d$, —NHS(O)$_2R^e$, —$C_1$-$C_6$alkyl-$R^f$, —$C_2$-$C_6$alkenyl-$R^g$, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ are each H. In any of the foregoing embodiments,

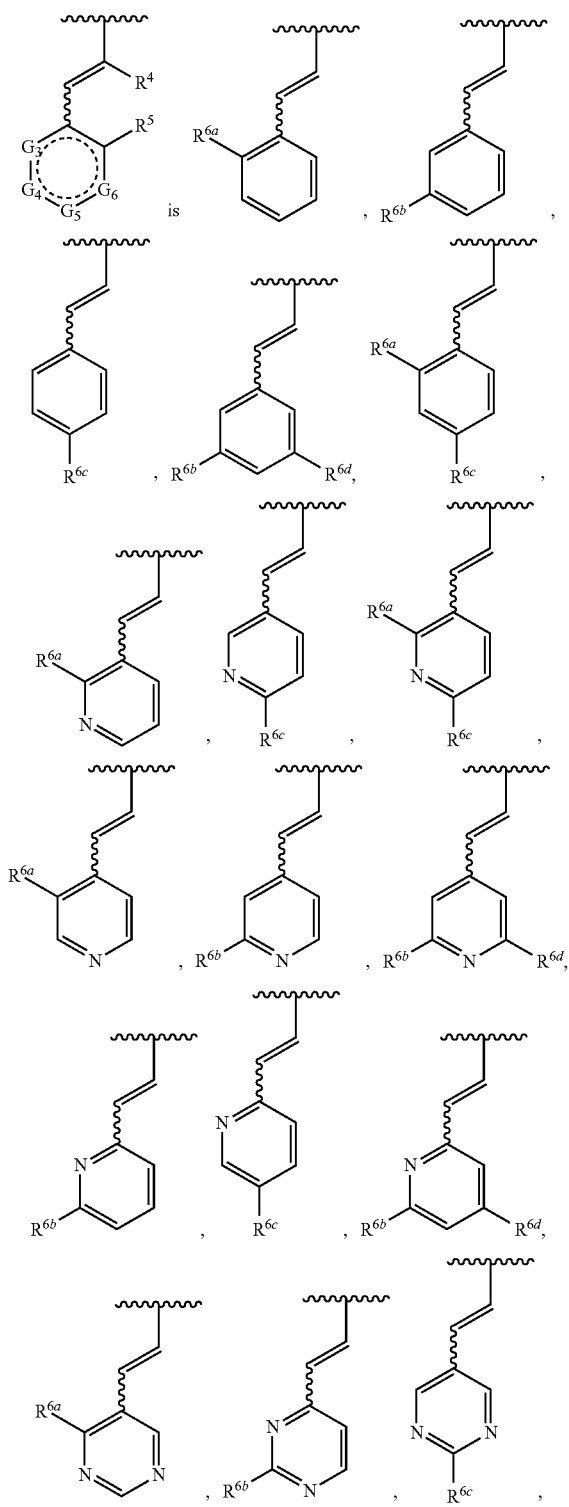

is

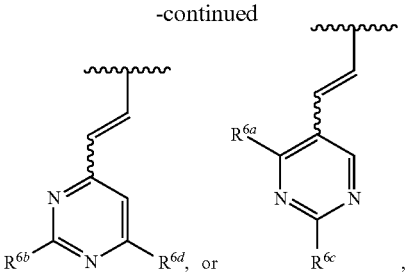

wherein $R^{6a}$, $R^{6b}$, $R^{6c}$, and $R^{6d}$ are each independently selected from the group consisting of C₁-C₆alkyl, C₁-C₆alkoxy, halo, or —C(O)R^h, wherein C₁-C₆alkyl is unsubstituted or substituted with cycloalkyl or halogen.

In some embodiments, one of G₁ and G₂ is N, and the other is CH; R¹ is —OH; R² is selected from the group consisting of —C(O)R^a, —S(O)R^b, —S(O)₂R^c, —NHC(O)R^d, —NHS(O)₂R^e, —C₁-C₆alkyl-R^f, —C₂-C₆alkenyl-R^g, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ come together to form —S—. In some embodiments, one of G₁ and G₂ is N, and the other is CH; R² is —OH; R¹ is selected from the group consisting of —C(O)R^a, —S(O)R^b, —S(O)₂R^c, —NHC(O)R^d, —NHS(O)₂R^e, —C₁-C₆alkyl-R^f, —C₂-C₆alkenyl-R^g, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ come together to form —S—. In any of the foregoing embodiments,

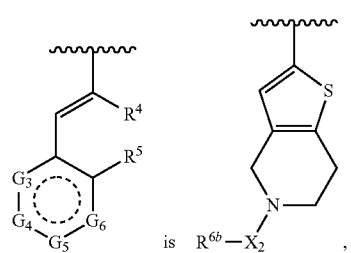

is $R^{6b}$—X₂

X₂ is absent, and $R^{6b}$ is selected from hydrogen —CH₃, —CH₂CH₂F, —CH(CH₃)₂, —C(O)OC(CH₃)₃, —C(O)CH₃,

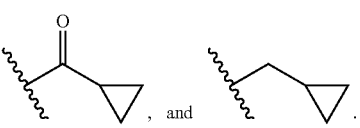 [SMILES: *C(=O)C1CC1 ; *CC1CC1]

, and

.

In some embodiments, G₁ and G₂ are both N; R¹ is —OH; R² is selected from the group consisting of —C(O)R^a, —S(O)R^b, —S(O)₂R^c, —NHC(O)R^d, —NHS(O)₂R^e, —C₁-C₆alkyl-R^f, —C₂-C₆alkenyl-R^g, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ are each H. In some embodiments, G₁ and G₂ are both N; R² is —OH; R¹ is selected from the group consisting of —C(O)R^a, —S(O)R^b, —S(O)₂R^c, —NHC(O)R^d, —NHS(O)₂R^e, —C₁-C₆alkyl-R^f, —C₂-C₆alkenyl-R^g, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ are each H. In any of the foregoing embodiments,

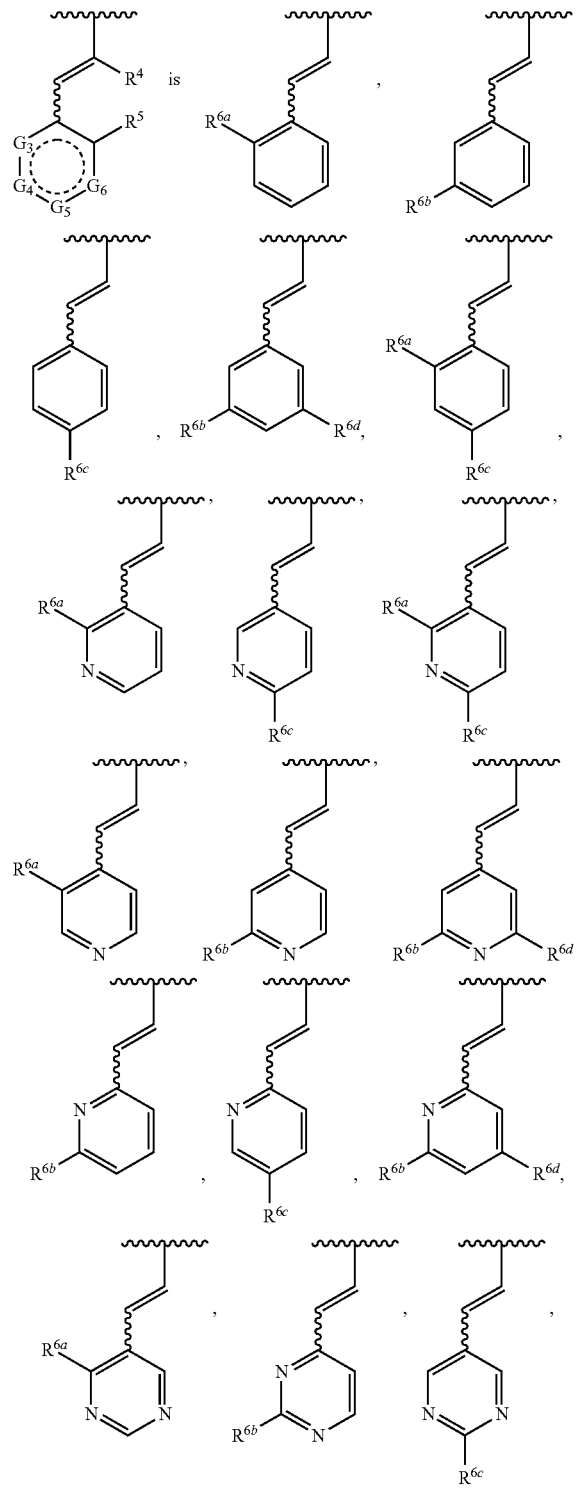

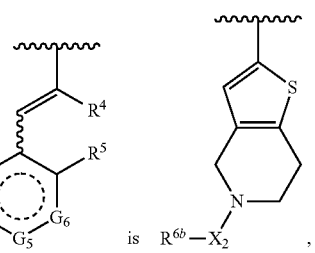

wherein $R^{6a}$, $R^{6b}$, $R^{6c}$, and $R^{6d}$ are each independently selected from the group consisting of $C_1$-$C_6$alkyl, $C_1$-$C_6$alkoxy, halo, or —C(O)R$^h$, wherein $C_1$-$C_6$alkyl is unsubstituted or substituted with cycloalkyl or halogen.

In some embodiments, $G_1$ and $G_2$ are both N; R¹ is —OH; R² is selected from the group consisting of —C(O)R$^a$, —S(O)R$^b$, —S(O)₂R$^c$, —NHC(O)R$^d$, —NHS(O)₂R$^e$, —C₁-C₆alkyl-R$^f$, —C₂-C₆alkenyl-R$^g$, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ come together to form —S—. In some embodiments, $G_1$ and $G_2$ are both N; R² is —OH; R¹ is selected from the group consisting of —C(O)R$^a$, —S(O)R$^b$, —S(O)₂R$^c$, —NHC(O)R$^d$, —NHS(O)₂R$^e$, —C₁-C₆alkyl-R$^f$, —C₂-C₆alkenyl-R$^g$, unsubstituted or substituted cycloalkyl, unsubstituted or substituted cycloalkenyl, and unsubstituted or substituted heterocycloalkyl; R³ is hydrogen, C₁-C₆alkoxy, or halogen; and R⁴ and R⁵ come together to form —S—. In any of the foregoing embodiments,

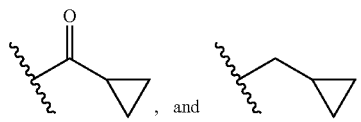 [SMILES: *C(=O)C1CC1 ; *CC1CC1]

X₂ is absent, and $R^{6b}$ is selected from hydrogen —CH₃, —CH₂CH₂F, —CH(CH₃)₂, —C(O)OC(CH₃)₃, —C(O)CH₃, In some embodiments, when R¹ is —OH; R² is —CHO; R³ is H; $G_1$, $G_2$, $G_3$, $G_4$, and $G_6$ are each CH; and R⁴ and R⁵ are each H, $G_5$ is not CH, CBr, COCH₃, CCH₃, CCl, or CF. In some embodiments, when R¹ is —OH; R² is —CHO; R³ is H; $G_1$, $G_2$, $G_3$, $G_5$, and $G_6$ are each CH; and R⁴ and R⁵ are each H, $G_4$ is not —CF₃. In some embodiments, when R¹ is —CHO; R² is —OH; R³ is H; $G_1$, $G_2$, $G_4$, and $G_6$ are each CH; R⁴ and R⁵ are each H; and $G_3$ is —OCH₃, $G_5$ is not n-propyl. In some embodiments, when R¹ is —NHC(O)CH₃; R² is —OH; R³ is H; $G_1$ and $G_2$ are each CH; and R⁴ and R⁵ are each H; at least one of $G_3$, $G_4$, $G_5$, and $G_6$ is other than CH.

In one aspect, the compound of Formula (I) is a compound of Formula (Ia):

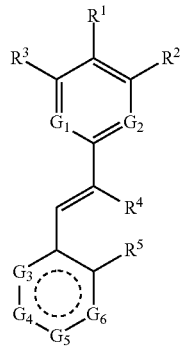

(Ia)

or a tautomer, or a pharmaceutically acceptable salt of any of the foregoing, wherein $R^1$, $R^2$, $R^3$, $R^4$, $R^5$, $G_1$, $G_2$, $G_3$, $G_4$, $G_5$, and $G_6$, are as defined for Formula (I) or any variation or embodiment thereof, and wherein the stereochemistry with respect to the double bond shown in Formula (Ia) is as represented in the formula as drawn.

In another aspect, the compound of Formula (I) is a compound of Formula (Ib):

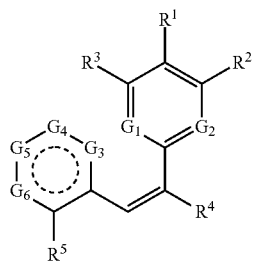

(Ib)

or a tautomer, or a pharmaceutically acceptable salt of any of the foregoing, wherein $R^1$, $R^2$, $R^3$, $R^4$, $R^5$, $G_1$, $G_2$, $G_3$, $G_4$, $G_5$, and $G_6$, are as defined for Formula (I) or any variation or embodiment thereof, and wherein the stereochemistry with respect to the double bond shown in Formula (Ib) is as represented in the formula as drawn.

It is understood that unless otherwise stated, any of the embodiments described herein, such as those described with respect to Formula (A), Formula (A-1), Formula (A-2), Formula (I), Formula (Ia), and Formula (Ib) are also intended to apply to any other formula described herein, including Formula (A), Formula (A-1), Formula (A-2), Formula (I), Formula (Ia), and Formula (Ib).

In some embodiments, provided herein are compounds and salts thereof described in Table 1.

TABLE 1

| Cmpd # | Chemical Structure | Chemical Name |
|---|---|---|
| 1 | (structure) | (E)-2-hydroxy-3-methoxy-5-(4-methoxystyryl)benzaldehyde |
| 2 | (structure) | (E)-2-hydroxy-3-methoxy-5-(3-(trifluoromethyl)styryl)benzaldehyde |

TABLE 1-continued
| Cmpd # | Chemical Structure | Chemical Name |
|---|---|---|
| 3 | 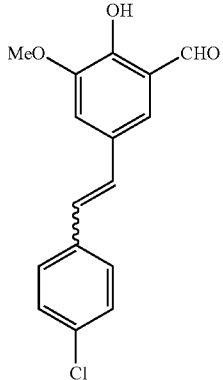 | 5-(4-chlorostyryl)-2-hydroxy-3-methoxybenzaldehyde |
| 4 | 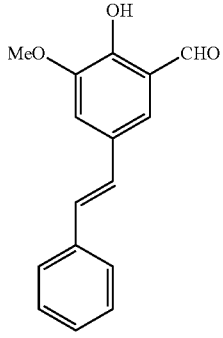 [SMILES: COc1cc(/C=C/c2ccccc2)cc(C=O)c1O] | (E)-2-hydroxy-3-methoxy-5-styrylbenzaldehyde |
| 5 | 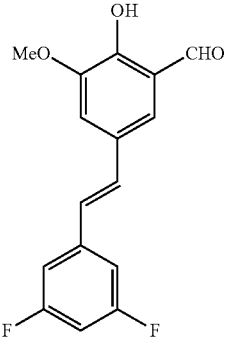 [SMILES: COc1cc(/C=C/c2cc(F)cc(F)c2)cc(C=O)c1O] | (E)-5-(3,5-difluorostyryl)-2-hydroxy-3-methoxybenzaldehyde |
| 6 | 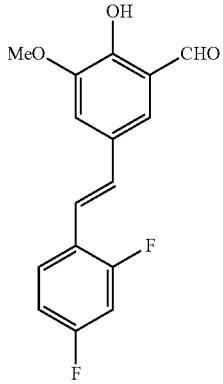 [SMILES: COc1cc(/C=C/c2ccc(F)cc2F)cc(C=O)c1O] | (E)-5-(2,4-difluorostyryl)-2-hydroxy-3-methoxybenzaldehyde |

TABLE 1-continued
| Cmpd # | Chemical Structure | Chemical Name |
|---|---|---|
| 7 | 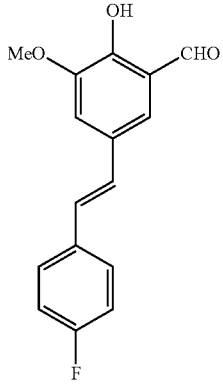 [SMILES: COc1cc(/C=C/c2ccc(F)cc2)cc(C=O)c1O] | (E)-5-(4-fluorostyryl)-2-hydroxy-3-methoxybenzaldehyde |
| 8 | 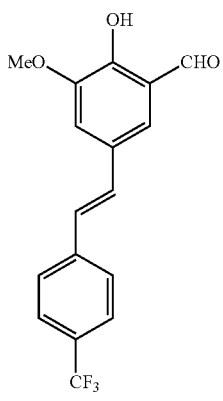 [SMILES: COc1cc(/C=C/c2ccc(C(F)(F)F)cc2)cc(C=O)c1O] | (E)-2-hydroxy-3-methoxy-5-(4-(trifluoromethyl)styryl)benzaldehyde |
| 9 | 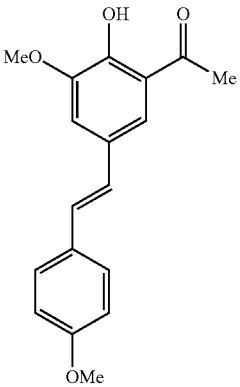 [SMILES: COc1ccc(/C=C/c2cc(OC)c(O)c(C(C)=O)c2)cc1] | (E)-1-(2-hydroxy-3-methoxy-5-(4-methoxystyryl)phenyl)ethan-1-one |
| 10 | 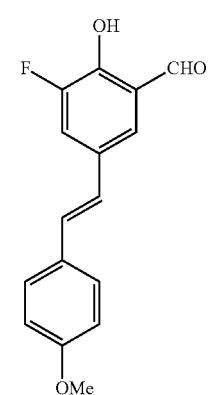 [SMILES: COc1ccc(/C=C/c2cc(F)c(O)c(C=O)c2)cc1] | (E)-3-fluoro-2-hydroxy-5-(4-methoxystyryl)benzaldehyde |

TABLE 1-continued

| Cmpd # | Chemical Structure | Chemical Name |
|---|---|---|
| 11 | 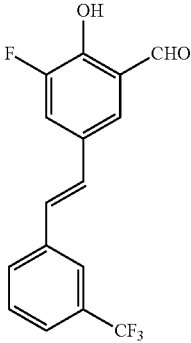 [SMILES: O=Cc1cc(/C=C/c2cccc(C(F)(F)F)c2)cc(F)c1O] | (E)-3-fluoro-2-hydroxy-5-(3-(trifluoromethyl)styryl)benzaldehyde |
| 12 | 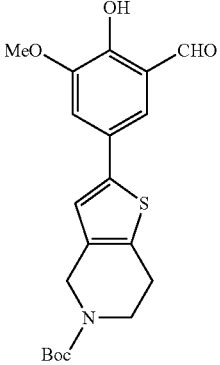 [SMILES: COc1cc(-c2cc3c(s2)CCN(C(=O)OC(C)(C)C)C3)cc(C=O)c1O] | tert-butyl 2-(3-formyl-4-hydroxy-5-methoxyphenyl)-6,7-dihydrothieno[3,2-c]pyridine-5(4H)-carboxylate |
| 13 | 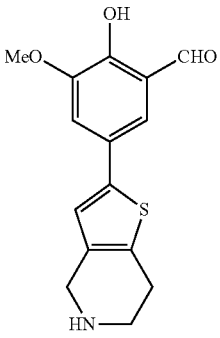 [SMILES: COc1cc(-c2cc3c(s2)CCNC3)cc(C=O)c1O] | 2-hydroxy-3-methoxy-5-(4,5,6,7-tetrahydrothieno[3,2-c]pyridin-2-yl)benzaldehyde hydrochloride |
| 14 | 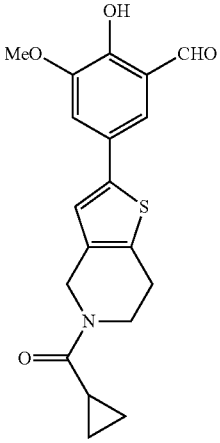 [SMILES: COc1cc(-c2cc3c(s2)CCN(C(=O)C2CC2)C3)cc(C=O)c1O] | 5-(5-(cyclopropanecarbonyl)-4,5,6,7-tetrahydrothieno[3,2-c]pyridin-2-yl)-2-hydroxy-3-methoxybenzaldehyde |

TABLE 1-continued
| Cmpd # | Chemical Structure | Chemical Name |
|---|---|---|
| 15 | 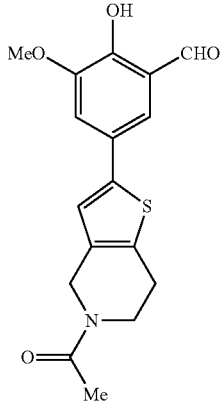 | 5-(5-acetyl-4,5,6,7-tetrahydrothieno[3,2-c]pyridin-2-yl)-2-hydroxy-3-methoxybenzaldehyde |
| 16 | 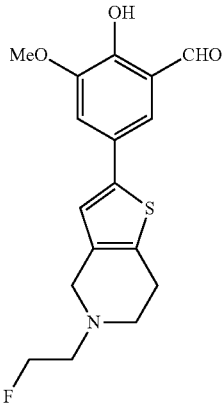 [SMILES: COc1cc(-c2cc3c(s2)CCN(CCF)C3)cc(C=O)c1O] | 5-(5-(2-fluoroethyl)-4,5,6,7-tetrahydrothieno[3,2-c]pyridin-2-yl)-2-hydroxy-3-methoxybenzaldehyde |
| 17 | 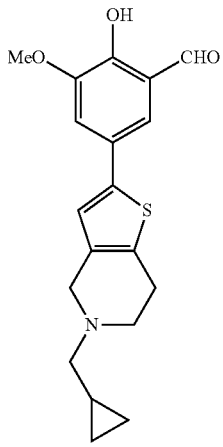 [SMILES: COc1cc(-c2cc3c(s2)CCN(CC2CC2)C3)cc(C=O)c1O] | 5-(5-(cyclopropylmethyl)-4,5,6,7-tetrahydrothieno[3,2-c]pyridin-2-yl)-2-hydroxy-3-methoxybenzaldehyde |

TABLE 1-continued
| Cmpd # | Chemical Structure | Chemical Name |
|---|---|---|
| 18 | 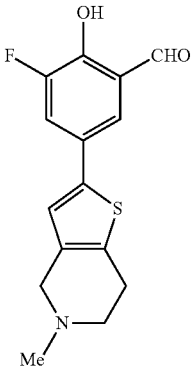 [SMILES: CN1CCc2sc(-c3cc(F)c(O)c(C=O)c3)cc2C1] | 3-fluoro-2-hydroxy-5-(5-methyl-4,5,6,7-tetrahydrothieno[3,2-c]pyridin-2-yl)benzaldehyde |
| 19 | 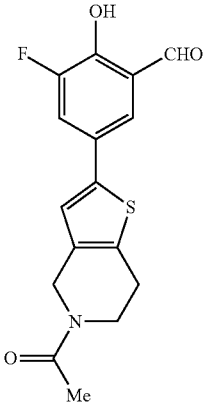 [SMILES: CC(=O)N1CCc2sc(-c3cc(F)c(O)c(C=O)c3)cc2C1] | 5-(5-acetyl-4,5,6,7-tetrahydrothieno[3,2-c]pyridin-2-yl)-3-fluoro-2-hydroxybenzaldehyde |
| 20 | 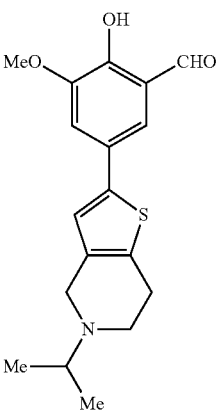 | 2-hydroxy-5-(5-isopropyl-4,5,6,7-tetrahydrothieno[3,2-c]pyridin-2-yl)-3-methoxybenzaldehyde |
| 21 | 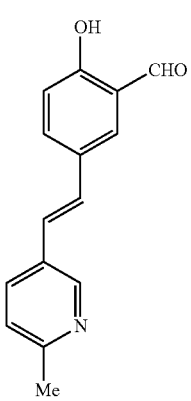 [SMILES: Cc1ccc(/C=C/c2ccc(O)c(C=O)c2)cn1] | (E)-2-hydroxy-5-(2-(6-methylpyridin-3-yl)vinyl)benzaldehyde |

TABLE 1-continued

| Cmpd # | Chemical Structure | Chemical Name |
|---|---|---|
| 22 | 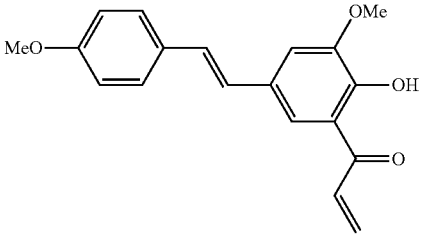 [SMILES: C=CC(=O)c1cc(/C=C/c2ccc(OC)cc2)cc(OC)c1O] | (E)-1-(2-hydroxy-3-methoxy-5-(4-methoxystyryl)phenyl)prop-2-en-1-one |
| 23 | 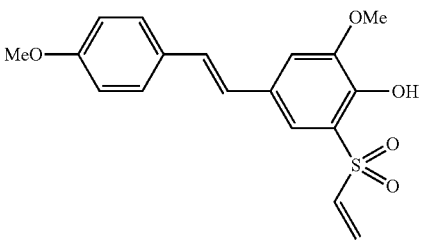 [SMILES: C=CS(=O)(=O)c1cc(/C=C/c2ccc(OC)cc2)cc(OC)c1O] | (E)-2-methoxy-4-(4-methoxystyryl)-6-(vinylsulfonyl)phenol |
| 24 | 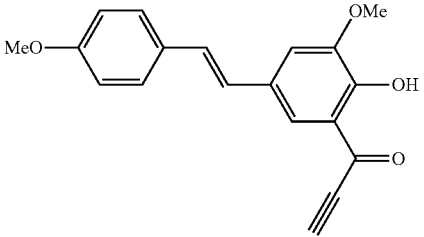 [SMILES: C#CC(=O)c1cc(/C=C/c2ccc(OC)cc2)cc(OC)c1O] | (E)-1-(2-hydroxy-3-methoxy-5-(4-methoxystyryl)phenyl)prop-2-yn-1-one |
| 25 | 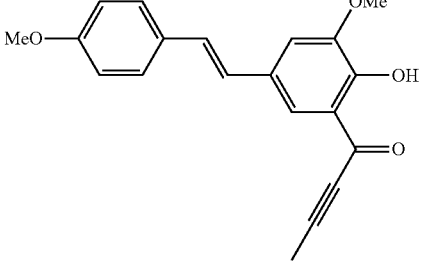 | (E)-1-(2-hydroxy-3-methoxy-5-(4-methoxystyryl)phenyl)but-2-yn-1-one |
| 26 | 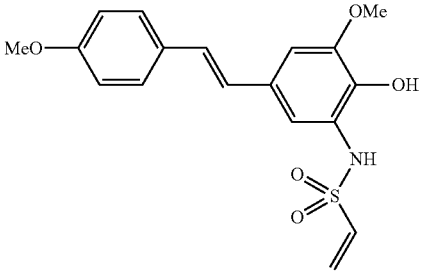 [SMILES: C=CS(=O)(=O)Nc1cc(/C=C/c2ccc(OC)cc2)cc(OC)c1O] | (E)-N-(2-hydroxy-3-methoxy-5-(4-methoxystyryl)phenyl)ethenesulfonamide |
| 27 | 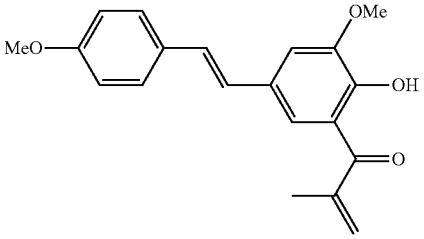 [SMILES: C=C(C)C(=O)c1cc(/C=C/c2ccc(OC)cc2)cc(OC)c1O] | (E)-1-(2-hydroxy-3-methoxy-5-(4-methoxystyryl)phenyl)-2-methylprop-2-en-1-one |

TABLE 1-continued

| Cmpd # | Chemical Structure | Chemical Name |
| --- | --- | --- |
| 28 | 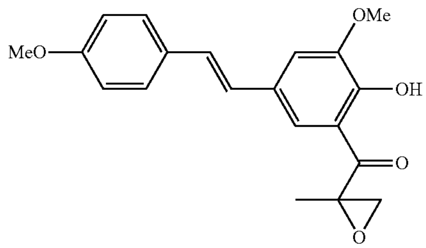 [SMILES: COc1ccc(/C=C/c2cc(OC)c(O)c(C(=O)C3(C)CO3)c2)cc1] | (E)-(2-hydroxy-3-methoxy-5-(4-methoxystyryl)phenyl)(2-methyloxiran-2-yl)methanone |
| 29 | 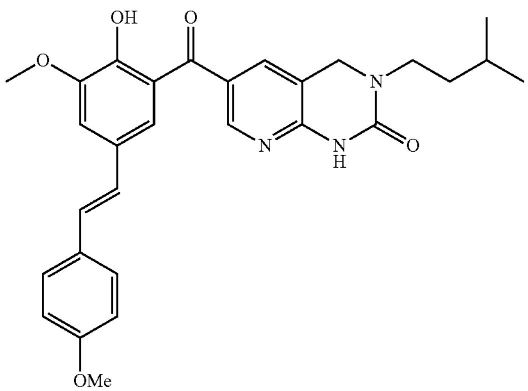 [SMILES: COc1ccc(/C=C/c2cc(OC)c(O)c(C(=O)c3cnc4c(c3)CN(CCC(C)C)C(=O)N4)c2)cc1] | (E)-6-(2-hydroxy-3-methoxy-5-(4-methoxystyryl)benzoyl)-3-isopentyl-3,4-dihydropyrido[2,3-d]pyrimidin-2(1H)-one |
| 30 | 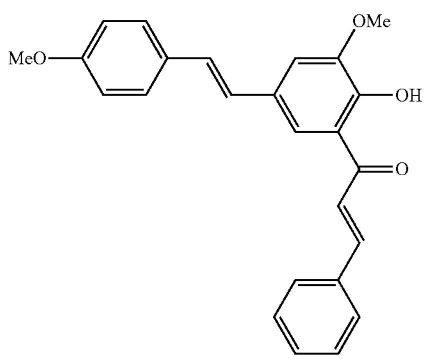 [SMILES: COc1ccc(/C=C/c2cc(OC)c(O)c(C(=O)/C=C/c3ccccc3)c2)cc1] | (E)-1-(2-hydroxy-3-methoxy-5-((E)-4-methoxystyryl)phenyl)-3-phenylprop-2-en-1-one |
| 31 | 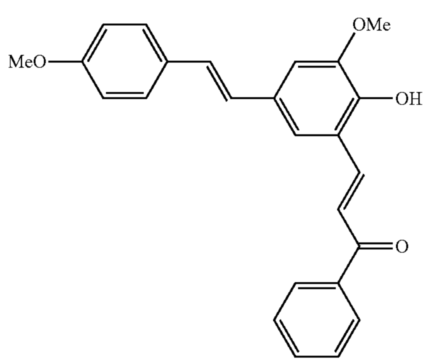 [SMILES: COc1ccc(/C=C/c2cc(/C=C/C(=O)c3ccccc3)c(O)c(OC)c2)cc1] | (E)-3-(2-hydroxy-3-methoxy-5-((E)-4-methoxystyryl)phenyl)-1-phenylprop-2-en-1-one |

TABLE 1-continued

| Cmpd # | Chemical Structure | Chemical Name |
| --- | --- | --- |
| 32 | 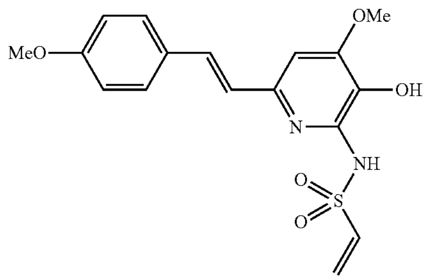 [SMILES: C=CS(=O)(=O)Nc1nc(/C=C/c2ccc(OC)cc2)cc(OC)c1O] | (E)-N-(3-hydroxy-4-methoxy-6-(4-methoxystyryl)pyridin-2-yl)ethenesulfonamide |
| 33 | 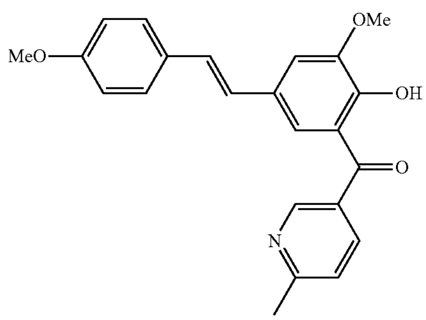 [SMILES: COc1ccc(/C=C/c2cc(OC)c(O)c(C(=O)c3ccc(C)nc3)c2)cc1] | (E)-(2-hydroxy-3-methoxy-5-(4-methoxystyryl)phenyl)(6-methylpyridin-3-yl)methanone |
| 34 | 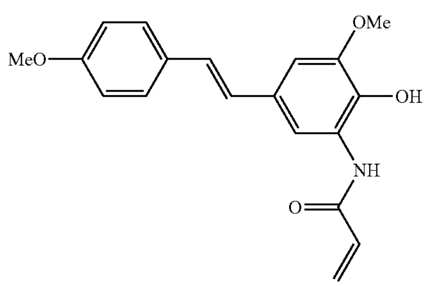 [SMILES: C=CC(=O)Nc1cc(/C=C/c2ccc(OC)cc2)cc(OC)c1O] | (E)-N-(2-hydroxy-3-methoxy-5-(4-methoxystyryl)phenyl)acrylamide |
| 35 | 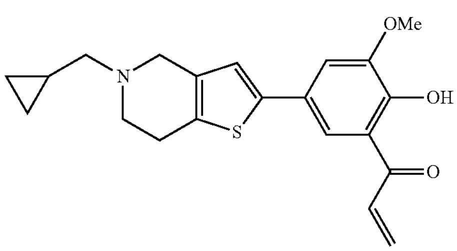 [SMILES: C=CC(=O)c1cc(-c2cc3c(s2)CCN(CC2CC2)C3)cc(OC)c1O] | 1-(5-(5-(cyclopropylmethyl)-4,5,6,7-tetrahydrothieno[3,2-c]pyridin-2-yl)-2-hydroxy-3-methoxyphenyl)prop-2-en-1-one |
| 36 | 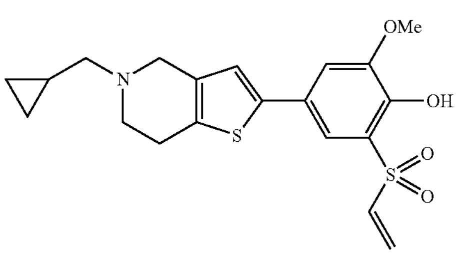 [SMILES: C=CS(=O)(=O)c1cc(-c2cc3c(s2)CCN(CC2CC2)C3)cc(OC)c1O] | 4-(5-(cyclopropylmethyl)-4,5,6,7-tetrahydrothieno[3,2-c]pyridin-2-yl)-2-methoxy-6-(vinylsulfonyl)phenol |

TABLE 1-continued

| Cmpd # | Chemical Structure | Chemical Name |
|---|---|---|
| 37 | 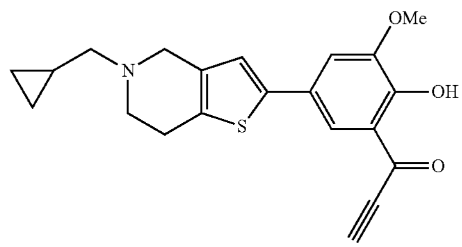 [SMILES: C#CC(=O)c1cc(-c2cc3c(s2)CCN(CC2CC2)C3)cc(OC)c1O] | 1-(5-(5-(cyclopropylmethyl)-4,5,6,7-tetrahydrothieno[3,2-c]pyridin-2-yl)-2-hydroxy-3-methoxyphenyl)prop-2-yn-1-one |
| 38 | 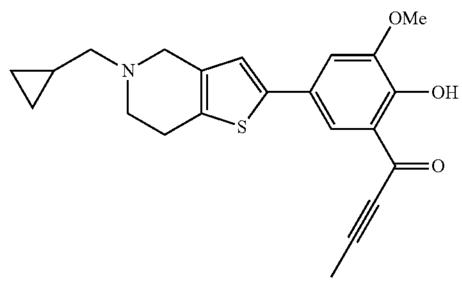 [SMILES: CC#CC(=O)c1cc(-c2cc3c(s2)CCN(CC2CC2)C3)cc(OC)c1O] | 1-(5-(5-(cyclopropylmethyl)-4,5,6,7-tetrahydrothieno[3,2-c]pyridin-2-yl)-2-hydroxy-3-methoxyphenyl)but-2-yn-1-one |
| 39 | 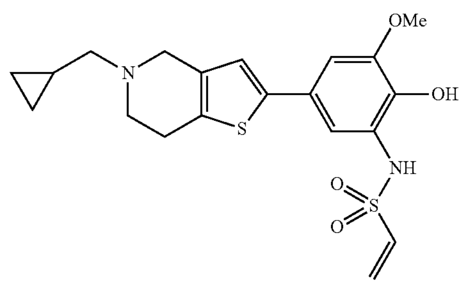 [SMILES: C=CS(=O)(=O)Nc1cc(-c2cc3c(s2)CCN(CC2CC2)C3)cc(OC)c1O] | N-(5-(5-(cyclopropylmethyl)-4,5,6,7-tetrahydrothieno[3,2-c]pyridin-2-yl)-2-hydroxy-3-methoxyphenyl)ethenesulfonamide |
| 40 | 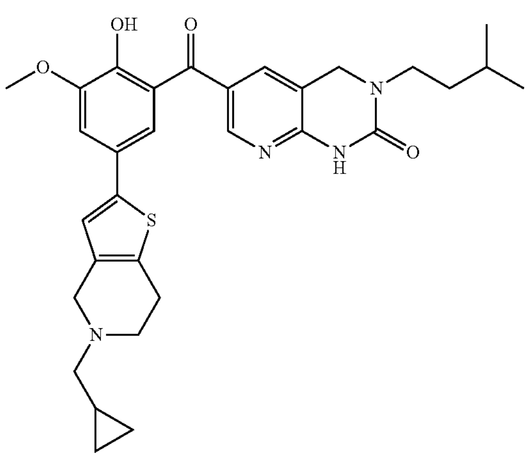 [SMILES: COc1cc(-c2cc3c(s2)CCN(CC2CC2)C3)cc(C(=O)c2cnc3c(c2)CN(CCC(C)C)C(=O)N3)c1O] | 6-(5-(5-(cyclopropylmethyl)-4,5,6,7-tetrahydrothieno[3,2-c]pyridin-2-yl)-2-hydroxy-3-methoxybenzoyl)-3-isopentyl-3,4-dihydropyrido[2,3-d]pyrimidin-2(1H)-one |
| 41 | 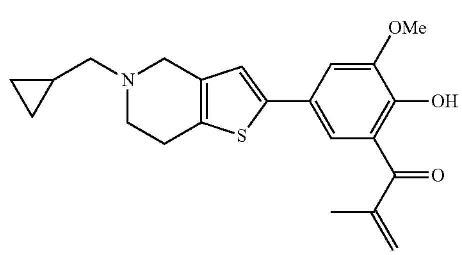 [SMILES: C=C(C)C(=O)c1cc(-c2cc3c(s2)CCN(CC2CC2)C3)cc(OC)c1O] | 1-(5-(5-(cyclopropylmethyl)-4,5,6,7-tetrahydrothieno[3,2-c]pyridin-2-yl)-2-hydroxy-3-methoxyphenyl)-2-methylprop-2-en-1-one |

TABLE 1-continued

| Cmpd # | Chemical Structure | Chemical Name |
| --- | --- | --- |
| 42 | 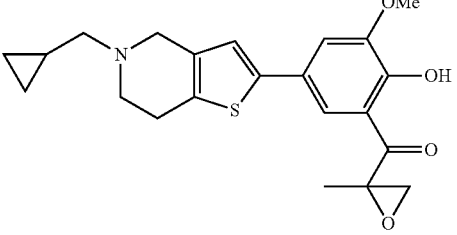 | (5-(5-(cyclopropylmethyl)-4,5,6,7-tetrahydrothieno[3,2-c]pyridin-2-yl)-2-hydroxy-3-methoxyphenyl)(2-methyloxiran-2-yl)methanone |
| 43 | 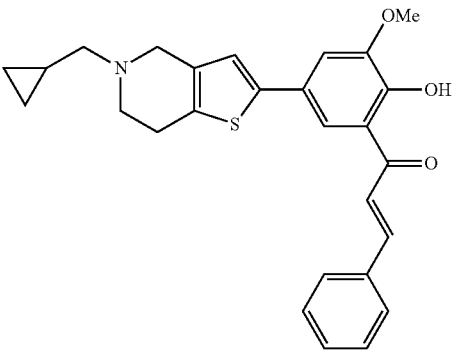 [SMILES: COc1cc(-c2cc3c(s2)CCN(CC2CC2)C3)cc(C(=O)/C=C/c2ccccc2)c1O] | (E)-1-(5-(5-(cyclopropylmethyl)-4,5,6,7-tetrahydrothieno[3,2-c]pyridin-2-yl)-2-hydroxy-3-methoxyphenyl)-3-phenylprop-2-en-1-one |
| 44 | 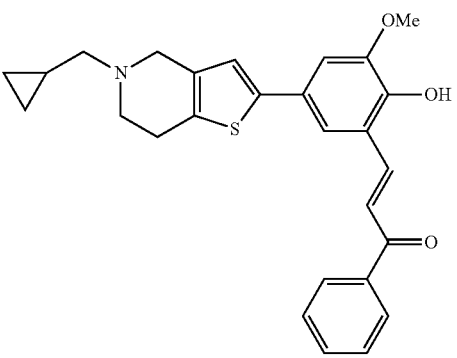 [SMILES: COc1cc(-c2cc3c(s2)CCN(CC2CC2)C3)cc(/C=C/C(=O)c2ccccc2)c1O] | (E)-3-(5-(5-(cyclopropylmethyl)-4,5,6,7-tetrahydrothieno[3,2-c]pyridin-2-yl)-2-hydroxy-3-methoxyphenyl)-1-phenylprop-2-en-1-one |
| 45 | 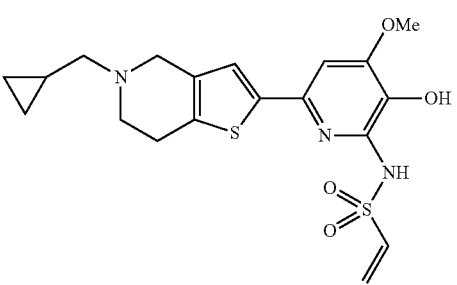 [SMILES: C=CS(=O)(=O)Nc1nc(-c2cc3c(s2)CCN(CC2CC2)C3)cc(OC)c1O] | N-(6-(5-(cyclopropylmethyl)-4,5,6,7-tetrahydrothieno[3,2-c]pyridin-2-yl)-3-hydroxy-4-methoxypyridin-2-yl)ethenesulfonamide |
| 46 | 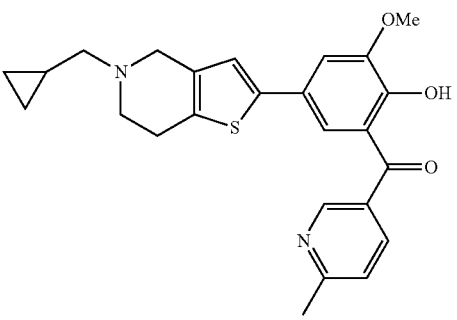 [SMILES: COc1cc(-c2cc3c(s2)CCN(CC2CC2)C3)cc(C(=O)c2ccc(C)nc2)c1O] | (5-(5-(cyclopropylmethyl)-4,5,6,7-tetrahydrothieno[3,2-c]pyridin-2-yl)-2-hydroxy-3-methoxyphenyl)(6-methylpyridin-3-yl)methanone |

TABLE 1-continued

| Cmpd # | Chemical Structure | Chemical Name |
|---|---|---|
| 47 | 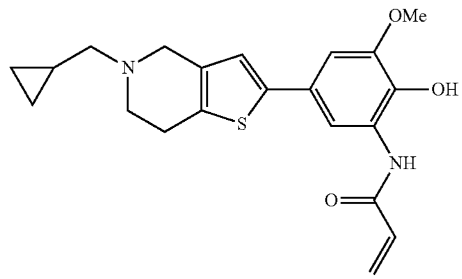 [SMILES: C=CC(=O)Nc1cc(-c2cc3c(s2)CCN(CC2CC2)C3)cc(OC)c1O] | N-(5-(5-(cyclopropylmethyl)-4,5,6,7-tetrahydrothieno[3,2-c]pyridin-2-yl)-2-hydroxy-3-methoxyphenyl)acrylamide |
| 48 | 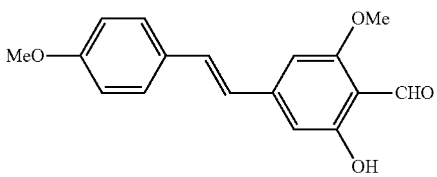 [SMILES: COc1ccc(/C=C/c2cc(O)c(C=O)c(OC)c2)cc1] | (E)-2-hydroxy-6-methoxy-4-(4-methoxystyryl)benzaldehyde |
| 49 | 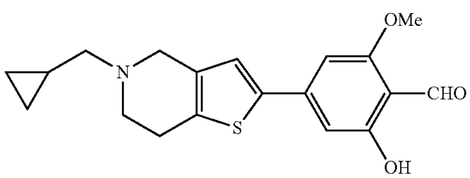 [SMILES: COc1cc(-c2cc3c(s2)CCN(CC2CC2)C3)cc(O)c1C=O] | 4-(5-(cyclopropylmethyl)-4,5,6,7-tetrahydrothieno[3,2-c]pyridin-2-yl)-2-hydroxy-6-methoxybenzaldehyde |
| 50 | 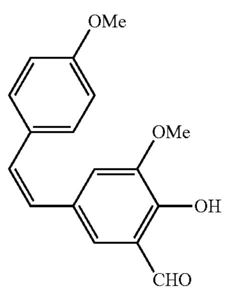 [SMILES: COc1ccc(/C=C\c2cc(C=O)c(O)c(OC)c2)cc1] | (Z)-2-hydroxy-3-methoxy-5-(4-methoxystyryl)benzaldehyde |
| 51 | 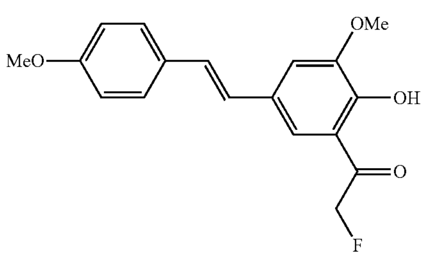 [SMILES: COc1ccc(/C=C/c2cc(OC)c(O)c(C(=O)CF)c2)cc1] | (E)-2-fluoro-1-(2-hydroxy-3-methoxy-5-(4-methoxystyryl)phenyl)ethan-1-one |
| 52 | 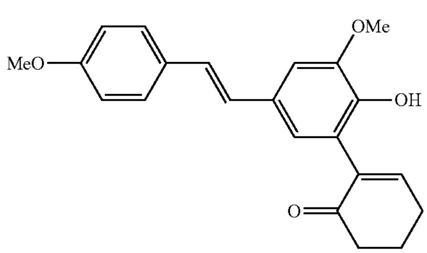 [SMILES: COc1ccc(/C=C/c2cc(OC)c(O)c(C3=CCCCC3=O)c2)cc1] | (E)-2'-hydroxy-3'-methoxy-5'-(4-methoxystyryl)-4,5-dihydro-[1,1'-biphenyl]-2(3H)-one |

TABLE 1-continued

| Cmpd # | Chemical Structure | Chemical Name |
| --- | --- | --- |
| 53 | 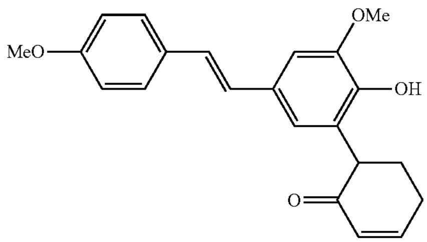 [SMILES: COc1ccc(/C=C/c2cc(OC)c(O)c(C3CCC=CC3=O)c2)cc1] | (E)-2'-hydroxy-3'-methoxy-5'-(4-methoxystyryl)-5,6-dihydro-[1,1'-biphenyl]-2(1H)-one |
| 54 | 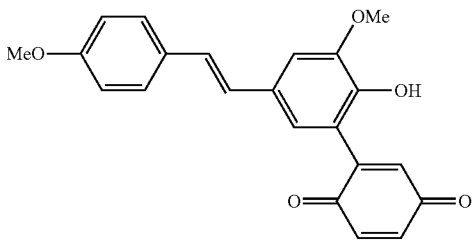 [SMILES: COc1ccc(/C=C/c2cc(OC)c(O)c(C3=CC(=O)C=CC3=O)c2)cc1] | (E)-2'-hydroxy-3'-methoxy-5'-(4-methoxystyryl)-[1,1'-biphenyl]-2,5-dione |
| 55 | 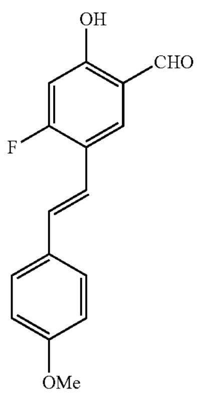 [SMILES: COc1ccc(/C=C/c2cc(C=O)c(O)cc2F)cc1] | (E)-4-fluoro-2-hydroxy-5-(4-methoxystyryl)benzaldehyde |
| 56 | 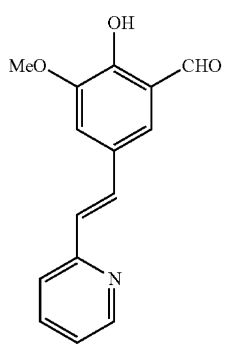 [SMILES: COc1cc(/C=C/c2ccccn2)cc(C=O)c1O] | (E)-2-hydroxy-3-methoxy-5-(2-(pyridin-2-yl)vinyl)benzaldehyde |
| 57 | 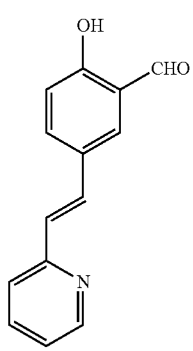 [SMILES: O=Cc1cc(/C=C/c2ccccn2)ccc1O] | (E)-2-hydroxy-5-(2-(pyridin-2-yl)vinyl)benzaldehyde |

TABLE 1-continued

| Cmpd # | Chemical Structure | Chemical Name |
| --- | --- | --- |
| 58 | 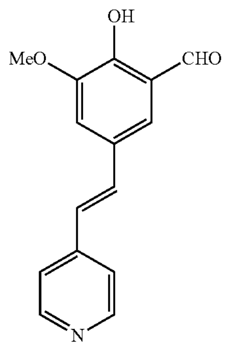 [SMILES: COc1cc(/C=C/c2ccncc2)cc(C=O)c1O] | (E)-2-hydroxy-3-methoxy-5-(2-(pyridin-4-yl)vinyl)benzaldehyde |
| 59 | 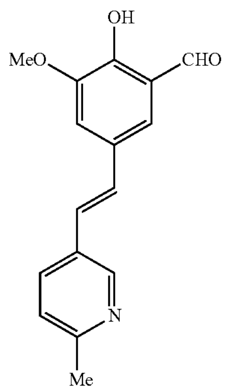 [SMILES: COc1cc(/C=C/c2ccc(C)nc2)cc(C=O)c1O] | (E)-2-hydroxy-3-methoxy-5-(2-(6-methylpyridin-3-yl)vinyl)benzaldehyde |
| 60 | 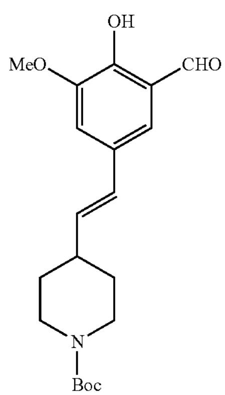 [SMILES: COc1cc(/C=C/C2CCN(C(=O)OC(C)(C)C)CC2)cc(C=O)c1O] | tert-butyl (E)-4-(3-formyl-4-hydroxy-5-methoxystyryl)piperidine-1-carboxylate |
| 61 | 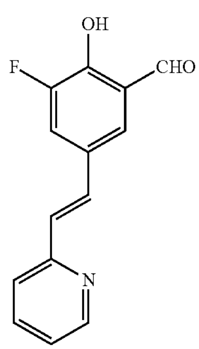 [SMILES: O=Cc1cc(/C=C/c2ccccn2)cc(F)c1O] | (E)-3-fluoro-2-hydroxy-5-(2-(pyridin-2-yl)vinyl)benzaldehyde |

TABLE 1-continued
| Cmpd # | Chemical Structure | Chemical Name |
|---|---|---|
| 62 | 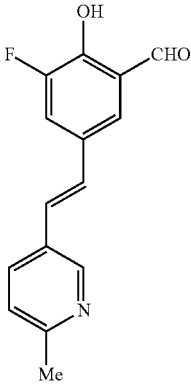 [SMILES: Cc1ccc(/C=C/c2cc(F)c(O)c(C=O)c2)cn1] | (E)-3-fluoro-2-hydroxy-5-(2-(6-methylpyridin-3-yl)vinyl)benzaldehyde |
| 63 | 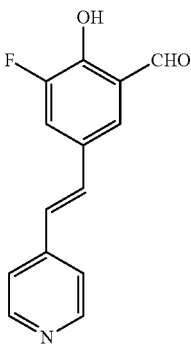 [SMILES: O=Cc1cc(/C=C/c2ccncc2)cc(F)c1O] | (E)-3-fluoro-2-hydroxy-5-(2-(pyridin-4-yl)vinyl)benzaldehyde |
| 64 | 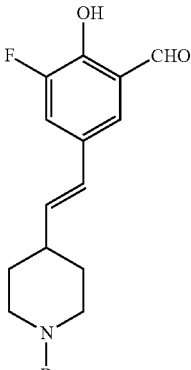 | tert-butyl (E)-4-(3-fluoro-5-formyl-4-hydroxystyryl)piperidine-1-carboxylate |
| 65 | 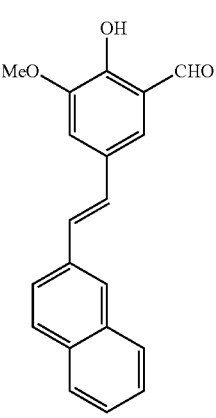 [SMILES: COc1cc(/C=C/c2ccc3ccccc3c2)cc(C=O)c1O] | (E)-2-hydroxy-3-methoxy-5-(2-(naphthalen-2-yl)vinyl)benzaldehyde |

TABLE 1-continued
| Cmpd # | Chemical Structure | Chemical Name |
|---|---|---|
| 66 | 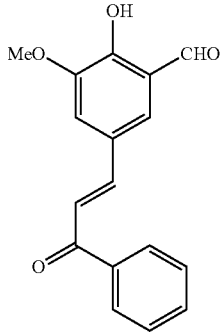 [SMILES: COc1cc(/C=C/C(=O)c2ccccc2)cc(C=O)c1O] | (E)-2-hydroxy-3-methoxy-5-(3-oxo-3-phenylprop-1-en-1-yl)benzaldehyde |
| 67 | 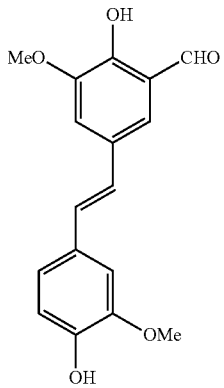 [SMILES: COc1cc(/C=C/c2cc(C=O)c(O)c(OC)c2)ccc1O] | (E)-2-hydroxy-5-(4-hydroxy-3-methoxystyryl)-3-methoxybenzaldehyde |
| 68 | 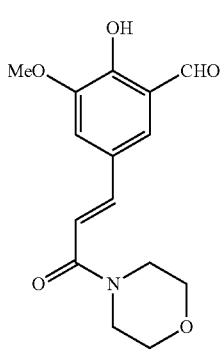 [SMILES: COc1cc(/C=C/C(=O)N2CCOCC2)cc(C=O)c1O] | (E)-2-hydroxy-3-methoxy-5-(3-morpholino-3-oxoprop-1-en-1-yl)benzaldehyde |
| 69 | 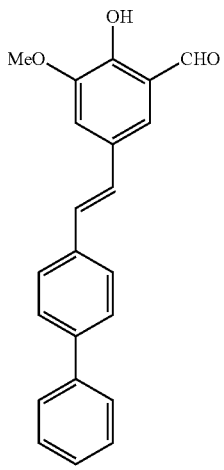 [SMILES: COc1cc(/C=C/c2ccc(-c3ccccc3)cc2)cc(C=O)c1O] | (E)-5-(2-([1,1'-biphenyl]-4-yl)vinyl)-2-hydroxy-3-methoxybenzaldehyde |

TABLE 1-continued
| Cmpd # | Chemical Structure | Chemical Name |
| --- | --- | --- |
| 70 | 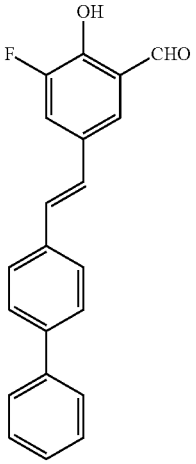 [SMILES: O=Cc1cc(/C=C/c2ccc(-c3ccccc3)cc2)cc(F)c1O] | (E)-5-(2-([1,1'-biphenyl]-4-yl)vinyl)-3-fluoro-2-hydroxybenzaldehyde |
| 71 | 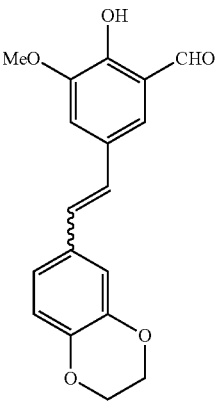 [SMILES: COc1cc(C=Cc2ccc3c(c2)OCCO3)cc(C=O)c1O] | 5-(2-(2,3-dihydrobenzo[b][1,4]dioxin-6-yl)vinyl)-2-hydroxy-3-methoxybenzaldehyde |
| 72 | 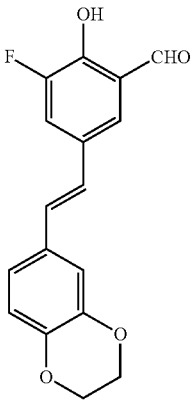 | (E)-5-(2-(2,3-dihydrobenzo[b][1,4]dioxin-6-yl)vinyl)-3-fluoro-2-hydroxybenzaldehyde |

TABLE 1-continued
| Cmpd # | Chemical Structure | Chemical Name |
| --- | --- | --- |
| 73 | 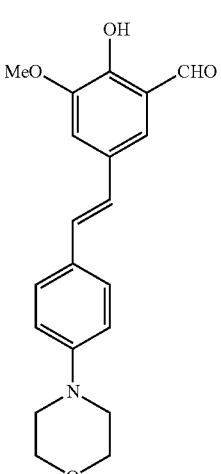 | (E)-2-hydroxy-3-methoxy-5-(4-morpholinostyryl)benzaldehyde |
| 74 | 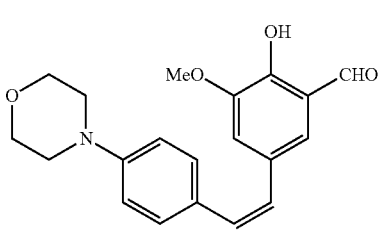 [SMILES: COc1cc(/C=C\c2ccc(N3CCOCC3)cc2)cc(C=O)c1O] | (Z)-2-hydroxy-3-methoxy-5-(4-morpholinostyryl)benzaldehyde |
| 75 | 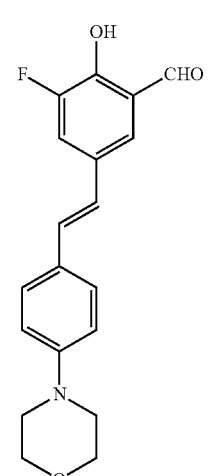 | (E)-3-fluoro-2-hydroxy-5-(4-morpholinostyryl)benzaldehyde |
| 76 | 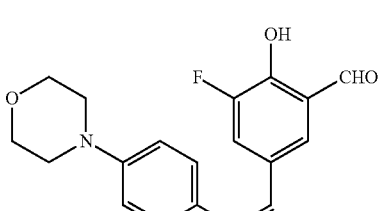 | (Z)-3-fluoro-2-hydroxy-5-(4-morpholinostyryl)benzaldehyde |

TABLE 1-continued
| Cmpd # | Chemical Structure | Chemical Name |
|---|---|---|
| 77 | 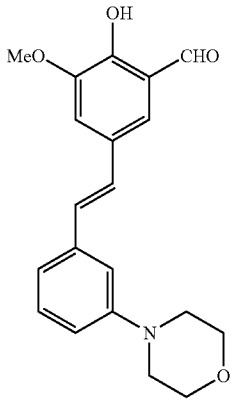 [SMILES: COc1cc(/C=C/c2cccc(N3CCOCC3)c2)cc(C=O)c1O] | (E)-2-hydroxy-3-methoxy-5-(3-morpholinostyryl)benzaldehyde |
| 78 | 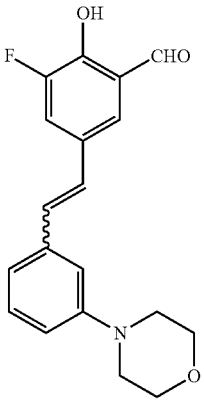 [SMILES: O=Cc1cc(C=Cc2cccc(N3CCOCC3)c2)cc(F)c1O] | (E)-3-fluoro-2-hydroxy-5-(3-morpholinostyryl)benzaldehyde |
| 79 | 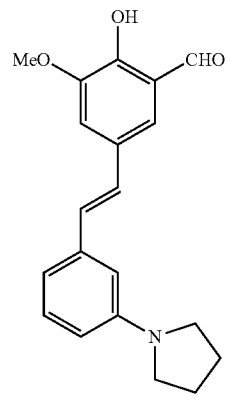 [SMILES: COc1cc(/C=C/c2cccc(N3CCCC3)c2)cc(C=O)c1O] | (E)-2-hydroxy-3-methoxy-5-(3-(pyrrolidin-1-yl)styryl)benzaldehyde |
| 80 | 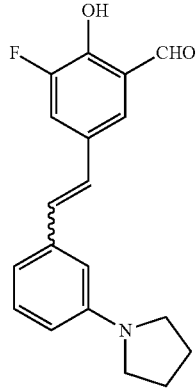 [SMILES: O=Cc1cc(C=Cc2cccc(N3CCCC3)c2)cc(F)c1O] | (E)-3-fluoro-2-hydroxy-5-(3-(pyrrolidin-1-yl)styryl)benzaldehyde |

TABLE 1-continued
| Cmpd # | Chemical Structure | Chemical Name |
| --- | --- | --- |
| 81 | 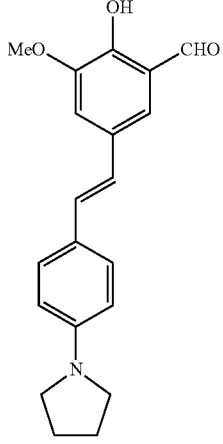 | (E)-2-hydroxy-3-methoxy-5-(4-(pyrrolidin-1-yl)styryl)benzaldehyde |
| 82 | 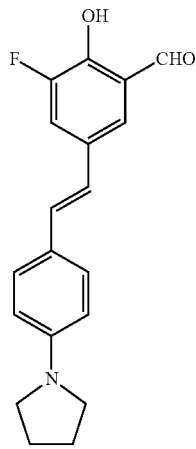 [SMILES: O=Cc1cc(/C=C/c2ccc(N3CCCC3)cc2)cc(F)c1O] | (E)-3-fluoro-2-hydroxy-5-(4-(pyrrolidin-1-yl)styryl)benzaldehyde |
| 83 | 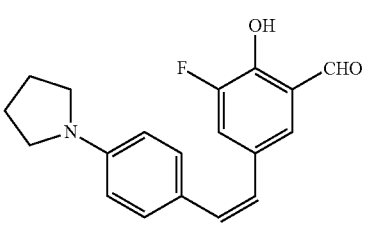 [SMILES: O=Cc1cc(/C=C\c2ccc(N3CCCC3)cc2)cc(F)c1O] | (Z)-3-fluoro-2-hydroxy-5-(4-(pyrrolidin-1-yl)styryl)benzaldehyde |
| 84 | 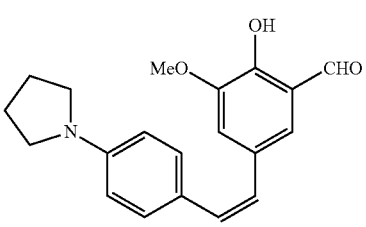 [SMILES: COc1cc(/C=C\c2ccc(N3CCCC3)cc2)cc(C=O)c1O] | (Z)-2-hydroxy-3-methoxy-5-(4-(pyrrolidin-1-yl)styryl)benzaldehyde |

TABLE 1-continued
| Cmpd # | Chemical Structure | Chemical Name |
| --- | --- | --- |
| 85 | 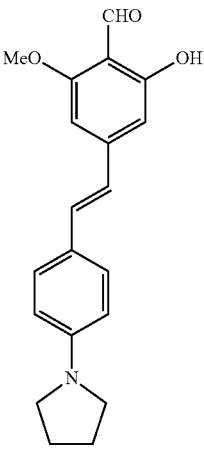 [SMILES: COc1cc(/C=C/c2ccc(N3CCCC3)cc2)cc(O)c1C=O] | (E)-2-hydroxy-6-methoxy-4-(4-(pyrrolidin-1-yl)styryl)benzaldehyde |
| 86 | 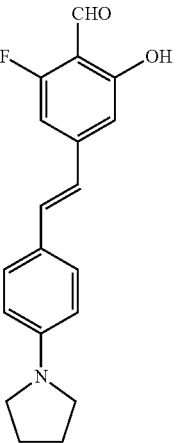 [SMILES: O=Cc1c(O)cc(/C=C/c2ccc(N3CCCC3)cc2)cc1F] | (E)-2-fluoro-6-hydroxy-4-(4-(pyrrolidin-1-yl)styryl)benzaldehyde |
| 87 | 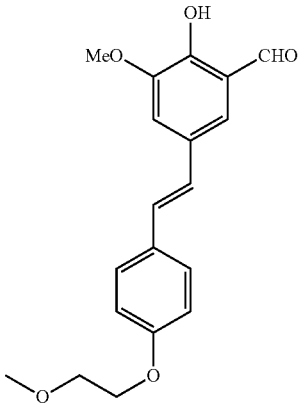 [SMILES: COCCOc1ccc(/C=C/c2cc(C=O)c(O)c(OC)c2)cc1] | (E)-2-hydroxy-3-methoxy-5-(4-(2-methoxyethoxy)styryl)benzaldehyde |

TABLE 1-continued

| Cmpd # | Chemical Structure | Chemical Name |
| --- | --- | --- |
| 88 | 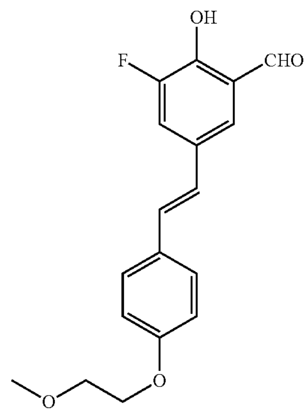 [SMILES: COCCOc1ccc(/C=C/c2cc(F)c(O)c(C=O)c2)cc1] | (E)-3-fluoro-2-hydroxy-5-(4-(2-methoxyethoxy)styryl)benzaldehyde |
| 89 | 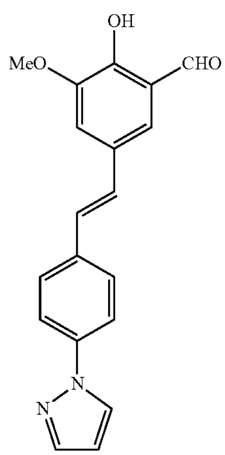 [SMILES: COc1cc(/C=C/c2ccc(-n3cccn3)cc2)cc(C=O)c1O] | (E)-5-(4-(1H-pyrazol-1-yl)styryl)-2-hydroxy-3-methoxybenzaldehyde |
| 90 | 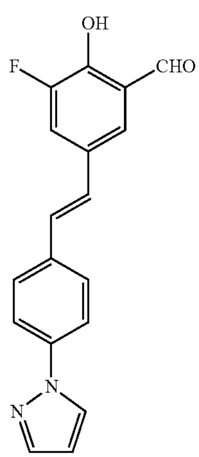 [SMILES: O=Cc1cc(/C=C/c2ccc(-n3cccn3)cc2)cc(F)c1O] | (E)-5-(4-(1H-pyrazol-1-yl)styryl)-3-fluoro-2-hydroxybenzaldehyde |

TABLE 1-continued
| Cmpd # | Chemical Structure | Chemical Name |
|---|---|---|
| 91 | 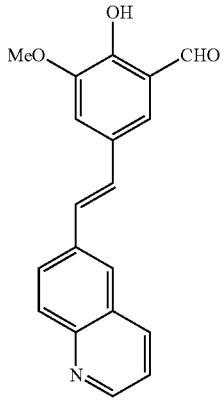 | (E)-2-hydroxy-3-methoxy-5-(2-(quinolin-6-yl)vinyl)benzaldehyde |
| 92 | 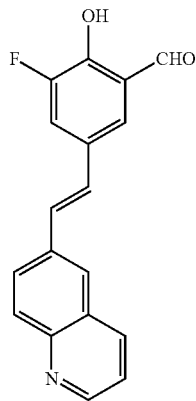 [SMILES: O=Cc1cc(/C=C/c2ccc3ncccc3c2)cc(F)c1O] | (E)-3-fluoro-2-hydroxy-5-(2-(quinolin-6-yl)vinyl)benzaldehyde |
| 93 | 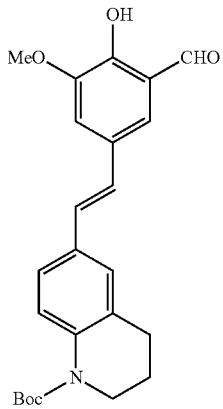 [SMILES: COc1cc(/C=C/c2ccc3c(c2)CCCN3C(=O)OC(C)(C)C)cc(C=O)c1O] | tert-butyl (E)-6-(3-formyl-4-hydroxy-5-methoxystyryl)-3,4-dihydroquinoline-1(2H)-carboxylate |

TABLE 1-continued
| Cmpd # | Chemical Structure | Chemical Name |
|---|---|---|
| 94 | 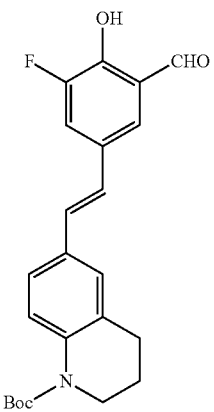 [SMILES: CC(C)(C)OC(=O)N1CCCc2cc(/C=C/c3cc(F)c(O)c(C=O)c3)ccc21] | tert-butyl (E)-6-(3-fluoro-5-formyl-4-hydroxystyryl)-3,4-dihydroquinoline-1(2H)-carboxylate |
| 95 | 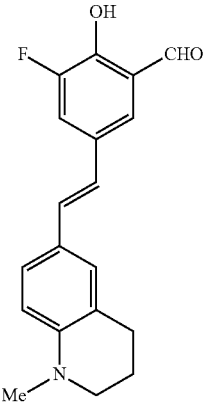 [SMILES: CN1CCCc2cc(/C=C/c3cc(F)c(O)c(C=O)c3)ccc21] | (E)-3-fluoro-2-hydroxy-5-(2-(1-methyl-1,2,3,4-tetrahydroquinolin-6-yl)vinyl)benzaldehyde |
| 96 | 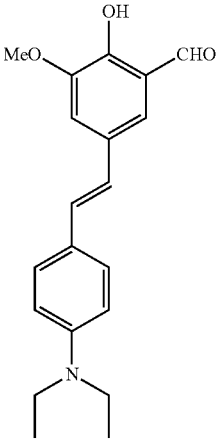 | (E)-5-(4-(diethylamino)styryl)-2-hydroxy-3-methoxybenzaldehyde |

TABLE 1-continued
| Cmpd # | Chemical Structure | Chemical Name |
| --- | --- | --- |
| 97 | 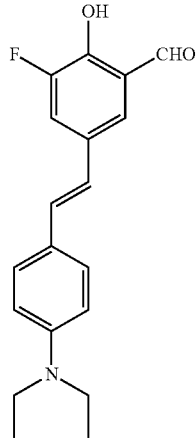 [SMILES: CCN(CC)c1ccc(/C=C/c2cc(F)c(O)c(C=O)c2)cc1] | (E)-5-(4-(diethylamino)styryl)-3-fluoro-2-hydroxybenzaldehyde |
| 98 | 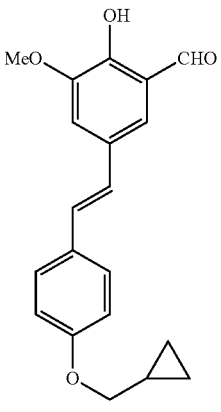 [SMILES: COc1cc(/C=C/c2ccc(OCC3CC3)cc2)cc(C=O)c1O] | (E)-5-(4-(cyclopropylmethoxy)styryl)-2-hydroxy-3-methoxybenzaldehyde |
| 99 | 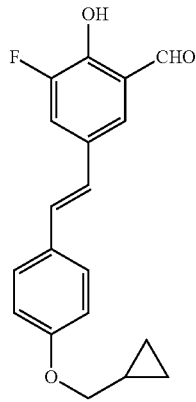 [SMILES: O=Cc1cc(/C=C/c2ccc(OCC3CC3)cc2)cc(F)c1O] | (E)-5-(4-(cyclopropylmethoxy)styryl)-3-fluoro-2-hydroxybenzaldehyde |

TABLE 1-continued
| Cmpd # | Chemical Structure | Chemical Name |
|---|---|---|
| 100 | 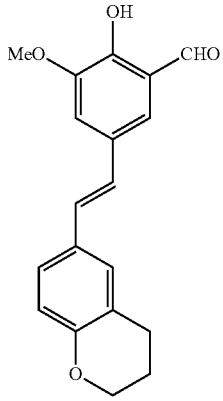 [SMILES: COc1cc(/C=C/c2ccc3c(c2)CCCO3)cc(C=O)c1O] | (E)-5-(2-(chroman-6-yl)vinyl)-2-hydroxy-3-methoxybenzaldehyde |
| 101 | 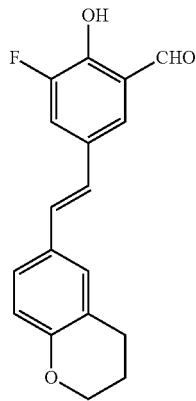 [SMILES: O=Cc1cc(/C=C/c2ccc3c(c2)CCCO3)cc(F)c1O] | (E)-5-(2-(chroman-6-yl)vinyl)-3-fluoro-2-hydroxybenzaldehyde |
| 102 | 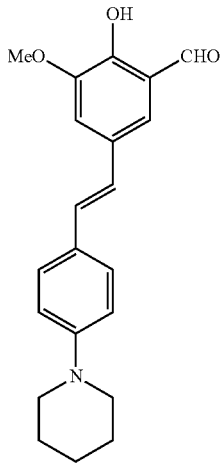 [SMILES: COc1cc(/C=C/c2ccc(N3CCCCC3)cc2)cc(C=O)c1O] | (E)-2-hydroxy-3-methoxy-5-(4-(piperidin-1-yl)styryl)benzaldehyde |

TABLE 1-continued
| Cmpd # | Chemical Structure | Chemical Name |
|---|---|---|
| 103 | 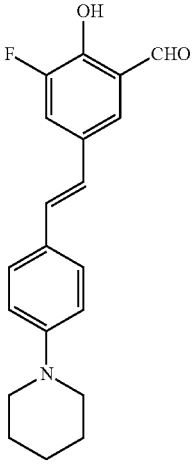 [SMILES: O=Cc1cc(/C=C/c2ccc(N3CCCCC3)cc2)cc(F)c1O] | (E)-3-fluoro-2-hydroxy-5-(4-(piperidin-1-yl)styryl)benzaldehyde |
| 104 | 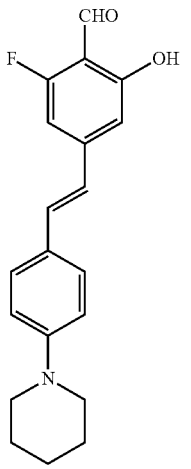 [SMILES: O=Cc1c(O)cc(/C=C/c2ccc(N3CCCCC3)cc2)cc1F] | (E)-2-fluoro-6-hydroxy-4-(4-(piperidin-1-yl)styryl)benzaldehyde |
| 105 | 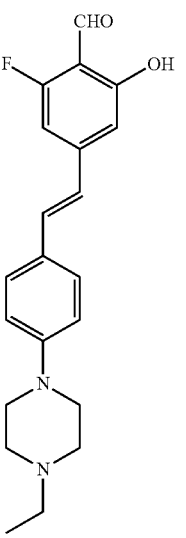 [SMILES: CCN1CCN(c2ccc(/C=C/c3cc(O)c(C=O)c(F)c3)cc2)CC1] | (E)-4-(4-(4-ethylpiperazin-1-yl)styryl)-2-fluoro-6-hydroxybenzaldehyde |

TABLE 1-continued
| Cmpd # | Chemical Structure | Chemical Name |
|---|---|---|
| 106 | 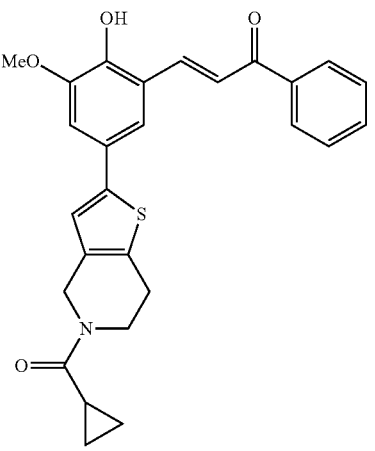 [SMILES: COc1cc(-c2cc3c(s2)CCN(C(=O)C2CC2)C3)cc(/C=C/C(=O)c2ccccc2)c1O] | (E)-3-(5-(5-(cyclopropanecarbonyl)-4,5,6,7-tetrahydrothieno[3,2-c]pyridin-2-yl)-2-hydroxy-3-methoxyphenyl)-1-phenylprop-2-en-1-one |
| 107 | 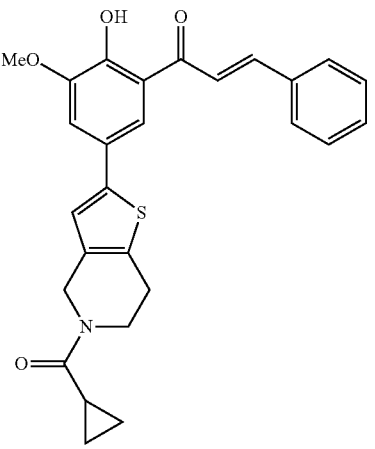 [SMILES: COc1cc(-c2cc3c(s2)CCN(C(=O)C2CC2)C3)cc(C(=O)/C=C/c2ccccc2)c1O] | (E)-1-(5-(5-(cyclopropanecarbonyl)-4,5,6,7-tetrahydrothieno[3,2-c]pyridin-2-yl)-2-hydroxy-3-methoxyphenyl)-3-phenylprop-2-en-1-one |
| 108 | 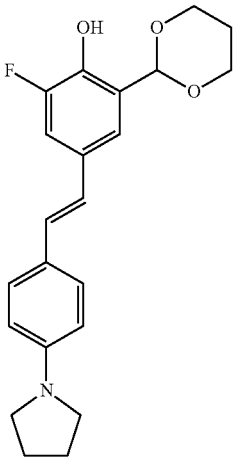 [SMILES: Oc1c(F)cc(/C=C/c2ccc(N3CCCC3)cc2)cc1C1OCCCO1] | (E)-2-(1,3-dioxan-2-yl)-6-fluoro-4-(4-(pyrrolidin-1-yl)styryl)phenol |

TABLE 1-continued
| Cmpd # | Chemical Structure | Chemical Name |
| --- | --- | --- |
| 109 | 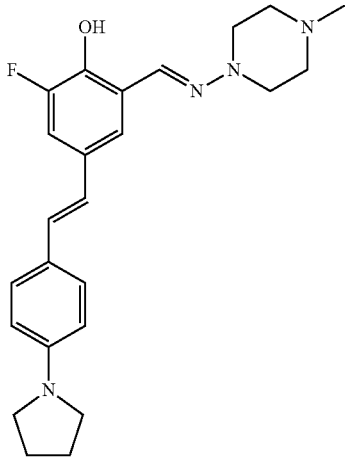 [SMILES: CN1CCN(/N=C/c2cc(/C=C/c3ccc(N4CCCC4)cc3)cc(F)c2O)CC1] | 2-fluoro-6-((E)-((4-methylpiperazin-1-yl)imino)methyl)-4-((E)-4-(pyrrolidin-1-yl)styryl)phenol |
| 110 | 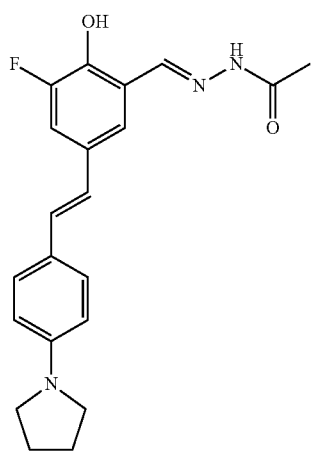 [SMILES: CC(=O)N/N=C/c1cc(/C=C/c2ccc(N3CCCC3)cc2)cc(F)c1O] | N'-((E)-3-fluoro-2-hydroxy-5-((E)-4-(pyrrolidin-1-yl)styryl)benzylidene)acetohydrazide |
| 111 | 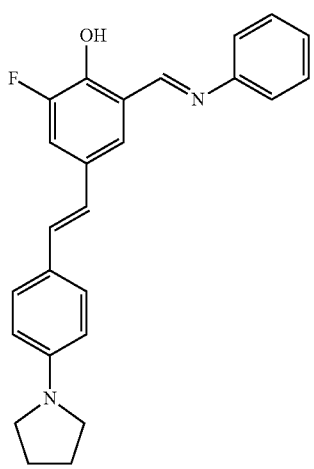 [SMILES: Oc1c(F)cc(/C=C/c2ccc(N3CCCC3)cc2)cc1/C=N/c1ccccc1] | 2-fluoro-6-((E)-(phenylimino)methyl)-4-((E)-4-(pyrrolidin-1-yl)styryl)phenol |

TABLE 1-continued
| Cmpd # | Chemical Structure | Chemical Name |
|---|---|---|
| 112 | 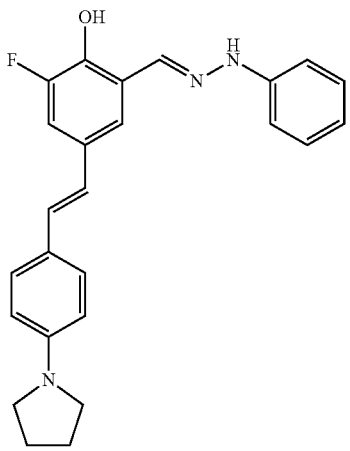 [SMILES: Oc1c(F)cc(/C=C/c2ccc(N3CCCC3)cc2)cc1/C=N/Nc1ccccc1] | 2-fluoro-6-((E)-(2-phenylhydrazono)methyl)-4-((E)-4-(pyrrolidin-1-yl)styryl)phenol |
| 113 | 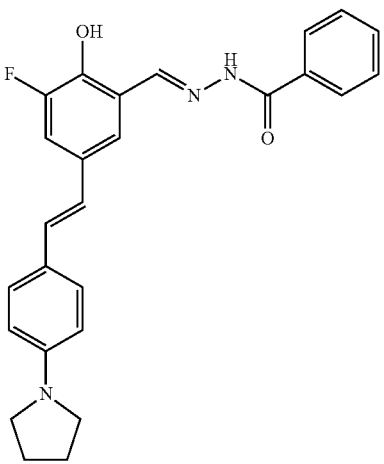 [SMILES: O=C(N/N=C/c1cc(/C=C/c2ccc(N3CCCC3)cc2)cc(F)c1O)c1ccccc1] | N'-((E)-3-fluoro-2-hydroxy-5-((E)-4-(pyrrolidin-1-yl)styryl)benzylidene)benzohydrazide |
| 114 | 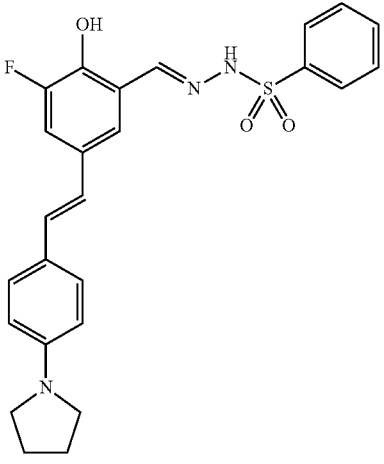 [SMILES: O=S(=O)(N/N=C/c1cc(/C=C/c2ccc(N3CCCC3)cc2)cc(F)c1O)c1ccccc1] | N'-((E)-3-fluoro-2-hydroxy-5-((E)-4-(pyrrolidin-1-yl)styryl)benzylidene)benzenesulfonohydrazide |

TABLE 1-continued
| Cmpd # | Chemical Structure | Chemical Name |
|---|---|---|
| 115 | 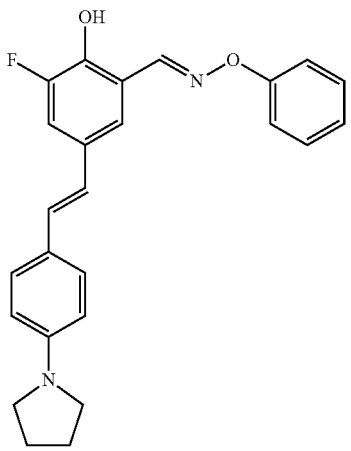 [SMILES: Oc1c(F)cc(/C=C/c2ccc(N3CCCC3)cc2)cc1/C=N/Oc1ccccc1] | (E)-3-fluoro-2-hydroxy-5-((E)-4-(pyrrolidin-1-yl)styryl)benzaldehyde O-phenyl oxime |
| 116 | 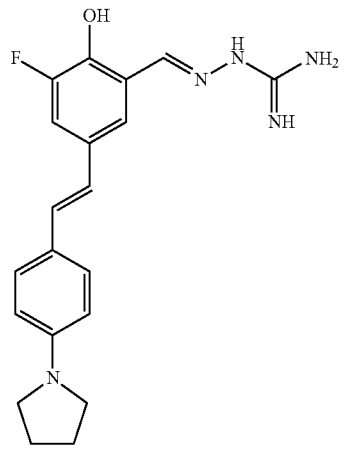 [SMILES: N=C(N)N/N=C/c1cc(/C=C/c2ccc(N3CCCC3)cc2)cc(F)c1O] | 2-((E)-3-fluoro-2-hydroxy-5-((E)-4-(pyrrolidin-1-yl)styryl)benzylidene)hydrazine-1-carboximidamide |
| 117 | 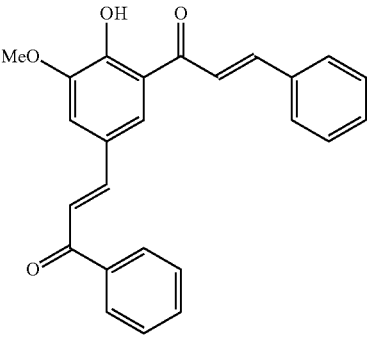 [SMILES: COc1cc(/C=C/C(=O)c2ccccc2)cc(C(=O)/C=C/c2ccccc2)c1O] | (E)-3-(3-cinnamoyl-4-hydroxy-5-methoxyphenyl)-1-phenylprop-2-en-1-one |

TABLE 1-continued

| Cmpd # | Chemical Structure | Chemical Name |
|---|---|---|
| 118 | 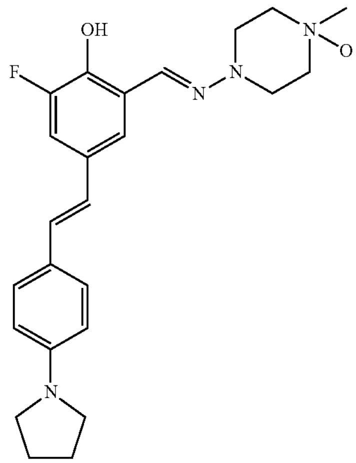 | 4-(((E)-3-fluoro-2-hydroxy-5-((E)-4-(pyrrolidin-1-yl)styryl)benzylidene)amino)-1-methylpiperazine 1-oxide |
| 119 | 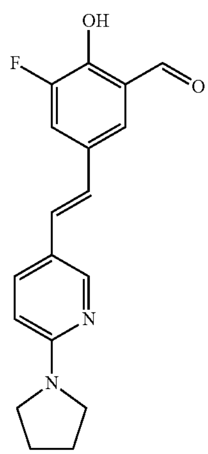 [SMILES: O=Cc1cc(/C=C/c2ccc(N3CCCC3)nc2)cc(F)c1O] | (E)-3-fluoro-2-hydroxy-5-(2-(6-(pyrrolidin-1-yl)pyridin-3-yl)vinyl)benzaldehyde |
| 120 | 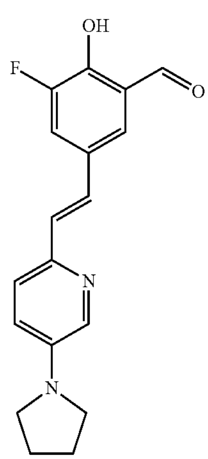 [SMILES: O=Cc1cc(/C=C/c2ccc(N3CCCC3)cn2)cc(F)c1O] | (E)-3-fluoro-2-hydroxy-5-(2-(5-(pyrrolidin-1-yl)pyridin-2-yl)vinyl)benzaldehyde |

TABLE 1-continued
| Cmpd # | Chemical Structure | Chemical Name |
|---|---|---|
| 121 | 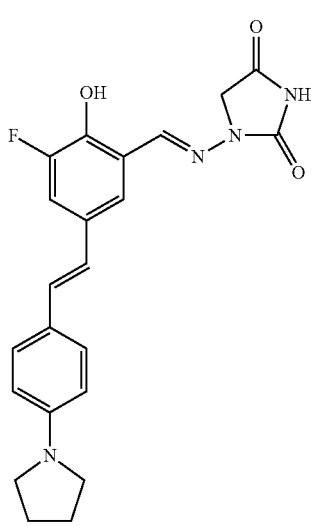 [SMILES: O=C1CN(/N=C/c2cc(/C=C/c3ccc(N4CCCC4)cc3)cc(F)c2O)C(=O)N1] | 1-(((E)-3-fluoro-2-hydroxy-5-((E)-4-(pyrrolidin-1-yl)styryl)benzylidene)amino)imidazolidine-2,4-dione |
| 122 | 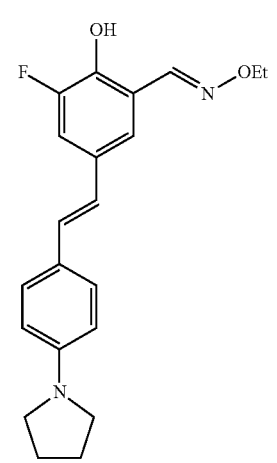 | (E)-3-fluoro-2-hydroxy-5-((E)-4-(pyrrolidin-1-yl)styryl)benzaldehyde O-ethyl oxime |
| 123 | 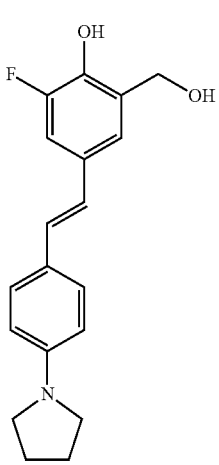 | (E)-2-fluoro-6-(hydroxymethyl)-4-(4-(pyrrolidin-1-yl)styryl)phenol |

TABLE 1-continued

| Cmpd # | Chemical Structure | Chemical Name |
| --- | --- | --- |
| 124 | 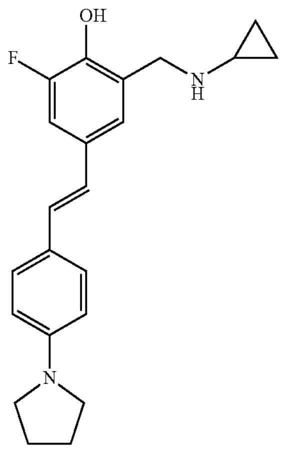 [SMILES: Oc1c(F)cc(/C=C/c2ccc(N3CCCC3)cc2)cc1CNC1CC1] | (E)-2-((cyclopropylamino)methyl)-6-fluoro-4-(4-(pyrrolidin-1-yl)styryl)phenol |
| 125 | 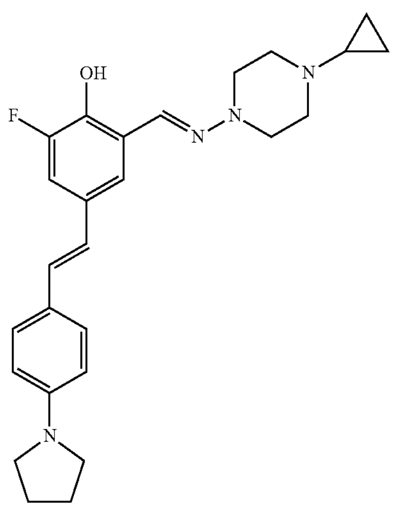 [SMILES: Oc1c(F)cc(/C=C/c2ccc(N3CCCC3)cc2)cc1/C=N/N1CCN(C2CC2)CC1] | 2-((E)-((4-cyclopropylpiperazin-1-yl)imino)methyl)-6-fluoro-4-((E)-4-(pyrrolidin-1-yl)styryl)phenol |
| 126 | 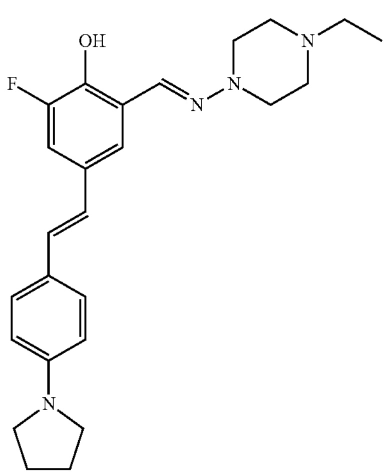 [SMILES: CCN1CCN(/N=C/c2cc(/C=C/c3ccc(N4CCCC4)cc3)cc(F)c2O)CC1] | 2-((E)-((4-ethylpiperazin-1-yl)imino)methyl)-6-fluoro-4-((E)-4-(pyrrolidin-1-yl)styryl)phenol |

TABLE 1-continued
| Cmpd # | Chemical Structure | Chemical Name |
|---|---|---|
| 127 | 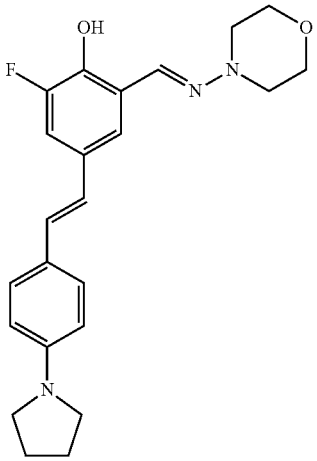 [SMILES: Oc1c(F)cc(/C=C/c2ccc(N3CCCC3)cc2)cc1/C=N/N1CCOCC1] | 2-fluoro-6-((E)-(morpholinoimino)methyl)-4-((E)-4-(pyrrolidin-1-yl)styryl)phenol |
| 128 | 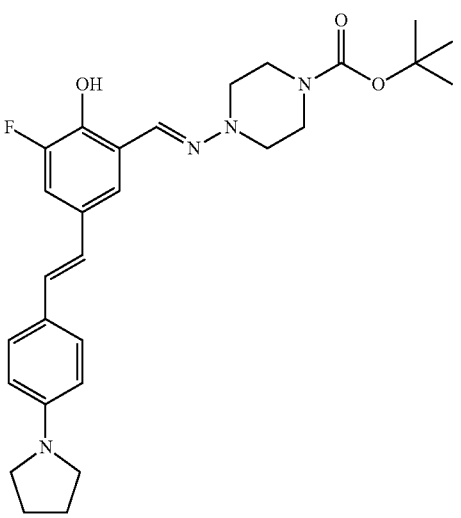 [SMILES: CC(C)(C)OC(=O)N1CCN(/N=C/c2cc(/C=C/c3ccc(N4CCCC4)cc3)cc(F)c2O)CC1] | tert-butyl 4-(((E)-3-fluoro-2-hydroxy-5-((E)-4-(pyrrolidin-1-yl)styryl)benzylidene)amino)piperazine-1-carboxylate |
| 129 | 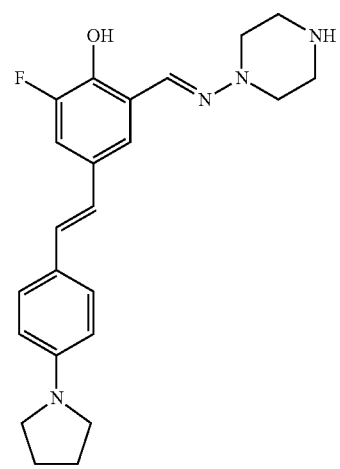 [SMILES: Oc1c(F)cc(/C=C/c2ccc(N3CCCC3)cc2)cc1/C=N/N1CCNCC1] | 2-fluoro-6-((E)-(piperazin-1-ylimino)methyl)-4-((E)-4-(pyrrolidin-1-yl)styryl)phenol hydrochloride |

TABLE 1-continued
| Cmpd # | Chemical Structure | Chemical Name |
|---|---|---|
| 130 | 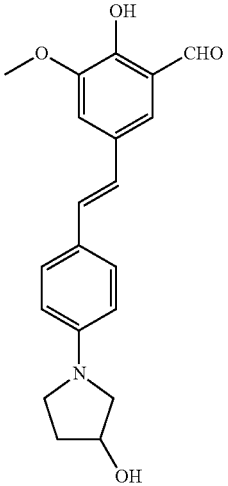 [SMILES: COc1cc(/C=C/c2ccc(N3CCC(O)C3)cc2)cc(C=O)c1O] | (E)-2-hydroxy-5-(4-(3-hydroxypyrrolidin-1-yl)styryl)-3-methoxybenzaldehyde |
| 131 | 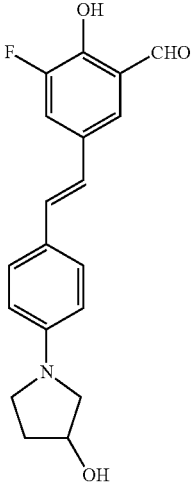 [SMILES: O=Cc1cc(/C=C/c2ccc(N3CCC(O)C3)cc2)cc(F)c1O] | (E)-3-fluoro-2-hydroxy-5-(4-(3-hydroxypyrrolidin-1-yl)styryl)benzaldehyde |
| 132 | 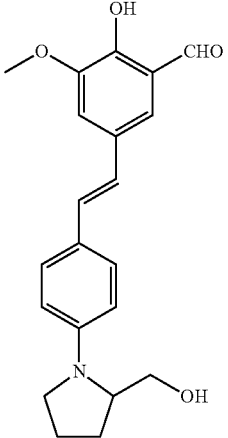 [SMILES: COc1cc(/C=C/c2ccc(N3CCCC3CO)cc2)cc(C=O)c1O] | (E)-2-hydroxy-5-(4-(2-(hydroxymethyl)pyrrolidin-1-yl)styryl)-3-methoxybenzaldehyde |

TABLE 1-continued
| Cmpd # | Chemical Structure | Chemical Name |
|---|---|---|
| 133 | 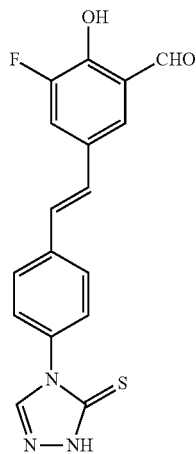 [SMILES: O=Cc1cc(/C=C/c2ccc(-n3cn[nH]c3=S)cc2)cc(F)c1O] | (E)-3-fluoro-2-hydroxy-5-(4-(5-thioxo-1,5-dihydro-4H-1,2,4-triazol-4-yl)styryl)benzaldehyde |
| 134 | 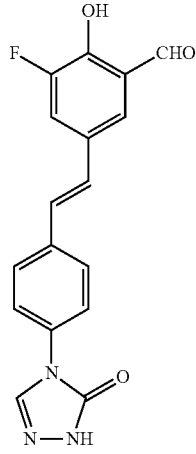 [SMILES: O=Cc1cc(/C=C/c2ccc(-n3cn[nH]c3=O)cc2)cc(F)c1O] | (E)-3-fluoro-2-hydroxy-5-(4-(5-oxo-1,5-dihydro-4H-1,2,4-triazol-4-yl)styryl)benzaldehyde |
| 135 | 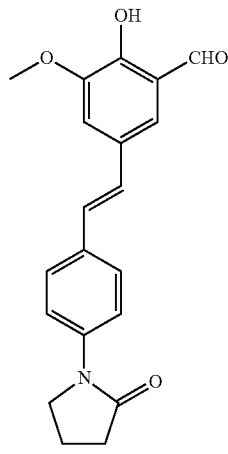 [SMILES: COc1cc(/C=C/c2ccc(N3CCCC3=O)cc2)cc(C=O)c1O] | (E)-2-hydroxy-3-methoxy-5-(4-(2-oxopyrrolidin-1-yl)styryl)benzaldehyde |

TABLE 1-continued
| Cmpd # | Chemical Structure | Chemical Name |
|---|---|---|
| 136 | 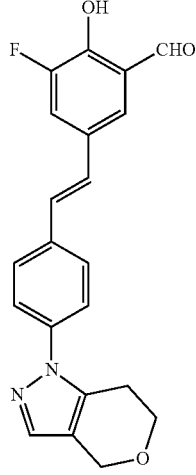 [SMILES: O=Cc1cc(/C=C/c2ccc(-n3ncc4c3CCOC4)cc2)cc(F)c1O] | E)-5-(4-(6,7-dihydropyrano[4,3-c]pyrazol-1(4H)-yl)styryl)-3-fluoro-2-hydroxybenzaldehyde |
| 137 | 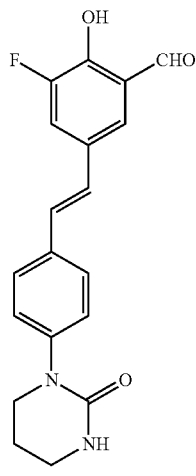 [SMILES: O=Cc1cc(/C=C/c2ccc(N3CCCNC3=O)cc2)cc(F)c1O] | (E)-3-fluoro-2-hydroxy-5-(4-(2-oxotetrahydropyrimidin-1(2H)-yl)styryl)benzaldehyde |
| 138 | 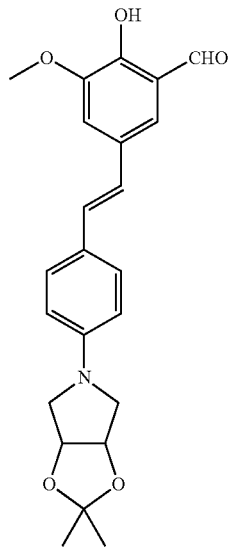 [SMILES: COc1cc(/C=C/c2ccc(N3CC4OC(C)(C)OC4C3)cc2)cc(C=O)c1O] | (E)-5-(4-(2,2-dimethyltetrahydro-5H-[1,3]dioxolo[4,5-c]pyrrol-5-yl)styryl)-2-hydroxy-3-methoxybenzaldehyde |

TABLE 1-continued
| Cmpd # | Chemical Structure | Chemical Name |
| --- | --- | --- |
| 139 | 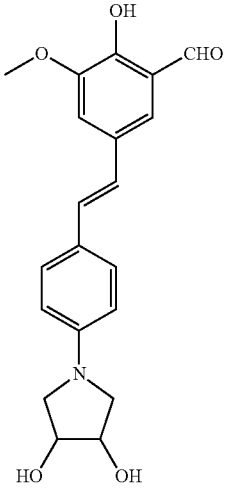 [SMILES: COc1cc(/C=C/c2ccc(N3CC(O)C(O)C3)cc2)cc(C=O)c1O] | (E)-5-(4-(3,4-dihydroxypyrrolidin-1-yl)styryl)-2-hydroxy-3-methoxybenzaldehyde |
| 140 | 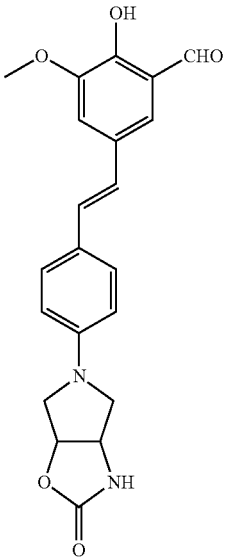 [SMILES: COc1cc(/C=C/c2ccc(N3CC4NC(=O)OC4C3)cc2)cc(C=O)c1O] | (E)-2-hydroxy-3-methoxy-5-(4-(2-oxohexahydro-5H-pyrrolo[3,4-d]oxazol-5-yl)styryl)benzaldehyde |
| 141 | 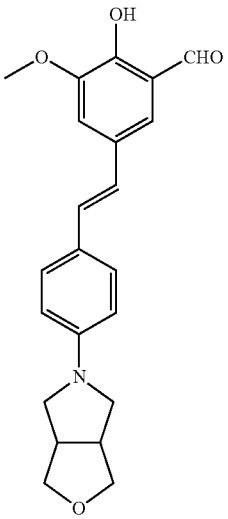 [SMILES: COc1cc(/C=C/c2ccc(N3CC4COCC4C3)cc2)cc(C=O)c1O] | (E)-2-hydroxy-3-methoxy-5-(4-(tetrahydro-1H-furo[3,4-c]pyrrol-5(3H)-yl)styryl)benzaldehyde |

TABLE 1-continued

| Cmpd # | Chemical Structure | Chemical Name |
|---|---|---|
| 142 | 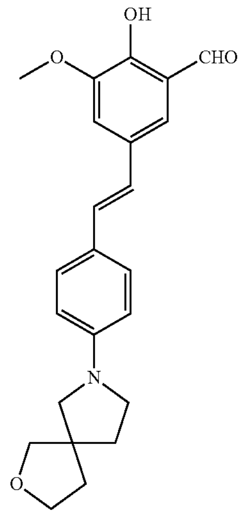 [SMILES: COc1cc(/C=C/c2ccc(N3CCC4(CCOC4)C3)cc2)cc(C=O)c1O] | (E)-5-(4-(2-oxa-7-azaspiro[4.4]nonan-7-yl)styryl)-2-hydroxy-3-methoxybenzaldehyde |
| 143 | 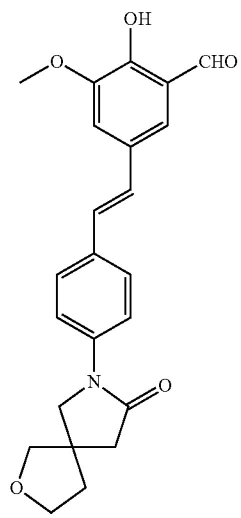 [SMILES: COc1cc(/C=C/c2ccc(N3CC4(CCOC4)CC3=O)cc2)cc(C=O)c1O] | (E)-2-hydroxy-3-methoxy-5-(4-(8-oxo-2-oxa-7-azaspiro[4.4]nonan-7-yl)styryl)benzaldehyde |
| 144 | 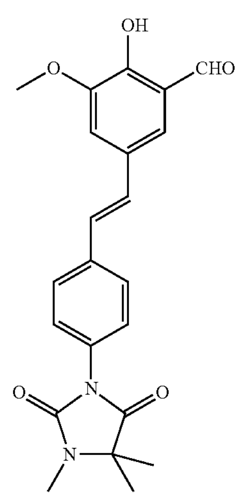 [SMILES: COc1cc(/C=C/c2ccc(N3C(=O)N(C)C(C)(C)C3=O)cc2)cc(C=O)c1O] | (E)-2-hydroxy-3-methoxy-5-(4-(3,4,4-trimethyl-2,5-dioxoimidazolidin-1-yl)styryl)benzaldehyde |

TABLE 1-continued
| Cmpd # | Chemical Structure | Chemical Name |
|---|---|---|
| 145 | 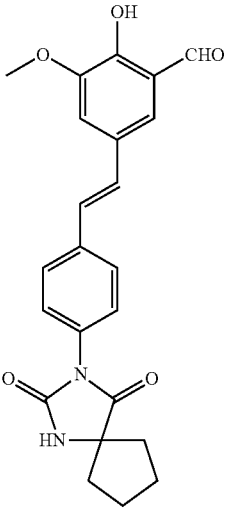 [SMILES: COc1cc(/C=C/c2ccc(N3C(=O)NC4(CCCC4)C3=O)cc2)cc(C=O)c1O] | (E)-5-(4-(2,4-dioxo-1,3-diazaspiro[4.4]nonan-3-yl)styryl)-2-hydroxy-3-methoxybenzaldehyde |
| 146 | 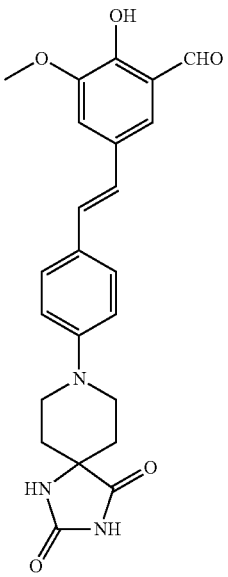 [SMILES: COc1cc(/C=C/c2ccc(N3CCC4(CC3)NC(=O)NC4=O)cc2)cc(C=O)c1O] | (E)-5-(4-(2,4-dioxo-1,3,8-triazaspiro[4.5]decan-8-yl)styryl)-2-hydroxy-3-methoxybenzaldehyde |
| 147 | 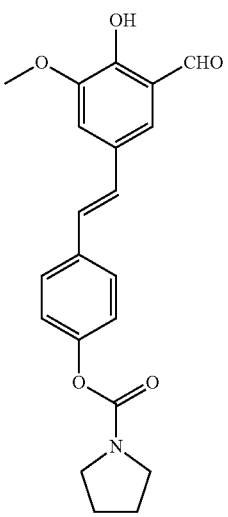 [SMILES: COc1cc(/C=C/c2ccc(OC(=O)N3CCCC3)cc2)cc(C=O)c1O] | (E)-4-(3-formyl-4-hydroxy-5-methoxystyryl)phenyl pyrrolidine-1-carboxylate |

TABLE 1-continued
| Cmpd # | Chemical Structure | Chemical Name |
|---|---|---|
| 148 | 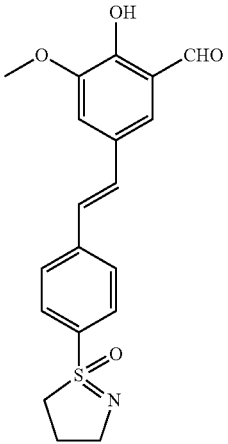 [SMILES: COc1cc(/C=C/c2ccc(S3(=O)=NCCC3)cc2)cc(C=O)c1O] | (E)-2-hydroxy-3-methoxy-5-(4-(1-oxido-4,5-dihydro-3H-1l6-isothiazol-1-yl)styryl)benzaldehyde |
| 149 | 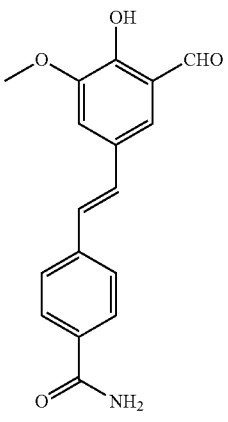 [SMILES: COc1cc(/C=C/c2ccc(C(N)=O)cc2)cc(C=O)c1O] | (E)-4-(3-formyl-4-hydroxy-5-methoxystyryl)benzamide |
| 150 | 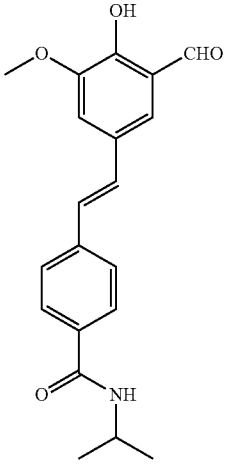 [SMILES: COc1cc(/C=C/c2ccc(C(=O)NC(C)C)cc2)cc(C=O)c1O] | (E)-4-(3-formyl-4-hydroxy-5-methoxystyryl)-N-isopropylbenzamide |

TABLE 1-continued
| Cmpd # | Chemical Structure | Chemical Name |
| --- | --- | --- |
| 151 | 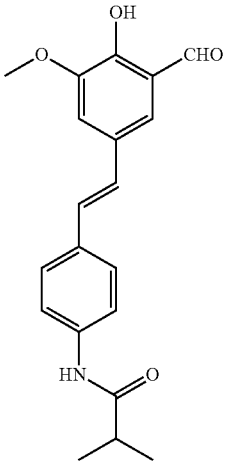 [SMILES: COc1cc(/C=C/c2ccc(NC(=O)C(C)C)cc2)cc(C=O)c1O] | (E)-N-(4-(3-formyl-4-hydroxy-5-methoxystyryl)phenyl)isobutyramide |
| 152 | 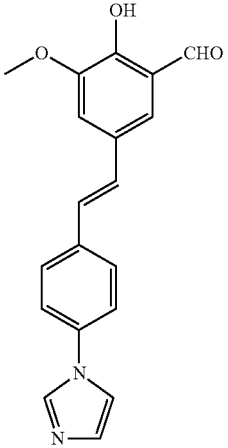 [SMILES: COc1cc(/C=C/c2ccc(-n3ccnc3)cc2)cc(C=O)c1O] | (E)-5-(4-(1H-imidazol-1-yl)styryl)-2-hydroxy-3-methoxybenzaldehyde |
| 153 | 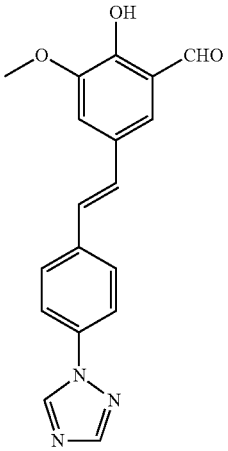 [SMILES: COc1cc(/C=C/c2ccc(-n3cncn3)cc2)cc(C=O)c1O] | (E)-5-(4-(1H-1,2,4-triazol-1-yl)styryl)-2-hydroxy-3-methoxybenzaldehyde |

TABLE 1-continued

| Cmpd # | Chemical Structure | Chemical Name |
|---|---|---|
| 154 | 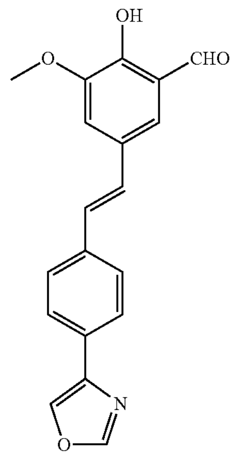 [SMILES: COc1cc(/C=C/c2ccc(-c3cocn3)cc2)cc(C=O)c1O] | (E)-2-hydroxy-3-methoxy-5-(4-(oxazol-4-yl)styryl)benzaldehyde |
| 155 | 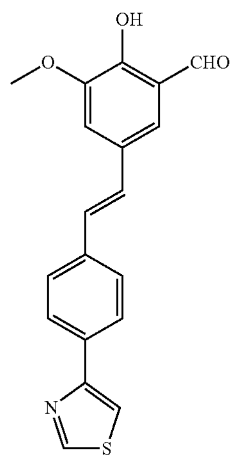 [SMILES: COc1cc(/C=C/c2ccc(-c3cscn3)cc2)cc(C=O)c1O] | (E)-2-hydroxy-3-methoxy-5-(4-(thiazol-4-yl)styryl)benzaldehyde |
| 156 | 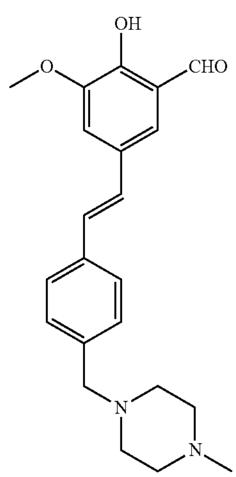 | (E)-2-hydroxy-3-methoxy-5-(4-((4-methylpiperazin-1-yl)methyl)styryl)benzaldehyde |

TABLE 1-continued
| Cmpd # | Chemical Structure | Chemical Name |
|---|---|---|
| 157 | 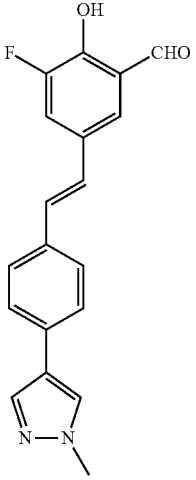 [SMILES: Cn1cc(-c2ccc(/C=C/c3cc(F)c(O)c(C=O)c3)cc2)cn1] | (E)-3-fluoro-2-hydroxy-5-(4-(1-methyl-1H-pyrazol-4-yl)styryl)benzaldehyde |
| 158 | 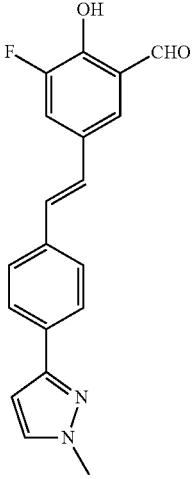 [SMILES: Cn1ccc(-c2ccc(/C=C/c3cc(F)c(O)c(C=O)c3)cc2)n1] | (E)-3-fluoro-2-hydroxy-5-(4-(1-methyl-1H-pyrazol-3-yl)styryl)benzaldehyde |
| 159 | 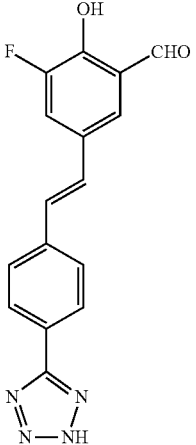 [SMILES: O=Cc1cc(/C=C/c2ccc(-c3nn[nH]n3)cc2)cc(F)c1O] | (E)-5-(4-(2H-tetrazol-5-yl)styryl)-3-fluoro-2-hydroxybenzaldehyde |

TABLE 1-continued

| Cmpd # | Chemical Structure | Chemical Name |
| --- | --- | --- |
| 160 | 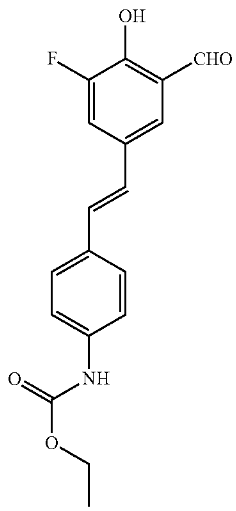 [SMILES: CCOC(=O)Nc1ccc(/C=C/c2cc(F)c(O)c(C=O)c2)cc1] | ethyl (E)-(4-(3-fluoro-5-formyl-4-hydroxystyryl)phenyl)carbamate |
| 161 | 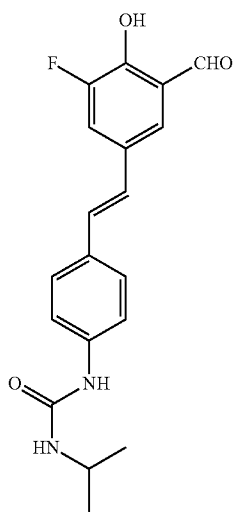 [SMILES: CC(C)NC(=O)Nc1ccc(/C=C/c2cc(F)c(O)c(C=O)c2)cc1] | (E)-1-(4-(3-fluoro-5-formyl-4-hydroxystyryl)phenyl)-3-isopropylurea |
| 162 | 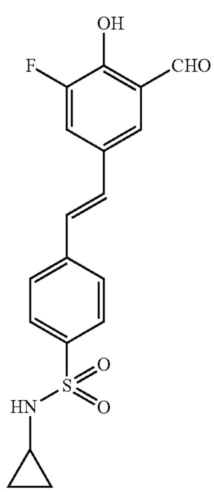 [SMILES: O=Cc1cc(/C=C/c2ccc(S(=O)(=O)NC3CC3)cc2)cc(F)c1O] | (E)-N-cyclopropyl-4-(3-fluoro-5-formyl-4-hydroxystyryl)benzenesulfonamide |

| Cmpd # | Chemical Structure | Chemical Name |
|---|---|---|
| 163 | 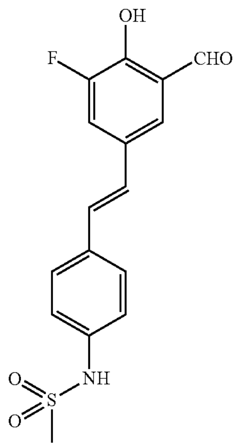 [SMILES: CS(=O)(=O)Nc1ccc(/C=C/c2cc(F)c(O)c(C=O)c2)cc1] | (E)-N-(4-(3-fluoro-5-formyl-4-hydroxystyryl)phenyl)methanesulfonamide |
| 164 | 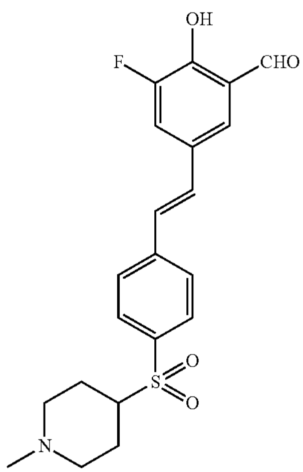 [SMILES: CN1CCC(S(=O)(=O)c2ccc(/C=C/c3cc(F)c(O)c(C=O)c3)cc2)CC1] | (E)-3-fluoro-2-hydroxy-5-(4-((1-methylpiperidin-4-yl)sulfonyl)styryl)benzaldehyde |
and pharmaceutically acceptable salts thereof.
In some embodiments, the compound is not a compound of Table 1X.
TABLE 1X
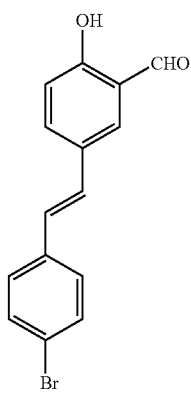
X1
TABLE 1X-continued
X2

TABLE 1X-continued
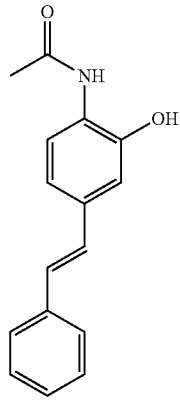 [SMILES: CC(=O)Nc1ccc(/C=C/c2ccccc2)cc1O] X3
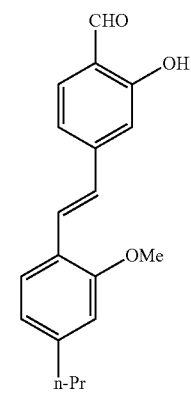 X4
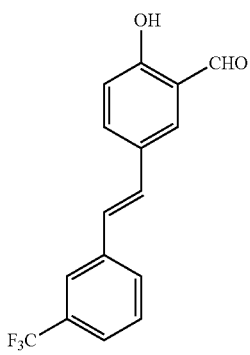 [SMILES: O=Cc1cc(/C=C/c2cccc(C(F)(F)F)c2)ccc1O] X5
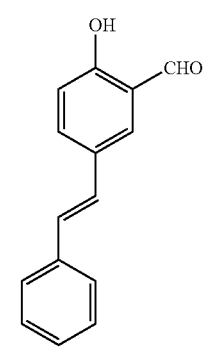 [SMILES: O=Cc1cc(/C=C/c2ccccc2)ccc1O] X6
TABLE 1X-continued
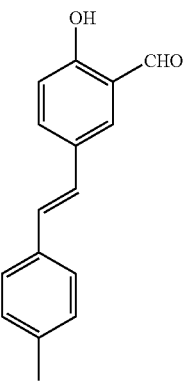 [SMILES: Cc1ccc(/C=C/c2ccc(O)c(C=O)c2)cc1] X7
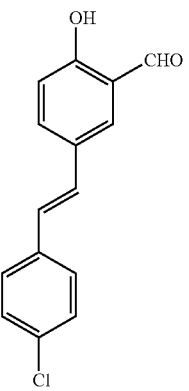 [SMILES: O=Cc1cc(/C=C/c2ccc(Cl)cc2)ccc1O] X8
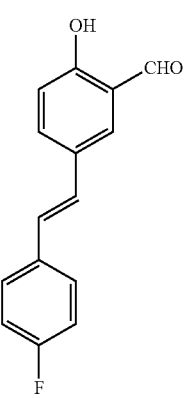 [SMILES: O=Cc1cc(/C=C/c2ccc(F)cc2)ccc1O] X9
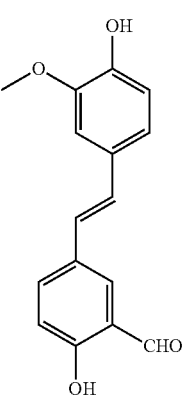 [SMILES: COc1cc(/C=C/c2ccc(O)c(C=O)c2)ccc1O] X10

TABLE 1X-continued

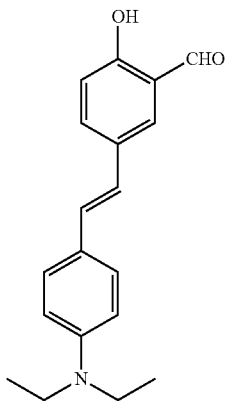 [SMILES: CCN(CC)c1ccc(/C=C/c2ccc(O)c(C=O)c2)cc1]

X11

Any formula or compound given herein, such as Formula (A), (A-1), (A-2), (I), (Ia), or (Ib), or compounds of Table 1, is intended to represent compounds having structures depicted by the structural formula as well as certain variations or forms. In particular, compounds of any formula given herein may contain bonds with restricted rotation and therefore exist in different geometric configurations. Where a compound of Table 1 is depicted as a particular geometric isomer (e.g., E or Z isomer, or cis or trans isomer), also provided herein is any alternative geometric configuration of the compound, as well as a mixture of geometric isomers of the compound in any ratio. For example, where a compound of Table 1 is depicted as a "Z" isomer, also provided herein is the "E" isomer of the compound. Likewise, where a compound of Table 1 is depicted as a "E" isomer, also provided herein is the "Z" isomer of the compound. Also provided are mixtures of the compound with both the "E" and the "Z" stereochemical configuration, wherein the mixtures are in any ratio. Similarly, where a compound of Table 1 is depicted as a "cis" isomer, also provided herein is the "trans" isomer of the compound; and where a compound is depicted as a "trans" isomer, also provided herein is the "cis" isomer of the compound. Also provided are mixtures of the compound with both the "cis" and the "trans" stereochemical configuration, wherein the mixtures are in any ratio. Additionally, compounds of any formula provided herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms (e.g., geoisomeric forms), and mixtures thereof in any ratio. Where a compound of Table 1 is depicted with a particular stereochemical configuration, also provided herein is any alternative stereochemical configuration of the compound, as well as a mixture of stereoisomers of the compound in any ratio. Any compound of Table 1 is intended to represent a racemate, one or more enantiomeric forms, one or more diastereomeric forms, one or more atropisomeric forms (e.g., geoisomeric forms), and mixtures thereof in any ratio. Furthermore, certain structures may exist as tautomers or as atropisomers. Additionally, any formula given herein is intended to refer to hydrates, solvates, and amorphous forms of such compounds, and mixtures thereof, even if such forms are not listed explicitly. In some embodiments, the solvent is water and the solvates are hydrates.

The compounds of Formula (A), (A-1), (A-2), (I), (Ia), or (Ib), or Table 1 may be prepared and/or formulated as pharmaceutically acceptable salts. In some embodiments, pharmaceutically acceptable salts include acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like. These salts may be derived from inorganic or organic acids. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. In some embodiments, pharmaceutically acceptable salts are formed when an acidic proton present in the parent compound either is replaced by a metal ion, e.g., an alkali metal ion, an alkaline earth ion, or an aluminum ion; or coordinates with an organic base. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, trimethamine, dicyclohexylamine, caffeine, procaine, hydrabamine, choline, betaine, ethylenediamine, glucosamine, N-ethylglucamine, N-methylglucamine, theobromine, purines, piperazine, piperidine, N-ethylpiperidine, polyamine resins, amino acids such as lysine, arginine, histidine, and the like. Examples of pharmaceutically acceptable base addition salts include those derived from inorganic bases such as sodium, potassium, lithium, ammonium, calcium, magnesium, iron, zinc, copper, manganese, aluminum salts and the like. In some embodiments, the organic non-toxic bases are L-amino acids, such as L-lysine and L-arginine, tromethamine, N-ethylglucamine and N-methylglucamine. Acceptable inorganic bases include aluminum hydroxide, calcium hydroxide, potassium hydroxide, sodium carbonate, sodium hydroxide, and the like. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, benzenesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The compounds depicted herein may be present as salts even if salts are not depicted, and it is understood that the compositions and methods provided herein embrace all salts and solvates of the compounds depicted here, as well as the non-salt and non-solvate form of the compound, as is well understood by the skilled artisan. In some embodiments, the salts of the compounds provided herein are pharmaceutically acceptable salts.

Representative examples of compounds detailed herein, including intermediates and final compounds, are depicted in the tables and elsewhere herein. It is understood that in one aspect, any of the compounds may be used in the methods detailed herein, including, where applicable, intermediate compounds that may be isolated and administered to an individual.

In one variation, the compounds herein are synthetic compounds prepared for administration to an individual. In another variation, compositions are provided containing a compound in substantially pure form. In another variation, provided are pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Any variation or embodiment of $R^1$, $R^2$, $R^3$, $R^4$, $R^5$, Y, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R^r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m $R^{6a}$, $R^{6b}$, $R^{6c}$, and $R^{6d}$ provided herein can be combined with every other variation or embodiment of $R^1$, $R^2$, $R^3$, $R^4$, $R^5$, Y, $G_1$, $G_2$, $G_3$, $G_4$, $G_5$, $G_6$, $G_7$, $R^a$, $R^b$, $R^c$, $R^d$, $R^e$, $R^f$, $R^g$, $R^h$, $R^j$, $R^k$, $R^m$, $R^n$, $R^p$, $R^q$, $R^r$, $R^s$, $R^t$, $R^u$, $R^v$, $R^{w1}$, $R^{w2}$, $R^x$, $R^y$, $R^{z1}$, $R^{z2}$, $X_1$, $X_2$, $X_3$, $X_4$, m, $R^{6a}$, $R^{6b}$, $R^{6c}$, and $R^{6d}$, as if each combination had been individually and specifically described. Any variation or embodiment of $R^1$, $R^2$, $R^3$, $R^4$, $R^5$, $G_1$, $G_2$, $G_3$, $G_4$, $G_5$, $G_6$, $R^a$, $R^b$, $R^c$, $R^d$, $R^e$, $R^f$, $R^g$, $R^h$, $X_1$, $X_2$, $X_3$, $X_4$, m, $R^{6a}$, $R^{6b}$, $R^{6c}$, and $R^{6d}$ provided herein can be combined with every other variation or embodiment of $R^1$, $R^2$, $R^3$, $R^4$, $R^5$, $G_1$, $G_2$, $G_3$, $G_4$, $G_5$, $G_6$, $R^a$, $R^b$, $R^c$, $R^d$, $R^e$, $R^f$, $R^g$, $R^h$, $X_1$, $X_2$, $X_3$, $X_4$, m, $R^{6a}$, $R^{6b}$, $R^{6c}$, and $R^{6d}$, as if each combination had been individually and specifically described.

The embodiments also relate to pharmaceutically acceptable prodrugs of the compounds described herein, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The embodiments also relate to pharmaceutically active metabolites of compounds described herein, and uses of such metabolites in the methods provided herein. A "pharmaceutically active metabolite" means a pharmacologically active product of metabolism in the body of a compound described herein or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Chemical Definitions

The following terms have the following meanings unless otherwise indicated. Any undefined terms have their art recognized meanings.

The term "alkyl" refers to a straight- or branched-chain univalent saturated hydrocarbon group, or combination thereof, having the number of carbon atoms designated (i.e., $C_1$-$C_{10}$ means one to ten carbon atoms). Examples of alkyl groups include, but are not limited to, methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an —O-alkyl. Examples of alkoxy include, but are not limited to, methoxy, ethoxy, n-propoxy, isopropoxy, n-butoxy, iso-butoxy, sec-butoxy, and tertbutoxy.

The term "alkenyl" refers to an unsaturated straight- or branched-chain hydrocarbon group, or combination thereof, having the indicated number of carbon atoms, and having one or more double bonds. Examples of alkenyl groups include, but are not limited to, ethenyl (or vinyl), allyl, and but-3-en-1-yl. Included within this term are cis and trans isomers and mixtures thereof.

The term "alkynyl" refers to an unsaturated straight- or branched-chain hydrocarbon group having the indicated number of carbon atoms (e.g., 2 to 8 or 2 to 6 carbon atoms) and at least one carbon-carbon triple bond. Examples of alkynyl groups include, but are not limited to, acetylenyl (—C≡CH) and propargyl (—CH2C≡CH).

The term "alkylene" refers to a divalent group that is a radical of an alkane. The alkylene can be a straight- or branched-chain divalent alkyl radical. "$C_{1-4}$ alkylene" refers to alkylene groups with 1 to 4 carbon atoms.

The term "aryl" refers to a monovalent aromatic carbocyclic group of from 6 to 18 annular carbon atoms having a single ring (a phenyl group) or a multiple condensed ring (such as napthyl, anthracenyl, or indanyl), in which condensed rings are optionally aromatic, provided that the point of attachment of the aryl group to the parent structure is through an atom of an aromatic ring. "Aryl" as defined herein encompasses groups such as phenyl and fluorenyl.

The term "cycloalkyl" refers to cyclic hydrocarbon groups of from 3 to 10 annular carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like. In some instances, the cycloalkyl is a monocyclic ring. In some instances, cycloalkyl is a 3- to 6-membered ring.

The term "cycloalkenyl" refers to a cyclic alkenyl group of from 4 to 10 annular carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

The term "haloalkyl" refers to an alkyl group as described above, wherein one or more hydrogen atoms on the alkyl group have been replaced with a halo group. Examples of such groups include, without limitation, fluoroalkyl groups, such as fluoroethyl, trifluoromethyl, difluoromethyl, trifluoroethyl, and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

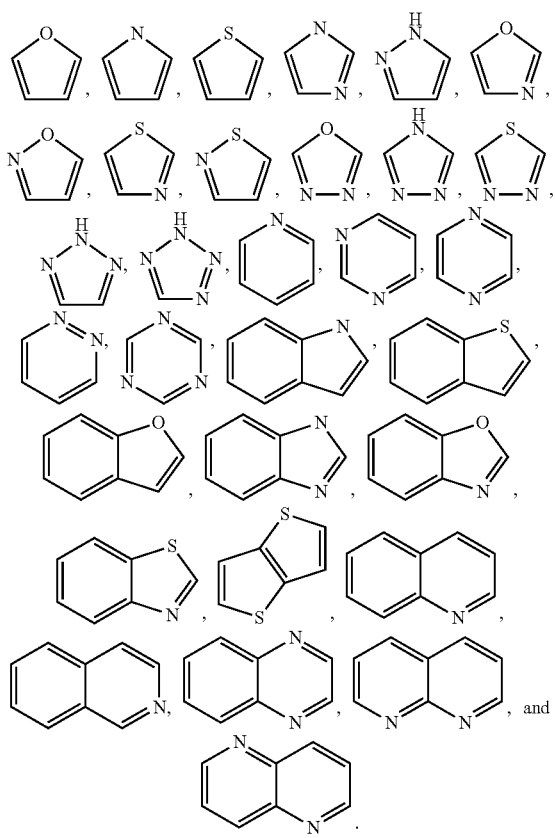

The terms "heterocyclyl" or "heterocycloalkyl" refer to a saturated or partially unsaturated group having a single ring or multiple condensed rings, including fused, bridged, or spiro ring systems, and having from 3 to 20 ring atoms, including 1 to 10 heteroatoms. These ring atoms are selected from the group consisting of carbon, nitrogen, sulfur, or oxygen. In certain embodiments, the nitrogen and/or sulfur atom(s) of the heterocyclic group are optionally oxidized to provide for N-oxide, —S(O)—, or —SO$_2$— moieties. Illustrative examples of heterocyclic groups include the following entities, in the form of properly bonded moieties:

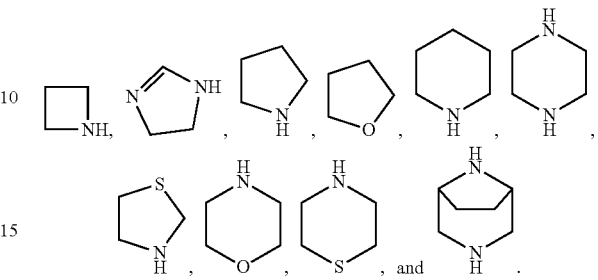

The term "halogen" represents chlorine, fluorine, bromine, or iodine. The term "halo" represents chloro, fluoro, bromo, or iodo.

The term "oxo" represents a carbonyl oxygen. For example, a cyclopentyl substituted with oxo is cyclopentanone.

Those skilled in the art will recognize that the species listed or illustrated above are not exhaustive, and that additional species within the scope of these defined terms may also be selected.

The term "substituted" means that the specified group or moiety bears one or more substituents including, but not limited to, substituents such as alkoxy, acyl, acyloxy, carbonylalkoxy, acylamino, amino, aminoacyl, aminocarbonylamino, aminocarbonyloxy, cycloalkyl, cycloalkenyl, aryl, heteroaryl, aryloxy, cyano, azido, halo, hydroxyl, nitro, carboxyl, thiol, thioalkyl, cycloalkyl, cycloalkenyl, alkyl, alkenyl, alkynyl, heterocyclyl, aralkyl, aminosulfonyl, sulfonylamino, sulfonyl, oxo, carbonylalkylenealkoxy and the like. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. When a group or moiety bears more than one substituent, it is understood that the substituents may be the same or different from one another. In some embodiments, a substituted group or moiety bears from one to five substituents. In some embodiments, a substituted group or moiety bears one substituent. In some embodiments, a substituted group or moiety bears two substituents. In some embodiments, a substituted group or moiety bears three substituents. In some embodiments, a substituted group or moiety bears four substituents. In some embodiments, a substituted group or moiety bears five substituents.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of the present disclosure and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of the present disclosure for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The present disclosure also includes pharmaceutically acceptable salts of the compounds represented by Formula (A), (A-1), (A-2), (I), (Ia), or (Ib), or the compounds of Table 1, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Particular pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (A), (A-1), (A-2), (I), (Ia), or (Ib), or a compound of Table 1 that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The present disclosure also relates to pharmaceutically acceptable prodrugs of the compounds of Formula (A), (A-1), (A-2), (I), (Ia), or (Ib), or the compounds of Table 1, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the formula compound). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula (A), (A-1), (A-2), (I), (Ia), or (Ib), or the compounds of Table 1, and uses of such metabolites in the methods provided herein. A "pharmaceutically active metabolite" means a pharmacologically active product of metabolism in the body of a compound of Formula (A), (A-1), (A-2), (I), (Ia), or (Ib), or the compounds of Table 1, or a salt of any of the foregoing. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In particular embodiments, pharmaceutical compositions according to the present disclosure are sterile compositions. Pharmaceutical compositions may be prepared using compounding techniques known or that become available to those skilled in the art.

Sterile compositions are also contemplated by the present disclosure, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the present disclosure may be administered by a suitable route of delivery, such as oral, parenteral, rectal, nasal, topical, or ocular routes, or by inhalation. In some embodiments, the compositions are formulated for intravenous or oral administration.

For oral administration, the compounds of the present disclosure may be provided in a solid form, such as a tablet or capsule, or as a solution, emulsion, or suspension. To prepare the oral compositions, the compounds of the present disclosure may be formulated to yield a dosage of, e.g., from about 0.01 to about 50 mg/kg daily, or from about 0.05 to about 20 mg/kg daily, or from about 0.1 to about 10 mg/kg daily. Additional dosages include from about 0.1 mg to 1 g daily, from about 1 mg to about 10 mg daily, from about 10 mg to about 50 mg daily, from about 50 mg to about 250 mg daily, or from about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the present disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present disclosure may be formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the present disclosure may utilize a patch formulation to effect transdermal delivery.

As used herein, "treatment" or "treating" is an approach for obtaining a beneficial or desired result, including clinical results. For purposes of this disclosure, beneficial or desired results include, but are not limited to: reducing the severity of or suppressing the worsening of a disease, symptom, or condition, alleviating a symptom and/or diminishing the extent of a symptom and/or preventing a worsening of a symptom associated with a condition, arresting the development of a disease, symptom, or condition, relieving the disease, symptom, or condition, causing regression of the disease, disorder, or symptom (in terms of severity or frequency of negative symptoms), or stopping the symptoms of the disease or condition. Beneficial or desired results can also be slowing, halting, or reversing the progressive course of a disease or condition. For example, beneficial effects may include slowing the progression of Parkinson's disease from an earlier stage (e.g., prodromal stage or stage 1, 2 or 3) to a later stage (e.g., stage 4 or 5), or halting Parkinson's disease at a prodromal or early stage.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Parkinson's disease (e.g., in a prodromal individual) is a method that reduces probability of disease development in a given time frame and/or reduces extent of the disease in a given time frame, when compared to not using the method.

The term "subject" refers to a mammalian patient in need of such treatment, such as a human. A "subject" may be a human, or may be a cat, dog, cow, rat, mouse, horse, or other domesticated mammal.

Exemplary diseases that are characterized by protein aggregation include Alzheimer's disease, Parkinson's disease, fronto-temporal dementia, dementia with Lewy bodies (Lewy body disease), Parkinson's disease with dementia, multiple system atrophy, amyotrophic lateral sclerosis, and Huntington's disease, as well inflammatory diseases, such as asthma, chronic obstructive pulmonary disease (COPD), chronic peptic ulcers, tuberculosis, rheumatoid arthritis, chronic sinusitis, hepatitis (such as hepatitis B or C), gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), atopic dermatitis, acne vulgaris, rosacea, non-alcoholic fatty liver disease, non-alcoholic steatohepatisis, corneal wounds, corneal disorders, Stargardt disease (Juvenile macular degeneration), age-related macular degeneration, sepsis, diabetic wounds, herpes simplex virus, and anti-fungal, anti-bacterial, antiviral and antitumor diseases or conditions. Additional exemplary diseases include Progressive Supranuclear Palsy (PSP), Niemann-Pick disease type C, irritable bowel disease, osteoarthritis, corneal HSV, stroke, and ischemic heart disease.

In one aspect, the compounds and pharmaceutical compositions of the present disclosure specifically target TLR2 protein dimers. Thus, these compounds and pharmaceutical compositions can be used to prevent, reverse, slow, or inhibit dimerization of TLR2 proteins with other natural protein ligands, and are used in methods of the present disclosure to treat neurological and inflammatory diseases related to or caused by such dimerization. In some embodiments, methods of treatment target Parkinson's disease, Alzheimer's disease, Lewy body disease, multiple system atrophy, atopic dermatitis, traumatic brain injury, or multiple sclerosis. The compounds, compositions, and method of the present disclosure are also used to mitigate deleterious effects that are secondary to protein dimerization and/or misfolding, such as neuronal cell death.

In some aspects, the compounds, compositions, and methods of the present disclosure are used to inhibit TLR2 dimerization. In alternative aspects, the compounds, compositions, and methods of the present disclosure are used to inhibit TLR2 dimerization with TLR1, or with TLR6, or both.

In the inhibitory methods of the present disclosure, an "effective amount" means an amount sufficient to reduce, slow the progression of, or reverse TLR2 dimerization. Measuring the amount of dimerization may be performed by routine analytical methods such as those described below. Such modulation is useful in a variety of settings, including in vitro assays. In some embodiments of such methods, the cell is a nerve cell or an HEK or THP cell.

In treatment methods according to the present disclosure, an "effective amount" means an amount or dose sufficient to generally bring about the desired therapeutic benefit in subjects needing such treatment. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, such as about 0.05 to 100 mg/kg/day, or about 1 to 35 mg/kg/day, or about 0.1 to 10 mg/kg/day. In alternative embodiments an exemplary dose is in the range of about 1 mg to about 1 g per day, or about 1-500, 1-250, 1-100, 1-50, 50-500, or 250-500 mg per day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. Further additional active ingredients for cancer applications include other cancer therapeutics or agents that mitigate adverse effects of cancer chemotherapeutic agents. Such combinations may serve to increase efficacy, ameliorate other disease symptoms, decrease one or more side effects, or decrease the required dose of an inventive compound. The additional active ingredients may be administered in a separate pharmaceutical composition from a compound of the present disclosure or may be included with a compound of the present disclosure in a single pharmaceutical composition. The additional active ingredients may be administered simultaneously with, prior to, or after administration of a compound of the present disclosure.

Combination agents include additional active ingredients are those that are known or discovered to be effective in treating the diseases, disorders, conditions, and symptoms discussed herein, including those active against another target associated with the disease, disorder, or symptom such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, compositions and formulations of the present disclosure, as well as methods of treatment, can further comprise other drugs or pharmaceuticals, e.g., other active agents useful for treating or palliative for a neurological or inflammatory diseases related to or caused by TLR2 dimerization, e.g., Parkinson's disease, Alzheimer's Disease (AD), Lewy body disease (LBD) and multiple system atrophy (MSA), or related symptoms or conditions. For example, the pharmaceutical compositions of the present disclosure may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monoamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present disclosure may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino)ethoxy]methyl] benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyridine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate), or a combination thereof.

Methods of Use

The compounds and pharmaceutical compositions herein may be used to treat or prevent a disease or condition in an individual. In some embodiments, provided are methods of treating a disease or condition associated with TLR2 heterodimerization, comprising administering to the individual in need thereof a compound of Formula (A), (A-1), (A-2), (I), (Ia), or (Ib), or a compound of Table 1, or a tautomer thereof, or a pharmaceutically acceptable salt of any of the foregoing. In some embodiments, provided are methods of treating a disease or condition associated with TLR2 heterodimerization comprising administering to the subject a therapeutically effective amount of at least one chemical entity as described herein.

In some embodiments, provided are compositions containing one or more compounds of Formula (A), (A-1), (A-2), (I), (Ia), or (Ib), or a compound of Table 1, or a tautomer thereof, or a pharmaceutically acceptable salt of any of the foregoing, for use in the treatment of a disease or condition associated with TLR2 heterodimerization. In some embodiments, provided are compositions containing at least one chemical entity as described herein for use in the treatment of a disease or condition associated with TLR2 heterodimerization.

Also provided herein is the use of a compound of Formula (A), (A-1), (A-2), (I), (Ia), or (Ib), or a compound of Table 1, or a tautomer thereof, or a pharmaceutically acceptable salt of any of the foregoing, in the manufacture of a medicament for treatment of a disease or condition associated with TLR2 heterodimerization. In some embodiments, provided is the use of at least one chemical entity as described herein in the manufacture of a medicament for treatment of a disease or condition associated with TLR2 heterodimerization.

In some embodiments, the disease or condition is selected from Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, Progressive Supranuclear Palsy (PSP), Niemann-Pick disease type C, inflammatory diseases, asthma, chronic obstructive pulmonary disease (COPD), chronic peptic ulcers, irritable bowel disease, tuberculosis, rheumatoid arthritis, osteoarthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), stroke, ischemic heart disease, atopic dermatitis, acne vulgaris, rosacea, non-alcoholic fatty liver disease, non-alcoholic steatohepatisis, corneal wounds, corneal disorders, corneal HSV, Stargardt disease (Juvenile macular degeneration), age-related macular degeneration, sepsis, diabetic wounds, herpes simplex virus, and anti-fungal, anti-bacterial, antiviral and antitumor diseases or conditions. In some embodiments, the disease or condition is selected from Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, inflammatory diseases, asthma, chronic obstructive pulmonary disease (COPD), chronic peptic ulcers, tuberculosis, rheumatoid arthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, and traumatic brain injury.

Also provided are methods for interfering with the heterodimerization of TLR2 in a cell, or modulating, preventing, slowing, reversing, or inhibiting TLR2 heterodimerization in a cell which involves contacting the cell with an effective amount of at least one compound of Formula (A), (A-1), (A-2), (I), (Ia), or (Ib), or a compound of Table 1, or a tautomer thereof, or a pharmaceutically acceptable salt of any of the foregoing. In some embodiments, provided are methods for interfering with the heterodimerization of TLR2 in a cell, or modulating, preventing, slowing, reversing, or inhibiting TLR2 heterodimerization in a cell which involves contacting the cell with an effective amount of at least one chemical entity as described herein.

Also provided herein are compositions containing one or more compounds of Formula (A), (A-1), (A-2), (I), (Ia), or (Ib), or a compound of Table 1, or a tautomer thereof, or a pharmaceutically acceptable salt of any of the foregoing for use in interfering with the heterodimerization of TLR2 in a cell, or modulating, preventing, slowing, reversing, or inhibiting TLR2 heterodimerization in a cell. In some embodiments, provided are compositions containing at least one chemical entity as described herein for use in interfering with the heterodimerization of TLR2 in a cell, or modulating, preventing, slowing, reversing, or inhibiting TLR2 heterodimerization in a cell.

Additionally provided herein is the use of at least one chemical entity as described herein, such as a compound of Formula (A), (A-1), (A-2), (I), (Ia), or (Ib), or a compound of Table 1, or a tautomer thereof, or a pharmaceutically acceptable salt of any of the foregoing, in the manufacture of a medicament for interfering with the heterodimerization of TLR2, or modulating, preventing, slowing, reversing, or inhibiting TLR2 heterodimerization.

Kits

Also provided are articles of manufacture and kits containing any of the compounds or pharmaceutical compositions provided herein. The article of manufacture may comprise a container with a label. Suitable containers include, for example, bottles, vials, and test tubes. The containers may be formed from a variety of materials such as glass or plastic. The container may hold a pharmaceutical composition provided herein. The label on the container may indicate that the pharmaceutical composition is used for preventing, treating or suppressing a condition described herein, and may also indicate directions for either in vivo or in vitro use.

In one aspect, provided herein are kits containing a compound or composition described herein and instructions for use. The kits may contain instructions for use in the treatment of a disease or condition associated with TLR2 heterodimerization in an individual in need thereof. A kit may additionally contain any materials or equipment that may be used in the administration of the compound or composition, such as vials, syringes, or IV bags. A kit may also contain sterile packaging.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

In some embodiments, compounds of the Formula (A), (A-1), or (A-2) may be synthesized according to Scheme A.

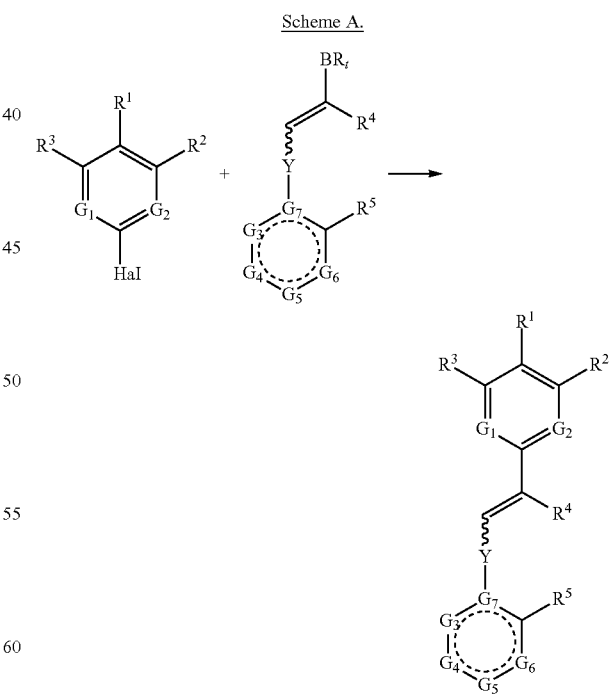

wherein $R^1$, $R^2$, $R^3$, $R^4$, $R^5$, Y, $G_1$, $G_2$, $G_3$, $G_4$, $G_5$, $G_6$, and $G_7$ are as defined for Formula (A), or any variation thereof detailed herein; Hal is a halogen, t is 2 or 3, and R is —OH, —Oalkyl, or halogen, or —$BR_t$ is

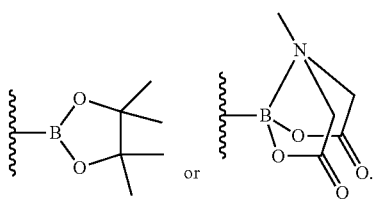

In some embodiments, compounds of the Formula (I), (Ia), or (Ib) may be synthesized according to Scheme 1.

Scheme 1.

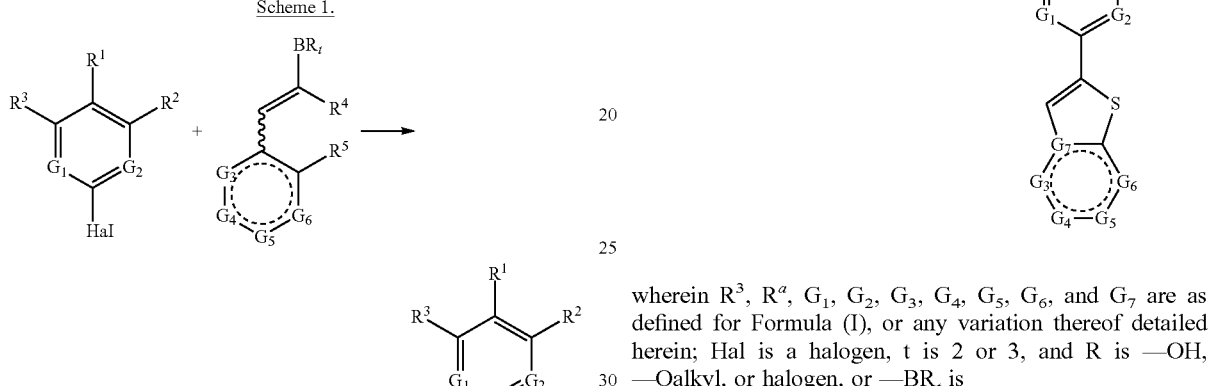

wherein $R^1$, $R^2$, $R^3$, $R^4$, $R^5$, $G_1$, $G_2$, $G_3$, $G_4$, $G_5$, and $G_6$ are as defined for Formula (I), or any variation thereof detailed herein; Hal is a halogen, t is 2 or 3, and R is —OH, —Oalkyl, or halogen, or —$BR_t$ is

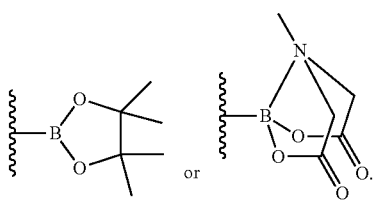

In some variations of the foregoing Scheme 1, compounds of the Formula (I) may be synthesized according to Scheme 1a.

Scheme 1a.

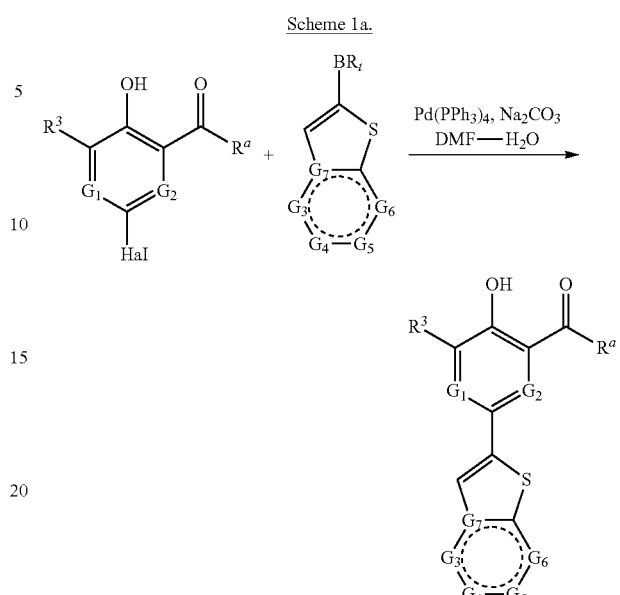

wherein $R^3$, $R^a$, $G_1$, $G_2$, $G_3$, $G_4$, $G_5$, $G_6$, and $G_7$ are as defined for Formula (I), or any variation thereof detailed herein; Hal is a halogen, t is 2 or 3, and R is —OH, —Oalkyl, or halogen, or —$BR_t$ is

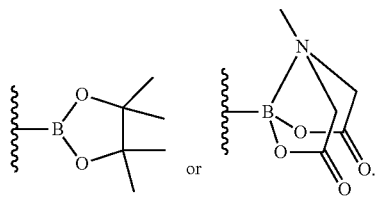

In some embodiments, compounds of the Formula (A), (A-1), or (A-2) may be synthesized according to Scheme B.

Scheme B.

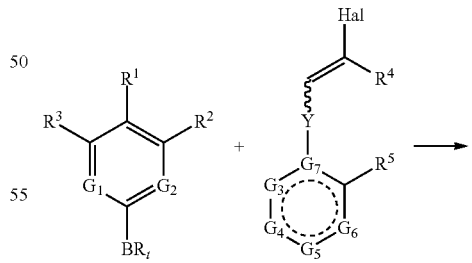

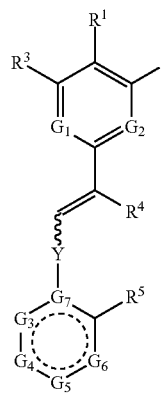

wherein $R^1$, $R^2$, $R^3$, $R^4$, $R^5$, Y, $G_1$, $G_2$, $G_3$, $G_4$, $G_5$, $G_6$, and $G_7$ are as defined for Formula (A), or any variation thereof detailed herein; Hal is a halogen, t is 2 or 3, and R is —OH, —Oalkyl, or halogen, or —$BR_t$ is

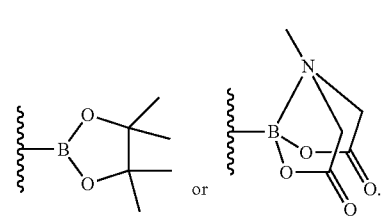

In some embodiments, compounds of the Formula (I), (Ia), or (Ib) may be synthesized according to Scheme 2.

Scheme 2.

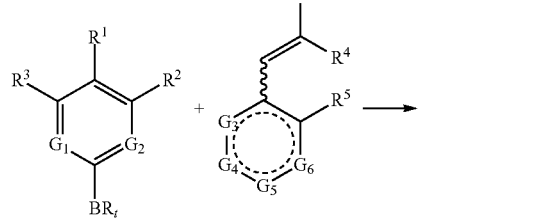

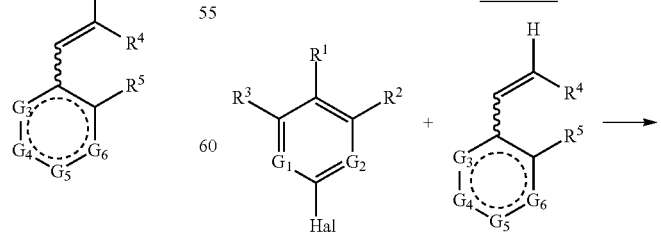

wherein $R^1$, $R^2$, $R^3$, $R^4$, $R^5$, $G_1$, $G_2$, $G_3$, $G_4$, $G_5$, and $G_6$ are as defined for Formula (I), or any variation thereof detailed herein; Hal is a halogen, t is 2 or 3, and R is —OH, —Oalkyl, or halogen, or —$BR_t$ is

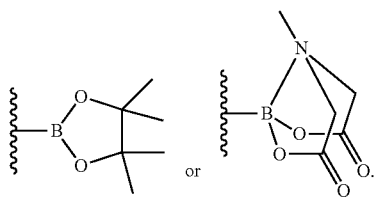

In some embodiments, compounds of the Formula (A), (A-1), or (A-2) may be synthesized according to Scheme C.

Scheme C.

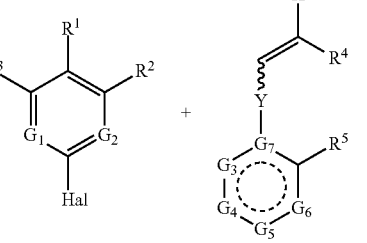

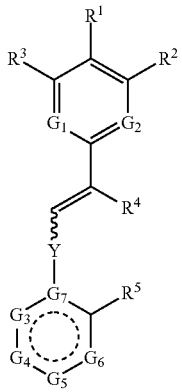

wherein $R^1$, $R^2$, $R^3$, $R^4$, $R^5$, Y, $G_1$, $G_2$, $G_3$, $G_4$, $G_5$, $G_6$, and $G_7$ are as defined for Formula (A), or any variation thereof detailed herein; and Hal is a halogen. In some embodiments, the compound of Formula (A), (A-1), or (A-2) is synthesized via Heck coupling.

In some embodiments, compounds of the Formula (I), (Ia), or (Ib) may be synthesized according to Scheme 3.

Scheme 3.

-continued

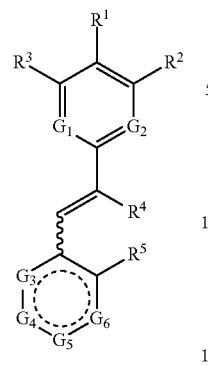

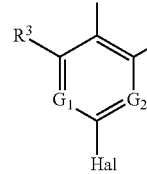

wherein $R^1$, $R^2$, $R^3$, $R^4$, $R^5$, $G_1$, $G_2$, $G_3$, $G_4$, $G_5$, and $G_6$ are as defined for Formula (I), or any variation thereof detailed herein; and Hal is a halogen. In some embodiments, the compound of Formula (I), (Ia), or (Ib) is synthesized via Heck coupling.

In some variations of the foregoing Scheme 3, compounds of the Formula (I), (Ia), or (Ib) may be synthesized according to Scheme 3a.

Scheme 3a.

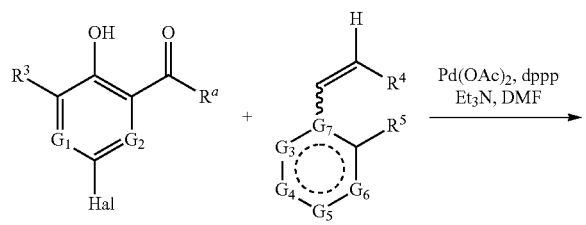

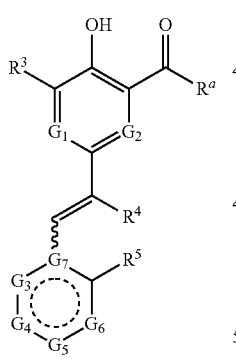

wherein $R^3$, $R^4$, $R^5$, $R^a$, $G_1$, $G_2$, $G_3$, $G_4$, $G_5$, $G_6$, and $G_7$ are as defined for Formula (I), or any variation thereof detailed herein, and Hal is a halogen.

In some variations of the foregoing Scheme 3, compounds of the Formula (I), (Ia), or (Ib) may be synthesized according to Scheme 3b.

Scheme 3b.

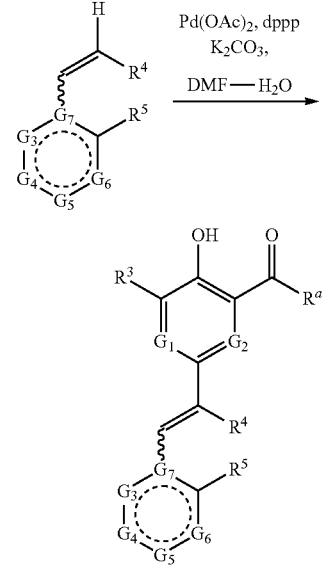

wherein $R^3$, $R^4$, $R^5$, $R^a$, $G_1$, $G_2$, $G_3$, $G_4$, $G_5$, $G_6$, and $G_7$ are as defined for Formula (I), or any variation thereof detailed herein, and Hal is a halogen.

In some embodiments, intermediates used in the synthesis of compounds of the Formula (A), (A-1), (A-2), (I), (Ia), or (Ib) may be synthesized according to Scheme 4.

Scheme 4

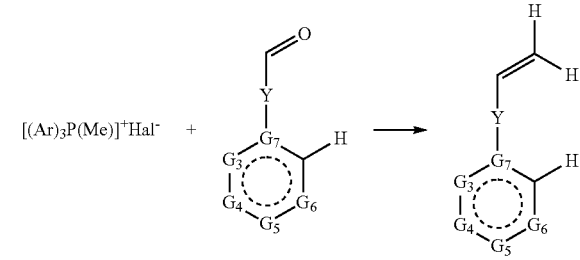

wherein $G_3$, $G_4$, $G_5$, $G_6$, $G_7$, and Y are as defined for Formula (A), or any variations thereof detailed herein; Hal is a halogen, and Ar is an aryl.

In some embodiments, compounds of the Formula (A) may be synthesized according to Scheme 5.

Scheme 5.

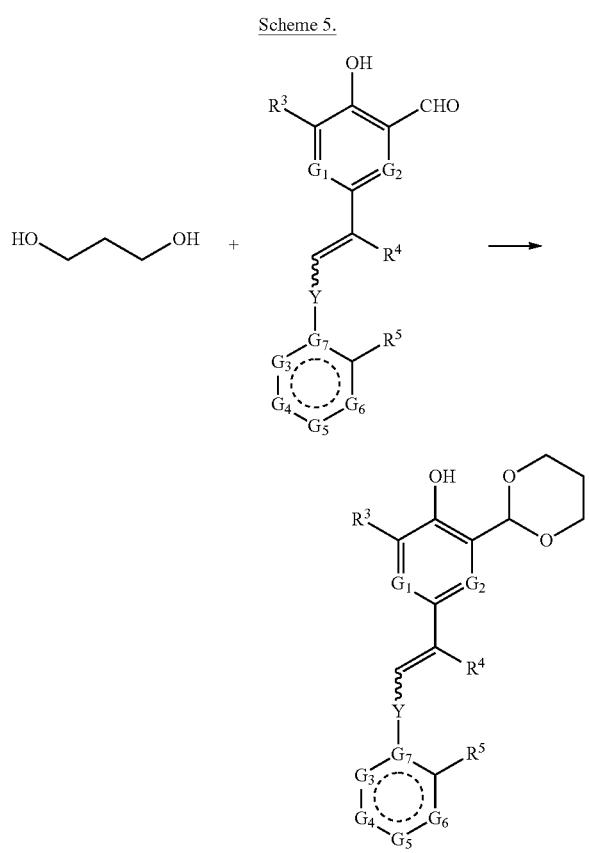

wherein $R^3$, $R^4$, $R^5$, $G_1$, $G_2$, $G_3$, $G_4$, $G_5$, $G_6$, $G_7$, and Y are as defined for Formula (A), or any variation thereof detailed herein.

In some embodiments, compounds of the Formula (A) may be synthesized according to Scheme 6.

Scheme 6.

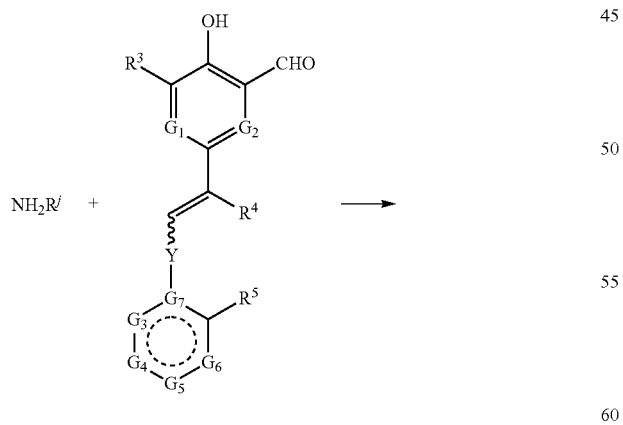

wherein $R^3$, $R^4$, $R^5$, $R^1$, $G_1$, $G_2$, $G_3$, $G_4$, $G_5$, $G_6$, $G_7$, and Y are as defined for Formula (A), or any variation thereof detailed herein.

In some variations of the foregoing Scheme 6, compounds of the Formula (I), (Ia), or (Ib) may be synthesized according to Scheme 6a.

Scheme 6a.

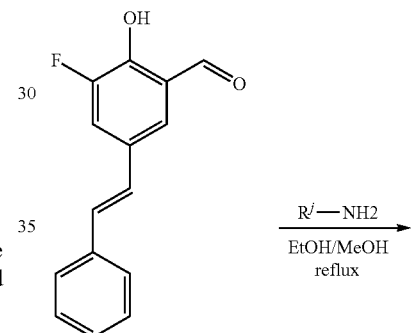

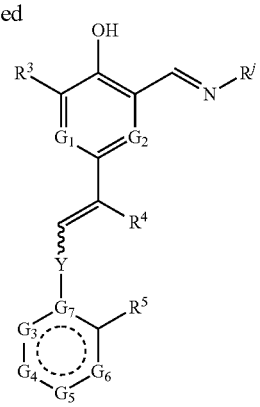

wherein $R^j$ is as defined for Formula (A), or any variation thereof detailed herein. In one embodiment of the procedure as described in Scheme 6a, (E)-3-fluoro-2-hydroxy-5-(4-(pyrrolidin-1-yl)styryl)benzaldehyde (1 eq.) and amine compound $R^j$—$NH_2$ (1 eq.) are dissolved in ethanol or methanol. The reaction is refluxed for 2 hours. The solvent is removed mostly, and the residue is filtered. The cake is washed with ethanol and dried in vacuo to give the desired product.

In some variations of Scheme 6, compounds of the Formula (I), (Ia), or (Ib) may be synthesized according to Scheme 6b.

Scheme 6b.

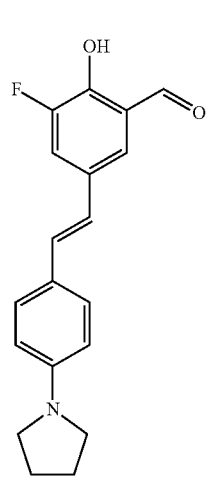

wherein $R^j$ is as defined for Formula (A), or any variation thereof detailed herein. In one embodiment of the procedure as described in Scheme 6b, (E)-3-fluoro-2-hydroxy-5-(4-(pyrrolidin-1-yl)styryl)benzaldehyde (1 eq.), the HCl salt of $R^j$—$NH_2$ (1.5 eq. or 2 eq.), and TEA (2 eq. or 3 eq.) are dissolved in ethanol. The reaction is refluxed for 2 hours. The solvent is removed mostly and the residue is filtered. The cake is washed with ethanol and dried in vacuo to give desired compound. In another embodiment of the procedure as described in Scheme 6b, (E)-3-fluoro-2-hydroxy-5-(4-(pyrrolidin-1-yl)styryl)benzaldehyde (1 eq.) and the free amine $R^j$—$NH_2$ or the HCl salt of the amine $R^j$—$NH_2$ (2 eq. or 1.2 eq.) are dissolved in ethanol with or without TEA (2 eq. or 3 eq.). The reaction is refluxed for 2 h. The resulting precipitate is filtered, washed with methanol, and dried in vacuo to give desired compound.

In some embodiments, compounds of the Formula (A) may be synthesized according to Scheme 7.

Scheme 7.

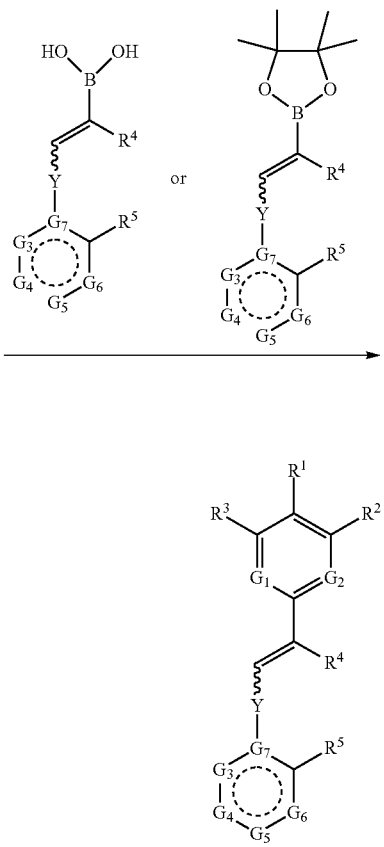

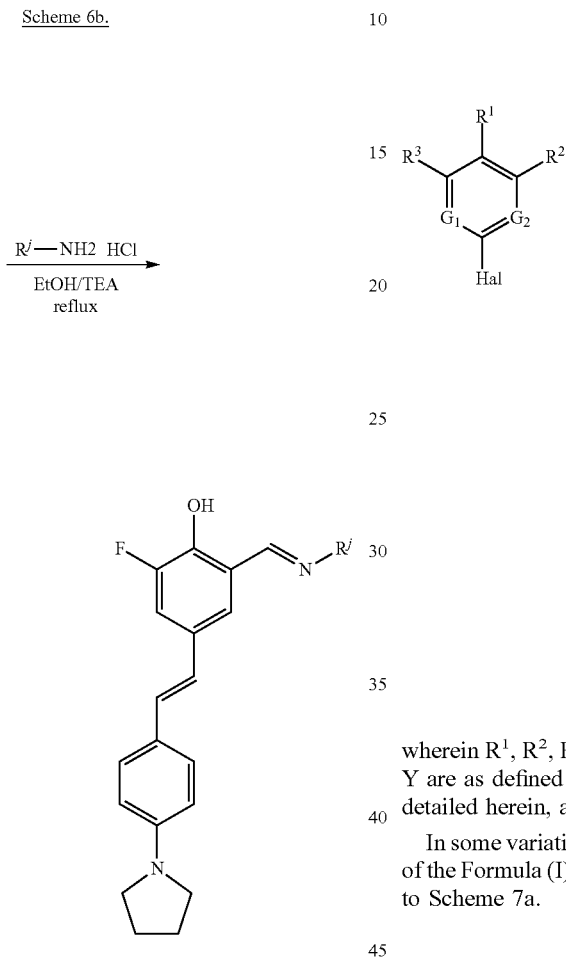

wherein $R^1$, $R^2$, $R^3$, $R^4$, $R^5$, $G_1$, $G_2$, $G_3$, $G_4$, $G_5$, $G_6$, $G_7$, and Y are as defined for Formula (A), or any variation thereof detailed herein, and Hal is a halogen.

In some variations of the foregoing Scheme 7, compounds of the Formula (I), (Ia), or (Ib) may be synthesized according to Scheme 7a.

Scheme 7a.

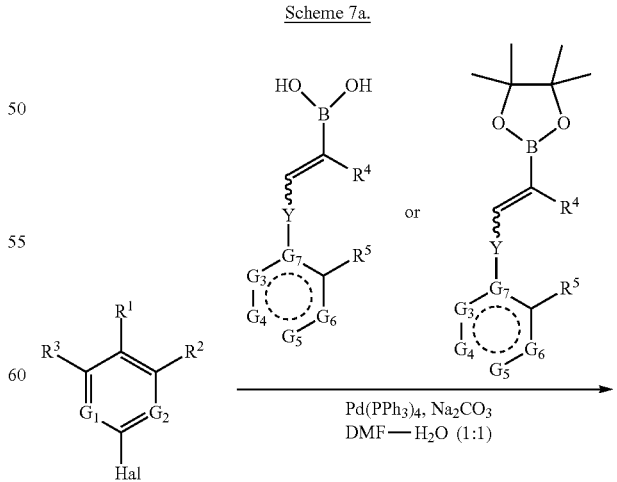

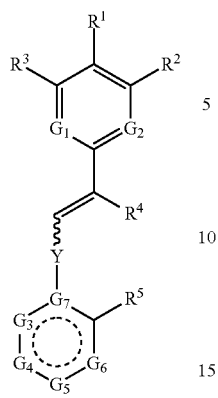

wherein $R^1$, $R^2$, $R^3$, $R^4$, $R^5$, $G_1$, $G_2$, $G_3$, $G_4$, $G_5$, $G_6$, $G_7$, and Y are as defined for Formula (A), or any variation thereof detailed herein.

Chemical Synthesis

Exemplary chemical entities useful in methods of the present disclosure will now be described by reference to the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes may be run at a temperature from about 0° C. to the reflux temperature of the organic solvent used. Isotopically labeled compounds as described herein are prepared according to the methods described below, using suitably labeled starting materials. Such materials are generally available from commercial suppliers of radiolabeled chemical reagents.

EXAMPLES

The following examples are offered to illustrate but not to limit the present disclosure. One of skill in the art will recognize that the following synthetic reactions and schemes may be modified by choice of suitable starting materials and reagents in order to access other compounds of Formula (A), (A-1), (A-2), (I), (Ia), or (Ib). The compounds are prepared using the general methods described above.

The following abbreviations are used throughout the Examples: Ac (acetate), Boc (tert-butyloxycarbonyl), dba (dibenzylideneacetone), DCM (dichloromethane), DMF (N,N-dimethylformamide), DMSO (dimethyl sulfoxide), dppf (1,1′-bis(diphenylphosphino)ferrocene), EA or EtOAc (Ethyl acetate), Et (ethyl), EtOH (ethanol), HPLC (high performance liquid chromatography), LAH (lithium aluminum hydride), mCPBA (meta-chloroperoxybenzoic acid), Me (methyl), MeOH (methanol), n-BuLi (n-butyllithium), OMe (methoxy), $PdCl_2(dppf)$ ((1,1′-bis(diphenylphosphino)ferrocene)palladium(II) dichloride), $Pd_2(dba)_3$ (tris(dibenzylideneacetone)dipalladium(0)), $Pd(OAc)_2$ (palladium(II) acetate), $Pd(PPh_3)_4$ (tetrakis(triphenylphosphine)palladium (0)), $PPh_3$ (triphenylphosphane), PinB (Bis(pinacolato)diboron), PMB (4-methoxybenzyl), PMB-Cl (4-methoxybenzyl chloride), TEA (trimethylamine), TFA (trifluoroacetic acid), THF (tetrahydrofuran), and TLC (thin layer chromatography).

Example 1: (E)-2-hydroxy-3-methoxy-5-(4-methoxystyryl)benzaldehyde

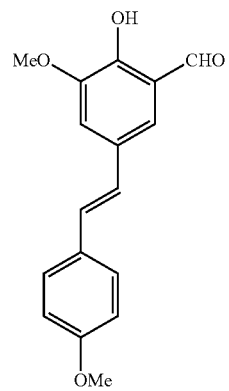

In a 30 mL sealed cap glass vial, 5-bromo-2-hydroxy-3-methoxybenzaldehyde (231 mg, 1.0 mmol), (E)-(4-methoxystyryl)boronic acid (214 mg, 1.2 mmol) and $Na_2CO_3$ (666 mg, 6.0 mmol) were suspended in DMF-water (10 mL). Then bubbled Argon gas for one to two minutes and added $Pd(PPh_3)_4$ (63 mg, 0.05 mmol) to the reaction vial and closed with sealed cap and continued at 105° C. for 16 hours on a stirrer plate with metallic beads contained dish. Then cooled to room temperature and diluted with water (20 mL) and transferred into a separating funnel using dichloromethane. Acidified the aqueous layer with 2.0 N HCl to pH~4.0 and extracted with additional dichloromethane (2×50 mL). Combined organic layer washed with brine, dried over sodium sulfate and evaporated completely. The resulted crude product purified using silica gel column chromatography (hexane through hexane-EtOAc (0-100%)) to give the title compound as a yellow solid (52 mg, 18% yield). $^1$H NMR (500 MHz, Chloroform-d) δ 11.06 (s, 1H), 9.95 (s, 1H), 7.55-7.35 (m, 2H), 7.27 (d, J=6.3 Hz, 2H), 6.97 (d, J=16.3 Hz, 1H), 6.94-6.87 (m, 3H), 3.99 (s, 3H), 3.84 (s, 3H); LC-MS m/z [M+H]$^+$ calc'd for $C_{17}H_{16}O_4$, 285; found, 285.

Example 2: (E)-2-hydroxy-3-methoxy-5-(3-(trifluoromethyl)styryl)benzaldehyde

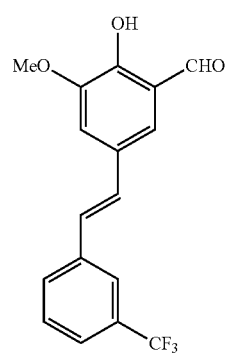

The title compound was prepared from 5-bromo-2-hydroxy-3-methoxybenzaldehyde (231 mg, 1.0 mmol) and (E)-4,4,5,5-tetramethyl-2-(3-(trifluoromethyl)styryl)-1,3,2-dioxaborolane (358 mg, 1.2 mmol) as described in Example 1 to give the title compound as a yellow solid (92 mg, 29% yield). $^1$H NMR (500 MHz, Chloroform-d) δ 11.14 (s, 1H), 9.96 (s, 1H), 7.75 (s, 1H), 7.70-7.61 (m, 1H), 7.50 (dt, J=15.3, 7.8 Hz, 2H), 7.36-7.29 (m, 2H), 7.13 (d, J=16.2 Hz, 1H), 7.03 (d, J=16.3 Hz, 1H), 4.00 (s, 3H); LC-MS m/z [M+H]$^+$ calc'd for $C_{17}H_{13}F_3O_3$, 323; found, 323.

Example 3:
5-(4-chlorostyryl)-2-hydroxy-3-methoxybenzaldehyde

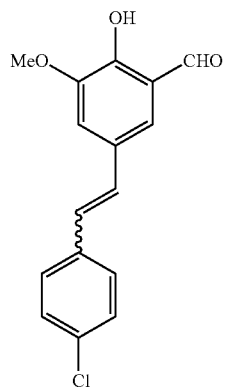

The title compound was prepared from 5-bromo-2-hydroxy-3-methoxybenzaldehyde (231 mg, 1.0 mmol) and (E)-2-(4-chlorostyryl)-4,4,5,5-tetramethyl-1,3,2-dioxaborolane (318 mg, 1.2 mmol) as described in Example 1 to give the title compound cis/trans mixture as a yellow solid (58 mg, 20% yield). $^1$H NMR (500 MHz, Chloroform-d) δ 11.22-10.92 (m, 1H), 10.04-9.73 (m, 1H), 7.53-7.36 (m, 1H), 7.36-7.32 (m, 1H), 7.31 (d, J=2.3 Hz, 1H), 7.28 (s, 1H), 7.21-7.17 (m, 1H), 7.12 (m, 1H), 7.06-6.93 (m, 2H), 3.99-3.92 (s, 3H); LC-MS m/z [M+Na]$^+$ calc'd for $C_{16}H_{13}ClO_3$, 311; found, 311.

Example 4:
(E)-2-hydroxy-3-methoxy-5-styrylbenzaldehyde

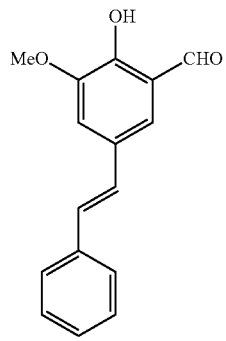

The title compound was prepared from 5-bromo-2-hydroxy-3-methoxybenzaldehyde (231 mg, 1.0 mmol) and (E)-styrylboronic acid (178 mg, 1.2 mmol) as described in Example 1 to give the title compound as a brownish yellow solid (122 mg, 48% yield). $^1$H NMR (500 MHz, Chloroform-d) δ 11.10 (s, 1H), 9.95 (s, 1H), 7.57-7.43 (m, 2H), 7.38 (t, J=7.6 Hz, 2H), 7.29 (dd, J=5.3, 3.2 Hz, 3H), 7.06 (d, J=16.3 Hz, 1H), 7.01 (d, J=16.3 Hz, 1H), 4.00 (s, 3H); LC-MS m/z [M+H]$^+$ calc'd for $C_{16}H_{14}O_3$, 255; found, 255.

Example 5: (E)-5-(3,5-difluorostyryl)-2-hydroxy-3-methoxybenzaldehyde

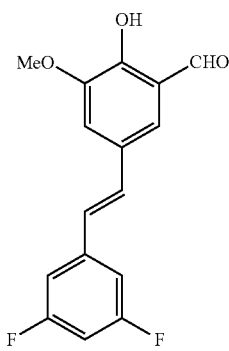

The title compound was prepared from 5-bromo-2-hydroxy-3-methoxybenzaldehyde (231 mg, 1.0 mmol) and (E)-2-(3,5-difluorostyryl)-4,4,5,5-tetramethyl-1,3,2-dioxaborolane (319 mg, 1.2 mmol) as described in Example 1 to give the title compound as a yellow solid (38 mg, 13% yield). $^1$H NMR (500 MHz, Chloroform-d) δ 11.15 (s, 1H), 9.96 (s, 1H), 7.30 (d, J=2.0 Hz, 1H), 7.27 (d, J=2.0 Hz, 1H), 7.05 (d, J=16.3 Hz, 1H), 7.01 (dt, J=7.0, 2.1 Hz, 2H), 6.91 (d, J=16.2 Hz, 1H), 6.72 (tt, J=8.8, 2.3 Hz, 1H), 4.00 (s, 3H); LC-MS m/z [M+H]$^+$ calc'd for $C_{16}H_{12}F_2O_3$, 291; found, 291.

Example 6: (E)-5-(2,4-difluorostyryl)-2-hydroxy-3-methoxybenzaldehyde

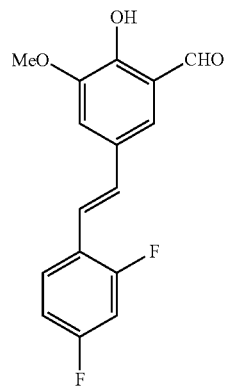

The title compound was prepared from 5-bromo-2-hydroxy-3-methoxybenzaldehyde (231 mg, 1.0 mmol) and (E)-2-(2,4-difluorostyryl)-4,4,5,5-tetramethyl-1,3,2-dioxaborolane (319 mg, 1.2 mmol) as described in Example 1 to give the title compound as a brownish yellow solid (152 mg, 52% yield). $^1$H NMR (500 MHz, Chloroform-d) δ 11.12 (s, 1H), 9.96 (s, 1H), 7.55 (td, J=8.6, 6.4 Hz, 1H), 7.29 (q, J=2.0 Hz, 2H), 7.09 (d, J=16.2 Hz, 1H), 7.05 (d, J=16.2 Hz, 1H), 6.90 (td, J=8.4, 2.7 Hz, 1H), 6.85 (ddd, J=11.1, 8.7, 2.6 Hz, 1H), 4.00 (s, 3H); LC-MS m/z [M+H]+ calc'd for C16H12F2O3, 291; found, 291.

Example 7: (E)-5-(4-fluorostyryl)-2-hydroxy-3-methoxybenzaldehyde

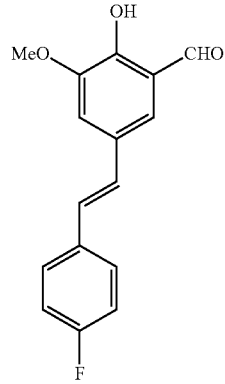

The title compound was prepared from 5-bromo-2-hydroxy-3-methoxybenzaldehyde (231 mg, 1.0 mmol) and (E)-(4-fluorostyryl)boronic acid (199 mg, 1.2 mmol) as described in Example 1 to give the title compound as a yellow solid (78 mg, 29% yield). $^1$H NMR (500 MHz, Chloroform-d) δ 11.09 (s, 1H), 9.95 (s, 1H), 7.52-7.41 (m, 2H), 7.28 (s, 2H), 7.10-7.02 (m, 2H), 6.97 (s, 2H), 3.99 (s, 3H); LC-MS m/z [M+H]+ calc'd for C16H13FO3, 273; found, 273.

Example 8: (E)-2-hydroxy-3-methoxy-5-(4-(trifluoromethyl)styryl)benzaldehyde

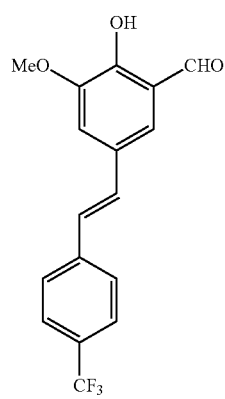

The title compound was prepared from 5-bromo-2-hydroxy-3-methoxybenzaldehyde (231 mg, 1.0 mmol) and (E)-(4-(trifluoromethyl)styryl)boronic acid (259 mg, 1.2 mmol) as described in Example 1 to give the title compound as a yellow solid (58 mg, 18% yield). $^1$H NMR (500 MHz, Chloroform-d) δ 11.14 (s, 1H), 9.97 (s, 1H), 7.65-7.57 (m, 4H), 7.33-7.28 (m, 2H), 7.14 (d, J=16.2 Hz, 1H), 7.03 (d, J=16.4 Hz, 1H), 3.96 (s, 3H); LC-MS m/z [M+H]+ calc'd for C17H13F3O3, 323; found, 323.

Example 9: (E)-1-(2-hydroxy-3-methoxy-5-(4-methoxystyryl)phenyl)ethan-1-one

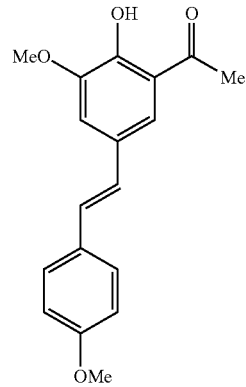

The title compound was prepared from 1-(5-bromo-2-hydroxy-3-methoxyphenyl)ethan-1-one (245 mg, 1.0 mmol) and (E)-(4-methoxystyryl)boronic acid (214 mg, 1.2 mmol) as described in Example 1 to give the title compound as a yellow solid (58 mg, 19% yield). $^1$H NMR (500 MHz, Chloroform-d) δ 12.59 (s, 1H), 7.51-7.41 (m, 2H), 7.38 (d, J=1.9 Hz, 1H), 7.25 (d, J=1.9 Hz, 1H), 6.96-6.85 (m, 4H), 3.97 (s, 3H), 3.84 (s, 3H), 2.68 (s, 3H); LC-MS m/z [M+H]+ calc'd for C18H18O4, 299; found, 299.

Example 10: (E)-3-fluoro-2-hydroxy-5-(4-methoxystyryl)benzaldehyde

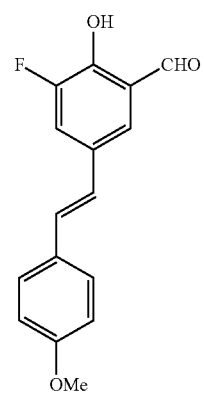

The title compound was prepared from 5-bromo-3-fluoro-2-hydroxybenzaldehyde (219 mg, 1.0 mmol) and (E)-(4-methoxystyryl)boronic acid (214 mg, 1.2 mmol) as described in Example 1 to give the title compound as a yellow solid (69 mg, 19% yield). $^1$H NMR (500 MHz, Chloroform-d) δ 10.90 (s, 1H), 9.95 (s, 1H), 7.53 (dd, J=11.8, 2.1 Hz, 1H), 7.46-7.41 (m, 3H), 6.97 (d, J=16.3 Hz, 1H), 6.94-6.90 (m, 2H), 6.87 (d, J=16.1 Hz, 1H), 3.84 (s, 3H); LC-MS m/z [M+H]+ calc'd for C16H13FO3, 273; found, 273.

Example 11: (E)-3-fluoro-2-hydroxy-5-(3-(trifluoromethyl)styryl)benzaldehyde

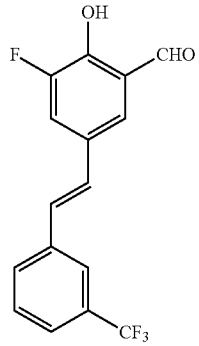

The title compound was prepared from 5-bromo-3-fluoro-2-hydroxybenzaldehyde (219 mg, 1.0 mmol) and (E)-4,4,5,5-tetramethyl-2-(3-(trifluoromethyl)styryl)-1,3,2-dioxaborolane (358 mg, 1.2 mmol) as described in Example 1 to give the title compound as a yellow solid (67 mg, 22% yield). $^1$H NMR (500 MHz, Chloroform-d) δ 10.99 (s, 1H), 9.97 (s, 1H), 7.74 (s, 1H), 7.66 (d, J=7.6 Hz, 1H), 7.57 (dd, J=11.6, 2.1 Hz, 1H), 7.55-7.46 (m, 3H), 7.09 (d, J=16.3 Hz, 1H), 7.03 (d, J=16.2 Hz, 1H); LC-MS m/z [M+H]$^+$ calc'd for $C_{16}H_{10}F_4O_2$, 311; found, 311.

Example 12: tert-butyl 2-(3-formyl-4-hydroxy-5-methoxyphenyl)-6,7-dihydrothieno[3,2-c]pyridine-5(4H)-carboxylate

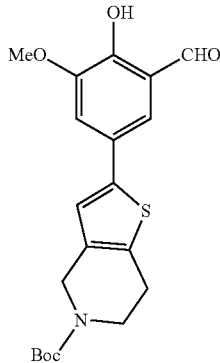 [SMILES: COc1cc(-c2cc3c(s2)CCN(C(=O)OC(C)(C)C)C3)cc(C=O)c1O]

The title compound was prepared from 5-bromo-2-hydroxy-3-methoxybenzaldehyde (462 mg, 2.0 mmol) and tert-butyl 2-(4,4,5,5-tetramethyl-1,3,2-dioxaborolan-2-yl)-6,7-dihydrothieno[3,2-c]pyridine-5(4H)-carboxylate (876 mg, 2.4 mmol) as described in Example 1 to give the title compound as a yellow solid (476 mg, 61% yield). $^1$H NMR (500 MHz, Chloroform-d) δ 11.06 (s, 1H), 9.95 (s, 1H), 7.33 (d, J=2.0 Hz, 1H), 6.94 (s, 1H), 4.50 (s, 2H), 3.97 (s, 3H), 3.75 (s, 2H), 2.86 (s, 2H), 1.50 (s, 9H); ESI-MS m/z [M+Na]$^+$ calc'd for $C_{20}H_{23}NO_5S$, 412; found, 412.

Example 13: 2-hydroxy-3-methoxy-5-(4,5,6,7-tetrahydrothieno[3,2-c]pyridin-2-yl)benzaldehyde hydrochloride

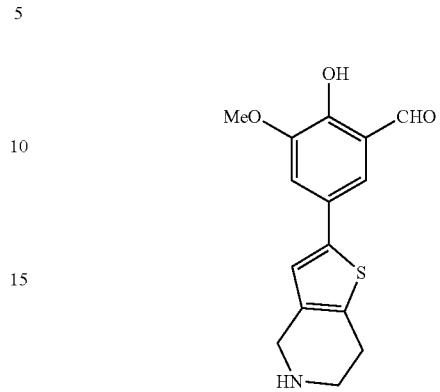

The title compound was prepared from above obtained Example 12, tert-butyl 2-(3-formyl-4-hydroxy-5-methoxyphenyl)-6,7-dihydrothieno[3,2-c]pyridine-5(4H)-carboxylate (97 mg, 0.25 mmol) in dichloromethane (2.0 mL) treated with 4 N HCl in dioxane (2.0 mL) for 3 hours at room temperature in a closed sealed cap glass vial (30 mL). Then evaporated volatiles completely and dried completely using lyophilizer to give the title compound as a yellow solid (48 mg). $^1$H NMR (500 MHz, DMSO-d$_6$) δ 10.44 (s, 1H), 10.31 (s, 1H), 9.48 (s, 2H), 7.43 (d, J=2.2 Hz, 1H), 7.37 (d, J=2.2 Hz, 1H), 7.31 (s, 1H), 4.17 (s, 2H), 3.94 (s, 3H), 3.57 (s, 1H), 3.43 (d, J=7.3 Hz, 2H), 3.05 (t, J=6.1 Hz, 2H); LC-MS m/z [M+H]$^+$ calc'd for $C_{15}H_{15}NO_3S$, 290; found, 290.

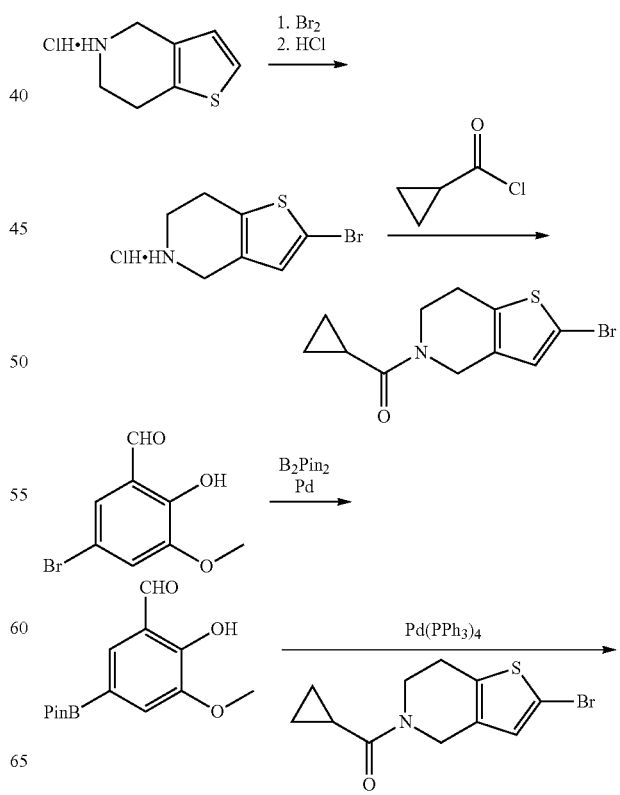

-continued

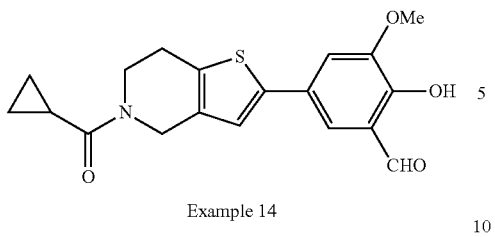

Example 14

Example 14: 5-(5-(cyclopropanecarbonyl)-4,5,6,7-tetrahydrothieno[3,2-c]pyridin-2-yl)-2-hydroxy-3-methoxybenzaldehyde

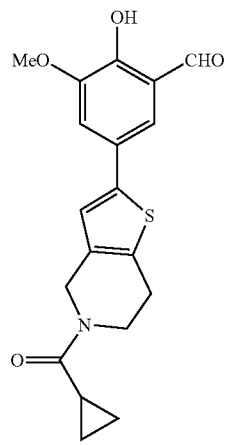 [SMILES: COc1cc(-c2cc3c(s2)CCN(C(=O)C2CC2)C3)cc(C=O)c1O]

Step 1: 2-Bromo-4,5,6,7-tetrahydrothieno[3,2-c]pyridine.HCl

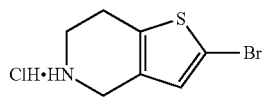

A solution of bromine (0.51 mL, 10.0 mmol) in acetic acid (1 mL) was added to a solution of 4,5,6,7-tetrahydrothieno[3,2-c]pyridine hydrochloride (1.75 g, 10.0 mmol) in acetic acid (5 mL). The reaction was stirred for 1.5 h. The reaction was quenched with sat. sodium bicarbonate (20 mL) and extracted with ethyl acetate (30 mL×3). The three organic extracts were combined, washed with brine (10 mL×2), dried over anhydrous sodium sulfate. 6 N HCl (gas)/dioxane (10 mL) was added and the mixture was concentrated in vacuo to give the desired product (1.7 g, 67% yield) as yellow solid. LC-MS m/z [M+H]$^+$ calc'd for $C_7H_8BrNS$, 219; found, 219.

Step 2: (2-bromo-6,7-dihydrothieno[3,2-c]pyridin-5(4H)-yl)(cyclopropyl)methanone

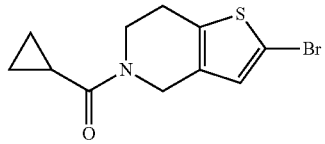 [SMILES: O=C(C1CC1)N1CCc2sc(Br)cc2C1]

TEA (1.65 mL, 11.9 mmol) and cyclopropanecarbonyl chloride (0.39 mL, 4.3 mmol) were added successively to a solution of 2-Bromo-4,5,6,7-tetrahydrothieno[3,2-c]pyridine.HCl (1 g, 3.95 mmol) in THF (10 mL) at 0° C. The reaction was stirred for 1 h at 0° C. The reaction mixture was quenched with water (30 mL) and extracted with ethyl acetate (30 mL×3). The organic extracts were combined, washed with brine (20 mL×2), dried over sodium sulfate, and concentrated. The residue was purified by silica gel column chromatography (petroleum ether/ethyl acetate=5:1 to 1:1) to give the desired product (0.97 g, 86% yield). LC-MS m/z [M+H]$^+$ calc'd for $C_{11}H_{12}BrNOS$, 287; found, 287.

Step 3: 2-Hydroxy-3-methoxy-5-(4,4,5,5-tetramethyl-1,3,2-dioxaborolan-2-yl)benzaldehyde

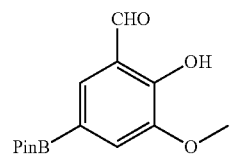

A mixture of 5-bromo-2-hydroxy-3-methoxybenzaldehyde (1.15 g, 5.0 mmol), Bis(pinacolato)diboron (1.4 g, 5.5 mmol), potassium acetate (1.5 g, 15.0 mmol), and $PdCl_2$(dppf) (0.4 g, 0.5 mmol) in dioxane (30 mL) was heated at 110° C. for 4 h. The reaction was quenched with water (50 mL) and extracted with ethyl acetate (50 mL×3). The organic extracts were combined, washed with brine (20 mL×2), dried over sodium sulfate, and concentrated. The residue was purified by silica gel column chromatography (petroleum ether/ethyl acetate=10:1 to 5:1) to give the desired product (310 mg, 22% yield) as yellow solid. $^1$H NMR (CDCl$_3$, 400 MHz) δ 11.37 (s, 1H), 9.93 (s, 1H), 7.69 (s, 1H), 7.49 (s, 1H), 3.96 (s, 3H), 1.35 (s, 12H).

Step 4: A mixture of 2-Hydroxy-3-methoxy-5-(4,4,5,5-tetramethyl-1,3,2-dioxaborolan-2-yl)benzaldehyde (50 mg, 0.18 mmol), (2-bromo-6,7-dihydrothieno[3,2-c]pyridin-5(4H)-yl)(cyclopropyl)methanone (51 mg, 0.18 mmol), $Na_2CO_3$ (96 mg, 0.9 mmol), and Pd(PPh$_3$)$_4$ (10 mg, 0.01 mmol) in DMF (2 mL) and H$_2$O (2 mL) was stirred at 95° C. for 2 h under N$_2$. The reaction mixture was poured into water (10 mL) and extracted with ethyl acetate (10 mL×3). The combined organics were washed with brine (10 mL), dried over sodium sulfate, and concentrated. The crude was purified by prep-TLC to afford the desired product (13 mg, 20% yield). $^1$H NMR (400 MHz, Chloroform-d) δ 11.07 (s, 1H), 9.95 (s, 1H), 7.33 (s, 1H), 6.95 (s, 1H), 4.74 (m, 2H), 3.98 (s, 5H), 2.93 (m, 2H), 1.82 (m, 1H), 1.04 (m, 2H), 0.84 (m, 2H); LC-MS m/z [M−H]$^-$ calc'd for $C_{19}H_{19}NO_4S$, 356; found, 356.

Example 15: 5-(5-acetyl-4,5,6,7-tetrahydrothieno[3,2-c]pyridin-2-yl)-2-hydroxy-3-methoxybenzaldehyde

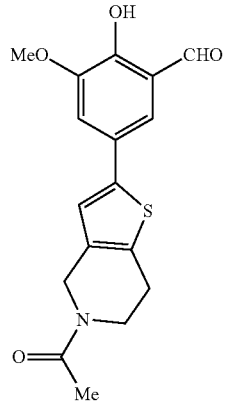 [SMILES: COc1cc(-c2cc3c(s2)CCN(C(C)=O)C3)cc(C=O)c1O]

Step 1: 1-(2-Bromo-6,7-dihydrothieno[3,2-c]pyridin-5(4H)-yl)ethanone

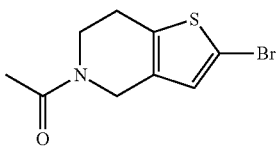

TEA (1.65 mL, 11.9 mmol) and acetyl chloride (0.35 mL, 4.3 mmol) were added successively to a solution of 2-bromo-4,5,6,7-tetrahydrothieno[3,2-c]pyridine hydrochloride (1 g, 3.95 mmol) prepared as in Example 14, in THF (10 mL) at 0° C. The reaction was stirred for 1 h at 0° C. The reaction mixture was quenched with water (30 mL) and extracted with ethyl acetate (30 mL×3). The organic extracts were combined, washed with brine (20 mL×2), dried over sodium sulfate, and concentrated. The residue was purified by silica gel column chromatography (petroleum ether/ethyl acetate=5:1 to 1:1) to give the desired product (0.93 g, 91% yield). LC-MS m/z [M+H]$^+$ calc'd for $C_9H_{10}BrNOS$, 261; found, 261.

Step 2: A mixture of 1-(2-Bromo-6,7-dihydrothieno[3,2-c]pyridin-5(4H)-yl)ethanone (259 mg, 1.0 mmol), 2-hydroxy-3-methoxy-5-(4,4,5,5-tetramethyl-1,3,2-dioxaborolan-2-yl)benzaldehyde (278 mg, 1.0 mmol) prepared as in Example 14, $Na_2CO_3$ (530 mg, 5.0 mmol), and $Pd(PPh_3)_4$ (58 mg, 0.05 mmol) in DMF (10 mL) and $H_2O$ (10 mL) was stirred at 95° C. for 2 h under $N_2$. The reaction mixture was poured into water (30 mL) and extracted with ethyl acetate (30 mL×3). The combined organics were washed with brine (30 mL), dried over sodium sulfate, and concentrated. The crude was purified by prep-TLC to afford the desired product (52 mg, 16% yield). $^1$H NMR (400 MHz, Chloroform-d) δ 11.07 (s, 1H), 9.95 (s, 1H), 7.33 (s, 1H), 7.24 (s, 1H), 6.94 (s, 1H), 4.68 (s, 1H), 4.55 (s, 1H), 3.98 (s, 3H), 3.94 (m, 1H), 3.78 (m, 1H), 2.94 (m, 2H), 2.19 (m, 3H); LC-MS m/z [M+H]$^+$ calc'd for $C_{17}H_{17}NO_4S$, 332; found, 332.

Example 16: 5-(5-(2-fluoroethyl)-4,5,6,7-tetrahydrothieno[3,2-c]pyridin-2-yl)-2-hydroxy-3-methoxybenzaldehyde

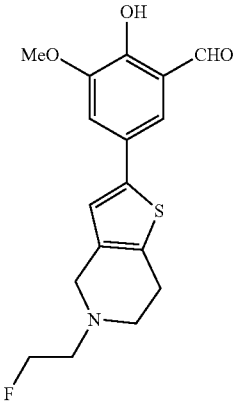 [SMILES: COc1cc(-c2cc3c(s2)CCN(CCF)C3)cc(C=O)c1O]

Step 1: 2-Bromo-5-(2-fluoroethyl)-4,5,6,7-tetrahydrothieno[3,2-c]pyridine

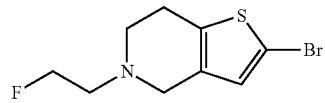 [SMILES: FCCN1CCc2sc(Br)cc2C1]

KOH (1.1 g, 19.75 mmol) and 1-bromo-2-fluoroethane (4.98 g, 39.5 mmol) were added to a solution of 2-bromo-4,5,6,7-tetrahydrothieno[3,2-c]pyridine hydrochloride (1 g, 3.95 mmol) prepared as in Example 14, in MeOH (40 mL). The reaction was stirred for 3 hours at room temperature. The reaction mixture was quenched with water (100 mL) and extracted with ethyl acetate (100 mL×3). The organic extracts were combined, washed with brine (100 mL×2), dried over sodium sulfate, and concentrated. The residue was purified by silica gel column chromatography (dichloromethane/methanol=20:1 to 10:1) to give the desired product (0.88 g, 85% yield). $^1$H NMR (400 MHz, Chloroform-d) δ 6.68 (s, 1H), 4.69 (m, 1H), 4.57 (m, 1H), 3.60 (s, 2H), 2.80-2.94 (m, 6H); LC-MS m/z [M+H]$^+$ calc'd for $C_9H_{11}BrFNS$, 265; found, 265.

Step 2: 3-Methoxy-2-(4-methoxybenzyloxy)-5-(4,4,5,5-tetramethyl-1,3,2-dioxaborolan-2-yl)benzaldehyde

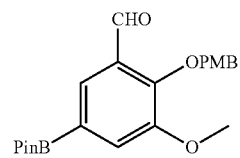

PMB-Cl (0.54 mL, 4.0 mmol) was added to a mixture of 2-hydroxy-3-methoxy-5-(4,4,5,5-tetramethyl-1,3,2-dioxaborolan-2-yl)benzaldehyde (532 mg, 2.0 mmol) prepared as in Example 14, and potassium carbonate (552 mg, 4.0 mmol) in DMF (10 mL). The reaction was stirred for 3 hours at room temperature. The reaction mixture was quenched with water (50 mL) and extracted with ethyl acetate (50 mL×3). The organic extracts were combined, washed with brine (30 mL×2), dried over sodium sulfate, and concentrated. The residue was purified by silica gel column chromatography (petroleum ether/ethyl acetate=20:1 to 10:1) to give the desired product (0.63 g, 82% yield).

Step 3: 5-(5-(2-fluoroethyl)-4,5,6,7-tetrahydrothieno[3,2-c]pyridin-2-yl)-3-methoxy-2-((4-methoxybenzyl)oxy)benzaldehyde

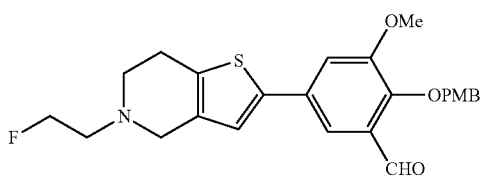

A mixture of 2-Bromo-5-(2-fluoroethyl)-4,5,6,7-tetrahydrothieno[3,2-c]pyridine (263 mg, 1.0 mmol), 3-Methoxy-2-(4-methoxybenzyloxy)-5-(4,4,5,5-tetramethyl-1,3,2-dioxaborolan-2-yl)benzaldehyde (398 mg, 1.0 mmol), $Na_2CO_3$ (320 mg, 3.0 mmol), and $Pd(PPh_3)_4$ (58 mg, 0.05 mmol) in DMF (10 mL) and $H_2O$ (10 mL) was stirred at 95° C. for 2 h under $N_2$. The reaction mixture was poured into water (30 mL) and extracted with ethyl acetate (30 mL×3). The combined organics were washed with brine (30 mL), dried over sodium sulfate, and concentrated. The crude was purified by prep-TLC to afford the desired product (160 mg, 36% yield). $^1$H NMR (400 MHz, Chloroform-d) δ 10.20 (s, 1H), 7.53 (s, 1H), 7.36 (m, 2H), 7.27 (m, 1H), 7.05 (m, 2H), 6.95 (s, 1H), 5.14 (s, 2H), 4.72 (m, 1H), 4.60 (m, 1H), 3.99 (s, 3H), 3.74 (m, 2H), 3.67 (m, 2H), 2.93 (m, 6H).

Step 4: 5-(5-(2-fluoroethyl)-4,5,6,7-tetrahydrothieno[3,2-c]pyridin-2-yl)-3-methoxy-2-((4-methoxybenzyl)oxy)benzaldehyde (160 mg, 0.36 mmol) was dissolved in DCM (2 mL) and TFA (1 mL) was added. The reaction was stirred for 30 min. The solution was concentrated in vacuo. The residue was dissolved in sat. sodium bicarbonate (5 mL) and extracted with ethyl acetate (5 mL×3). The organic extracts were combined, dried over anhydrous sodium sulfate, and concentrated. The crude was purified by prep-TLC to afford desired product (88 mg, 75% yield) as yellow solid. $^1$H NMR (400 MHz, Chloroform-d) δ 11.10 (br, 1H), 9.94 (s, 1H), 7.32 (s, 1H), 7.24 (s, 1H), 6.89 (s, 1H), 4.79 (m, 1H), 4.67 (m, 1H), 3.97 (s, 3H), 3.76 (s, 2H), 3.00 (m, 6H); LC-MS m/z [M+H]$^+$ calc'd for $C_{17}H_{18}FNO_3S$, 336; found, 336.

Example 17: 5-(5-(cyclopropylmethyl)-4,5,6,7-tetrahydrothieno[3,2-c]pyridin-2-yl)-2-hydroxy-3-methoxybenzaldehyde

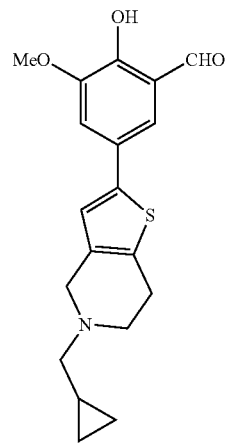 [SMILES: COc1cc(-c2cc3c(s2)CCN(CC2CC2)C3)cc(C=O)c1O]

Step 1: Cyclopropyl(6,7-dihydrothieno[3,2-c]pyridin-5(4H)-yl)methanone

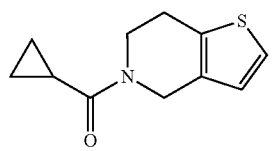 [SMILES: O=C(C1CC1)N1CCc2sccc2C1]

TEA (4.77 mL, 34.3 mmol) and cyclopropanecarbonyl chloride (1.14 mL, 12.6 mmol) were added successively to a solution of 4,5,6,7-tetrahydrothieno[3,2-c]pyridine hydrochloride (2 g, 11.4 mmol) in THF (10 mL) at 0° C. The reaction was stirred for 1 h at 0° C. The reaction mixture was quenched with water (30 mL) and extracted with ethyl acetate (30 mL×3). The organic extracts were combined, washed with brine (20 mL×2), dried over sodium sulfate, and concentrated. The residue was purified by silica gel column chromatography (petroleum ether/ethyl acetate=5:1 to 1:1) to give the titled compound (2.2 g, 93% yield). LC-MS m/z [M+H]$^+$ calc'd for $C_{11}H_{13}NOS$, 208; found, 208.

Step 2: 5-(cyclopropylmethyl)-4,5,6,7-tetrahydrothieno[3,2-c]pyridine

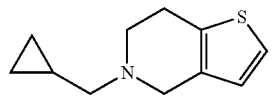 [SMILES: c1cc2c(s1)CCN(CC1CC1)C2]

LAH (700 mg, 18.4 mmol) was added to a solution of cyclopropyl(6,7-dihydrothieno[3,2-c]pyridin-5(4H)-yl)methanone (1 g, 4.8 mmol) in THF (10 mL) at 0° C. The reaction was heated at 60° C. for 1 h. The reaction mixture was cooled to rt, quenched with water (30 mL) and extracted with ethyl acetate (30 mL×3). The organic extracts were combined, washed with brine (20 mL×2), dried over sodium sulfate, and concentrated. The residue was purified by silica gel column chromatography (dichloromethane/methanol=100:1 to 20:1) to give the desired product (0.64 g, 69% yield). LC-MS m/z [M+H]+ calc'd for $C_{11}H_{15}NS$, 194; found, 194.

Step 3: 2-Bromo-5-(cyclopropylmethyl)-4,5,6,7-tetrahydrothieno[3,2-c]pyridine

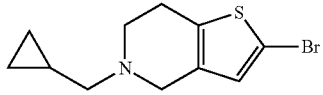 [SMILES: Brc1cc2c(s1)CCN(CC1CC1)C2]

Bromine (0.13 mL, 2.59 mmol) was added to a solution of compound 2 (500 mg, 2.59 mmol) in DMF/water (6 mL/12 mL) at 0° C. The reaction was stirred for 30 min at 0° C. The reaction was quenched with sat. sodium bicarbonate (20 mL) and extracted with ethyl acetate (30 mL×3). The three organic extracts were combined, washed with brine (10 mL×2), dried over anhydrous sodium sulfate. The residue was purified by silica gel column chromatography (dichloromethane/methanol=100:1 to 30:1) to give the desired product (0.41 g, 58% yield). LC-MS m/z [M+H]+ calc'd for $C_{11}H_{14}BrNS$, 272; found, 272.

Step 4: 5-(5-(cyclopropylmethyl)-4,5,6,7-tetrahydrothieno[3,2-c]pyridin-2-yl)-3-methoxy-2-((4-methoxybenzyl)oxy)benzaldehyde

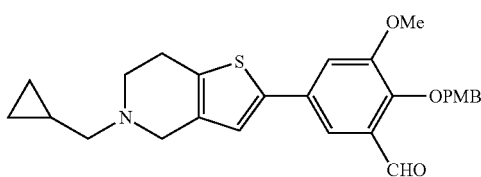

A mixture of 2-Bromo-5-(cyclopropylmethyl)-4,5,6,7-tetrahydrothieno[3,2-c]pyridine (271 mg, 1.0 mmol), 3-methoxy-2-(4-methoxybenzyloxy)-5-(4,4,5,5-tetramethyl-1,3,2-dioxaborolan-2-yl)benzaldehyde (398 mg, 1.0 mmol) prepared as in Example 16, $Na_2CO_3$ (320 mg, 3.0 mmol), and $Pd(PPh_3)_4$ (58 mg, 0.05 mmol) in DMF (10 mL) and $H_2O$ (10 mL) was stirred at 95° C. for 2 h under $N_2$. The reaction mixture was poured into water (30 mL) and extracted with ethyl acetate (30 mL×3). The combined organics were washed with brine (30 mL), dried over sodium sulfate, and concentrated. The crude was purified by prep-TLC to afford the desired product (90 mg, 19% yield).

Step 5: 5-(5-(cyclopropylmethyl)-4,5,6,7-tetrahydrothieno[3,2-c]pyridin-2-yl)-3-methoxy-2-((4-methoxybenzyl)oxy)benzaldehyde (90 mg, 0.19 mmol) was dissolved in DCM (2 mL) and TFA (1 mL) was added. The reaction was stirred for 30 min. The solution was concentrated in vacuo. The residue was dissolved in sat. sodium bicarbonate (5 mL) and extracted with ethyl acetate (5 mL×3). The organic extracts were combined, dried over anhydrous sodium sulfate, and concentrated. The crude was purified by prep-TLC to afford the desired product (57 mg, 85% yield) as yellow solid. 1H NMR (400 MHz, Chloroform-d) δ 10.31 (s, 1H), 7.44 (s, 1H), 7.36 (s, 1H), 7.30 (s, 1H), 3.94 (s, 3H), 3.27 (m, 4H), 3.03 (m, 4H), 1.09 (m, 1H), 0.61 (m, 2H), 0.29 (m, 2H); LC-MS m/z [M+H]+ calc'd for $C_{19}H_{21}NO_3S$, 344; found, 344.

Example 18: 3-fluoro-2-hydroxy-5-(5-methyl-4,5,6,7-tetrahydrothieno[3,2-c]pyridin-2-yl)benzaldehyde

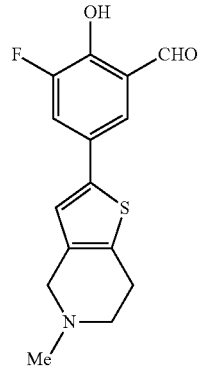 [SMILES: CN1CCc2sc(-c3cc(F)c(O)c(C=O)c3)cc2C1]

Step 1: 2-Bromo-5-methyl-4,5,6,7-tetrahydrothieno[3,2-c]pyridine

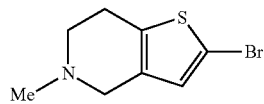

A mixture of formaldehyde aqueous solution (3.93 mL, 39.5 mmol, 37% concentration), acetic acid (2 mL), 2-bromo-4,5,6,7-tetrahydrothieno[3,2-c]pyridine hydrochloride (1 g, 3.95 mmol), prepared as in Example 14 and $NaBH_3CN$ (0.50 g, 79.0 mmol) in MeOH (12 mL) was stirred overnight at rt. The reaction mixture was quenched with water (30 mL) and extracted with ethyl acetate (30 mL×3). The organic extracts were combined, washed with brine (20 mL×2), dried over sodium sulfate, and concentrated. The residue was purified by silica gel column chromatography (petroleum ether/ethyl acetate/dichloromethane=20:1:1 to 5:1:1) gave the desired product (0.32 g, 35% yield). LC-MS m/z [M+H]+ calc'd for $C_8H_{10}BrNS$, 232; found, 232.

Step 2: 5-Bromo-3-fluoro-2-(4-methoxybenzyloxy)benzaldehyde

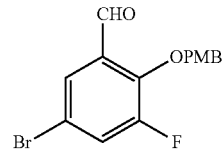

PMB-Cl (1.79 g, 11.5 mmol) was added to a mixture of 5-bromo-3-fluoro-2-hydroxybenzaldehyde (1 g, 4.6 mmol) and potassium carbonate (1.9 g, 13.8 mmol) in DMF (10 mL). The reaction was stirred for 3 h at rt. The reaction mixture was quenched with water (50 mL) and extracted with ethyl acetate (50 mL×3). The organic extracts were combined, washed with brine (30 mL×2), dried over sodium sulfate, and concentrated. The residue was purified by silica gel column chromatography (petroleum ether/ethyl acetate=100:1 to 20:1) gave the desired product (1.37 g, 88% yield).

Step 3: 3-Fluoro-2-(4-methoxybenzyloxy)-5-(4,4,5,5-tetramethyl-1,3,2-dioxaborolan-2-yl)benzaldehyde

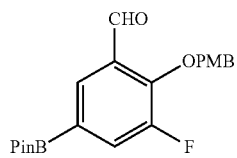

A mixture of 5-Bromo-3-fluoro-2-(4-methoxybenzyloxy)benzaldehyde (1.37 g, 4.1 mmol), Bis(pinacolato)diboron (1.1 g, 4.5 mmol), potassium acetate (1.2 g, 12.3 mmol), and $PdCl_2(dppf)$ (0.3 g, 0.4 mmol) in dioxane (30 mL) was heated at 110° C. for 4 h. The reaction was quenched with water (50 mL) and extracted with ethyl acetate (50 mL×3). The organic extracts were combined, washed with brine (20 mL×2), dried over sodium sulfate, and concentrated. The residue was purified by silica gel column chromatography (petroleum ether/ethyl acetate=10:1 to 5:1) gave the desired product (1.14 g, 73% yield).

Step 4: A mixture of 2-bromo-5-methyl-4,5,6,7-tetrahydrothieno[3,2-c]pyridine (84 mg, 0.36 mmol), 3-Fluoro-2-(4-methoxybenzyloxy)-5-(4,4,5,5-tetramethyl-1,3,2-dioxaborolan-2-yl)benzaldehyde (140 mg, 0.36 mmol), $Na_2CO_3$ (192 mg, 1.81 mmol), and $Pd(PPh_3)_4$ (21 mg, 0.02 mmol) in DMF (7 mL) and $H_2O$ (1 mL) was stirred at 95° C. for 2 h under $N_2$. PMB was off during the reaction. The reaction mixture was poured into water (30 mL) and extracted with ethyl acetate (30 mL×3). The combined organics were washed with brine (30 mL), dried over sodium sulfate, and concentrated. The crude was purified by prep-TLC to afford the desired product (15 mg, 10% yield) as yellow solid. $^1$H NMR (400 MHz, Chloroform-d) δ 10.28 (s, 1H), 7.76 (dd, J=12.0 Hz, 2.0 Hz, 1H), 7.57 (d, J=1.2 Hz, 1H), 7.20 (s, 1H), 3.60 (s, 2H), 3.27 (m, 4H), 2.88 (s, 3H); LC-MS m/z $[M+H]^+$ calc'd for $C_{15}H_{14}FNO_2S$, 292; found, 292.

Example 19: 5-(5-acetyl-4,5,6,7-tetrahydrothieno[3,2-c]pyridin-2-yl)-3-fluoro-2-hydroxybenzaldehyde

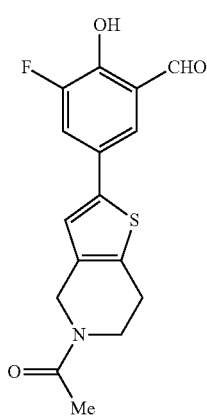 [SMILES: CC(=O)N1CCc2sc(-c3cc(F)c(O)c(C=O)c3)cc2C1]

A mixture of 1-(2-bromo-6,7-dihydrothieno[3,2-c]pyridin-5(4H)-yl)ethanone (67 mg, 0.26 mmol), prepared as in Example 15, 3-fluoro-2-(4-methoxybenzyloxy)-5-(4,4,5,5-tetramethyl-1,3,2-dioxaborolan-2-yl)benzaldehyde (100 mg, 0.26 mmol), prepared as in Example 18, $Na_2CO_3$ (137 mg, 1.30 mmol), and $Pd(PPh_3)_4$ (15 mg, 0.01 mmol) in DMF (5 mL) and $H_2O$ (1 mL) was stirred at 95° C. for 2 h under $N_2$. PMB was off during the reaction. The reaction mixture was poured into water (30 mL) and extracted with dichloromethane (30 mL×3). The combined organics were washed with brine (30 mL), dried over sodium sulfate, and concentrated. The crude was purified by prep-TLC to afford desired product (39 mg, 47% yield) as yellow solid. $^1$H NMR (DMSO-d6, 400 MHz) δ 11.12 (br, 1H), 10.30 (s, 1H), 7.80 (dd, J=12.0 Hz, 2.4 Hz, 1H), 7.60 (s, 1H), 7.28 (m, 1H), 4.52 (m, 2H), 3.74 (m, 2H), 2.76-2.88 (m, 2H), 2.08-2.11 (m, 3H); LC-MS m/z $[M-H]^-$ calc'd for $C_{16}H_{14}FNO_3S$, 318; found, 318.

Example 20: 2-hydroxy-5-(5-isopropyl-4,5,6,7-tetrahydrothieno[3,2-c]pyridin-2-yl)-3-methoxybenzaldehyde

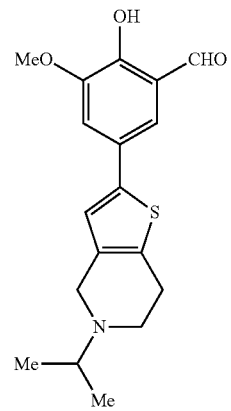

Step 1: 2-Bromo-5-isopropyl-4,5,6,7-tetrahydrothieno[3,2-c]pyridine

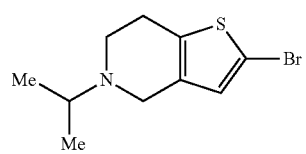 [SMILES: CC(C)N1CCc2sc(Br)cc2C1]

Acetone (1.83 g, 31.6 mmol) and acetic acid (1.81 mL, 31.6 mmol) were added to a solution of 2-bromo-4,5,6,7-tetrahydrothieno[3,2-c]pyridine hydrochloride (2 g, 7.9 mmol), prepared as in Example 14, and triethylamine (2.2 mL, 15.8 mmol) in MeOH (20 mL). The reaction was stirred for 20 min and $NaBH_3CN$ (2.49 g, 39.5 mmol) was added. The reaction was then stirred overnight at rt. The reaction mixture was quenched with water (30 mL) and extracted with ethyl acetate (30 mL×3). The organic extracts were combined, washed with brine (20 mL×2), dried over sodium sulfate, and concentrated. The residue was purified by silica gel column chromatography (petroleum ether/ethyl acetate/ dichloromethane=20:1:1 to 5:1:1) gave the desired product (1.9 g, 93% yield). LC-MS m/z [M+H]+ calc'd for $C_{10}H_{14}BrNS$, 261; found, 261.

Step 2: A mixture of 2-Bromo-5-isopropyl-4,5,6,7-tetrahydrothieno[3,2-c]pyridine (100 mg, 0.39 mmol), 2-hydroxy-3-methoxy-5-(4,4,5,5-tetramethyl-1,3,2-dioxaborolan-2-yl)benzaldehyde (107 mg, 0.39 mmol), prepared as in Example 13, $Na_2CO_3$ (204 mg, 1.96 mmol), and $Pd(PPh_3)_4$ (22 mg, 0.02 mmol) in DMF (3 mL) and $H_2O$ (2 mL) was stirred at 95° C. for 2 h under $N_2$. The reaction mixture was poured into water (30 mL) and extracted with ethyl acetate (30 mL×3). The combined organics were washed with brine (30 mL), dried over sodium sulfate, and concentrated. The crude was purified by prep-HPLC to afford desired product (23 mg, 18% yield) as yellow solid. $^1$H NMR (DMSO-d6, 400 MHz) δ 10.29 (s, 1H), 7.41 (s, 1H), 7.32 (s, 1H), 7.18 (s, 1H), 3.92 (s, 3H), 3.50 (m, 4H), 2.89 (m, 1H), 2.76 (m, 4H), 1.06 (d, J=6.4 Hz, 6H); LC-MS m/z [M+H]+ calc'd for $C_{18}H_{21}NO_3S$, 332; found, 332.

Example 21: (E)-2-hydroxy-5-(2-(6-methylpyridin-3-yl)vinyl)benzaldehyde

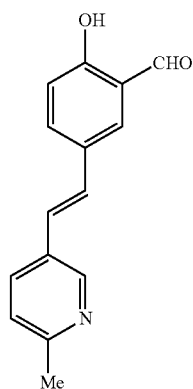

In a 30 mL sealed cap glass vial, 5-bromo-2-hydroxybenzaldehyde (201 mg, 1.0 mmol), 2-methyl-5-vinylpyridine (119 mg, 1.0 mmol), 1,3-bis(diphenylphosphino)propane (dppp) (82.4 mg, 0.2 mmol), trimethylamine (278 mg, 2.0 mmol) were dissolved in DMF (5.0 mL), then added Palladium acetate (22.4 mg, 0.1 mmol) to the vial. Then closed with sealed cap and continued at 95° C. for 16 hours on a stirrer plate with metallic beads contained dish. Then cooled to room temperature and diluted with water (20 mL) and transferred into a separating funnel using dichloromethane and extracted with additional dichloromethane (2×50 mL). Combined organic layer washed with brine, dried over sodium sulfate and evaporated completely. The resulted crude product purified using silica gel column chromatography (hexane through hexane-EtOAc (0-100%)) to give the title compound as a yellow solid (45 mg, 19% yield). $^1$H NMR (500 MHz, Chloroform-d) δ 11.04 (s, 1H), 9.95 (s, 1H), 8.59 (d, J=2.3 Hz, 1H), 7.73 (dt, J=8.5, 2.4 Hz, 2H), 7.67 (d, J=2.2 Hz, 1H), 7.16 (d, J=8.1 Hz, 1H), 7.07 (d, J=16.4 Hz, 1H), 7.02 (d, J=8.7 Hz, 1H), 6.98 (d, J=16.3 Hz, 1H), 2.57 (s, 3H); LC-MS m/z [M+H]+ calc'd for $C_{15}H_{13}NO_2$, 240; found, 240.

Example 22: (E)-4-fluoro-2-hydroxy-5-(4-methoxystyryl)benzaldehyde (Compound 55)

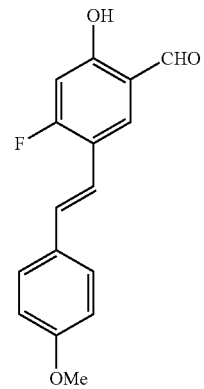

The title compound was prepared from 5-bromo-4-fluoro-2-hydroxybenzaldehyde (219 mg, 1.0 mmol) and (E)-(4-methoxystyryl)boronic acid (214 mg, 1.2 mmol) as described in Example 1 to give the title compound as a yellow solid (45 mg, 16% yield). $^1$H NMR (500 MHz, Chloroform-d) δ 11.22 (d, J=1.6 Hz, 1H), 9.89 (s, 1H), 7.78 (d, J=8.2 Hz, 1H), 7.51-7.37 (m, 2H), 7.07 (d, J=16.5 Hz, 1H), 7.00 (d, J=16.5 Hz, 1H), 6.95-6.87 (m, 2H), 6.70 (d, J=11.9 Hz, 1H), 3.84 (s, 3H); LC-MS m/z [M+H]+ calc'd for $C_{16}H_{13}FO_3$, 273; found, 273.

Example 23: (E)-2-hydroxy-3-methoxy-5-(2-(pyridin-2-yl)vinyl)benzaldehyde (Compound 56)

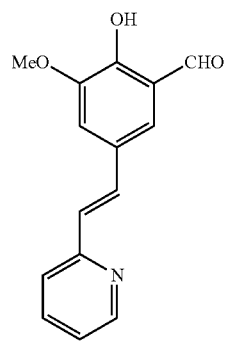

Compound 56 was prepared generally as described in Scheme 3a. In a 30 mL sealed cap glass vial, 5-bromo-2-hydroxy-3-methoxybenzaldehyde (231 mg, 1.0 mmol), 2-vinylpyridine (105 mg, 1.0 mmol), 1,3-Bis(diphenylphosphino)propane (dppp) (82 mg, 0.2 mmol) and $Et_3N$ (278 uL, 2.0 mmol) were suspended in DMF (5 mL). Then added $Pd(OAc)_2$ (22 mg, 0.1 mmol) to the reaction vial and closed with sealed cap and continued at 95° C. for 16 hours on a stirrer plate with metallic beads contained dish. Then cooled to room temperature and evaporated volatiles and transferred into a separating funnel using dichloromethane. Acidified the aqueous layer with 10% citric acid to pH~5 and extracted with additional dichloromethane (2×50 mL). Combined organic layer washed with brine, dried over sodium sulfate and evaporated. The resulted crude product purified using silica gel column chromatography (hexane through hexane-EtOAc (0-100%)) to give the title compound as a brown solid (36 mg, 13% yield). $^1$H NMR (500 MHz, Chloroform-d) δ 11.17 (s, 1H), 9.95 (s, 1H), 8.61 (d, J=4.8 Hz, 1H), 7.68 (t, J=7.9 Hz, 1H), 7.59 (d, J=16.0 Hz, 1H), 7.38 (dd, J=14.3, 5.9 Hz, 3H), 7.17 (dd, J=7.5, 5.0 Hz, 1H), 7.09 (d, J=16.0 Hz, 1H), 3.99 (s, 3H); LC-MS m/z [M+H]$^+$ calc'd for $C_{15}H_{13}NO_3$, 256; found, 256.

Example 24: (E)-2-hydroxy-5-(2-(pyridin-2-yl)vinyl)benzaldehyde (Compound 57)

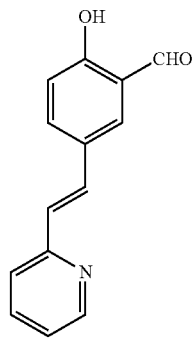

The title compound was prepared from 5-bromo-2-hydroxybenzaldehyde (201 mg, 1.0 mmol) and (2-vinylpyridine (105 mg, 1.0 mmol) as described in Example 23 to give the title compound as a yellow solid (37 mg, 16% yield). $^1$H NMR (500 MHz, Chloroform-d) δ 11.07 (s, 1H), 9.94 (s, 1H), 8.71-8.53 (m, 1H), 7.88-7.75 (m, 2H), 7.73 (d, J=2.3 Hz, 1H), 7.68 (td, J=7.7, 1.9 Hz, 1H), 7.62 (d, J=16.1 Hz, 1H), 7.50-7.39 (m, 2H), 7.36 (d, J=7.8 Hz, 1H), 7.20-7.13 (m, 1H), 7.09 (d, J=16.0 Hz, 1H), 7.03 (d, J=8.7 Hz, 1H); LC-MS m/z [M+H]$^+$ calc'd for $C_{14}H_{11}NO_2$, 226; found, 226.

Example 25: (E)-2-hydroxy-3-methoxy-5-(2-(pyridin-4-yl)vinyl)benzaldehyde (Compound 58)

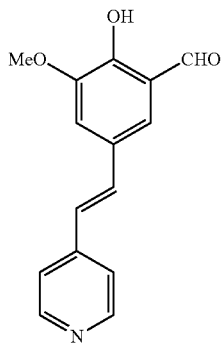

Compound 56 was prepared generally as described in Scheme 3a. In a 30 mL sealed cap glass vial, 5-bromo-2-hydroxy-3-methoxybenzaldehyde (231 mg, 1.0 mmol), 4-vinylpyridine (105 mg, 1.0 mmol), 1,3-Bis(diphenylphosphino)propane (dppp) (82 mg, 0.2 mmol) and $K_2CO_3$ (414 mg, 3.0 mmol) were suspended in DMF-$H_2O$ (3:1) (10 mL). Then added Pd(OAc)$_2$ (22 mg, 0.1 mmol) to the reaction vial and closed with sealed cap and continued at 95° C. for 5 hours on a stirrer plate with metallic beads contained dish. Then cooled to room temperature and diluted with water and transferred into a separating funnel using ethyl acetate. Acidified the aqueous layer with 10% citric acid to pH~5 and extracted with additional ethyl acetate (2×50 mL). Combined organic layer washed with brine, dried over sodium sulfate and evaporated. The resulted crude product purified using silica gel column chromatography (hexane through hexane-EtOAc (0-100%)) to give the title compound as a brown solid (58 mg, 23% yield). $^1$H NMR (500 MHz, Chloroform-d) δ 11.18 (s, 1H), 9.97 (s, 1H), 8.59 (d, J=5.1 Hz, 2H), 7.38-7.35 (m, 2H), 7.34 (d, J=1.9 Hz, 1H), 7.31 (d, J=1.9 Hz, 1H), 7.25 (d, J=16.3 Hz, 1H), 6.93 (d, J=16.3 Hz, 1H), 4.00 (s, 3H); LC-MS m/z [M+H]$^+$ calc'd for $C_{15}H_{13}NO_3$, 256; found, 256.

Example 26: (E)-2-hydroxy-3-methoxy-5-(2-(6-methylpyridin-3-yl)vinyl)benzaldehyde (Compound 59)

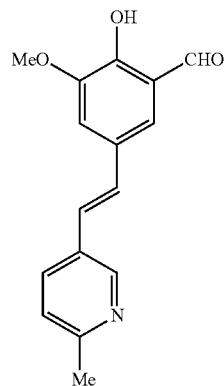

The title compound was prepared from 5-bromo-2-hydroxy-3-methoxybenzaldehyde (231 mg, 1.0 mmol) and 2-methyl-5-vinylpyridine (119 mg, 1.0 mmol) as described in Example 25 to give the title compound as a yellow solid (100 mg, 37% yield). $^1$H NMR (500 MHz, Chloroform-d) δ 11.12 (s, 1H), 9.95 (s, 1H), 8.60 (d, J=2.4 Hz, 1H), 7.73 (dd, J=8.1, 2.3 Hz, 1H), 7.29 (s, 2H), 7.17 (d, J=8.1 Hz, 1H), 7.06 (d, J=16.4 Hz, 1H), 6.96 (d, J=16.4 Hz, 1H), 4.00 (s, 3H), 2.58 (s, 3H); LC-MS m/z [M+H]$^+$ calc'd for $C_{16}H_{15}NO_3$, 270; found, 270.

Example 27: tert-butyl (E)-4-(3-formyl-4-hydroxy-5-methoxystyryl)piperidine-1-carboxylate (Compound 60)

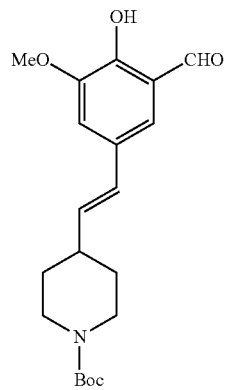

The title compound was prepared from 5-bromo-2-hydroxy-3-methoxybenzaldehyde (231 mg, 1.0 mmol) and tert-butyl 4-vinylpiperidine-1-carboxylate (211 mg, 1.0 mmol) as described in Example 23 to give the title compound as a yellow solid (58 mg, 16% yield). $^1$H NMR (500 MHz, Chloroform-d) δ 11.01 (s, 1H), 10.11-9.77 (m, 1H), 7.16-7.05 (m, 2H), 6.34 (dd, J=15.9, 1.3 Hz, 1H), 6.06 (dd, J=16.0, 6.9 Hz, 1H), 3.94 (s, 3H), 2.77 (d, J=12.9 Hz, 3H), 2.29 (m, 1H), 1.76 (d, J=13.0 Hz, 2H), 1.59 (d, J=8.8 Hz, 1H), 1.47 (s, 9H), 1.39 (m, 2H); LC-MS m/z [M+H]$^+$ calc'd for $C_{20}H_{27}NO_5$, 362; found, 362.

Example 28: (E)-3-fluoro-2-hydroxy-5-(2-(pyridin-2-yl)vinyl)benzaldehyde (Compound 61)

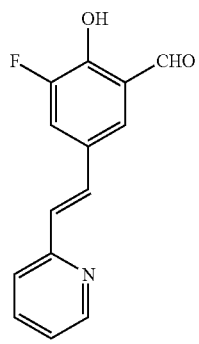

The title compound was prepared from 5-bromo-3-fluoro-2-hydroxybenzaldehyde (219 mg, 1.0 mmol) and 2-vinylpyridine (105 mg, 1.0 mmol) as described in Example 25 to give the title compound as a yellow solid (70 mg, 29% yield). $^1$H NMR (500 MHz, Chloroform-d) δ 10.97 (s, 1H), 9.96 (d, J=1.8 Hz, 1H), 8.61 (dd, J=4.8, 1.7 Hz, 1H), 7.68 (td, J=7.7, 1.9 Hz, 1H), 7.62-7.55 (m, 2H), 7.55-7.50 (m, 1H), 7.35 (d, J=7.8 Hz, 1H), 7.23-7.14 (m, 1H), 7.06 (d, J=15.9 Hz, 1H); LC-MS m/z [M+H]$^+$ calc'd for $C_{14}H_{10}FNO_2$, 244; found, 244.

Example 29: (E)-3-fluoro-2-hydroxy-5-(2-(6-methylpyridin-3-yl)vinyl)benzaldehyde (Compound 62)

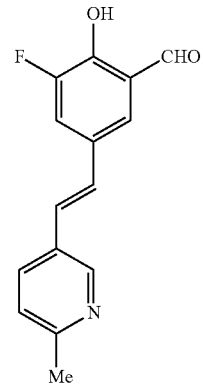

The title compound was prepared from 5-bromo-3-fluoro-2-hydroxybenzaldehyde (219 mg, 1.0 mmol) and 2-methyl-5-vinylpyridine (119 mg, 1.0 mmol) as described in Example 25 to give the title compound as a yellow solid (38 mg, 15% yield) and its citrate salt (58 mg). $^1$H NMR (500 MHz, Chloroform-d) δ 9.97 (d, J=1.8 Hz, 1H), 8.85-8.49 (m, 1H), 7.78 (dd, J=8.1, 2.2 Hz, 2H), 7.56 (dd, J=11.5, 2.1 Hz, 1H), 7.49 (s, 1H), 7.22 (d, J=8.0 Hz, 1H), 7.05 (d, J=16.4 Hz, 1H), 6.97 (d, J=16.4 Hz, 1H), 2.61 (s, 3H); LC-MS m/z [M+H]$^+$ calc'd for $C_{15}H_{12}FNO_2$, 258; found, 258.

Example 30: (E)-3-fluoro-2-hydroxy-5-(2-(pyridin-4-yl)vinyl)benzaldehyde (Compound 63)

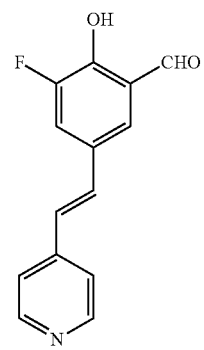

The title compound was prepared from 5-bromo-3-fluoro-2-hydroxybenzaldehyde (219 mg, 1.0 mmol) and 4-vinylpyridine (105 mg, 1.0 mmol) as described in Example 25 to give the title compound as a pink solid (22 mg, 9% yield). LC-MS m/z [M+H]$^+$ calc'd for $C_{14}H_{10}FNO_2$, 244; found, 244.

Example 31: tert-butyl (E)-4-(3-fluoro-5-formyl-4-hydroxystyryl)piperidine-1-carboxylate (Compound 64)

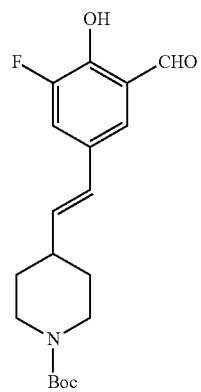

The title compound was prepared from 5-bromo-3-fluoro-2-hydroxybenzaldehyde (219 mg, 1.0 mmol) and tert-butyl 4-vinylpiperidine-1-carboxylate (211 mg, 1.0 mmol) as described in Example 25 to give the title compound as a yellow solid (48 mg, 14% yield). $^1$H NMR (500 MHz, Chloroform-d) δ 10.88 (d, J=13.6 Hz, 1H), 9.92 (dd, J=12.6, 1.9 Hz, 1H), 7.42-7.31 (m, 1H), 7.29 (t, J=1.4 Hz, 1H), 6.30 (d, J=15.9 Hz, 1H), 6.07 (dd, J=15.9, 6.8 Hz, 1H), 4.39-4.01 (m, 2H), 2.78 (t, J=12.6 Hz, 2H), 2.29 (qt, J=7.3, 3.5 Hz, 1H), 1.75 (dd, J=13.4, 3.7 Hz, 2H), 1.47 (d, J=4.4 Hz, 10H), 1.38 (qd, J=12.5, 4.2 Hz, 2H); LC-MS m/z [M+H]$^+$ calc'd for $C_{19}H_{24}FNO_4$, 350; found, 350.

Example 32: (E)-2-hydroxy-3-methoxy-5-(2-(naphthalen-2-yl)vinyl)benzaldehyde (Compound 65)

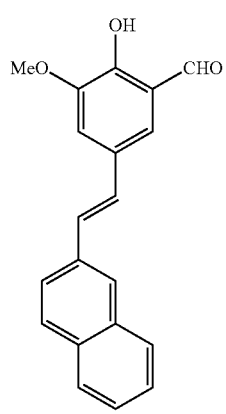

The title compound was prepared from 5-bromo-2-hydroxy-3-methoxybenzaldehyde (231 mg, 1.0 mmol) and 2-vinylnaphthalene (154 mg, 1.0 mmol) as described in Example 25 to give the title compound as a yellow solid (54 mg, 18% yield). $^1$H NMR (500 MHz, Chloroform-d) δ 11.12 (s, 1H), 9.97 (s, 1H), 7.90-7.79 (m, 4H), 7.73 (dd, J=8.6, 1.8 Hz, 1H), 7.54-7.42 (m, 2H), 7.39-7.31 (m, 2H), 7.19 (s, 2H), 4.02 (s, 3H); LC-MS m/z [M+H]$^+$ calc'd for $C_{20}H_{16}O_3$, 305; found, 305.

Example 33: (E)-2-hydroxy-3-methoxy-5-(3-oxo-3-phenylprop-1-en-1-yl)benzaldehyde (Compound 66)

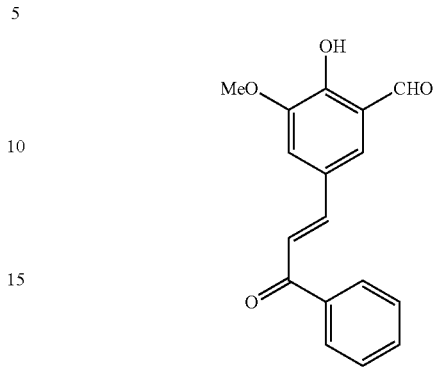

The title compound was prepared from 5-bromo-2-hydroxy-3-methoxybenzaldehyde (231 mg, 1.0 mmol) and 1-phenylprop-2-en-1-one (132 mg, 1.0 mmol) as described in Example 25 to give the title compound as a yellow solid (68 mg, 24% yield). $^1$H NMR (499 MHz, Chloroform-d) δ 11.35 (s, 1H), 9.98 (s, 1H), 8.15-7.95 (m, 2H), 7.77 (d, J=15.6 Hz, 1H), 7.64-7.58 (m, 1H), 7.56-7.46 (m, 3H), 7.44 (d, J=15.5 Hz, 1H), 7.37 (d, J=1.8 Hz, 1H), 4.01 (s, 3H); LC-MS m/z [M+H]$^+$ calc'd for $C_{17}H_{14}O_4$, 283; found, 283.

Example 34: (E)-2-hydroxy-5-(4-hydroxy-3-methoxystyryl)-3-methoxybenzaldehyde (Compound 67)

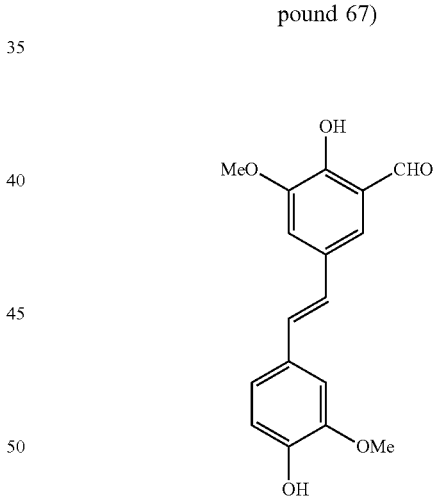

The title compound was prepared from 5-bromo-2-hydroxy-3-methoxybenzaldehyde (231 mg, 1.0 mmol) and 2-methoxy-4-vinylphenol (150 mg, 1.0 mmol) as described in Example 25 to give the title compound as a yellow solid (62 mg, 21% yield). $^1$H NMR (499 MHz, Chloroform-d) δ 11.06 (s, 1H), 9.94 (s, 1H), 7.27 (m, 2H), 7.05-7.00 (m, 2H), 6.95 (d, J=16.3 Hz, 1H), 6.93 (s, 1H), 6.90 (d, J=16.2 Hz, 1H), 5.67 (s, 1H), 3.99 (s, 3H), 3.96 (s, 3H); LC-MS m/z [M+H]$^+$ calc'd for $C_{17}H_{16}O_5$, 301; found, 301.

Example 35: (E)-2-hydroxy-3-methoxy-5-(3-morpholino-3-oxoprop-1-en-1-yl)benzaldehyde (Compound 68)

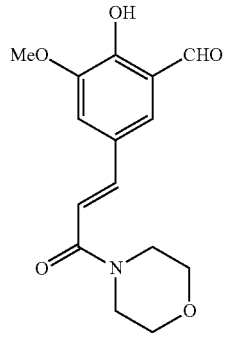

The title compound was prepared from 5-bromo-2-hydroxy-3-methoxybenzaldehyde (231 mg, 1.0 mmol) and 1-morpholinoprop-2-en-1-one (142 mg, 1.0 mmol) as described in Example 25 to give the title compound as a brown solid (165 mg, 21% yield). $^1$H NMR (499 MHz, Chloroform-d) δ 11.22 (s, 1H), 9.95 (s, 1H), 7.66 (d, J=15.3 Hz, 1H), 7.36 (d, J=1.8 Hz, 1H), 7.23 (d, J=2.0 Hz, 1H), 6.75 (d, J=15.4 Hz, 1H), 3.97 (s, 3H), 3.74 (dd, J=4.0, 2.1 Hz, 8H); LC-MS m/z [M+H]$^+$ calc'd for $C_{15}H_{17}NO_5$, 292; found, 292.

Example 36: (E)-5-(2-([1,1'-biphenyl]-4-yl)vinyl)-2-hydroxy-3-methoxybenzaldehyde (Compound 69)

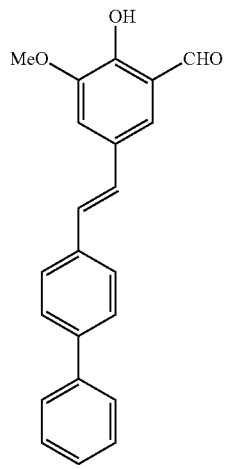

The title compound was prepared from 5-bromo-2-hydroxy-3-methoxybenzaldehyde (231 mg, 1.0 mmol) and 4-vinyl-1,1'-biphenyl (180 mg, 1.0 mmol) as described in Example 25 to give the title compound as a yellow solid (62 mg, 19% yield). $^1$H NMR (499 MHz, Chloroform-d) δ 11.11 (s, 1H), 9.97 (s, 1H), 7.63 (dd, J=8.0, 2.3 Hz, 4H), 7.58 (d, J=8.3 Hz, 2H), 7.46 (t, J=7.6 Hz, 2H), 7.39-7.33 (m, 1H), 7.32 (q, J=2.0 Hz, 2H), 7.11 (d, J=16.4 Hz, 1H), 7.05 (d, J=16.2 Hz, 1H), 4.01 (s, 3H); LC-MS m/z [M+H]$^+$ calc'd for $C_{22}H_{18}O_3$, 331; found, 331.

Example 37: (E)-5-(2-([1,1'-biphenyl]-4-yl)vinyl)-3-fluoro-2-hydroxybenzaldehyde (Compound 70)

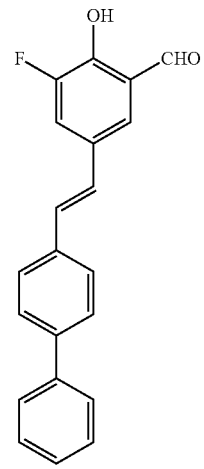

The title compound was prepared from 5-bromo-3-fluoro-2-hydroxybenzaldehyde (219 mg, 1.0 mmol) and 4-vinyl-1,1'-biphenyl (180 mg, 1.0 mmol) as described in Example 25 to give the title compound as a off-white solid (18 mg, 6% yield). $^1$H NMR (499 MHz, Chloroform-d) δ 10.95 (s, 1H), 9.97 (d, J=1.8 Hz, 1H), 7.63 (d, J=8.1 Hz, 4H), 7.60-7.55 (m, 3H), 7.50-7.48 (m, 1H), 7.46 (t, J=7.7 Hz, 2H), 7.36 (t, J=7.4 Hz, 1H), 7.06 (s, 2H); LC-MS m/z [M+H]$^+$ calc'd for $C_{21}H_{15}FO_2$, 319; found, 319.

Example 38: 5-(2-(2,3-dihydrobenzo[b][1,4]dioxin-6-yl)vinyl)-2-hydroxy-3-methoxybenzaldehyde (Compound 71)

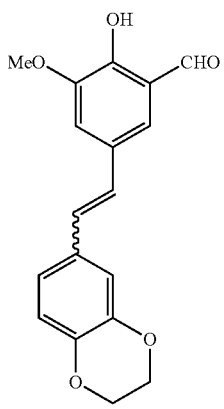

Step 1: Synthesis of 6-vinyl-2,3-dihydrobenzo[b][1,4]dioxine

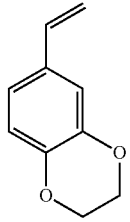

The intermediate 6-vinyl-2,3-dihydrobenzo[b][1,4]dioxine was prepared generally as described in Scheme 4. In a 250 mL round bottom flask fitted with addition funnel under argon atmosphere, methyltriphenylphosphonium bromide (7.14 g, 20 mmol) suspended in tetrahydrofuran (40 mL) at 0° C. in an ice bath. Then added n-BuLi solution (2.0 M solution in THF) to the reaction mixture using syringe and continued stirring for additional 15 min. Then added 2,3-dihydrobenzo[b][1,4]dioxine-6-carbaldehyde (1.64 g, 10 mmol) in 10 mL THF dropwise using addition funnel. Continued the reaction for 8 hours, then added saturated aq.NH$_4$Cl to the reaction mixture at 0° C. and extracted in EtOAc (2×75 mL). Combined organic layer washed with brine, dried over sodium sulfate and evaporated. The resulted crude product purified using silica gel column chromatography (hexane through hexane-EtOAc (0-100%)) to give the title compound as colorless oil (1.32 g, 81% yield). LC-MS m/z [M+H]$^+$ calc'd for C$_{10}$H$_{10}$O$_2$, 163; found, 163.

Step 2: The title compound was prepared from 5-bromo-2-hydroxy-3-methoxybenzaldehyde (231 mg, 1.0 mmol) and above obtained 6-vinyl-2,3-dihydrobenzo[b][1,4]dioxine (162 mg, 1.0 mmol) as described in Example 25 to give the title compound as yellow solid (71 mg, 23% yield). $^1$H NMR (499 MHz, Chloroform-d) δ 11.07 (s, 1H), 9.94 (s, 1H), 7.26-7.22 (m, 2H), 7.03 (d, J=2.1 Hz, 1H), 6.99 (dd, J=8.3, 2.1 Hz, 1H), 6.89 (s, 2H), 6.86 (d, J=8.3 Hz, 1H), 4.28 (s, 4H), 3.98 (s, 3H); LC-MS m/z [M+H]$^+$ calc'd for C$_{18}$H$_{16}$O$_5$, 313; found, 313.

Example 39: (E)-5-(2-(2,3-dihydrobenzo[b][1,4]dioxin-6-yl)vinyl)-3-fluoro-2-hydroxybenzaldehyde (Compound 72)

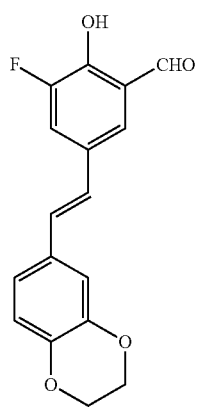

The title compound was prepared from 5-bromo-3-fluoro-2-hydroxybenzaldehyde (219 mg, 1.0 mmol) and 6-vinyl-2,3-dihydrobenzo[b][1,4]dioxine (162 mg, 1.0 mmol) as described in Example 25 to give the title compound as yellow solid (62 mg, 21% yield). $^1$H NMR (499 MHz, Chloroform-d) δ 10.91 (s, 1H), 9.95 (d, J=1.9 Hz, 1H), 7.51 (dd, J=11.8, 2.1 Hz, 1H), 7.42 (t, J=1.4 Hz, 1H), 7.02 (d, J=2.2 Hz, 1H), 6.98 (dd, J=8.3, 2.1 Hz, 1H), 6.90 (d, J=16.3 Hz, 1H), 6.86 (d, J=6.5 Hz, 1H), 6.84 (d, J=14.3 Hz, 1H), 4.28 (s, 4H); LC-MS m/z [M+H]$^+$ calc'd for C$_{17}$H$_{13}$FO$_4$, 301; found, 301.

Example 40: (E)-2-hydroxy-3-methoxy-5-(4-morpholinostyryl)benzaldehyde (Compound 73)

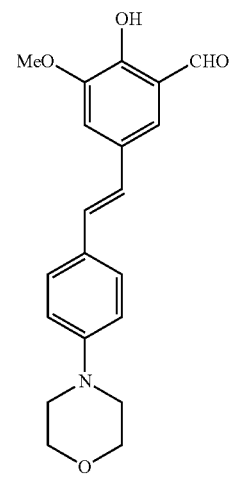 [SMILES: COc1cc(/C=C/c2ccc(N3CCOCC3)cc2)cc(C=O)c1O]

Step 1: Synthesis of 4-(4-vinylphenyl)morpholine

The title compound was prepared from 4-morpholinobenzaldehyde (1.912 g, 10 mmol) and methyltriphenylphosphonium bromide (7.14 g, 20 mmol) using the similar procedure mentioned as in step-1 of Example 38 to give the product as white solid (1.32 g, 70% yield). LC-MS m/z [M+H]$^+$ calc'd for C$_{12}$H$_{15}$NO, 190; found, 190.

Step 2: The title compound was prepared from 5-bromo-2-hydroxy-3-methoxybenzaldehyde (231 mg, 1.0 mmol) and 4-(4-vinylphenyl)morpholine (189 mg, 1.0 mmol) as described in Example 25 to give the title compound as a yellow solid (92 mg, 27% yield). $^1$H NMR (500 MHz, Chloroform-d) δ 11.05 (s, 1H), 9.94 (s, 1H), 7.49-7.40 (m, 2H), 7.28-7.21 (m, 2H), 6.96 (d, J=16.3 Hz, 1H), 6.93-6.86

(m, 3H), 3.98 (s, 3H), 3.92-3.73 (m, 4H), 3.32-3.06 (m, 4H); LC-MS m/z [M+H]⁺ calc'd for $C_{20}H_{21}NO_4$, 340; found, 340.

Example 41: (Z)-2-hydroxy-3-methoxy-5-(4-morpholinostyryl)benzaldehyde (Compound 74)

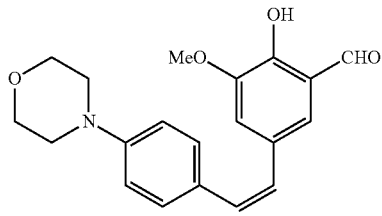 [SMILES: COc1cc(/C=C\c2ccc(N3CCOCC3)cc2)cc(C=O)c1O]

A mixture of 5-bromo-2-hydroxy-3-methoxybenzaldehyde (693 mg, 3.0 mmol), 4-(4-vinylphenyl)morpholine (567 mg, 3.0 mmol), 1,3-bis(diphenylphosphino)propane (dppp) (247 mg, 0.6 mmol), $K_2CO_3$ powder (1.24 g, 9.0 mmol), and palladium acetate (67 mg, 0.3 mmol) in DMF-water (3:1) (12 mL) was heated overnight at 85° C. The mixture was cooled to room temperature, diluted with water (50 mL), and extracted with ethyl acetate (50 mL×3). The organic extracts were combined, washed with brine (50 mL×2), dried over anhydrous sodium sulfate, and concentrated. The residue was purified by silica gel column chromatography (petroleum ether/ethyl acetate=100:1 to 10:1) to give the title product as a yellow solid (27 mg, 3% yield). ¹H NMR (CDCl₃, 400 MHz) δ: 11.16 (s, 1H), 9.87 (s, 1H), 7.29 (s, 2H), 7.12-7.15 (m, 2H), 6.95 (m, 2H), 5.40 (s, 1H), 5.31 (s, 1H), 3.90 (m, 7H), 3.23 (m, 4H); LC-MS m/z [M+H]⁺ calc'd for $C_{20}H_{21}NO_4$, 340; found, 340.

Example 42: (E)-3-fluoro-2-hydroxy-5-(4-morpholinostyryl)benzaldehyde (Compound 75)

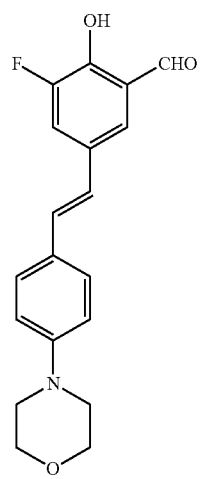

The title compound was prepared from 5-bromo-3-fluoro-2-hydroxybenzaldehyde (219 mg, 1.0 mmol) and 4-(4-vinylphenyl)morpholine (189 mg, 1.0 mmol) as described in Example 25 to give the title compound as a yellow solid (63 mg, 19% yield). ¹H NMR (500 MHz, Chloroform-d) δ 10.89 (s, 1H), 9.95 (d, J=1.9 Hz, 1H), 7.52 (dd, J=11.9, 2.1 Hz, 1H), 7.45-7.39 (m, 3H), 6.95 (d, J=16.3 Hz, 1H), 6.91 (d, J=8.4 Hz, 2H), 6.86 (d, J=16.2 Hz, 1H), 3.96-3.74 (m, 4H), 3.21 (dd, J=5.7, 3.9 Hz, 4H); LC-MS m/z [M+H]⁺ calc'd for $C_{19}H_{18}FNO_3$, 328; found, 328.

Example 43: (Z)-3-fluoro-2-hydroxy-5-(4-morpholinostyryl)benzaldehyde (Compound 76)

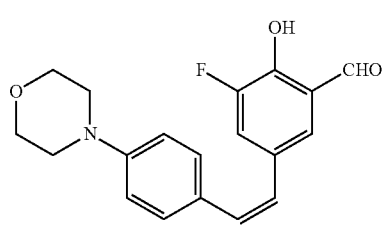 [SMILES: O=Cc1cc(/C=C\c2ccc(N3CCOCC3)cc2)cc(F)c1O]

A mixture of 5-bromo-3-fluoro-2-hydroxybenzaldehyde (1.73 g, 7.95 mmol), 4-(4-vinylphenyl)morpholine (500 mg, 2.65 mmol), 1,3-bis(diphenylphosphino)propane (dppp) (218 mg, 0.53 mmol), $K_2CO_3$ powder (1.1 g, 7.95 mmol), and palladium acetate (59 mg, 0.27 mmol) in DMF-water (10 mL:3 mL) was heated overnight at 90° C. The mixture was cooled to rt, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=100:1 to 30:1) and prep-HPLC to give the title product as a yellow solid (15 mg, 2% yield). ¹H NMR (CDCl₃, 400 MHz) δ: 10.97 (s, 1H), 9.88 (s, 1H), 7.29-7.37 (m, 2H), 7.24 (m, 2H), 6.93 (m, 2H), 5.41 (s, 1H), 5.34 (s, 1H), 3.90 (m, 4H), 3.23 (m, 4H); LC-MS m/z [M+H]⁺ calc'd for $C_{19}H_{18}FNO_3$, 328; found, 328.

Example 44: (E)-2-hydroxy-3-methoxy-5-(3-morpholinostyryl)benzaldehyde (Compound 77)

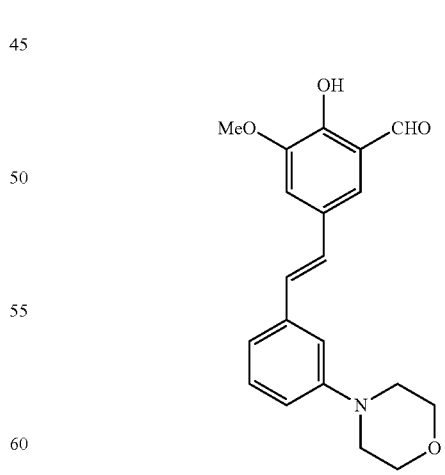

Step 1: Synthesis of 4-(3-vinylphenyl)morpholine

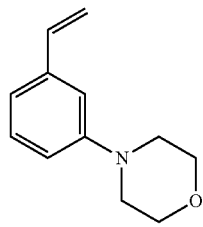

The title compound was prepared from 3-morpholinobenzaldehyde (1.912 g, 10 mmol) and methyltriphenylphosphonium bromide (7.14 g, 20 mmol) using the similar procedure mentioned as in step-1 of Example 38 to give the product as a colorless oil (1.26 g, 67% yield). LC-MS m/z [M+H]+ calc'd for $C_{12}H_{15}NO$, 190; found, 190.

Step 2: The title compound was prepared from 5-bromo-2-hydroxy-3-methoxybenzaldehyde (231 mg, 1.0 mmol) and 4-(3-vinylphenyl)morpholine (189 mg, 1.0 mmol) as described in Example 25 to give the title compound as yellow solid (98 mg, 29% yield). $^1$H NMR (500 MHz, Chloroform-d) δ 11.09 (s, 1H), 9.95 (s, 1H), 7.32-7.23 (m, 3H), 7.09-7.02 (m, 3H), 6.98 (d, J=16.3 Hz, 1H), 6.86 (d, J=7.8 Hz, 1H), 3.99 (s, 3H), 3.89 (t, J=4.7 Hz, 4H), 3.28-3.08 (m, 4H); LC-MS m/z [M+H]+ calc'd for $C_{20}H_{21}NO_4$, 340; found, 340.

Example 45: (E)-3-fluoro-2-hydroxy-5-(3-morpholinostyryl)benzaldehyde (Compound 78)

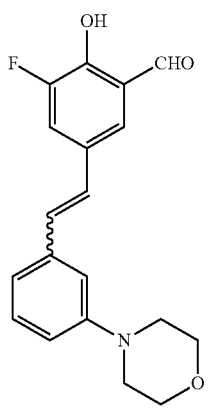 [SMILES: O=Cc1cc(C=Cc2cccc(N3CCOCC3)c2)cc(F)c1O]

The title compound was prepared from 5-bromo-3-fluoro-2-hydroxybenzaldehyde (219 mg, 1.0 mmol) and 4-(3-vinylphenyl)morpholine (189 mg, 1.0 mmol) as described in Example 25 to give the title compound as a yellow solid (56 mg, 17% yield). $^1$H NMR (500 MHz, Chloroform-d) δ 10.94 (s, 1H), 9.96 (d, J=1.9 Hz, 1H), 7.55 (dd, J=11.7, 2.1 Hz, 1H), 7.46 (t, J=1.5 Hz, 1H), 7.29 (t, J=7.9 Hz, 1H), 7.05 (t, J=8.4 Hz, 2H), 6.99 (s, 2H), 6.88 (d, J=8.2 Hz, 1H), 4.08-3.76 (m, 4H), 3.30-3.05 (m, 4H); LC-MS m/z [M+H]+ calc'd for $C_{19}H_{18}FNO_3$, 328; found, 328.

Example 46: (E)-2-hydroxy-3-methoxy-5-(3-(pyrrolidin-1-yl)styryl)benzaldehyde (Compound 79)

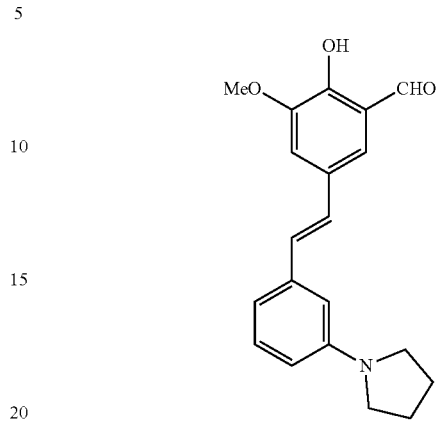

Step 1: Synthesis of 1-(3-vinylphenyl)pyrrolidine

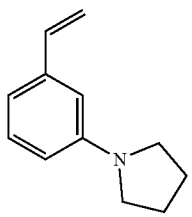

The title compound was prepared from 3-(pyrrolidin-1-yl)benzaldehyde (1.75 g, 10 mmol) and methyltriphenylphosphonium bromide (7.14 g, 20 mmol) using the similar procedure mentioned as in step-1 of Example 38 to give the product as a colorless oil (1.25 g, 72% yield). LC-MS m/z [M+H]+ calc'd for $C_{12}H_{15}N$, 174; found, 174.

Step 2: The title compound was prepared from 5-bromo-2-hydroxy-3-methoxybenzaldehyde (231 mg, 1.0 mmol) and 1-(3-vinylphenyl)pyrrolidine (173 mg, 1.0 mmol) as described in Example 25 to give the title compound as yellow solid (62 mg, 29% yield). $^1$H NMR (500 MHz, Chloroform-d) δ 11.08 (s, 1H), 9.94 (s, 1H), 7.33-7.27 (m, 2H), 7.23 (t, J=7.8 Hz, 1H), 7.04 (d, J=16.3 Hz, 1H), 6.99 (d, J=16.0 Hz, 1H), 6.84 (d, J=7.6 Hz, 1H), 6.67 (t, J=1.9 Hz, 1H), 6.52 (dd, J=8.2, 2.3 Hz, 1H), 4.00 (s, 3H), 3.41-3.20 (m, 4H), 2.09-1.90 (m, 4H); LC-MS m/z [M+H]+ calc'd for $C_{20}H_{21}NO_3$, 324; found, 324.

229

Example 47: (E)-3-fluoro-2-hydroxy-5-(3-(pyrrolidin-1-yl)styryl)benzaldehyde (Compound 80)

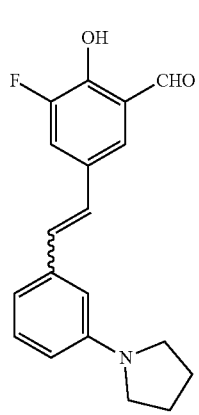

The title compound was prepared from 5-bromo-3-fluoro-2-hydroxybenzaldehyde (219 mg, 1.0 mmol) and 1-(3-vinylphenyl)pyrrolidine (173 mg, 1.0 mmol) as described in Example 25 to give the title compound as a yellow solid (48 mg, 15% yield). $^1$H NMR (500 MHz, Chloroform-d) δ 10.92 (s, 1H), 9.95 (d, J=1.9 Hz, 1H), 7.55 (dd, J=11.9, 2.1 Hz, 1H), 7.48-7.42 (m, 1H), 7.23 (t, J=7.8 Hz, 1H), 6.99 (s, 2H), 6.83 (d, J=7.5 Hz, 1H), 6.65 (t, J=2.0 Hz, 1H), 6.53 (dd, J=8.2, 2.4 Hz, 1H), 3.53-3.12 (m, 4H), 2.18-1.85 (m, 4H); LC-MS m/z [M+H]$^+$ calc'd for $C_{19}H_{18}FNO_2$, 312; found, 312.

Example 48: (E)-2-hydroxy-3-methoxy-5-(4-(pyrrolidin-1-yl)styryl)benzaldehyde (Compound 81)

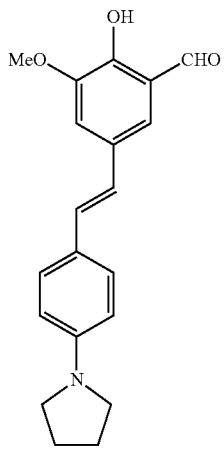

230

Step 1: Synthesis of 1-(4-vinylphenyl)pyrrolidine

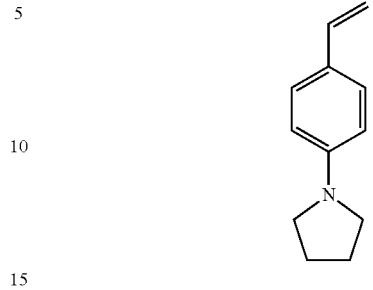

The title compound was prepared from 4-(pyrrolidin-1-yl)benzaldehyde (1.75 g, 10 mmol) and methyltriphenylphosphonium bromide (7.14 g, 20 mmol) using a similar procedure as described in step-1 of Example 38 to give the product as a colorless oil (1.38 g, 80% yield). LC-MS m/z [M+H]$^+$ calc'd for $C_{12}H_{15}N$, 174; found, 174.

Step 2: The title compound was prepared from 5-bromo-2-hydroxy-3-methoxybenzaldehyde (231 mg, 1.0 mmol) and 1-(4-vinylphenyl)pyrrolidine (173 mg, 1.0 mmol) as described in Example 25 to give the title compound as yellow solid (42 mg, 13% yield). $^1$H NMR (500 MHz, Chloroform-d) δ 11.02 (s, 1H), 9.93 (s, 1H), 7.46-7.30 (m, 2H), 7.27 (d, J=2.1 Hz, 1H), 7.23 (d, J=2.0 Hz, 1H), 6.95 (d, J=16.2 Hz, 1H), 6.83 (d, J=16.2 Hz, 1H), 6.64-6.48 (m, 2H), 3.98 (s, 3H), 3.38-3.23 (m, 4H), 2.12-1.88 (m, 4H); LC-MS m/z [M+H]$^+$ calc'd for $C_{20}H_{21}NO_3$, 324; found, 324.

Example 49: (E)-3-fluoro-2-hydroxy-5-(4-(pyrrolidin-1-yl)styryl)benzaldehyde (Compound 82)

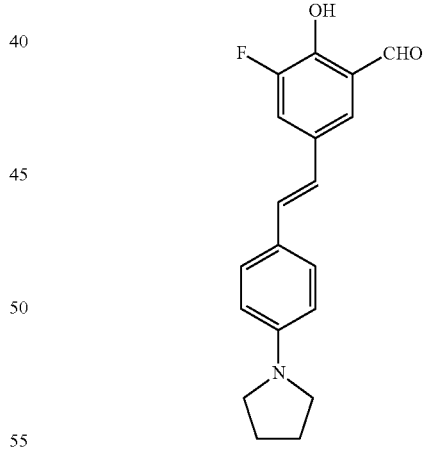

Example 49a—Synthesis Route (a)

The title compound was prepared from 5-bromo-3-fluoro-2-hydroxybenzaldehyde (219 mg, 1.0 mmol) and 1-(4-vinylphenyl)pyrrolidine (173 mg, 1.0 mmol) as described in Example 25 to give the title compound as a pinkish yellow solid (38 mg, 12% yield). $^1$H NMR (500 MHz, Chloroform-d) δ 10.84 (s, 1H), 9.94 (d, J=1.9 Hz, 1H), 7.50 (dd, J=12.0, 2.1 Hz, 1H), 7.41-7.35 (m, 3H), 6.94 (d, J=16.2 Hz, 1H), 6.77 (d, J=16.2 Hz, 1H), 6.59-6.52 (m, 2H), 3.35-3.29 (m, 4H), 2.05-2.00 (m, 4H); LC-MS m/z [M+H]+ calc'd for C19H18FNO2, 312; found, 312.

Example 49b—Synthesis Route (b)

A mixture of 5-bromo-3-fluoro-2-hydroxybenzaldehyde (4.36 g, 20.0 mmol), 1-(4-vinylphenyl)pyrrolidine (3.46 g, 20.0 mmol), 1,3-bis(diphenylphosphino)propane (dppp) (1.65 g, 4.0 mmol), K2CO3 powder (8.28 g, 60.0 mmol), and palladium acetate (448 mg, 2.0 mmol) in DMF-water (50 mL:17 mL) was heated overnight at 90° C. The mixture was cooled to rt, diluted with water (300 mL), and extracted with ethyl acetate (200 mL×3). The organic extracts were combined, washed with brine (100 mL×2), dried over anhydrous sodium sulfate, and concentrated. The residue was purified by silica gel column chromatography (petroleum ether/ethyl acetate=200:1 to 100:1) and prep-HPLC to give the title product as yellow solid (816 mg, 13% yield). 1H NMR (CDCl3, 400 MHz) δ: 10.87 (s, 1H), 9.94 (s, 1H), 7.51 (d, J=12.0 Hz, 1H), 7.41 (m, 3H), 6.94 (d, J=16.4 Hz, 1H), 6.80 (d, J=16.4 Hz, 1H), 6.68 (m, 2H), 3.37 (m, 4H), 2.06 (m, 4H); LC-MS m/z [M+H]+ calc'd for C19H18FNO2, 312; found, 312.

Example 49c—Synthesis of (E)-3-fluoro-2-hydroxy-5-(4-(pyrrolidin-1-yl)styryl)benzaldehyde hydrochloride (hydrochloride Salt of Compound 82)

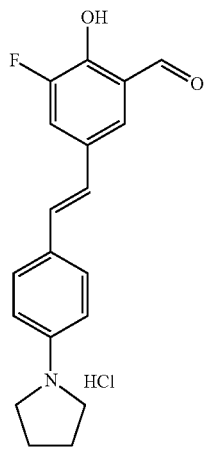 [SMILES: O=Cc1cc(/C=C/c2ccc(N3CCCC3)cc2)cc(F)c1O ; Cl]

The title compound was prepared by treating (E)-2-hydroxy-3-methoxy-5-(4-(pyrrolidin-1-yl)styryl)benzaldehyde (623 mg, 2.0 mmol) (from Example 49b above) with 4N HCl dioxane (1.0 mL) after dissolving in dichloromethane (25 mL) at room temperature. Yellow solution turned into light pink precipitate. Reaction mixture stirred for additional 5 min, then filtered and collected the precipitate to obtain desired product as a light pink solid (100% yield).

Example 50: (Z)-3-fluoro-2-hydroxy-5-(4-(pyrrolidin-1-yl)styryl)benzaldehyde (Compound 83)

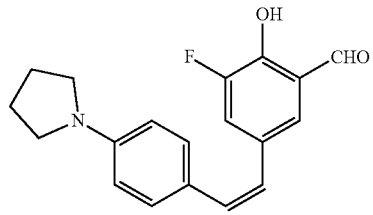 [SMILES: O=Cc1cc(/C=C\c2ccc(N3CCCC3)cc2)cc(F)c1O]

The crude upper spot on TLC (from Example 49b above) was collected and re-purified by prep-TLC to afford title product as a yellow solid (74 mg, 1% yield). 1H NMR (CDCl3, 400 MHz) δ: 10.97 (s, 1H), 9.88 (s, 1H), 7.38 (m, 2H), 7.22 (m, 2H), 6.70 (br, 2H), 5.37 (s, 1H), 5.26 (s, 1H), 3.38 (m, 4H), 2.07 (m, 4H); LC-MS m/z [M+H]+ calc'd for C19H18FNO2, 312; found, 312.

Example 51: (Z)-2-hydroxy-3-methoxy-5-(4-(pyrrolidin-1-yl)styryl)benzaldehyde (Compound 84)

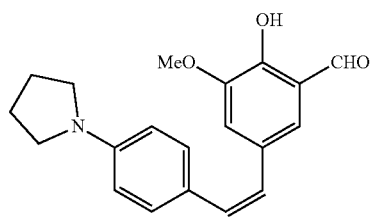 [SMILES: COc1cc(/C=C\c2ccc(N3CCCC3)cc2)cc(C=O)c1O]

A mixture of 5-bromo-2-hydroxy-3-methoxybenzaldehyde (1.44 g, 6.24 mmol), 1-(4-vinylphenyl)pyrrolidine (900 mg, 5.20 mmol), 1,3-bis(diphenylphosphino)propane (dppp) (429 mg, 1.04 mmol), K2CO3 powder (2.15 g, 15.6 mmol), and palladium acetate (117 mg, 0.52 mmol) in DMF-water (3:1) (12 mL) was heated overnight at 90° C. The mixture was cooled to room temperature, diluted with water (100 mL), and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=200:1 to 150:1) and prep-TLC to give the title product as a yellow solid (25 mg, 1% yield). 1H NMR (CDCl3, 400 MHz) δ: 11.16 (s, 1H), 9.87 (s, 1H), 7.08-7.25 (m, 4H), 6.69 (m, 2H), 5.37 (s, 1H), 5.24 (s, 1H), 3.89 (s, 3H), 3.38 (m, 4H), 2.07 (m, 4H); LC-MS m/z [M+H]+ calc'd for C20H21NO3, 324; found, 324.

Example 52: (E)-2-hydroxy-6-methoxy-4-(4-(pyrrolidin-1-yl)styryl)benzaldehyde (Compound 85)

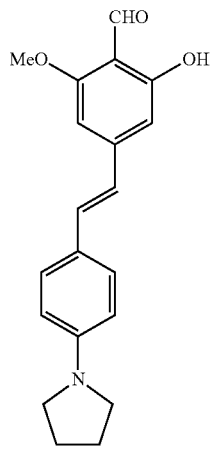 [SMILES: COc1cc(/C=C/c2ccc(N3CCCC3)cc2)cc(O)c1C=O]

Step 1: 4-bromo-2-hydroxy-6-methoxybenzaldehyde

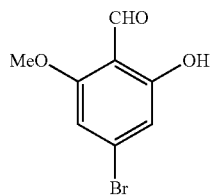 [SMILES: COc1cc(Br)cc(O)c1C=O]

A solution of 4-bromo-2,6-dimethoxybenzaldehyde (10 g, 40.8 mmol) and sodium iodide (12.2 g, 81.6 mmol) in MeCN/DCM (50 mL, 1:1) was cooled to 0° C. AlCl$_3$ (10.8 g, 81.6 mmol) was added slowly. The reaction was stirred at rt for 5 h and TLC showed the reaction was complete. The mixture was poured into sat. ammonium chloride and extracted with ethyl acetate (100 mL×3). The organic extracts were combined, washed with brine (50 mL×2), dried over anhydrous sodium sulfate, and concentrated. The residue was purified by silica gel column chromatography (petroleum ether/ethyl acetate=300:1 to 200:1) to give the desired product and its iodo-substitution compound (6.3 g, 67% yield). LC-MS m/z [M+H]$^+$ calc'd for C$_8$H$_7$BrO$_3$ and C$_8$H$_7$IO$_3$, 232 and 278; found, 232 and 278.

Step 2: A mixture of above obtained 4-bromo-2-hydroxy-6-methoxybenzaldehyde (300 mg, 0.93 mmol), 1-(4-vinylphenyl)pyrrolidine (254 mg, 0.93 mmol), Pd$_2$(dba)$_3$ (8 mg, 0.009 mmol), 1,3-bis(diphenylphosphino)propane (DPPP) (15.3 mg, 0.037 mmol) in dioxane (8 mL) was stirred for 10 min at rt under nitrogen protection. Formic acid (0.08 mL) was then added. The reaction was heated overnight at 80° C. under nitrogen protection. The mixture was cooled to rt, diluted with water (10 mL), and extracted with ethyl acetate (10 mL×3). The organic extracts were combined, washed with brine (10 mL×2), dried over anhydrous sodium sulfate, and concentrated. The residue was purified by silica gel column chromatography (petroleum ether/ethyl acetate=100:1 to 10:1) to give the title product as an orange solid (145 mg, 48% yield). $^1$H NMR (CDCl$_3$, 400 MHz) δ: 12.07 (s, 1H), 10.26 (s, 1H), 7.53 (d, J=8.0 Hz, 2H), 7.19 (m, 3H), 6.92 (m, 1H), 6.65 (s, 1H), 6.49 (s, 1H), 3.96 (s, 3H), 3.54 (m, 4H), 2.21 (m, 4H); LC-MS m/z [M+H]$^+$ calc'd for C$_{20}$H$_{21}$NO$_3$, 324; found, 324.

Example 53: (E)-2-fluoro-6-hydroxy-4-(4-(pyrrolidin-1-yl)styryl)benzaldehyde (Compound 86)

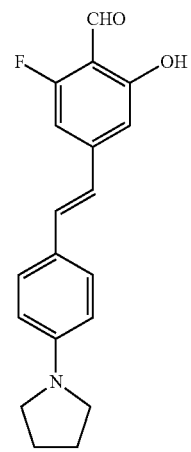

A mixture of 4-bromo-2-fluoro-6-hydroxybenzaldehyde (200 mg, 0.91 mmol), 1-(4-vinylphenyl)pyrrolidine (249 mg, 0.91 mmol), Pd$_2$(dba)$_3$ (6 mg, 0.007 mmol), 1,3-bis(diphenylphosphino)propane (dppp) (10.7 mg, 0.026 mmol) in dioxane (5 mL) was stirred for 10 min at rt under nitrogen protection. Formic acid (0.05 mL) was then added. The reaction was heated overnight at 80° C. under nitrogen protection. The mixture was cooled to rt, diluted with water (10 mL), and extracted with ethyl acetate (10 mL×3). The organic extracts were combined, washed with brine (10 mL×2), dried over anhydrous sodium sulfate, and concentrated. The residue was purified by silica gel column chromatography (petroleum ether/ethyl acetate=100:1 to 10:1) to give the title product as a brown solid (77 mg, 38% yield). $^1$H NMR (CDCl$_3$, 400 MHz) δ: 11.57 (s, 1H), 10.18 (s, 1H), 7.52 (d, J=8.0 Hz, 2H), 7.12-7.20 (m, 3H), 6.76-6.90 (m, 3H), 3.53 (m, 4H), 2.20 (m, 4H); LC-MS m/z [M+H]$^+$ calc'd for C$_{19}$H$_{18}$FNO$_2$, 312; found, 312.

Example 54: (E)-2-hydroxy-3-methoxy-5-(4-(2-methoxyethoxy)styryl)benzaldehyde (Compound 87)

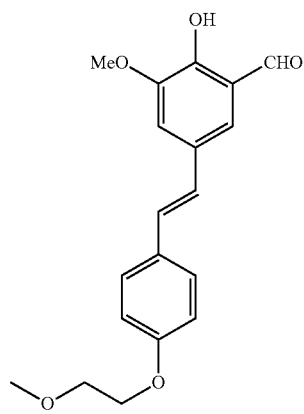 [SMILES: COCCOc1ccc(/C=C/c2cc(C=O)c(O)c(OC)c2)cc1]

Step 1: 1-(2-methoxyethoxy)-4-vinylbenzene

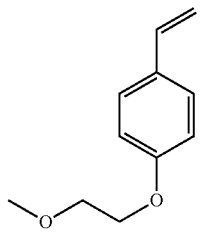

The title compound was prepared from 4-(2-methoxyethoxy)benzaldehyde (1.80 g, 10 mmol) and methyltriphenylphosphonium bromide (7.14 g, 20 mmol) using the similar procedure mentioned as in step-1 of Example 38 to give the product as colorless oil (0.93 g, 22% yield). LC-MS m/z [M+H]$^+$ calc'd for $C_{11}H_{14}O_2$, 179; found, 179.

Step 2: The title compound was prepared from 5-bromo-2-hydroxy-3-methoxybenzaldehyde (231 mg, 1.0 mmol) and 1-(2-methoxyethoxy)-4-vinylbenzene (178 mg, 1.0 mmol) as described in Example 25 to give the title compound as a yellow solid (72 mg, 22% yield). $^1$H NMR (500 MHz, Chloroform-d) δ 11.06 (s, 1H), 9.94 (s, 1H), 7.46-7.40 (m, 2H), 7.29-7.23 (m, 2H), 6.96 (d, J=16.9 Hz, 2H), 6.93 (s, 2H), 4.15 (dd, J=5.6, 3.8 Hz, 2H), 3.98 (s, 3H), 3.84-3.68 (m, 2H), 3.46 (s, 3H); LC-MS m/z [M+H]$^+$ calc'd for $C_{19}H_{20}O_5$, 329; found, 329.

Example 55: (E)-3-fluoro-2-hydroxy-5-(4-(2-methoxyethoxy)styryl)benzaldehyde (Compound 88)

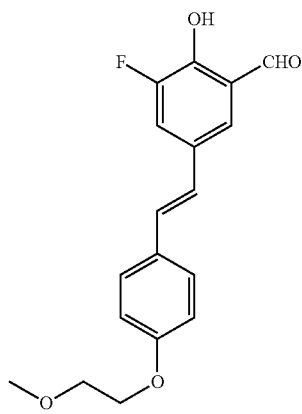 [SMILES: COCCOc1ccc(/C=C/c2cc(F)c(O)c(C=O)c2)cc1]

The title compound was prepared from 5-bromo-3-fluoro-2-hydroxybenzaldehyde (219 mg, 1.0 mmol) and 1-(2-methoxyethoxy)-4-vinylbenzene (178 mg, 1.0 mmol) as described in Example 25 to give the title compound as yellow solid (68 mg, 22% yield). $^1$H NMR (500 MHz, Chloroform-d) δ 10.90 (s, 1H), 9.95 (d, J=1.8 Hz, 1H), 7.52 (dd, J=11.8, 2.1 Hz, 1H), 7.45-7.40 (m, 3H), 6.96 (d, J=14.0 Hz, 1H), 6.93 (d, 2H), 6.87 (d, J=16.2 Hz, 1H), 4.23-4.07 (m, 2H), 3.81-3.69 (m, 2H), 3.47 (s, 3H); LC-MS m/z [M+H]$^+$ calc'd for $C_{18}H_{17}FO_4$, 317; found, 317.

Example 56: (E)-5-(4-(1H-pyrazol-1-yl)styryl)-2-hydroxy-3-methoxybenzaldehyde (Compound 89)

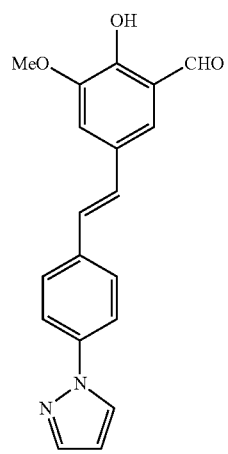

Step 1: 1-(4-vinylphenyl)-1H-pyrazole

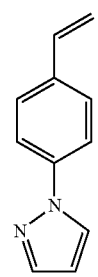

The title compound was prepared from 4-(1H-pyrazol-1-yl)benzaldehyde (1.72 g, 10 mmol) and methyltriphenylphosphonium bromide (7.14 g, 20 mmol) using the similar procedure mentioned as in step-1 of Example 38 to give the product as white solid (1.08 g, 63% yield). LC-MS m/z [M+H]$^+$ calc'd for $C_{11}H_{10}N_2$, 171; found, 171.

Step 2: The title compound was prepared from 5-bromo-2-hydroxy-3-methoxybenzaldehyde (231 mg, 1.0 mmol) and 1-(4-vinylphenyl)-1H-pyrazole (170 mg, 1.0 mmol) as described in Example 25 to give the title compound as yellow solid (108 mg, 34% yield). $^1$H NMR (500 MHz, Chloroform-d) δ 11.11 (s, 1H), 9.96 (s, 1H), 7.95 (d, J=2.5 Hz, 1H), 7.74 (d, J=1.8 Hz, 1H), 7.73-7.69 (m, 2H), 7.62-7.55 (m, 2H), 7.30 (s, 2H), 7.07 (d, J=16.3 Hz, 1H), 7.02 (d, J=16.3 Hz, 1H), 6.49 (t, J=2.2 Hz, 1H), 4.00 (s, 3H); LC-MS m/z [M+H]$^+$ calc'd for $C_{19}H_{16}N_2O_3$, 321; found, 321.

Example 57: (E)-5-(4-(1H-pyrazol-1-yl)styryl)-3-fluoro-2-hydroxybenzaldehyde (Compound 90)

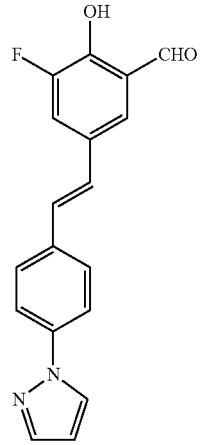

The title compound was prepared from 5-bromo-3-fluoro-2-hydroxybenzaldehyde (219 mg, 1.0 mmol) and 1-(4-vinylphenyl)-1H-pyrazole (170 mg, 1.0 mmol) as described in Example 25 to give the title compound as yellow solid (78 mg, 25% yield). $^1$H NMR (500 MHz, Chloroform-d) δ 10.96 (s, 1H), 9.97 (d, J=1.8 Hz, 1H), 7.95 (d, J=2.5 Hz, 1H), 7.75 (d, J=1.8 Hz, 1H), 7.73-7.69 (m, 2H), 7.61-7.53 (m, 3H), 7.50-7.45 (m, 1H), 7.02 (s, 2H), 6.49 (t, J=2.2 Hz, 1H); LC-MS m/z [M+H]$^+$ calc'd for $C_{18}H_{13}FN_2O_2$, 309; found, 309.

Example 58: (E)-2-hydroxy-3-methoxy-5-(2-(quinolin-6-yl)vinyl)benzaldehyde (Compound 91)

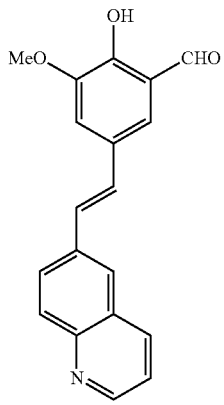

Step 1: 6-vinylquinoline

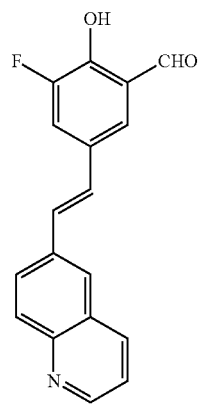

The title compound was prepared from quinoline-6-carbaldehyde (1.57 g, 10 mmol) and methyltriphenylphosphonium bromide (7.14 g, 20 mmol) using a similar procedure as described in step-1 of Example 38 to give the product as a colorless liquid (1.28 g, 82% yield). LC-MS m/z [M+H]$^+$ calc'd for $C_{11}H_9N$, 156; found, 156.

Step 2: The title compound was prepared from 5-bromo-2-hydroxy-3-methoxybenzaldehyde (231 mg, 1.0 mmol) and 6-vinylquinoline (155 mg, 1.0 mmol) as described in Example 25 to give the title compound as a brown solid (18 mg, 6% yield). $^1$H NMR (500 MHz, Chloroform-d) δ 11.14 (s, 1H), 9.98 (s, 1H), 8.88 (dd, J=4.3, 1.7 Hz, 1H), 8.15 (dd, J=20.9, 8.6 Hz, 2H), 7.97 (dd, J=8.9, 2.0 Hz, 1H), 7.84 (d, J=1.9 Hz, 1H), 7.43 (dd, J=8.3, 4.3 Hz, 1H), 7.35 (d, J=1.5 Hz, 2H), 7.22 (d, J=16.3 Hz, 1H), 7.18 (d, J=16.3 Hz, 1H), 4.02 (s, 3H); LC-MS m/z [M+H]$^+$ calc'd for $C_{19}H_{15}NO_3$, 306; found, 306.

Example 59: (E)-3-fluoro-2-hydroxy-5-(2-(quinolin-6-yl)vinyl)benzaldehyde (Compound 92)

The title compound was prepared from 5-bromo-3-fluoro-2-hydroxybenzaldehyde (219 mg, 1.0 mmol) and 6-vinylquinoline (155 mg, 1.0 mmol) as described in Example 25 to give the title compound as a yellow solid (52 mg, 18% yield). $^1$H NMR (500 MHz, Chloroform-d) δ 10.99 (s, 1H), 9.99 (d, J=1.8 Hz, 1H), 8.90 (dd, J=4.3, 1.7 Hz, 1H), 8.19 (dd, J=8.4, 1.6 Hz, 1H), 8.15 (d, J=8.8 Hz, 1H), 7.96 (dd, J=8.9, 2.0 Hz, 1H), 7.84 (d, J=2.1 Hz, 1H), 7.61 (dd, J=11.6, 2.1 Hz, 1H), 7.56-7.49 (m, 1H), 7.45 (dd, J=8.3, 4.3 Hz, 1H), 7.18 (s, 2H); LC-MS m/z [M+H]$^+$ calc'd for $C_{18}H_{12}FNO_2$, 294; found, 294.

Example 60: tert-butyl (E)-6-(3-formyl-4-hydroxy-5-methoxystyryl)-3,4-dihydroquinoline-1(2H)-carboxylate (Compound 93)

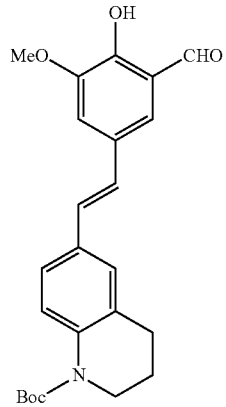

Step 1: tert-butyl 6-vinyl-3,4-dihydroquinoline-1(2H)-carboxylate

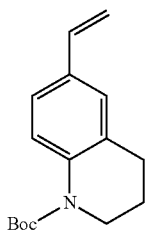

The title compound was prepared from tert-butyl 6-formyl-3,4-dihydroquinoline-1(2H)-carboxylate (0.91 g, 3.5 mmol) and methyltriphenylphosphonium bromide (2.5 g, 7 mmol) using a similar procedure as described in step-1 of Example 38 to give the product as a white solid (0.68 g, 75% yield). LC-MS m/z [M+H]$^+$ calc'd for $C_{16}H_{21}NO_2$, 260; found, 260.

Step 2: The title compound was prepared from 5-bromo-2-hydroxy-3-methoxybenzaldehyde (231 mg, 1.0 mmol) and tert-butyl 6-vinyl-3,4-dihydroquinoline-1(2H)-carboxylate (259 mg, 1.0 mmol) as described in Example 25 to give the title compound as a yellow solid (148 mg, 36% yield). $^1$H NMR (500 MHz, Chloroform-d) δ 11.07 (s, 1H), 9.94 (s, 1H), 7.70 (d, J=8.5 Hz, 1H), 7.29 (dd, J=8.7, 2.3 Hz, 1H), 7.28-7.26 (m, 2H), 7.22 (d, J=2.0 Hz, 1H), 6.96 (d, J=16 Hz, 1H), 6.95 (d, J=16 Hz, 1H), 3.99 (s, 3H), 3.81-3.65 (m, 2H), 2.79 (t, J=6.6 Hz, 2H), 1.94 (p, J=6.4 Hz, 2H), 1.54 (s, 9H); LC-MS m/z [M+H]$^+$ calc'd for $C_{24}H_{27}NO_5$, 410; found, 410.

Example 61: tert-butyl (E)-6-(3-fluoro-5-formyl-4-hydroxystyryl)-3,4-dihydroquinoline-1(2H)-carboxylate (Compound 94)

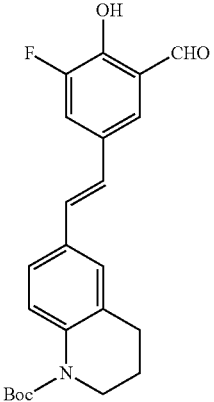 [SMILES: CC(C)(C)OC(=O)N1CCCc2cc(/C=C/c3cc(F)c(O)c(C=O)c3)ccc21]

The title compound was prepared from 5-bromo-3-fluoro-2-hydroxybenzaldehyde (219 mg, 1.0 mmol) and 6-vinyl-3,4-dihydroquinoline-1(2H)-carboxylate (259 mg, 1.0 mmol) as described in Example 25 to give the title compound as a yellow solid (28 mg, 7% yield). $^1$H NMR (500 MHz, Chloroform-d) δ 10.91 (s, 1H), 9.95 (d, J=1.9 Hz, 1H), 7.70 (d, J=8.6 Hz, 1H), 7.53 (dd, J=11.8, 2.1 Hz, 1H), 7.45-7.41 (m, 1H), 7.28 (dd, J=8.7, 2.2 Hz, 1H), 7.20 (d, J=2.0 Hz, 1H), 6.93 (m, 2H), 3.81-3.57 (m, 2H), 2.79 (t, J=6.5 Hz, 2H), 1.94 (p, J=6.4 Hz, 2H), 1.54 (s, 9H); LC-MS m/z [M+H]$^+$ calc'd for $C_{23}H_{24}FNO_4$, 398; found, 398.

Example 62: (E)-3-fluoro-2-hydroxy-5-(2-(1-methyl-1,2,3,4-tetrahydroquinolin-6-yl)vinyl)benzaldehyde (Compound 95)

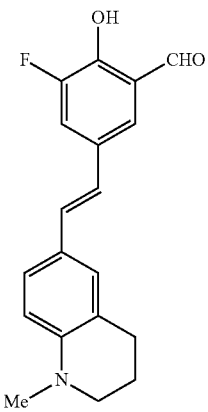 [SMILES: CN1CCCc2cc(/C=C/c3cc(F)c(O)c(C=O)c3)ccc21]

Step 1:
1-methyl-6-vinyl-1,2,3,4-tetrahydroquinoline

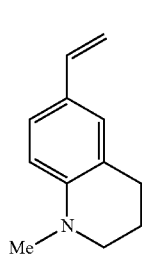

The title compound was prepared from 1-methyl-1,2,3,4-tetrahydroquinoline-6-carbaldehyde (1.75 g, 10 mmol) and methyltriphenylphosphonium bromide (7.14 g, 20 mmol) using a similar procedure as described in step-1 of Example 38 to give the product as a brown liquid (1.01 g, 58% yield). LC-MS m/z [M+H]$^+$ calc'd for $C_{12}H_{15}N$, 174; found, 174.

Step 2: The title compound was prepared from 5-bromo-3-fluoro-2-hydroxybenzaldehyde (219 mg, 1.0 mmol) and 1-methyl-6-vinyl-1,2,3,4-tetrahydroquinoline (173 mg, 1.0 mmol) as described in Example 25 to give the title compound as a red solid (25 mg, 8% yield). $^1$H NMR (500 MHz, Chloroform-d) δ 10.84 (s, 1H), 9.93 (d, J=1.8 Hz, 1H), 7.49 (dd, J=12.0, 2.1 Hz, 1H), 7.39 (t, J=1.5 Hz, 1H), 7.21 (dd, J=8.3, 2.2 Hz, 1H), 7.13 (d, J=2.0 Hz, 1H), 6.89 (d, J=16.1 Hz, 1H), 6.77 (d, J=16.1 Hz, 1H), 6.57 (d, J=8.5 Hz, 1H), 3.35-3.17 (m, 2H), 2.93 (s, 3H), 2.79 (t, J=6.4 Hz, 2H), 2.08-1.82 (m, 2H); LC-MS m/z [M+H]$^+$ calc'd for $C_{19}H_{18}FNO_2$, 312; found, 312.

Example 63: (E)-5-(4-(diethylamino)styryl)-2-hydroxy-3-methoxybenzaldehyde (Compound 96)

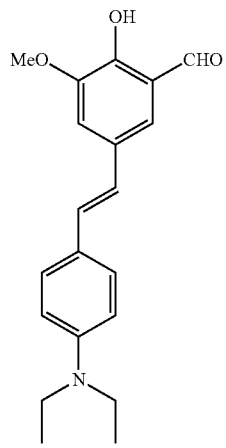 [SMILES: CCN(CC)c1ccc(/C=C/c2cc(C=O)c(O)c(OC)c2)cc1]

Step 1: N,N-diethyl-4-vinylaniline

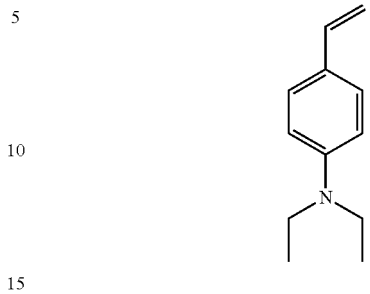

The title compound was prepared from 4-(diethylamino)benzaldehyde (1.77 g, 10 mmol) and methyltriphenylphosphonium bromide (7.14 g, 20 mmol) using a similar procedure as described in step-1 of Example 38 to give the product as a colorless liquid (1.72 g, 98% yield). LC-MS m/z [M+H]$^+$ calc'd for $C_{12}H_{17}N$, 176; found, 176.

Step 2: The title compound was prepared from 5-bromo-2-hydroxy-3-methoxybenzaldehyde (231 mg, 1.0 mmol) and N,N-diethyl-4-vinylaniline (176 mg, 1.0 mmol) as described in Example 25 to give the title compound as a yellow solid (48 mg, 15% yield). $^1$H NMR (500 MHz, Chloroform-d) δ 11.02 (s, 1H), 9.93 (s, 1H), 7.42-7.34 (m, 2H), 7.26 (s, 1H), 7.23 (d, J=1.9 Hz, 1H), 6.93 (d, J=16.2 Hz, 1H), 6.82 (d, J=16.2 Hz, 1H), 6.71-6.49 (m, 2H), 3.98 (s, 3H), 3.39 (q, J=7.1 Hz, 4H), 1.19 (t, J=7.0 Hz, 6H); LC-MS m/z [M+H]$^+$ calc'd for $C_{20}H_{23}NO_3$, 326; found, 326.

Example 64: (E)-5-(4-(diethylamino)styryl)-3-fluoro-2-hydroxybenzaldehyde (Compound 97)

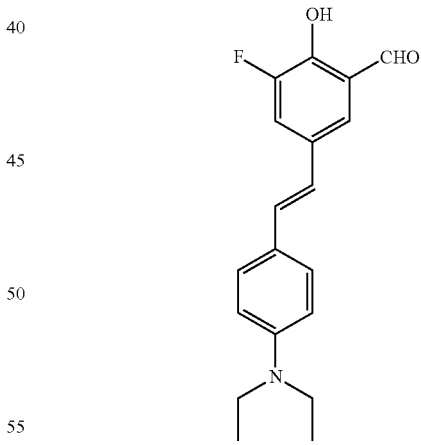

The title compound was prepared from 5-bromo-3-fluoro-2-hydroxybenzaldehyde (219 mg, 1.0 mmol) and N,N-diethyl-4-vinylaniline (176 mg, 1.0 mmol) as described in Example 25 to give the title compound as an orange solid (38 mg, 12% yield). $^1$H NMR (500 MHz, Chloroform-d) δ 10.84 (s, 1H), 9.94 (d, J=1.9 Hz, 1H), 7.50 (dd, J=12.1, 2.0 Hz, 1H), 7.39 (t, J=1.4 Hz, 1H), 7.38-7.33 (m, 2H), 6.92 (d, J=16.1 Hz, 1H), 6.77 (d, J=16.2 Hz, 1H), 6.70-6.64 (m, 2H), 3.39 (q, J=7.1 Hz, 4H), 1.19 (t, J=7.0 Hz, 6H); LC-MS m/z [M+H]$^+$ calc'd for $C_{19}H_{20}FNO_2$, 314; found, 314.

Example 65: (E)-5-(4-(cyclopropylmethoxy)styryl)-2-hydroxy-3-methoxybenzaldehyde (Compound 98)

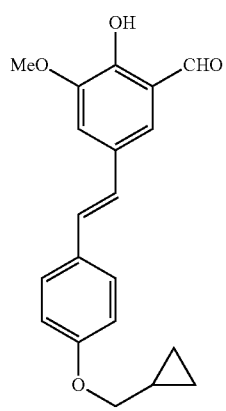 [SMILES: COc1cc(/C=C/c2ccc(OCC3CC3)cc2)cc(C=O)c1O]

Step 1: 1-(cyclopropylmethoxy)-4-vinylbenzene

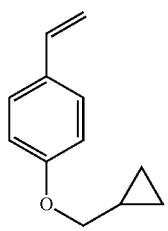

The title compound was prepared from 4-(cyclopropylmethoxy)benzaldehyde (1.76 g, 10 mmol) and methyltriphenylphosphonium bromide (7.14 g, 20 mmol) using a similar procedure as described in step-1 of Example 38 to give the product as a white solid (1.67 g, 96% yield). LC-MS m/z [M+H]$^+$ calc'd for $C_{12}H_{14}O$, 175; found, 175.

Step 2: The title compound was prepared from 5-bromo-2-hydroxy-3-methoxybenzaldehyde (231 mg, 1.0 mmol) and 1-(cyclopropylmethoxy)-4-vinylbenzene (175 mg, 1.0 mmol) as described in Example 25 to give the title compound as a yellow solid (58 mg, 18% yield). $^1$H NMR (500 MHz, Chloroform-d) δ 11.06 (s, 1H), 9.94 (s, 1H), 7.47-7.40 (m, 2H), 7.29-7.23 (m, 2H), 6.96 (d, J=16.3 Hz, 1H), 6.93-6.88 (m, 3H), 3.99 (s, 3H), 3.83 (d, J=6.9 Hz, 2H), 1.37-1.12 (m, 1H), 0.73-0.56 (m, 2H), 0.36 (dt, J=6.2, 4.7 Hz, 2H); LC-MS m/z [M+H]$^+$ calc'd for $C_{20}H_{20}O_4$, 325; found, 325.

Example 66: (E)-5-(4-(cyclopropylmethoxy)styryl)-3-fluoro-2-hydroxybenzaldehyde (Compound 99)

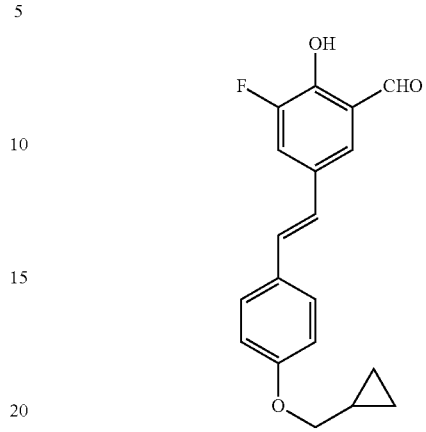

The title compound was prepared from 5-bromo-3-fluoro-2-hydroxybenzaldehyde (219 mg, 1.0 mmol) and 1-(cyclopropylmethoxy)-4-vinylbenzene (175 mg, 1.0 mmol) as described in Example 25 to give the title compound as an off-white solid (43 mg, 14% yield). $^1$H NMR (500 MHz, Chloroform-d) δ 10.90 (s, 1H), 9.95 (d, J=1.9 Hz, 1H), 7.52 (dd, J=11.8, 2.1 Hz, 1H), 7.45-7.39 (m, 3H), 6.96 (d, J=16.3 Hz, 1H), 6.92-6.89 (m, 2H), 6.86 (d, J=16.2 Hz, 1H), 3.83 (d, J=6.9 Hz, 2H), 1.29 (dddd, J=15.1, 6.9, 5.1, 2.8 Hz, 1H), 0.78-0.57 (m, 2H), 0.37 (dt, J=6.1, 4.6 Hz, 2H); LC-MS m/z [M+H]$^+$ calc'd for $C_{19}H_{17}FO_3$, 313; found, 313.

Example 67: (E)-5-(2-(chroman-6-yl)vinyl)-2-hydroxy-3-methoxybenzaldehyde (Compound 100)

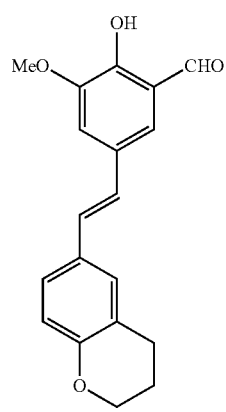 [SMILES: COc1cc(/C=C/c2ccc3c(c2)CCCO3)cc(C=O)c1O]

245

Step 1: 6-vinylchromane

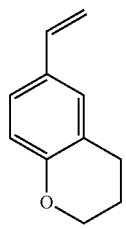

The title compound was prepared from chromane-6-carbaldehyde (1.62 g, 10 mmol) and methyltriphenylphosphonium bromide (7.14 g, 20 mmol) using the similar procedure mentioned as in step-1 of Example 38 to give the product as a colorless oil (1.6 g, 100% yield). LC-MS m/z [M+H]$^+$ calc'd for C$_H$H$_{12}$O, 161; found, 161.

Step 2: The title compound was prepared from 5-bromo-2-hydroxy-3-methoxybenzaldehyde (231 mg, 1.0 mmol) and 6-vinylchromane (160 mg, 1.0 mmol) as described in Example 25 to give the title compound as a yellow solid (56 mg, 18% yield). $^1$H NMR (500 MHz, Chloroform-d) δ 11.05 (s, 1H), 9.94 (s, 1H), 7.26 (s, 1H), 7.24 (d, J=1.9 Hz, 2H), 7.19 (d, J=2.1 Hz, 1H), 6.93 (d, J=16.2 Hz, 1H), 6.88 (d, J=16.2 Hz, 1H), 6.79 (d, J=8.5 Hz, 1H), 4.39-4.14 (m, 2H), 3.98 (s, 3H), 2.82 (t, J=6.4 Hz, 2H), 2.13-1.91 (m, 2H); LC-MS m/z [M+H]$^+$ calc'd for C$_{19}$H$_{18}$O$_4$, 311; found, 311.

Example 68: (E)-5-(2-(chroman-6-yl)vinyl)-3-fluoro-2-hydroxybenzaldehyde (Compound 101)

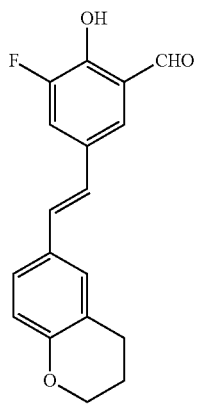 [SMILES: O=Cc1cc(/C=C/c2ccc3c(c2)CCCO3)cc(F)c1O]

The title compound was prepared from 5-bromo-3-fluoro-2-hydroxybenzaldehyde (219 mg, 1.0 mmol) and 6-vinylchromane (160 mg, 1.0 mmol) as described in Example 25 to give the title compound as an off-white solid (58 mg, 19% yield). $^1$H NMR (500 MHz, Chloroform-d) δ 10.89 (s, 1H), 9.95 (d, J=1.7 Hz, 1H), 7.51 (dd, J=11.8, 2.1 Hz, 1H), 7.43-7.39 (m, 1H), 7.24 (dd, J=9.3, 3.1 Hz, 1H), 7.17 (d, J=2.1 Hz, 1H), 6.92 (d, J=16.3 Hz, 1H), 6.84 (d, J=16.3 Hz, 1H), 6.80 (d, J=8.5 Hz, 1H), 4.36-4.07 (m, 2H), 2.82 (t, J=6.5 Hz, 2H), 2.19-1.85 (m, 2H); LC-MS m/z [M+H]$^+$ calc'd for C$_{18}$H$_{15}$FO$_3$, 299; found, 299.

246

Example 69: (E)-2-hydroxy-3-methoxy-5-(4-(piperidin-1-yl)styryl)benzaldehyde (Compound 102)

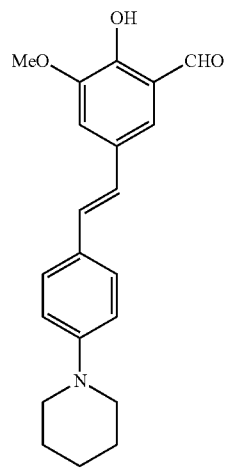 [SMILES: COc1cc(/C=C/c2ccc(N3CCCCC3)cc2)cc(C=O)c1O]

Step 1: 1-(4-vinylphenyl)piperidine

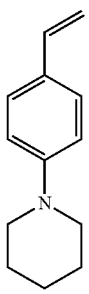

The title compound was prepared from 4-(piperidin-1-yl)benzaldehyde (1.89 g, 10 mmol) and methyltriphenylphosphonium bromide (7.14 g, 20 mmol) using a similar procedure as described in step-1 of Example 38 to give the product as a colorless oil (1.62 g, 87% yield). LC-MS m/z [M+H]$^+$ calc'd for C$_{13}$H$_{17}$N, 188; found, 188.

Step 2: The title compound was prepared from 5-bromo-2-hydroxy-3-methoxybenzaldehyde (231 mg, 1.0 mmol) and 1-(4-vinylphenyl)piperidine (188 mg, 1.0 mmol) as described in Example 25 to give the title compound as a yellow solid (58 mg, 17% yield). $^1$H NMR (500 MHz, Chloroform-d) δ 11.04 (s, 1H), 9.94 (s, 1H), 7.47-7.33 (m, 2H), 7.29-7.22 (m, 2H), 6.95 (d, J=16.3 Hz, 1H), 6.91 (s, 2H), 6.88 (d, J=16.2 Hz, 1H), 3.98 (s, 3H), 3.32-3.13 (m, 4H), 1.71 (p, J=5.6 Hz, 4H), 1.61 (q, J=8.6, 7.3 Hz, 2H); LC-MS m/z [M+H]$^+$ calc'd for C$_{21}$H$_{23}$NO$_3$, 338; found, 338.

Example 70: (E)-3-fluoro-2-hydroxy-5-(4-(piperidin-1-yl)styryl)benzaldehyde (Compound 103)

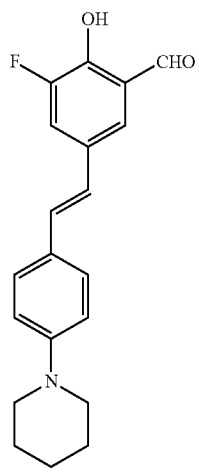

The title compound was prepared from 5-bromo-3-fluoro-2-hydroxybenzaldehyde (219 mg, 1.0 mmol) and 1-(4-vinylphenyl)piperidine (188 mg, 1.0 mmol) as described in Example 25 to give the title compound as a yellow solid (42 mg, 13% yield). $^1$H NMR (500 MHz, Chloroform-d) δ 10.87 (s, 1H), 9.94 (d, J=1.9 Hz, 1H), 7.51 (dd, J=11.8, 2.1 Hz, 1H), 7.41 (d, J=1.6 Hz, 1H), 7.40-7.37 (m, 2H), 6.94 (d, J=16.2 Hz, 1H), 6.91 (s, 2H), 6.83 (d, J=16.3 Hz, 1H), 3.23 (t, J=5.5 Hz, 4H), 1.72 (t, J=8.2 Hz, 4H), 1.61 (q, J=5.7 Hz, 2H); LC-MS m/z [M+H]$^+$ calc'd for $C_{20}H_{20}FNO_2$, 326; found, 326.

Example 71: (E)-2-fluoro-6-hydroxy-4-(4-(piperidin-1-yl)styryl)benzaldehyde (Compound 104)

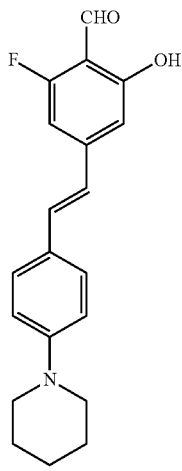

The title compound was prepared from 4-bromo-2-fluoro-6-hydroxybenzaldehyde (219 mg, 1.0 mmol) and 1-(4-vinylphenyl)piperidine (188 mg, 1.0 mmol) as described in Example 25 to give the title compound as an orange solid (140 mg, 43% yield). $^1$H NMR (500 MHz, Chloroform-d) δ 11.56 (s, 1H), 10.15 (s, 1H), 7.46-7.39 (m, 2H), 7.16 (d, J=16.2 Hz, 1H), 6.90 (d, J=8.3 Hz, 2H), 6.85-6.70 (m, 3H), 3.33-3.14 (m, 4H), 1.70 (h, J=5.0 Hz, 4H), 1.62 (q, J=5.6 Hz, 2H); LC-MS m/z [M+H]$^+$ calc'd for $C_{20}H_{20}FNO_2$, 326; found, 326.

Example 72: (E)-4-(4-(4-ethylpiperazin-1-yl)styryl)-2-fluoro-6-hydroxybenzaldehyde (Compound 105)

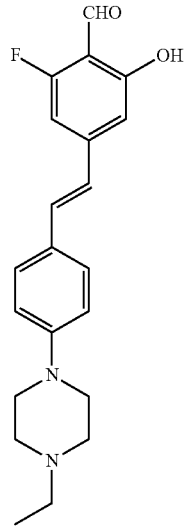

Step 1: 1-ethyl-4-(4-vinylphenyl)piperazine

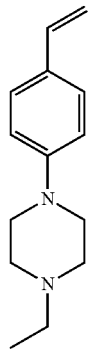

The title compound was prepared from 4-(4-ethylpiperazin-1-yl)benzaldehyde (2.18 g, 10 mmol) and methyltriphenylphosphonium bromide (7.14 g, 20 mmol) using a similar procedure as described in step-1 of Example 38 to give the product as a white solid (1.58 g, 73% yield). LC-MS m/z [M+H]$^+$ calc'd for $C_{14}H_{20}N_2$, 217; found, 217.

Step 2: The title compound was prepared from 5-bromo-3-fluoro-2-hydroxybenzaldehyde (219 mg, 1.0 mmol) and 1-ethyl-4-(4-vinylphenyl)piperazine (217 mg, 1.0 mmol) as described in Example 25 to give the title compound as a brown solid (198 mg, 56% yield). $^1$H NMR (500 MHz, Chloroform-d) δ 11.55 (s, 1H), 10.16 (s, 1H), 7.46-7.39 (m, 2H), 7.16 (d, J=16.1 Hz, 1H), 6.94-6.88 (m, 2H), 6.82 (d, J=16.3 Hz, 1H), 6.80 (s, 1H), 6.76 (dd, J=11.7, 1.5 Hz, 1H), 3.35 (t, J=5.1 Hz, 4H), 2.70 (t, J=5.0 Hz, 4H), 2.56 (q, J=7.3 Hz, 2H), 1.18 (t, J=7.2 Hz, 3H); LC-MS m/z [M+H]$^+$ calc'd for $C_{21}H_{23}FN_2O_2$, 355; found, 355.

Example 73: (E)-3-(5-(5-(cyclopropanecarbonyl)-4,5,6,7-tetrahydrothieno[3,2-c]pyridin-2-yl)-2-hydroxy-3-methoxyphenyl)-1-phenylprop-2-en-1-one (Compound 106)

Example 74: (E)-1-(5-(5-(cyclopropanecarbonyl)-4,5,6,7-tetrahydrothieno[3,2-c]pyridin-2-yl)-2-hydroxy-3-methoxyphenyl)-3-phenylprop-2-en-1-one (Compound 107)

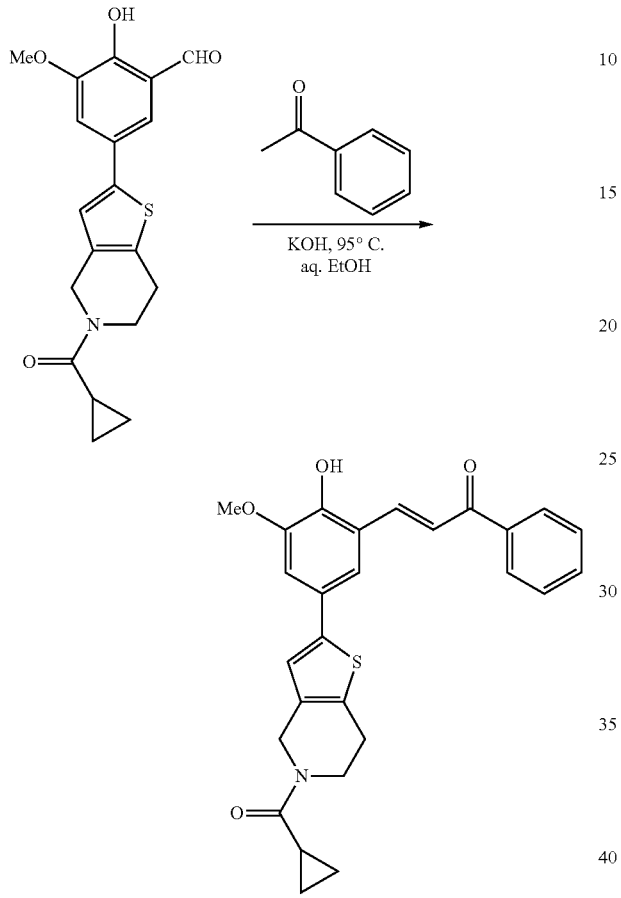

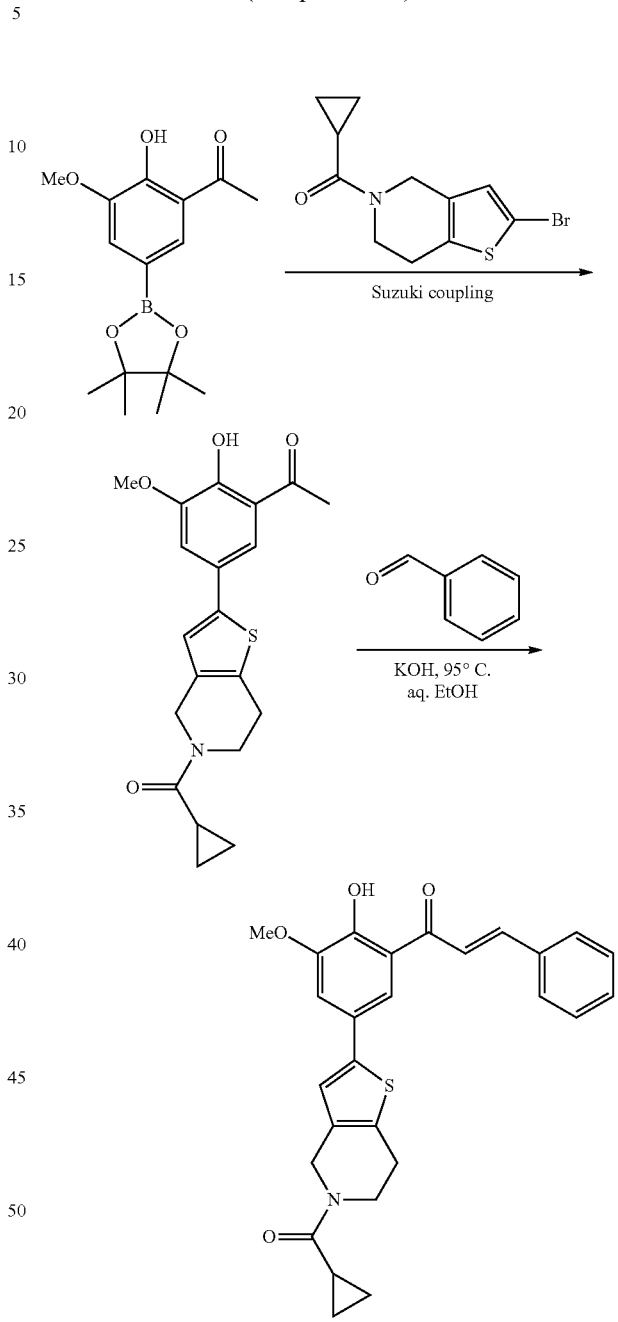

KOH (403 mg, 7.2 mmol) was added to a mixture of 5-(5-(cyclopropanecarbonyl)-4,5,6,7-tetrahydrothieno[3,2-c]pyridin-2-yl)-2-hydroxy-3-methoxybenzaldehyde (650 mg, 1.8 mmol) and acetophenone (216 mg, 1.8 mmol) in EtOH/water (20 mL/7 mL). The reaction was heated overnight at 95° C. Ethanol was removed in vacuo and the residue was diluted with water (20 mL). The mixture was then extracted with ethyl acetate (20 mL×3). The organic extracts were combined, dried over anhydrous sodium sulfate, and concentrated. The crude was purified by prep-HPLC to give desired product as a brown solid (73 mg, 9% yield). $^1$H NMR (DMSO-d6, 400 MHz) δ: 9.75 (br, 1H), 8.14 (m, 2H), 8.07 (s, 1H), 7.92 (m, 1H), 7.68 (m, 2H), 7.58 (m, 2H), 7.33 (s, 1H), 7.19 (s, 1H), 4.82 (br, 1H), 4.57 (s, 1H), 4.01 (m, 1H), 3.91 (s, 3H), 3.82 (m, 1H), 2.92 (m, 1H), 2.78 (m, 1H), 1.98-2.15 (m, 1H), 0.77 (m, 4H); LC-MS m/z [M+H]$^+$ calc'd for $C_{27}H_{25}NO_4S$, 460; found, 460.

Step 1: 1-(5-(5-(cyclopropanecarbonyl)-4,5,6,7-tetrahydrothieno[3,2-c]pyridin-2-yl)-2-hydroxy-3-methoxyphenyl)ethan-1-one

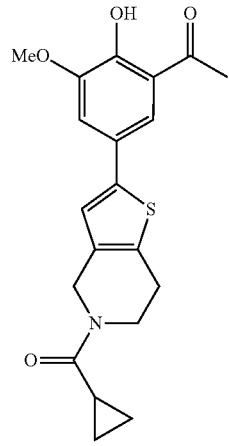 [SMILES: COc1cc(-c2cc3c(s2)CCN(C(=O)C2CC2)C3)cc(C(C)=O)c1O]

A mixture of 1-(2-hydroxy-3-methoxy-5-(4,4,5,5-tetramethyl-1,3-dioxolan-2-yl)phenyl)ethanone (300 mg, 1.0 mmol), (2-bromo-6,7-dihydrothieno[3,2-c]pyridin-5(4H)-yl)(cyclopropyl)methanone (342 mg, 1.2 mmol), K$_2$CO$_3$ (284 mg, 2.1 mmol), and Pd(dppf)$_2$Cl$_2$ (84 mg, 0.1 mmol) in dioxane (20 mL)/water (6 mL) was stirred overnight at 110° C. under N$_2$. The mixture was cooled to rt, diluted with water (50 mL), and extracted with ethyl acetate (50 mL×3). The organic extracts were combined, washed with brine (50 mL), dried over anhydrous sodium sulfate, and concentrated. The residue was purified by silica gel column chromatography (petroleum ether/ethyl acetate=20:1 to 10:1) to afford the desired intermediate (213 mg, 56% yield).

Step 2: KOH (120 mg, 2.16 mmol) was added to a mixture of the desired intermediate of Step 1 above (200 mg, 0.54 mmol) and benzaldehyde (57 mg, 0.54 mmol) in EtOH/water (10 mL/3 mL). The reaction was heated overnight at 95° C. Ethanol was removed in vacuo and the residue was diluted with water (20 mL). The mixture was then extracted with ethyl acetate (20 mL×3). The organic extracts were combined, dried over anhydrous sodium sulfate, and concentrated. The crude was purified by prep-HPLC to give the desired final product as a brown solid (93 mg, 38% yield). $^1$H NMR (CDCl$_3$, 400 MHz) δ 13.21 (br, 1H), 7.95 (d, J=15.2 Hz, 1H), 7.58-7.69 (m, 4H), 7.46 (m, 3H), 7.20 (m, 1H), 6.96 (s, 1H), 4.82 (m, 1H), 4.71 (m, 1H), 3.97-4.02 (m, 5H), 2.99 (m, 1H), 2.88 (m, 1H), 1.86 (m, 1H), 1.08 (m, 2H), 0.87 (m, 2H); LC-MS m/z [M+H]$^+$ calc'd for C$_{27}$H$_{25}$NO$_4$S, 460; found, 460.

Example 75: (E)-2-(1,3-dioxan-2-yl)-6-fluoro-4-(4-(pyrrolidin-1-yl)styryl)phenol (Compound 108)

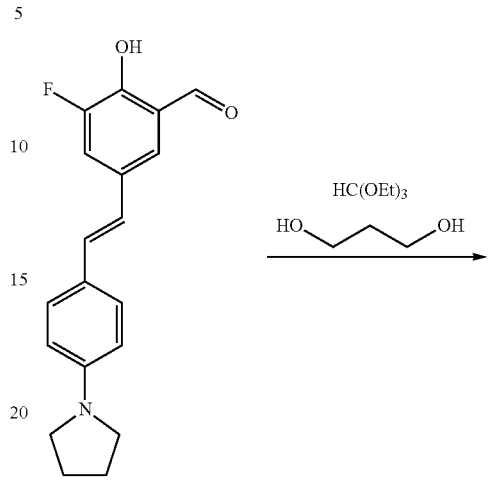

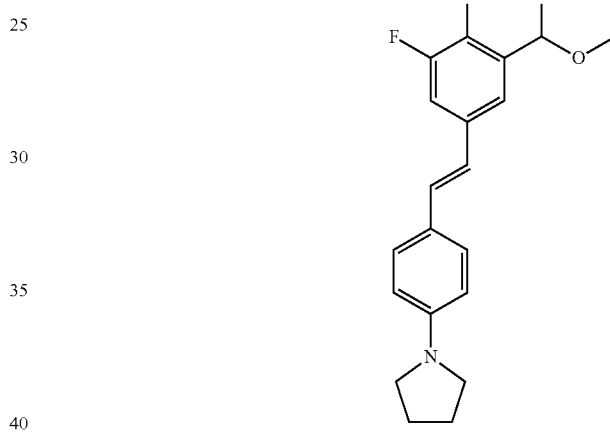

A suspension of (E)-3-fluoro-2-hydroxy-5-(4-(pyrrolidin-1-yl)styryl)benzaldehyde (200 mg, 0.64 mmol), triethyl orthoformate (105 mg, 0.71 mmol), and Bu$_4$NBr (2 mg, 0.005 mmol) in propane-1,3-diol (5 mL) was stirred for 3 hours at rt. The solvent was removed in vacuo and the cake was purified by prep-TLC to give the title product as yellow solid (90 mg, 38% yield). $^1$H NMR (DMSO-d6, 400 MHz) δ 9.62 (s, 1H), 7.29-7.39 (m, 4H), 6.81-6.94 (m, 2H), 6.52 (d, J=8.4 Hz, 2H), 5.76 (s, 1H), 4.13 (m, 2H), 3.93 (m, 2H), 3.25 (m, 4H), 2.00 (m, 1H), 1.95 (m, 4H), 1.43 (m, 1H); LC-MS m/z [M+H]$^+$ calc'd for C$_{22}$H$_{24}$FNO$_3$, 370; found, 370.

Example 76: 2-fluoro-6-((E)-((4-methylpiperazin-1-yl)imino)methyl)-4-((E)-4-(pyrrolidin-1-yl)styryl)phenol (Compound 109)

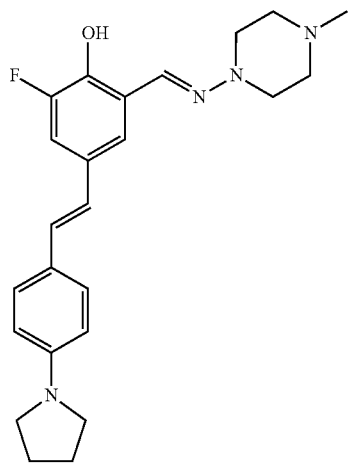 [SMILES: CN1CCN(/N=C/c2cc(/C=C/c3ccc(N4CCCC4)cc3)cc(F)c2O)CC1]

Compound 109 was prepared generally as described in Scheme 6a. (E)-3-fluoro-2-hydroxy-5-(4-(pyrrolidin-1-yl)styryl)benzaldehyde (200 mg, 0.64 mmol) and 4-methylpiperazin-1-amine (74 mg, 0.64 mmol) were dissolved in ethanol. The reaction was refluxed for 2 hours. The solvent was removed, and the residue was filtered. The cake was washed with ethanol and dried in vacuo to give the title compound as a pale yellow solid (210 mg, 80% yield). $^1$H NMR (CDCl$_3$, 400 MHz) δ 11.65 (br, 1H), 7.67 (s, 1H), 7.36 (d, J=8.4 Hz, 2H), 7.18 (m, 1H), 7.00 (s, 1H), 6.87 (d, J=16.0 Hz, 1H), 6.74 (d, J=16.0 Hz, 1H), 6.54 (d, J=8.4 Hz, 2H), 3.32 (m, 4H), 3.27 (m, 4H), 2.71 (m, 4H), 2.42 (s, 3H), 2.01 (m, 4H); LC-MS m/z [M+H]$^+$ calc'd for C$_{24}$H$_{29}$FN$_4$O, 409; found, 409.

Example 77: N'-((E)-3-fluoro-2-hydroxy-5-((E)-4-(pyrrolidin-1-yl)styryl)benzylidene)acetohydrazide (Compound 110)

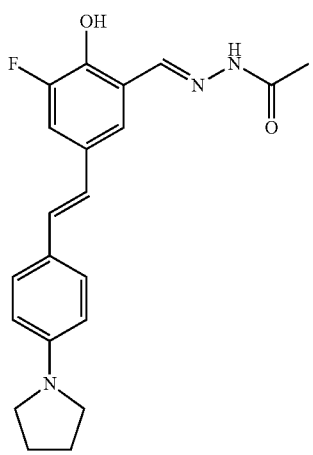

The title compound was prepared using a similar method as that described in Example 76 and generally as described in Scheme 6a using (E)-3-fluoro-2-hydroxy-5-(4-(pyrrolidin-1-yl)styryl)benzaldehyde (200 mg, 0.64 mmol) and acetohydrazide (48 mg, 0.64 mmol) to give the title compound as a pale yellow solid (210 mg, 89% yield). $^1$H NMR (DMSO-d6, 400 MHz) δ: 11.79 (s, 0.6H), 11.47 (s, 0.6H), 11.37 (s, 0.4H), 10.30 (s, 0.4H), 8.35 (s, 0.6H), 8.28 (s, 0.4H), 7.46-7.53 (m, 2H), 7.38 (m, 2H), 7.04 (m, 1H), 6.89 (m, 1H), 6.85 (m, 2H), 3.25 (m, 4H), 2.23 (s, 1H), 1.95-2.00 (m, 6H); LC-MS m/z [M+H]$^+$ calc'd for C$_{21}$H$_{22}$FN$_3$O$_2$, 368; found, 368.

Example 78: 2-fluoro-6-((E)-(phenylimino)methyl)-4-((E)-4-(pyrrolidin-1-yl)styryl)phenol (Compound 111)

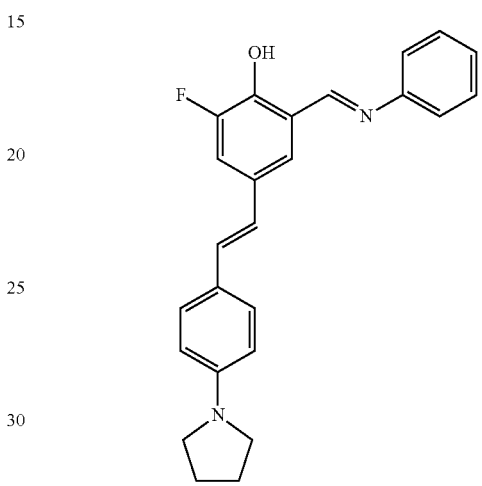

The title compound was prepared using a similar method as that described in Example 76 and generally as described in Scheme 6a using (E)-3-fluoro-2-hydroxy-5-(4-(pyrrolidin-1-yl)styryl)benzaldehyde (200 mg, 0.64 mmol) and aniline (60 mg, 0.64 mmol) to give the title compound as a pale yellow solid (200 mg, 81% yield). $^1$H NMR (CDCl$_3$, 400 MHz) δ: 13.63 (br, 1H), 8.66 (s, 1H), 7.30-7.47 (m, 9H), 6.71-6.95 (m, 4H), 3.41 (m, 4H), 2.10 (m, 4H); LC-MS m/z [M+H]$^+$ calc'd for C$_{25}$H$_{23}$FN$_2$O, 387; found, 387.

Example 79: 2-fluoro-6-((E)-(2-phenylhydrazono)methyl)-4-((E)-4-(pyrrolidin-1-yl)styryl)phenol (Compound 112)

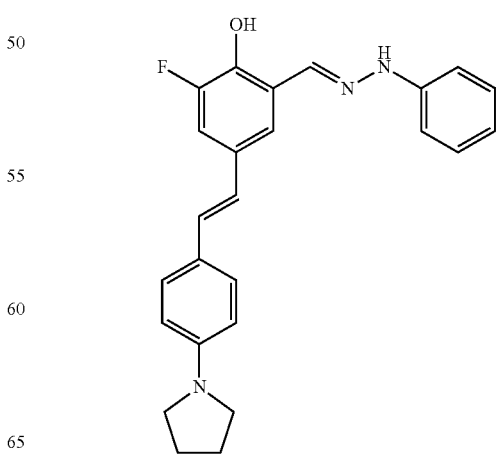

The title compound was prepared using a similar method as that described in Example 76 and generally as described in Scheme 6a using (E)-3-fluoro-2-hydroxy-5-(4-(pyrrolidin-1-yl)styryl)benzaldehyde (200 mg, 0.64 mmol) and phenylhydrazine (70 mg, 0.64 mmol) to give the title compound as a pale yellow solid (180 mg, 70% yield). $^1$H NMR (DMSO-d$_6$, 400 MHz) δ: 10.67 (s, 1H), 10.59 (s, 1H), 8.15 (s, 1H), 7.49 (s, 1H), 7.38 (m, 3H), 7.28 (m, 2H), 7.03 (m, 3H), 6.90 (m, 1H), 6.54 (d, J=8.4 Hz, 2H), 3.26 (m, 4H), 1.96 (m, 4H); LC-MS m/z [M+H]$^+$ calc'd for C$_{25}$H$_{24}$FN$_3$O, 402; found, 402.

Example 80: N'-((E)-3-fluoro-2-hydroxy-5-((E)-4-(pyrrolidin-1-yl)styryl)benzylidene)benzohydrazide (Compound 113)

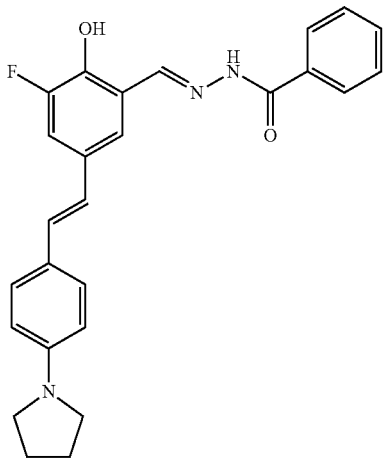 [SMILES: O=C(N/N=C/c1cc(/C=C/c2ccc(N3CCCC3)cc2)cc(F)c1O)c1ccccc1]

The title compound was prepared using a similar method as that described in Example 76 and generally as described in Scheme 6a using (E)-3-fluoro-2-hydroxy-5-(4-(pyrrolidin-1-yl)styryl)benzaldehyde (200 mg, 0.64 mmol) and benzohydrazide (88 mg, 0.64 mmol) to give the title compound as a yellow solid (240 mg, 87% yield). $^1$H NMR (DMSO-d$_6$, 400 MHz) δ: 12.29 (s, 1H), 11.58 (s, 1H), 8.67 (s, 1H), 7.96 (d, J=7.2 Hz, 2H), 7.51-7.64 (m, 5H), 7.39 (d, J=8.0 Hz, 2H), 7.06 (d, J=16.4 Hz, 1H), 6.90 (d, J=16.4 Hz, 1H), 6.54 (d, J=8.4 Hz, 2H), 3.26 (m, 4H), 1.96 (m, 4H); LC-MS m/z [M+H]$^+$ calc'd for C$_{26}$H$_{24}$FN$_3$O$_2$, 430; found, 430.

Example 81: N'-((E)-3-fluoro-2-hydroxy-5-((E)-4-(pyrrolidin-1-yl)styryl)benzylidene)benzenesulfonohydrazide (Compound 114)

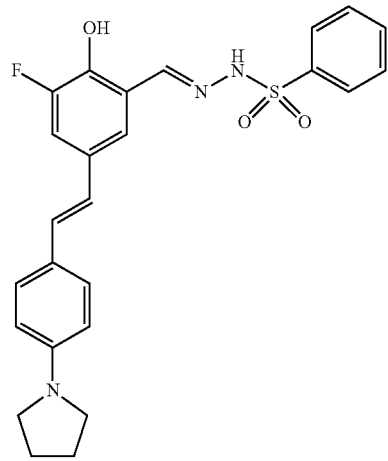 [SMILES: O=S(=O)(N/N=C/c1cc(/C=C/c2ccc(N3CCCC3)cc2)cc(F)c1O)c1ccccc1]

The title compound was prepared using a similar method as that described in Example 76 and generally as described in Scheme 6a from (E)-3-fluoro-2-hydroxy-5-(4-(pyrrolidin-1-yl)styryl)benzaldehyde (200 mg, 0.64 mmol) and benzenesulfonohydrazide (111 mg, 0.64 mmol) to give the title compound as a yellow solid (230 mg, 77% yield). $^1$H NMR (DMSO-d$_6$, 400 MHz) δ: 11.74 (s, 1H), 10.36 (s, 1H), 8.19 (s, 1H), 7.90 (d, J=7.2 Hz, 2H), 7.65 (m, 3H), 7.48 (d, J=12.4 Hz, 1H), 7.39 (m, 3H), 6.97 (d, J=16.0 Hz, 1H), 6.85 (d, J=16.0 Hz, 1H), 6.53 (d, J=8.0 Hz, 2H), 3.25 (m, 4H), 1.96 (m, 4H); LC-MS m/z [M+H]$^+$ calc'd for C$_{25}$H$_{24}$FN$_3$O$_3$S, 466; found, 466.

Example 82: (E)-3-fluoro-2-hydroxy-5-((E)-4-(pyrrolidin-1-yl)styryl)benzaldehyde O-phenyl oxime (Compound 115)

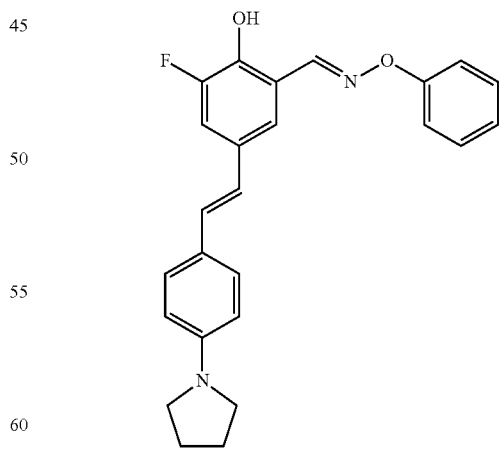

The title compound was prepared using a similar method as that described in Example 76 and generally as described in Scheme 6a from (E)-3-fluoro-2-hydroxy-5-(4-(pyrrolidin-1-yl)styryl)benzaldehyde (400 mg, 1.28 mmol) and O-phenylhydroxylamine (140 mg, 1.28 mmol) to give the title compound as orange solid (200 mg, 39% yield). ¹H NMR (DMSO-d₆, 400 MHz) δ: 10.37 (br, 1H), 8.81 (s, 1H), 7.67 (s, 1H), 7.58 (d, J=12.0 Hz, 1H), 7.39 (m, 4H), 7.28 (d, J=8.0 Hz, 2H), 7.04 (m, 2H), 6.94 (m, 1H), 6.54 (d, J=8.4 Hz, 2H), 3.25 (m, 4H), 1.96 (m, 4H); LC-MS m/z [M+H]⁺ calc'd for $C_{25}H_{23}FN_2O_2$, 403; found, 403.

Example 83: 2-((E)-3-fluoro-2-hydroxy-5-((E)-4-(pyrrolidin-1-yl)styryl)benzylidene)hydrazine-1-carboximidamide (Compound 116)

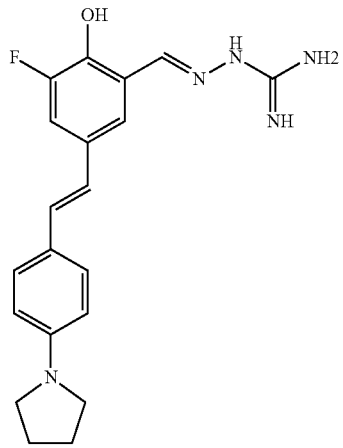

A mixture of (E)-3-fluoro-2-hydroxy-5-(4-(pyrrolidin-1-yl)styryl)benzaldehyde (200 mg, 0.64 mmol), hydrazinecarboximidamide hydrochloride (70 mg, 0.64 mmol), and sodium acetate (53 mg, 0.64 mmol) in ethanol (5 mL) was refluxed for 5 hours. The mixture was cooled to room temperature and filtered. The cake was washed with ethanol (5 mL), water (1 mL), and dried in vacuo to give the title product as a green solid (130 mg, 55% yield). ¹H NMR (DMSO-d6, 400 MHz) δ: 11.39 (br, 1H), 8.29 (s, 1H), 7.53 (s, 1H), 7.36 (m, 3H), 7.01 (m, 1H), 6.84 (m, 1H), 6.54 (d, J=8.4 Hz, 2H), 6.43 (br, 2H), 3.25 (m, 4H), 1.96 (m, 4H); LC-MS m/z [M+H]⁺ calc'd for $C_{20}H_{22}FN_5O$, 368; found, 368.

Example 84: (E)-3-(3-cinnamoyl-4-hydroxy-5-methoxyphenyl)-1-phenylprop-2-en-1-one (Compound 117)

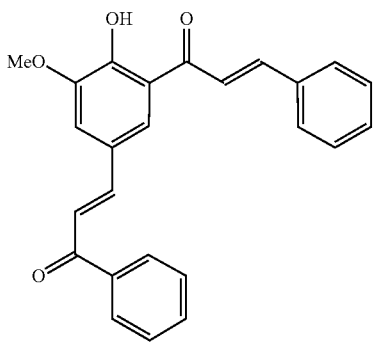 [SMILES: COc1cc(/C=C/C(=O)c2ccccc2)cc(C(=O)/C=C/c2ccccc2)c1O]

Step 1: N-Methoxy-N-methylbenzamide

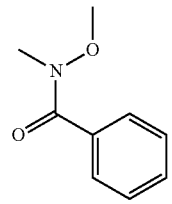

CDI (7.13 g, 44.0 mmol) was added to a solution of benzoic acid (4.88 g, 44.0 mmol) in DCM (100 mL). The reaction was stirred for 2 hours at room temperature. N,O-dimethylhydroxylamine.HCl (4.66 g, 48.0 mmol) was added. The reaction was stirred overnight at room temperature. The mixture was diluted with sat. sodium bicarbonate (100 mL). The organic layer was separated and the water phase was re-extracted with dichloromethane (100 mL×2). The organic extracts were washed with brine (100 mL), dried over anhydrous sodium sulfate, and concentrated to give title product as color less oil (4.9 g, 74% yield), which was used for next reaction without further purification.

Step 2: 1-Phenylprop-2-yn-1-one

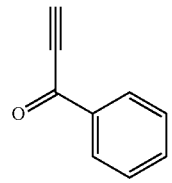

Ethynylmagnesium bromide (109 mL, 54.54 mmol, 0.5 M in THF) was added dropwise to a solution of a mixture of N-Methoxy-N-methylbenzamide (3 g, 18.18 mmol) in THF (20 mL) at 0° C. The reaction was stirred for 1 hour at room temperature. The reaction was quenched with water (50 mL) and pH of the system was adjusted 7-8 with 5% KHSO₄. THF was removed in vacuo and the water phase was extracted with ethyl acetate (50 mL×3). The organic extracts were combined, washed with brine (50 mL), dried over anhydrous sodium sulfate, and concentrated to give crude desired product (7.4 g, 97% yield), which was used for next reaction without further purification.

Step 3: 3-Iodo-1-phenylprop-2-en-1-one

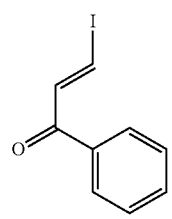 [SMILES: O=C(/C=C/I)c1ccccc1]

NaI (534 mg, 3.54 mmol) was added to a solution of 1-Phenylprop-2-yn-1-one (460 mg, 3.54 mmol) in TFA (3 mL). The reaction was stirred for 2 hours at room temperature. The solution was added dropwise to a solution of sat. sodium bicarbonate (20 mL) and then extracted with ethyl acetate (20 mL×3). The organic extracts were combined, washed with brine (20 mL), dried over anhydrous sodium sulfate, and concentrated. The residue was purified by silica gel column chromatography (petroleum ether/ethyl acetate=200:1 to 100:1) to give the desired product (900 mg, ~60% purity, 59% yield).

Step 4: (E)-1-(5-Bromo-3-methoxy-2-(4-methoxybenzyloxy)phenyl)-3-phenylprop-2-en-1-one

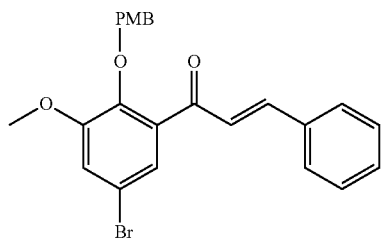

A mixture of 1-(5-bromo-2-hydroxy-3-methoxyphenyl) ethanone (2 g, 8.7 mmol), PMBCl (2.7 g, 17.4 mmol), and $K_2CO_3$ (3.6 g, 26.1 mmol) in DMF (10 mL) was stirred for 1 hour at 90° C. The mixture was cooled to room temperature, diluted with water (50 mL). The resulting precipitate was collected with filtration and dried to give PMB-protected ketone (3.2 g, quantitative yield), which was used for next reaction without further purification. The PMB-ketone (1.2 g, 3.3 mmol) was dissolved in EtOH/water (20 mL/7 mL). KOH (739 mg, 13.2 mmol) and benzaldehyde (350 mg, 0.54 mmol) were added. The reaction was heated overnight at 95° C. Ethanol was removed in vacuo and the residue was diluted with water (20 mL). The mixture was then extracted with ethyl acetate (20 mL×3). The organic extracts were combined, dried over anhydrous sodium sulfate, and concentrated to give crude compound 4 (1.2 g, 81% yield), which was used for next reaction without further purification. LC-MS m/z $[M+Na]^+$ calc'd for $C_{24}H_{21}BrO_4$, 476; found, 476.

Step 5: (E)-1-(3-Methoxy-2-(4-methoxybenzyloxy)-5-(4,4,5,5-tetramethyl-1,3,2-dioxaborolan-2-yl)phenyl)-3-phenylprop-2-en-1-one

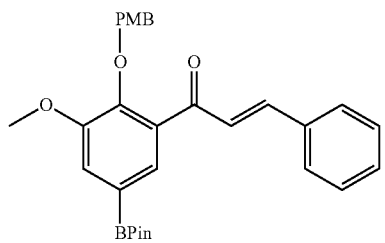

A mixture of above step 4 product (1.2 g, 2.7 mmol), bis(pinacolato)diboron (686 mg, 2.7 mmol), KOAc (778 mg, 8.1 mmol), and $Pd(dppf)_2Cl_2$ (221 mg, 0.27 mmol) in dioxane (30 mL) was stirred at 110° C. for 2 hours under $N_2$. The mixture was cooled to room temperature, diluted with water (50 mL), and extracted with ethyl acetate (50 mL×3). The organic extracts were combined, washed with brine (50 mL), dried over anhydrous sodium sulfate, and concentrated. The residue was purified by silica gel column chromatography (petroleum ether/ethyl acetate=20:1 to 10:1) to afford titled product (710 mg, 53% yield). LC-MS m/z $[M+Na]^+$ calc'd for $C_{30}H_{33}BO_6$, 523; found, 523.

Step 6: A mixture of above step 5 product (500 mg, 1.0 mmol), 3-Iodo-1-phenylprop-2-en-1-one (358 mg, 1.0 mmol), $K_2CO_3$ (414 mg, 3.0 mmol), and $Pd(dppf)_2Cl_2$ (41 mg, 0.1 mmol) in dioxane (20 mL) and $H_2O$ (7 mL) was stirred at 110° C. for 3 hours under $N_2$. The mixture was cooled to room temperature, diluted with water (50 mL) and ethyl acetate (100 mL). The resulting precipitate was filtered off. The organic layer of the filtrate was collected, fried over anhydrous sodium sulfate, and concentrated. The residue was purified by silica gel column chromatography (petroleum ether/ethyl acetate=20:1 to 10:1) to afford crude PMB-protected product (307 mg, 61% yield). PMB-protected product (300 mg, 0.60 mmol) was dissolved in dichloromethane (5 mL) and TFA (3 mL) was added. The reaction was stirred for 1 hour at room temperature. The solvent was removed and the residue purified by prep-TLC to afford desired titled final product as yellow solid (51 mg, 22% yield). $^1$H NMR ($CDCl_3$, 400 MHz) δ: 13.63 (s, 1H), 7.98-8.05 (m, 3H), 7.34-7.84 (m, 13H), 4.02 (s, 3H); LC-MS m/z $[M+H]^+$ calc'd for $C_{25}H_{20}O_4$, 385; found, 385.

Example 85: 4-(((E)-3-fluoro-2-hydroxy-5-((E)-4-(pyrrolidin-1-yl)styryl)benzylidene)amino)-1-methylpiperazine 1-oxide (Compound 118)

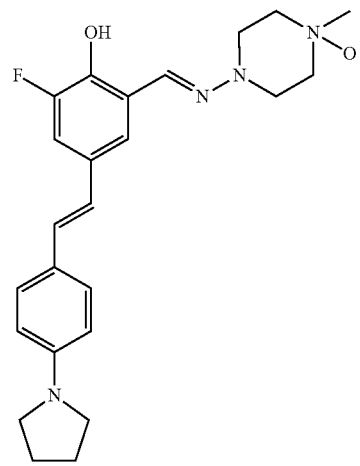

In a 20 mL glass vial, compound 2-fluoro-6-((E)-((4-methylpiperazin-1-yl)imino)methyl)-4-((E)-4-(pyrrolidin-1-yl)styryl)phenol (from Example 110 above) (102 mg, 0.25 mmol) dissolved in chloroform (5.0 mL) and added mCPBA (67 mg, 0.3 mmol) to the vial. Then closed the vial and stirred at room temperature for 10 min. Without any workup, reaction solution directly loaded on wet alumina column and eluted with dichloromethane-methanol (0-15%). Pure product fractions combined and evaporated to get the desired product as a light yellow solid (35 mg, 33% yield). $^1$H NMR (500 MHz, Chloroform-d) δ 11.36 (s, 1H), 7.77 (s, 1H), 7.36 (d, J=8.4 Hz, 2H), 7.21 (d, J=12.0 Hz, 1H), 7.02 (s, 1H), 6.88 (d, J=16.2 Hz, 1H), 6.74 (d, J=16.2 Hz, 1H), 6.54 (d, J=8.3 Hz, 2H), 3.80 (t, J=12.5 Hz, 2H), 3.53 (d, J=11.4 Hz, 4H), 3.40 (d, J=11.2 Hz, 2H), 3.32 (dd, J=14.7, 8.1 Hz, 4H), 2.30-1.86 (m, 7H); LC-MS m/z [M+H]+ calc'd for C24H29FN4O2, 425; found, 425.

Example 86: (E)-3-fluoro-2-hydroxy-5-(2-(6-(pyrrolidin-1-yl)pyridin-3-yl)vinyl)benzaldehyde (Compound 119)

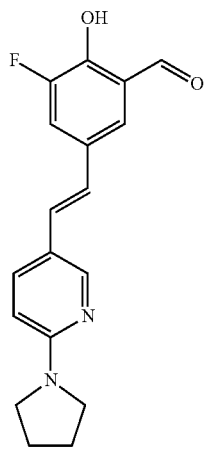

Step 1: 6-(Pyrrolidin-1-yl)nicotinaldehyde

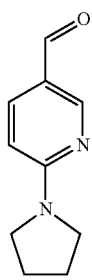

A mixture of 6-chloronicotinaldehyde (141 mg, 1.0 mmol), pyrrolidine (142 mg, 2.0 mmol), and potassium phosphate (848 mg, 4.0 mmol) in dioxane (10 mL) was heated overnight at 95° C. The reaction was cooled to room temperature, diluted with water (20 mL) and extracted with EtOAc (20 mL×3). The organic layers were combined, washed with brine (20 mL), dried over anhydrous sodium sulfate, and concentrated. The residue was purified by silica gel column chromatography (petroleum ether/ethyl acetate=50:1 to 15:1) to give the desired product (130 mg, 74% yield). 1H NMR (DMSO-d6, 400 MHz) δ: 9.71 (s, 1H), 8.57 (s, 1H), 7.85 (d, J=9.2 Hz, 1H), 6.57 (d, J=9.6 Hz, 1H), 3.49 (m, 4H), 1.97 (m, 4H).

Step 2: 2-(Pyrrolidin-1-yl)-5-vinylpyridine

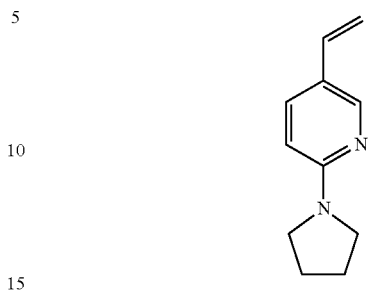

Methyltriphenylphosphonium bromide (405 mg, 1.14 mmol) was suspended in THF (5 mL) and cooled to 0° C. in an ice bath under nitrogen. Then, n-BuLi (0.46 mL, 1.14 mmol, 2.5 M in THF) was added dropwise. The reaction was stirred for 1 hour at 0° C. Then, a solution of 6-(pyrrolidin-1-yl)nicotinaldehyde (100 mg, 0.57 mmol) in THF (5 mL) was added dropwise. The reaction was stirred for 1 hour at room temperature. The reaction was quenched with saturated ammonium chloride solution (20 mL) and extracted with EtOAc (20 mL×3). The organic layers were combined, washed with brine (20 mL), dried over anhydrous sodium sulfate, and concentrated. The residue was used for the next reaction without further purification. LC-MS m/z [M+H]+ calc'd for C11H14N2, 175; found, 175.

Step 3: A mixture of 5-bromo-3-fluoro-2-hydroxybenzaldehyde (124.3 mg, 0.57 mmol), 2-(Pyrrolidin-1-yl)-5-vinylpyridine (crude, 0.57 mmol), 1,3-bis(diphenylphosphino)propane (dppp) (47.0 mg, 0.11 mmol), K2CO3 powder (236.0 mg, 1.71 mmol), and palladium acetate (12.8 mg, 0.06 mmol) in DMF-water (2 mL:0.6 mL) was heated overnight at 90° C. The mixture was cooled to room temperature, diluted with water (10 mL), and extracted with ethyl acetate (10 mL×3). The organic extracts were combined, washed with brine (10 mL×3), dried over anhydrous sodium sulfate, and concentrated. The residue was purified by silica gel column chromatography (petroleum ether/ethyl acetate=10:1 to 3:1) to give the desired product as an orange solid (26 mg, 15% yield overall yield in two steps). 1H NMR (CDCl3, 400 MHz) δ: 9.97 (s, 1H), 8.24 (s, 1H), 7.69 (d, J=8.8 Hz, 1H), 7.52 (d, J=11.6 Hz, 1H), 7.44 (s, 1H), 6.91 (d, J=16.0 Hz, 1H), 6.78 (d, J=16.4 Hz, 1H), 6.44 (d, J=9.2 Hz, 1H), 3.54 (m, 4H), 2.06 (m, 4H); LC-MS m/z [M+H]+ calc'd for C18H17FN2O2, 313; found, 313.

Example 87: (E)-3-fluoro-2-hydroxy-5-(2-(5-(pyrrolidin-1-yl)pyridin-2-yl)vinyl)benzaldehyde (Compound 120)

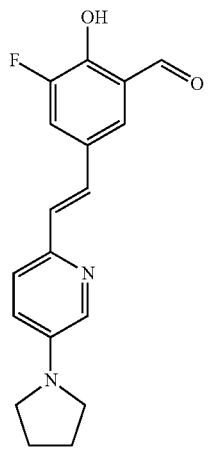

Step 1: 5-(Pyrrolidin-1-yl)picolinaldehyde

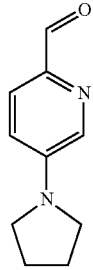

A mixture of 5-fluoropicolinaldehyde (141 mg, 1.0 mmol), pyrrolidine (142 mg, 2.0 mmol), and potassium phosphate (848 mg, 4.0 mmol) in dioxane (10 mL) was heated overnight at 95° C. The reaction was cooled to room temperature, diluted with water (20 mL) and extracted with EtOAc (20 mL×3). The organic layers were combined, washed with brine (20 mL), dried over anhydrous sodium sulfate, and concentrated. The residue was purified by silica gel column chromatography (petroleum ether/ethyl acetate=50:1 to 15:1) to give the desired product (120 mg, 68% yield).

Step 2: 5-(Pyrrolidin-1-yl)-2-vinylpyridine

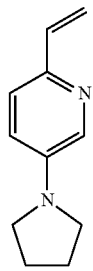

Methyltriphenylphosphonium bromide (1.21 g, 3.42 mmol) was suspended in THF (10 mL) and cooled to 0° C. in an ice bath under nitrogen. Then n-BuLi (1.38 mL, 3.42 mmol, 2.5 M in THF) was added dropwise. The reaction was stirred for 1 hour at 0° C. Then a solution of 5-(pyrrolidin-1-yl)picolinaldehyde (300 mg, 1.71 mmol) in THF (5 mL) was added dropwise. The reaction was stirred for 1 hour at room temperature. The reaction was quenched with saturated ammonium chloride solution (30 mL) and extracted with EtOAc (30 mL×3). The organic layers were combined, washed with brine (30 mL), dried over anhydrous sodium sulfate, and concentrated. The residue was used for the next reaction without further purification.

Step 3: A mixture of 5-bromo-3-fluoro-2-hydroxybenzaldehyde (373 mg, 1.71 mmol), 5-(Pyrrolidin-1-yl)-2-vinylpyridine (crude, 1.71 mmol), 1,3-bis(diphenylphosphino)propane (dppp) (141 mg, 0.33 mmol), $K_2CO_3$ powder (708 mg, 5.13 mmol), and palladium acetate (38.4 mg, 0.18 mmol) in DMF-water (6 mL:1.8 mL) was heated overnight at 90° C. The mixture was cooled to rt, diluted with water (10 mL), and extracted with ethyl acetate (10 mL×3). The organic extracts were combined, washed with brine (10 mL×3), dried over anhydrous sodium sulfate, and concentrated. The residue was purified by silica gel column chromatography (petroleum ether/ethyl acetate=10:1 to 3:1) and washed with a combination of petroleum ether/dichloromethane to give the desired product as pale yellow solid (45 mg, 8% yield via two steps). $^1$H NMR (DMSO-d6, 400 MHz) δ: 10.99 (br, 1H), 10.29 (s, 1H), 7.96 (s, 1H), 7.84 (d, J=12.4 Hz, 1H), 7.64 (s, 1H), 7.35 (d, J=8.4 Hz, 1H), 7.28 (d, J=16.4 Hz, 1H), 7.14 (d, J=16.0 Hz, 1H), 6.90 (d, J=8.8 Hz, 1H), 3.30 (m, 4H), 1.97 (m, 4H); LC-MS m/z [M+H]$^+$ calc'd for $C_{18}H_{17}FN_2O_2$, 313; found, 313.

Example 88: 1-(((E)-3-fluoro-2-hydroxy-5-((E)-4-(pyrrolidin-1-yl)styryl)benzylidene)amino)imidazolidine-2,4-dione (Compound 121)

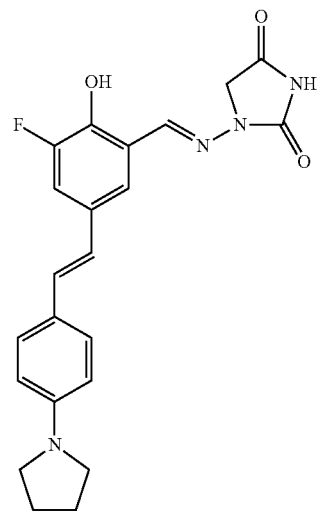

The title compound was prepared generally as described in Scheme 6b. (E)-3-fluoro-2-hydroxy-5-(4-(pyrrolidin-1-yl)styryl)benzaldehyde (200 mg, 0.64 mmol), 1-aminoimidazolidine-2,4-dione hydrochloride (195 mg, 1.28 mmol), and TEA (195 mg, 1.92 mmol) were dissolved in ethanol. The reaction was refluxed for 2 hours. The solvent was removed, and the residue was filtered. The cake was washed with ethanol and dried in vacuo to give the title compound as orange solid (200 mg, 76% yield). $^1$H NMR (DMSO-d6, 400 MHz) δ: 11.42 (br, 1H), 10.78 (br, 1H), 8.01 (s, 1H), 7.51 (s, 1H), 7.40 (d, J=8.8 Hz, 2H), 7.02 (d, J=16.4 Hz, 1H), 6.89 (d, J=16.4 Hz, 1H), 6.54 (d, J=8.8 Hz, 2H), 4.41 (s, 2H), 3.26 (m, 4H), 1.95 (m, 4H); LC-MS m/z [M+H]$^+$ calc'd for $C_{22}H_{21}FN_4O_3$, 409; found, 409.

Example 89: (E)-3-fluoro-2-hydroxy-5-((E)-4-(pyrrolidin-1-yl)styryl)benzaldehyde O-ethyl oxime (Compound 122)

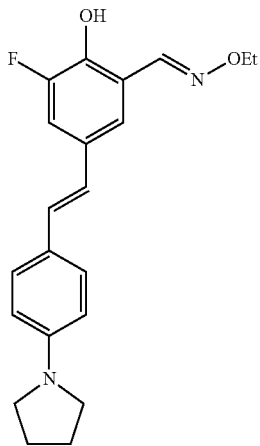 [SMILES: CCO/N=C/c1cc(/C=C/c2ccc(N3CCCC3)cc2)cc(F)c1O]

The title compound was prepared using a similar method as that described in Example 88 and generally as described in Scheme 6b using (E)-3-fluoro-2-hydroxy-5-(4-(pyrrolidin-1-yl)styryl)benzaldehyde (200 mg, 0.64 mmol), O-ethylhydroxylamine hydrochloride (75 mg, 0.77 mmol), and TEA (129 mg, 1.28 mmol) to give the title compound as pale yellow solid (140 mg, 61% yield). $^1$H NMR (CDCl$_3$, 400 MHz) δ: 10.08 (br, 1H), 8.19 (s, 1H), 7.40 (d, J=8.4 Hz, 2H), 7.30 (m, 1H), 7.03 (s, 1H), 6.91 (d, J=16.0 Hz, 1H), 6.78 (d, J=16.0 Hz, 1H), 6.61 (m, 2H), 4.28 (q, J=7.1 Hz, 2H), 3.36 (m, 4H), 2.07 (m, 4H), 1.38 (t, J=7.0 Hz, 3H); LC-MS m/z [M+H]$^+$ calc'd for $C_{21}H_{23}FN_2O_2$, 355; found, 355.

Example 90: (E)-2-fluoro-6-(hydroxymethyl)-4-(4-(pyrrolidin-1-yl)styryl)phenol (Compound 123)

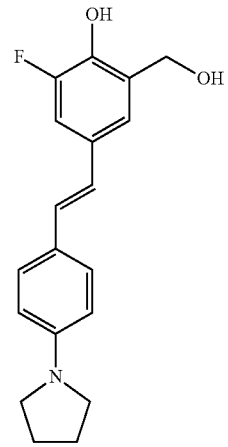

In a 25 ml round bottom flask, LiAlH$_4$ (26 mg, 0.64 mmol) was added to a solution of (E)-3-fluoro-2-hydroxy-5-(4-(pyrrolidin-1-yl)styryl)benzaldehyde (100 mg, 0.32 mmol) in THF (5 mL) at 0° C. The reaction was stirred for 30 min at room temperature and quenched with ice-water. The mixture was extracted with ethyl acetate for three times. The organic extracts were combined, washed with brine, dried over anhydrous sodium sulfate, and concentrated. The residue was stirred in a combination of petroleum ether/dichloromethane and filtered. The cake was dried in vacuo to give the title product as green solid (50 mg, 50% yield). $^1$H NMR (DMSO-d6, 400 MHz) δ: 9.48 (br, 1H), 7.37 (d, J=8.8 Hz, 2H), 7.24 (m, 2H), 6.95 (d, J=16.4 Hz, 1H), 6.84 (d, J=16.4 Hz, 1H), 6.53 (d, J=8.8 Hz, 2H), 4.52 (s, 2H), 3.25 (m, 4H), 1.98 (m, 4H); LC-MS m/z [M+H]$^+$ calc'd for $C_{19}H_{20}FNO_2$, 314; found, 314.

Example 91: (E)-2-((cyclopropylamino)methyl)-6-fluoro-4-(4-(pyrrolidin-1-yl)styryl)phenol (Compound 124)

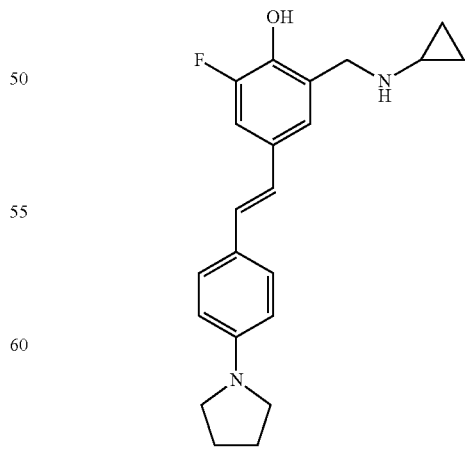

A solution of (E)-3-fluoro-2-hydroxy-5-(4-(pyrrolidin-1-yl)styryl)benzaldehyde (120 mg, 0.39 mmol) and cyclopropanamine (27 mg, 0.47 mmol) in methanol (5 mL) was stirred for 2 hours at room temperature. Sodium cyanoborohydride (121 mg, 1.93 mmol) was added and the reaction was heated overnight at 50° C. The solvent was removed in vacuo and the residue was diluted in water. The system was acidified to pH 5-6 and extracted with dichloromethane for two times. The organic extracts were combined, dried over anhydrous sodium sulfate, and concentrated. The residue was purified by prep-TLC to give the title product as white solid (55 mg, 38% yield). $^1$H NMR (CDCl$_3$, 400 MHz) δ: 7.38 (d, J=8.8 Hz, 2H), 7.15 (d, J=12.0 Hz, 1H), 6.92 (s, 1H), 6.88 (d, J=16.0 Hz, 1H), 6.75 (d, J=16.4 Hz, 1H), 6.56 (d, J=8.8 Hz, 2H), 4.13 (s, 2H), 3.34 (m, 4H), 2.27 (m, 1H), 2.03 (m, 4H), 0.58 (m, 4H); LC-MS m/z [M+H]$^+$ calc'd for C$_{22}$H$_{25}$FN$_2$O, 353; found, 353.

Example 92: 2-((E)-((4-cyclopropylpiperazin-1-yl)imino)methyl)-6-fluoro-4-((E)-4-(pyrrolidin-1-yl)styryl)phenol (Compound 125)

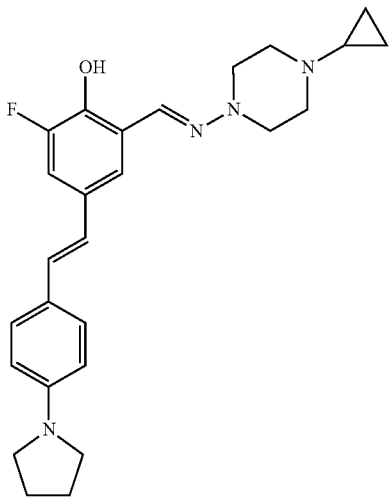

The title compound was prepared using a similar method as that described in Example 88 and generally as described in Scheme 6b using (E)-3-fluoro-2-hydroxy-5-(4-(pyrrolidin-1-yl)styryl)benzaldehyde (200 mg, 0.64 mmol), 4-cyclopropylpiperazin-1-amine dihydrochloride (165 mg, 0.77 mmol), and TEA (195 mg, 1.93 mmol) to give the title compound as pale yellow solid (240 mg, 86% yield). $^1$H NMR (DMSO-d6, 400 MHz) δ: 11.56 (br, 1H), 7.92 (s, 1H), 7.34 (m, 4H), 6.99 (d, J=16.4 Hz, 1H), 6.83 (d, J=16.4 Hz, 1H), 6.54 (d, J=8.4 Hz, 2H), 3.25 (m, 4H), 3.11 (m, 4H), 2.74 (m, 4H), 1.96 (m, 4H), 1.70 (m, 1H), 0.45 (m, 2H), 0.36 (m, 2H); LC-MS m/z [M−H]$^-$ calc'd for C$_{26}$H$_{31}$FN$_4$O, 433; found, 433.

Example 93: 2-((E)-((4-ethylpiperazin-1-yl)imino)methyl)-6-fluoro-4-((E)-4-(pyrrolidin-1-yl)styryl)phenol (Compound 126)

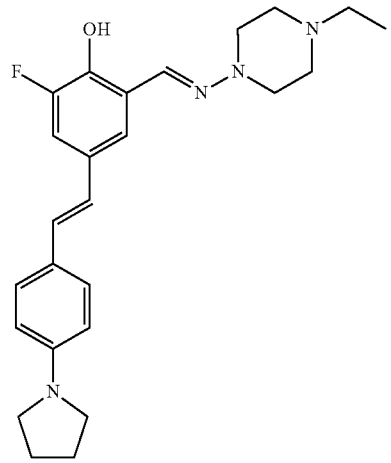 [SMILES: CCN1CCN(/N=C/c2cc(/C=C/c3ccc(N4CCCC4)cc3)cc(F)c2O)CC1]

The title compound was prepared using a similar method as that described in Example 88 and generally as described in Scheme 6b using (E)-3-fluoro-2-hydroxy-5-(4-(pyrrolidin-1-yl)styryl)benzaldehyde (100 mg, 0.32 mmol), 4-ethylpiperazin-1-amine dihydrochloride (78 mg, 0.38 mmol), and TEA (97 mg, 0.96 mmol) to give the title compound as pale yellow solid (100 mg, 74% yield). $^1$H NMR (DMSO-d6, 400 MHz) δ: 11.57 (br, 1H), 7.92 (s, 1H), 7.36 (m, 4H), 6.99 (d, J=16.4 Hz, 1H), 6.83 (d, J=16.4 Hz, 1H), 6.54 (d, J=8.4 Hz, 2H), 3.25 (m, 4H), 3.16 (m, 4H), 2.56 (m, 4H), 2.39 (q, J=7.2 Hz, 2H), 1.96 (m, 4H), 1.04 (t, J=7.2 Hz, 3H); LC-MS m/z [M−H]$^-$ calc'd for C$_{25}$H$_{31}$FN$_4$O, 421; found, 421.

Example 94: 2-fluoro-6-((E)-(morpholinoimino)methyl)-4-((E)-4-(pyrrolidin-1-yl)styryl)phenol (Compound 127)

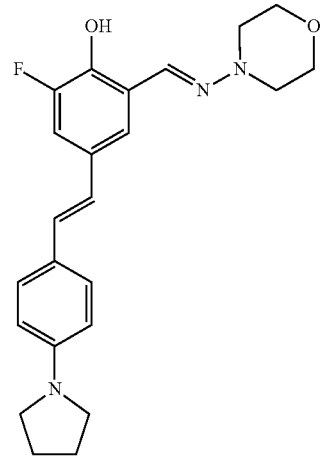

The title compound was prepared using a similar method as that described in Example 88 and generally as described in Scheme 6b using (E)-3-fluoro-2-hydroxy-5-(4-(pyrrolidin-1-yl)styryl)benzaldehyde (200 mg, 0.64 mmol) and morpholin-4-amine (130 mg, 1.28 mmol) to give the title compound as a pale yellow solid (220 mg, 87% yield). $^1$H NMR (DMSO-d6, 400 MHz) δ: 11.44 (br, 1H), 7.99 (s, 1H), 7.36 (m, 4H), 6.99 (d, J=16.4 Hz, 1H), 6.83 (d, J=16.4 Hz, 1H), 6.54 (d, J=8.8 Hz, 2H), 3.79 (m, 4H), 3.25 (m, 4H), 3.15 (m, 4H), 1.96 (m, 4H); LC-MS m/z [M+H]$^+$ calc'd for $C_{23}H_{26}FN_3O_2$, 396; found, 396.

Example 95: tert-butyl 4-(((E)-3-fluoro-2-hydroxy-5-((E)-4-(pyrrolidin-1-yl)styryl)benzylidene)amino)piperazine-1-carboxylate (Compound 128)

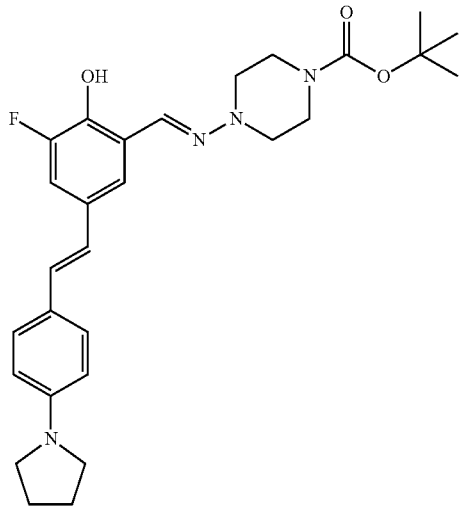 [SMILES: CC(C)(C)OC(=O)N1CCN(/N=C/c2cc(/C=C/c3ccc(N4CCCC4)cc3)cc(F)c2O)CC1]

The title compound was prepared using a similar method as that described in Example 88 and generally as described in Scheme 6b using (E)-3-fluoro-2-hydroxy-5-(4-(pyrrolidin-1-yl)styryl)benzaldehyde (200 mg, 0.64 mmol) and tert-butyl 4-aminopiperazine-1-carboxylate (259 mg, 1.28 mmol) to give the title compound as white solid (155 mg, 49% yield). $^1$H NMR (DMSO-d6, 400 MHz) δ: 11.42 (br, 1H), 7.98 (s, 1H), 7.36 (m, 4H), 6.99 (d, J=16.0 Hz, 1H), 6.84 (d, J=16.8 Hz, 1H), 6.54 (d, J=8.8 Hz, 2H), 3.53 (m, 4H), 3.25 (m, 4H), 3.14 (m, 4H), 1.96 (m, 4H), 1.43 (s, 9H); LC-MS m/z [M+H]$^+$ calc'd for $C_{28}H_{35}FN_4O_3$, 495; found, 495.

Example 96: 2-fluoro-6-((E)-(piperazin-1-ylimino)methyl)-44E)-4-(pyrrolidin-1-yl)styryl)phenol hydrochloride (hydrochloride Salt of Compound 129)

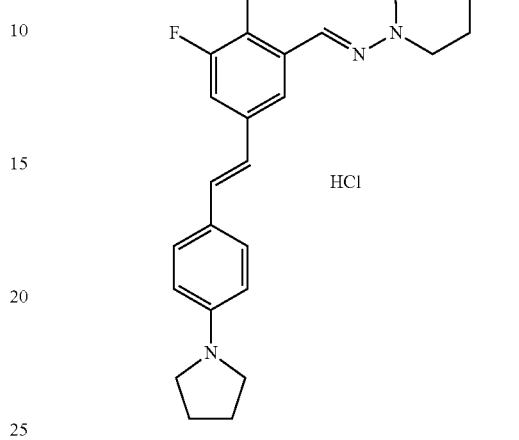

Above obtained tert-butyl 4-(((E)-3-fluoro-2-hydroxy-5-((E)-4-(pyrrolidin-1-yl)styryl) benzylidene)amino)piperazine-1-carboxylate (90 mg, 0.18 mmol) (see Example 96 above) was treated with 6N HCl/Dioxane (5 mL) and filtered and washed with small dichloromethane to get the Boc-deproted hydrochloride salt as white solid (55 mg, 70% yield). $^1$H NMR (DMSO-d6, 400 MHz) δ: 11.13 (br, 2H), 9.97 (br, 1H), 9.20 (br, 2H), 8.04 (s, 1H), 7.41 (m, 4H), 7.00 (d, J=16.4 Hz, 1H), 6.84 (d, J=16.8 Hz, 1H), 6.58 (d, J=8.4 Hz, 2H), 3.41 (m, 4H), 3.28 (m, 8H), 1.97 (m, 4H); LC-MS m/z [M−H]$^-$ calc'd for $C_{23}H_{27}FN_4O$, 393; found, 393.

Biological Example 1: In Vitro Assay

Synthetic diacylated lipoprotein (Pam2CSK4, TLR2/6 agonist) and synthetic triacylated lipoprotein (Pam3CSK4, TLR1/2 agonist) were obtained from InvivoGen and were dissolved in endotoxin-free water to a concentration 1 mg/mL, vortexed until complete solubilization, and stored in aliquots at −20° C. Prior to addition to cells, an aliquot of the dissolved ligand was vortexed shortly and then was diluted in medium to 25 ng/mL Pam2CSK4 or 1000 ng/mL Pam3CSK4. The $EC_{50}$ of the agonists for each assay run was determined by using 3-fold dilutions of each agonist from the following starting concentrations: 5 ng/mL for Pam2CSK4, and 200 ng/mL for Pam3CSK4.

Test compounds were solubilized fresh to 10-20 mM stocks in DMSO and sonicated for 5-10 minutes in a water bath sonicator. Serial dilutions were prepared in DMSO, and then diluted in medium. The final concentration of DMSO used in the assay was 1%.

HEK-Blue hTLR2 reporter cells (InvivoGen) are HEK-293 cells stably expressing both the human TLR2 gene and a secreted embryonic alkaline phosphatase (SEAP) reporter construct downstream of NFκB promotor sites. HEK-Blue hTLR2 reporters were cultured according to manufacturer's protocol using Dulbecco's Modified Eagle Medium (DMEM; Gibco) containing 1× GlutaMax (Gibco), 10% heat-inactivated Fetal Bovine Serum (Gibco), Pen-Strep (50 U/mL penicillin, 50 μg/mL streptomycin, Gibco), 100 μg/mL Normocin (InvivoGen), and the selective antibiotic, 1× HEK-Blue Selection (InvivoGen). Quanti-Blue reagent (InvivoGen) for detection and quantification of secreted alkaline phosphatase was dissolved in 100 mL of endotoxin-free water, warmed to 37° C. for 30 minutes and then filtered using a 0.2 µm membrane.

Biological Example 2: HEK-Blue hTLR2 Antagonism Assay

On day 1, 50 µL of each test compound dilution in duplicates or a vehicle control was added to each well of a 96-well plate followed by addition of 150 µL of HEK-Blue hTLR2 cell suspension (1×10$^5$ cells/well) and incubated at 37° C./5% $CO_2$ for 2 h. Next, 50 µL of an approximate 3×$EC_{50}$ concentration of each agonist (Pam2CSK4 or Pam3CSK4) was added to the wells containing test compounds or the vehicle control. The plates were then incubated at 37° C./5% $CO_2$ for 18 h. For each assay run, non-treated HEK-Blue hTLR2 cells were treated with serial dilutions of agonists to determine $EC_{50}$ values for the respective run.

On day 2, secreted alkaline phosphatase (SEAP) activity was detected in cell culture supernatants. In brief, 20 µL was collected from each well and transferred to a 96-well plate. Next, 200 µL of Quanti-Blue detection reagent was added to each well. Plates were incubated at room temperature for 15 min and SEAP activity was assessed by spectrophotometer OD reading at 655 nm. Table A shows the activities of the compounds tested in HEK cells using Pam2CSK4 and Pam3CSK4 as agonists. The activities of the compounds against Pam2CSK4 and Pam3CSK4 are presented as $IC_{50}$ values for the response from cells treated with agonists with the background signal subtracted.

TABLE A

| Compound of Example No. | $IC_{50}$ (µM) with Pam2CSK4 | $IC_{50}$ (µM) with Pam3CSK4 |
| --- | --- | --- |
| 1 | 3.2 | 1.7 |
| 2 | 5.3 | 1.4 |
| 3 | 4.8 | 3.1 |
| 4 | 5.5 | 4 |
| 5 | 4 | 3.2 |
| 6 | 2.5 | 2.3 |
| 7 | 7.9 | 6.2 |
| 8 | 6.3 | 5.5 |
| 9 | >100 | >100 |
| 10 | 4.6 | 3.8 |
| 11 | 1.1 | 1 |
| 12 | 1.4 | 1.3 |
| 13 | 4.5 | 3.8 |
| 14 | 5.7 | 4.2 |
| 15 | 14.7 | 12.6 |
| 16 | 5.9 | 6.9 |
| 17 | 2.0 | 2.1 |
| 18 | 10.4 | 12.2 |
| 19 | 26.7 | 38.1 |
| 20 | 11.2 | 10.0 |
| 21 | 40 | 57.3 |
| 22 | 17.8 | 6.3 |
| 23 | 11.8 | 11.5 |
| 24 | >100 | >100 |
| 25 | 15.2 | 16.4 |
| 26 | 7.4 | 9.3 |
| 27 | 4.4 | 7.7 |
| 28 | 19.5 | 29.4 |
| 29 | 9.1 | 10 |
| 30 | 20.6 | 18.8 |
| 31 | 3.8 | 6 |
| 32 | 1.1 | 1 |
| 33 | 6.2 | 6.4 |
| 34 | 9.7 | 7.5 |
| 35 | 68.5 | 62.6 |
| 36 | 0.6 | 0.4 |
| 37 | 1 | 0.3 |
| 38 | 4.4 | 5 |
| 39 | 12.8 | 15.4 |
| 40 | 2.3 | 2.5 |
| 41 | 35.1 | 29.8 |
| 42 | 3.4 | 4.5 |
| 43 | 32.8 | 40.7 |
| 44 | 3 | 3.2 |
| 45 | 5 | 6.7 |
| 46 | 1.4 | 1 |
| 47 | 1.3 | 0.9 |
| 48 | 1 | 0.6 |
| 49a | 0.5 | 0.6 |
| 49b | 0.8 | 0.8 |
| 50 | 10 | 6.7 |
| 51 | 71.3 | 70.1 |
| 52 | >100 | >100 |
| 53 | 1.3 | 1.5 |
| 54 | 4 | 4.6 |
| 55 | 3.6 | 4.1 |
| 56 | 1.8 | 1.7 |
| 57 | 1.7 | 1.9 |
| 58 | 4.9 | 5 |
| 59 | 4.1 | 2.6 |
| 60 | 2.3 | 0.9 |
| 61 | 1 | 0.4 |
| 62 | 1.5 | 0.8 |
| 63 | 1.5 | 0.6 |
| 64 | 1.1 | 0.5 |
| 65 | 1.7 | 0.5 |
| 66 | 0.9 | 0.3 |
| 67 | 1.7 | 1.2 |
| 68 | 1.6 | 1.3 |
| 69 | 0.7 | 0.6 |
| 70 | 0.9 | 0.4 |
| 71 | 13.7 | 2.5 |
| 72 | 8.2 | 11.2 |
| 73 | 4.5 | 4.8 |
| 74 | 6.3 | 7 |
| 75 | 1.2 | 1.3 |
| 76 | 0.4 | 0.5 |
| 77 | 1.4 | 1.1 |
| 78 | 1 | 0.9 |
| 79 | 4.4 | 6 |
| 80 | 28.4 | 14.8 |
| 81 | 16.4 | 13.2 |
| 82 | 2.1 | 2.1 |
| 83 | 36.7 | 88.9 |
| 84 | 3.4 | 3.1 |
| 85 | 4.5 | 1.9 |
| 86 | 3.8 | 4.1 |
| 87 | 3.9 | 3.3 |
| 88 | 11.2 | 7.9 |
| 89 | 29.5 | 29.6 |
| 90 | 5.4 | 8.5 |
| 91 | 30.6 | 82.1 |
| 92 | 26.6 | 32.3 |
| 93 | 24.5 | 3.2 |
| 94 | 2.9 | 1.4 |
| 95 | 4.4 | 3.6 |
| 96 | 3.2 | 1.3 |

The invention claimed is:

1. A compound of Formula (A)

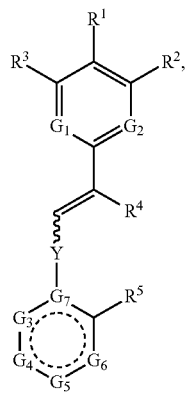

(A)

or a tautomer, or a pharmaceutically acceptable salt of any of the foregoing, wherein

indicates that the ring is saturated, partially unsaturated, or fully unsaturated;

indicates that the

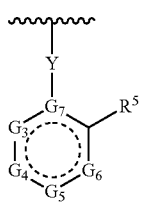

is attached in either the E or Z configuration;
$G_1$ and $G_2$ are each independently $CR^x$;
$R^x$ is hydrogen or halogen;
$R^1$ is —OH;
$R^2$ is CHO;
$R^3$ is $C_1$-$C_6$alkoxy or halogen, wherein the $C_1$-$C_6$alkoxy of $R^3$ is unsubstituted or substituted with one or more halogen;
Y is —C(O)— or absent and $R^4$ and $R^5$ are each H,
$G_3$ is $CH(X_1$—$R^{6a})$, $C(X_1$—$R^{6a})$, N, $N(X_1$—$R^{6a})$, S, or O;
$G_4$ is $CH(X_2$—$R^{6b})$, $C(X_2$—$R^{6b})$, N, $N(X_2$—$R^{6b})$, S, or O;
$G_5$ is $CH(X_3$—$R^{6c})$, $C(X_3$—$R^{6c})$, N, $N(X_3$—$R^{6c})$, S, or O;
$G_6$ is $CH(X_4$—$R^{6d})$, $C(X_4$—$R^{6d})$, N, $N(X_4$—$R^{6d})$, S, O, or absent;
$G_7$ is N, C, or CH;
  wherein when $G_5$ is N, at least one of (i), (ii), and (iii) applies:
  (i) at least one of $G_3$, $G_4$, and $G_6$ is not CH;
  (ii) $R^4$ and $R^5$ come together to form —S—; and
  (iii) $R^3$ is —OCH$_3$ or halo;

$X_1$, $X_2$, $X_3$, and $X_4$ are each independently absent,

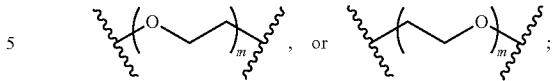

m is 1-6;
$R^{6a}$, $R^{6b}$, $R^{6c}$, and $R^{6d}$ are each independently hydrogen, $C_1$-$C_6$alkyl, $C_1$-$C_6$alkoxy, halo, —OH, —NR$^p$R$^q$, aryl, heterocyclyl, heteroaryl, —$C_1$-$C_6$alkyl-heterocyclyl, —OC(O)-heterocyclyl, —C(O)R$^h$, —S(O)$_2$NR$^{w1}$R$^{w2}$, —S(O)$_2$R$^y$, or —NR$^{z1}$S(O)$_2$R$^{z2}$, wherein the $C_1$-$C_6$alkyl and $C_1$-$C_6$alkoxy of $R^{6a}$, $R^{6b}$, $R^{6c}$, and $R^{6d}$ are each independently unsubstituted or substituted with one or more groups selected from the group consisting of cycloalkyl and halogen; the aryl and heteroaryl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, and $C_1$-$C_6$alkyl-OH; and the heterocyclyl, —$C_1$-$C_6$alkyl-heterocyclyl, and —OC(O)-heterocyclyl of $R^{6a}$, $R^{6b}$, $R^{6c}$, and $R^{6d}$ are each independently unsubstituted or substituted with one or more groups selected from the group consisting of $C_1$-$C_6$alkyl, $C_1$-$C_6$alkoxy, —OH, $C_1$-$C_6$alkyl-OH, =O, and =S;
$R^h$ is selected from the group consisting of H, $C_1$-$C_6$alkyl, $C_1$-$C_6$alkoxy, $C_3$-$C_8$cycloalkyl, and —NR$^r$R$^s$;
$R^p$ is H or $C_1$-$C_6$alkyl;
$R^q$ is $C_2$-$C_3$alkyl, —C(O)R$^t$, —C(O)OR$^u$, or —C(O)NR$^v$;
$R^r$, $R^s$, $R^{w1}$, and $R^{z1}$ each independently selected from H and $C_1$-$C_6$alkyl; and
$R^t$, $R^u$, $R^v$, $R^{w2}$, $R^y$, and $R^{z2}$ are each independently selected from H, $C_1$-$C_6$alkyl, unsubstituted or substituted $C_3$-$C_8$cycloalkyl, and unsubstituted or substituted heterocyclyl;
or
$G_5$ is $CH(X_3$—$R^{6c})$ or $C(X_3$—$R^{6c})$, $G_6$ is $CH(X_4$—$R^{6d})$ or $C(X_4$—$R^{6d})$, and $R^{6c}$ and $R^{6d}$ are taken together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted;
wherein no more than one of $R^{6a}$, $R^{6b}$, $R^{6c}$, and $R^{6d}$ is $C_1$-$C_6$alkoxy or —OH; and
wherein the compound is not a compound of Table 1X.

2. The compound of claim 1, or a tautomer thereof, or a pharmaceutically acceptable salt of any of the foregoing, wherein Y is absent.

3. The compound of claim 1, or a tautomer thereof, or a pharmaceutically acceptable salt of any of the foregoing, wherein $G_5$ is $CH(X_3$—$R^{6c})$ or $C(X_3$—$R^{6c})$, $G_6$ is $CH(X_4$—$R^{6d})$ or $C(X_4$—$R^{6d})$, and $R^{6c}$ and $R^{6d}$ come together with the carbons to which they are attached to form a 6-membered aryl, a 6-membered heterocyclyl, or a 6-membered heteroaryl ring; wherein the 6-membered aryl, 6-membered heterocyclyl, and 6-membered heteroaryl rings are each independently unsubstituted or substituted.

4. The compound of claim 1, or a tautomer thereof, or a pharmaceutically acceptable salt of any of the foregoing, wherein $G_7$ is C or CH.

5. The compound of claim 1, or a tautomer thereof, or a pharmaceutically acceptable salt of any of the foregoing, wherein $G_3$ is $CH(X_1-R^{6a})$ or $C(X_1-R^{6a})$; $X_1$ is absent; m is 1-6; $R^{6a}$ is hydrogen, $C_1$-$C_6$alkyl, $C_1$-$C_6$alkoxy, halo, or $-C(O)R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl.

6. The compound of claim 1, or a tautomer thereof, or a pharmaceutically acceptable salt of any of the foregoing, wherein $G_4$ is $CH(X_2-R^{6b})$ or $C(X_2-R^{6b})$; $X_2$ is absent; m is 1-6; $R^{6b}$ is hydrogen, $C_1$-$C_6$alkyl, $C_1$-$C_6$alkoxy, halo, or $-C(O)R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl.

7. The compound of claim 1, or a tautomer thereof, or a pharmaceutically acceptable salt of any of the foregoing, wherein $G_5$ is $CH(X_3-R^{6c})$ or $C(X_3-R^{6c})$; $X_3$ is absent; m is 1-6; $R^{6c}$ is hydrogen, $C_1$-$C_6$alkyl, $C_1$-$C_6$alkoxy, halo, or $-C(O)R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl.

8. The compound of claim 1, or a tautomer thereof, or a pharmaceutically acceptable salt of any of the foregoing, wherein $G_6$ is $CH(X_4-R^{6d})$ or $C(X_4-R^{6d})$; $X_4$ is absent; m is 1-6; $R^{6d}$ is hydrogen, $C_1$-$C_6$alkyl, $C_1$-$C_6$alkoxy, halo, or $-C(O)R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl.

9. The compound of claim 1, or a tautomer thereof, or a pharmaceutically acceptable salt of any of the foregoing, wherein $R^{6a}$, $R^{6b}$, $R^{6c}$ and $R^{6d}$ are each independently hydrogen, $C_1$-$C_6$alkyl, $C_1$-$C_6$alkoxy, halo, or $-C(O)R^h$, wherein $C_1$-$C_6$alkyl is unsubstituted or substituted with cycloalkyl or halogen; and $R^h$ is selected from the group consisting of H, $C_1$-$C_6$alkyl, $C_1$-$C_6$alkoxy, and $C_3$-$C_8$cycloalkyl.

10. The compound of claim 1, or a tautomer thereof, or a pharmaceutically acceptable salt of any of the foregoing, wherein the compound is

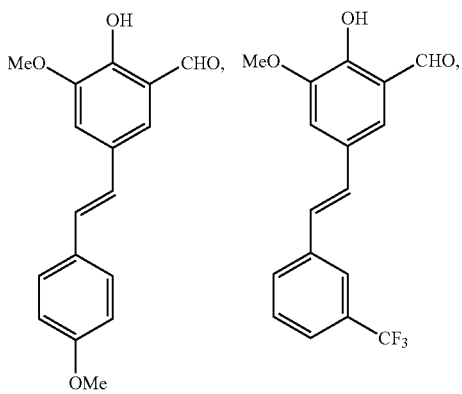

-continued

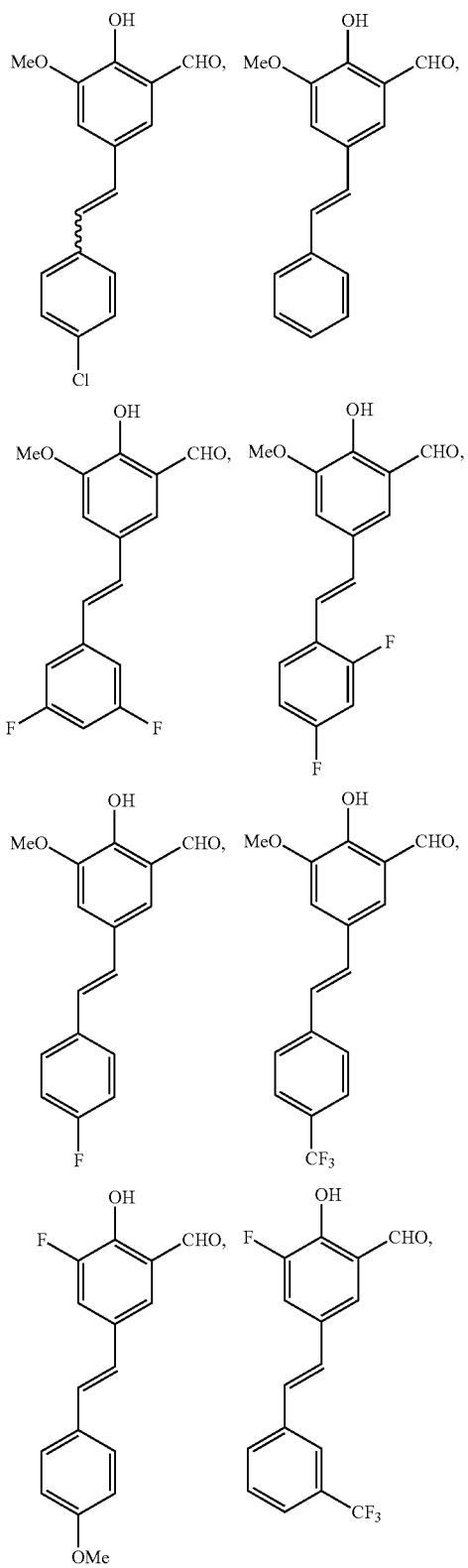

277
-continued
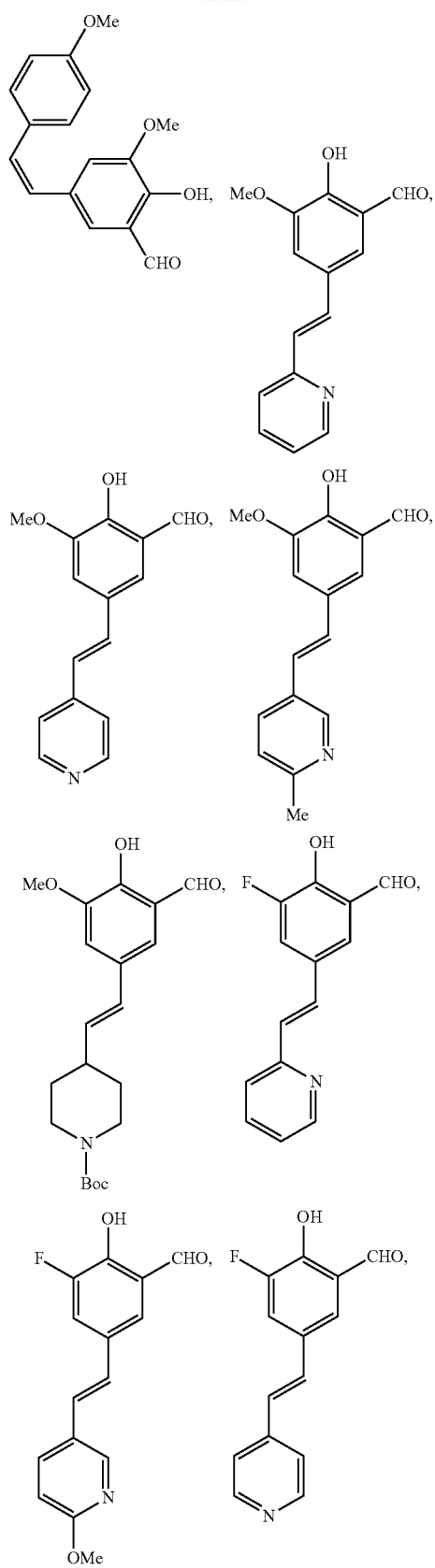
278
-continued
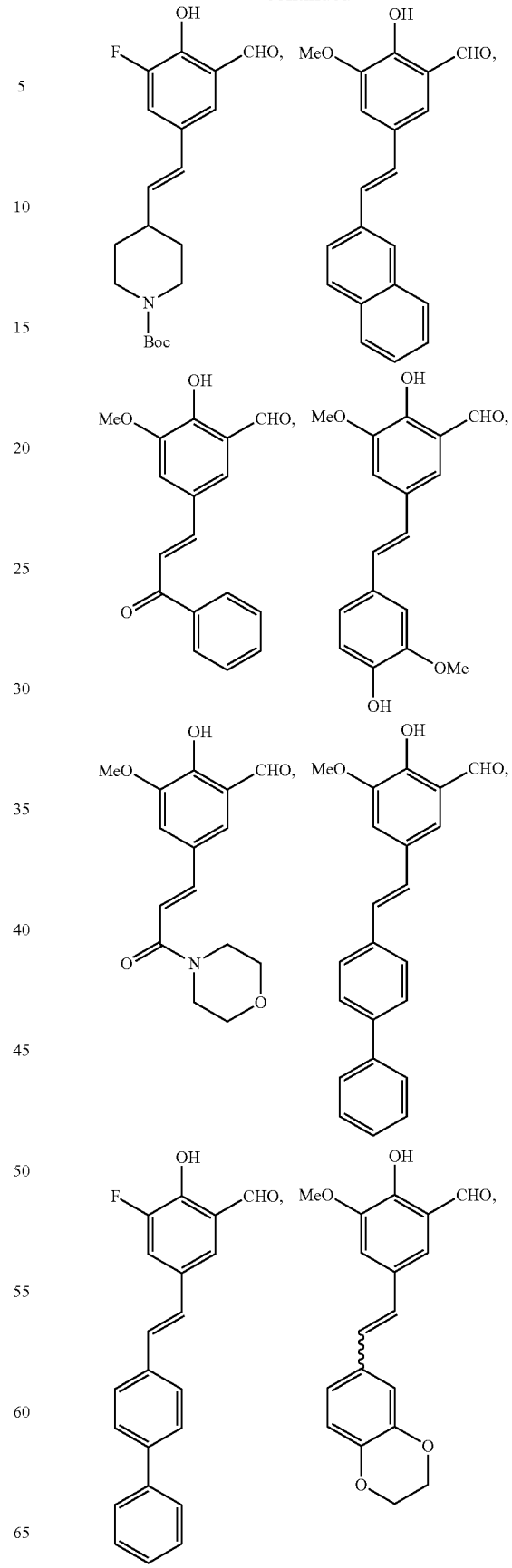

279
-continued
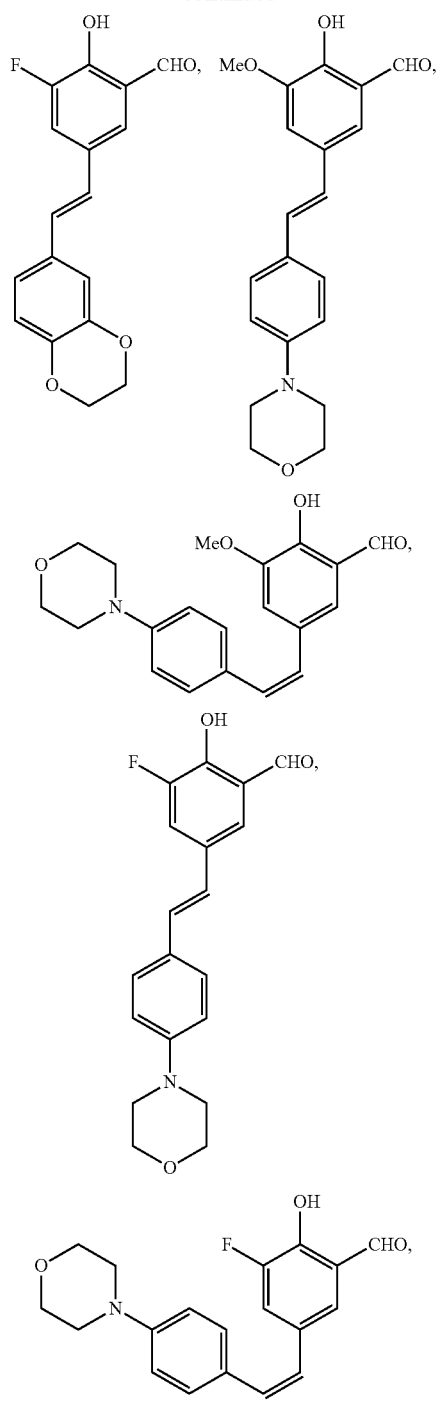
280
-continued
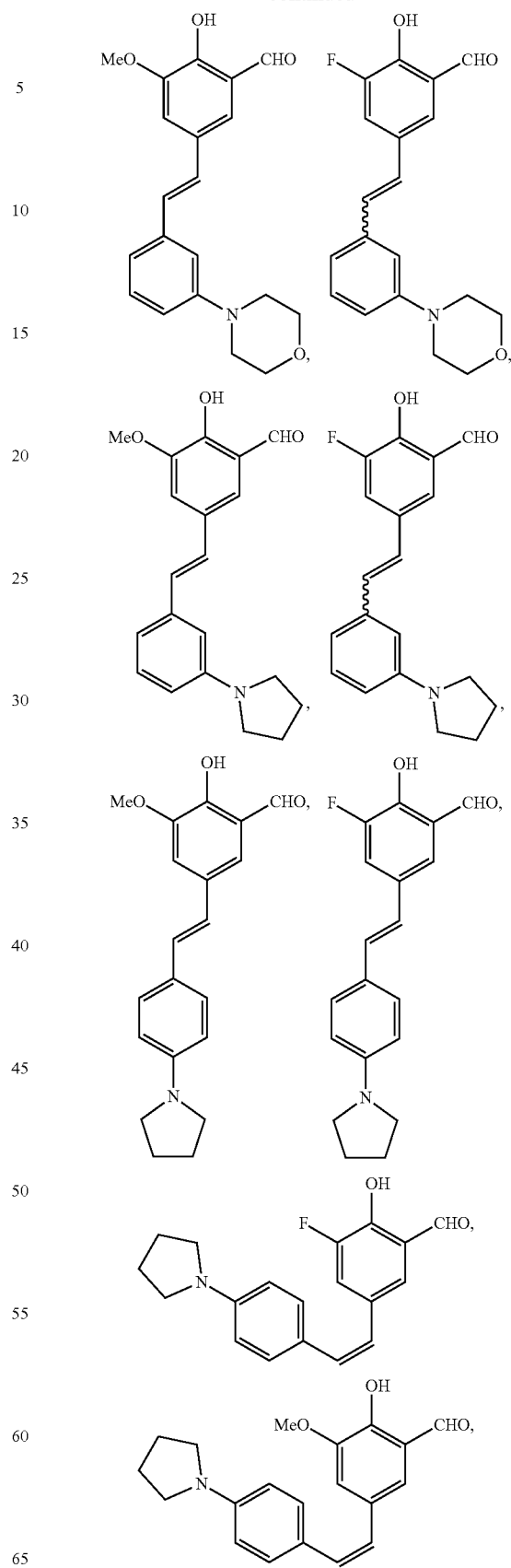

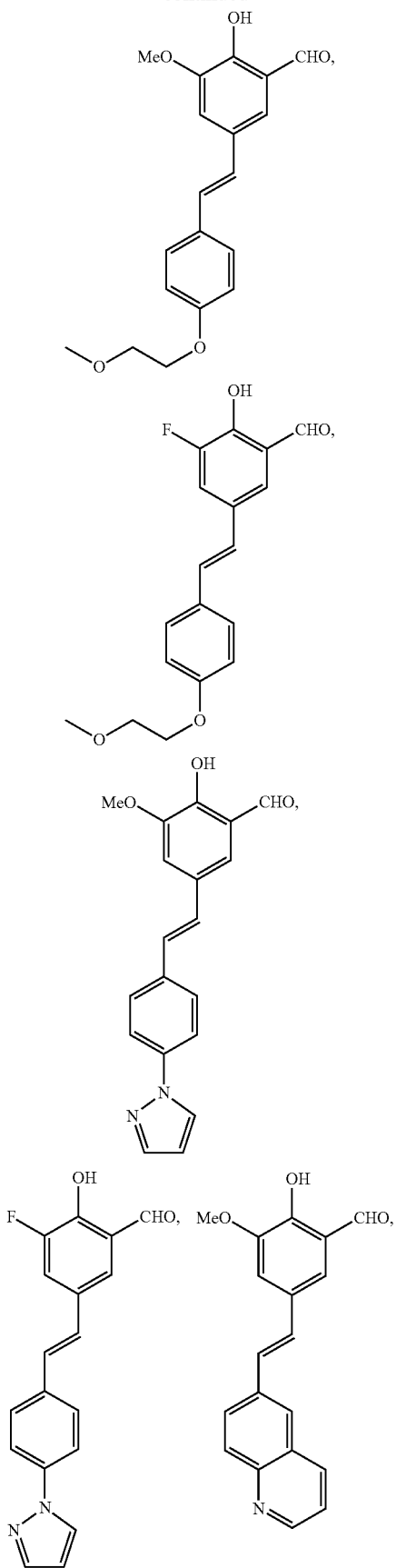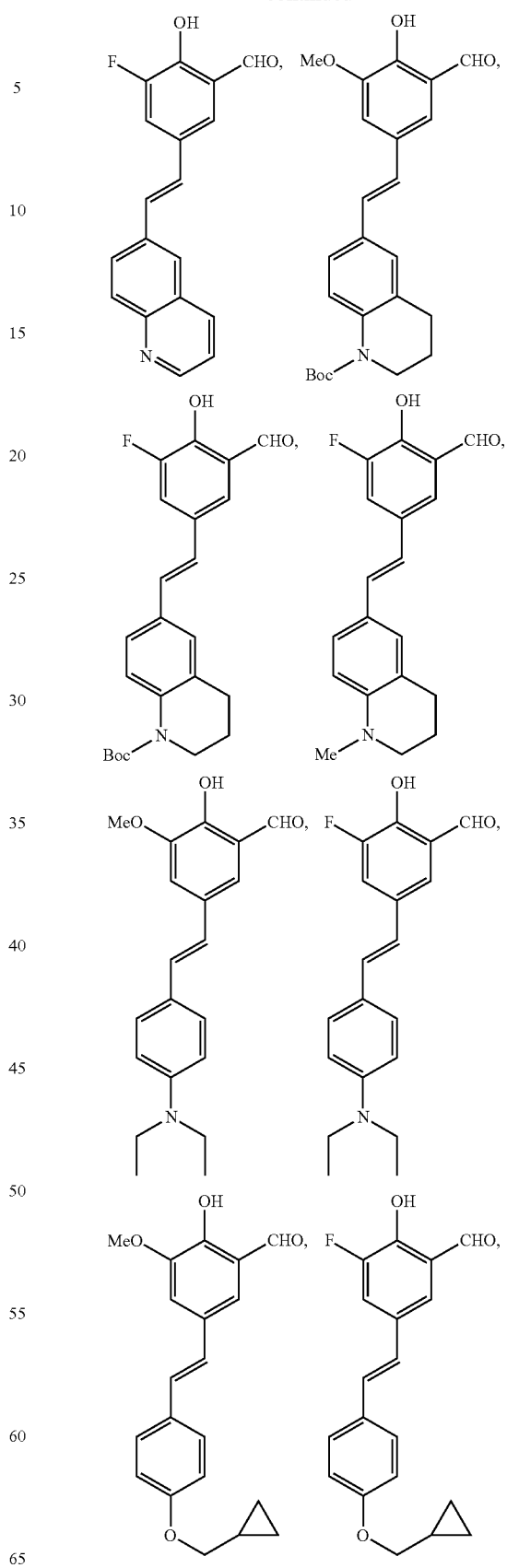

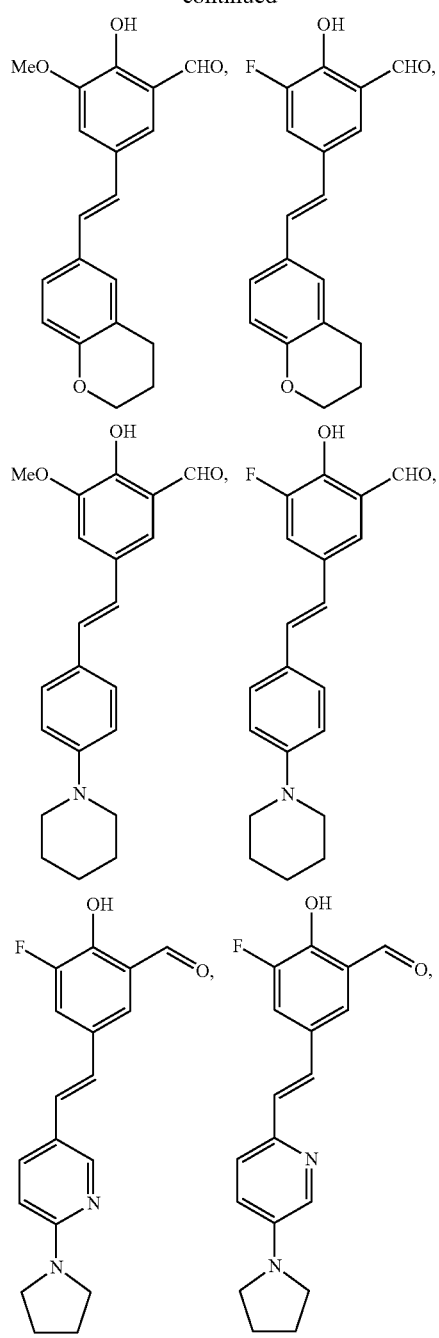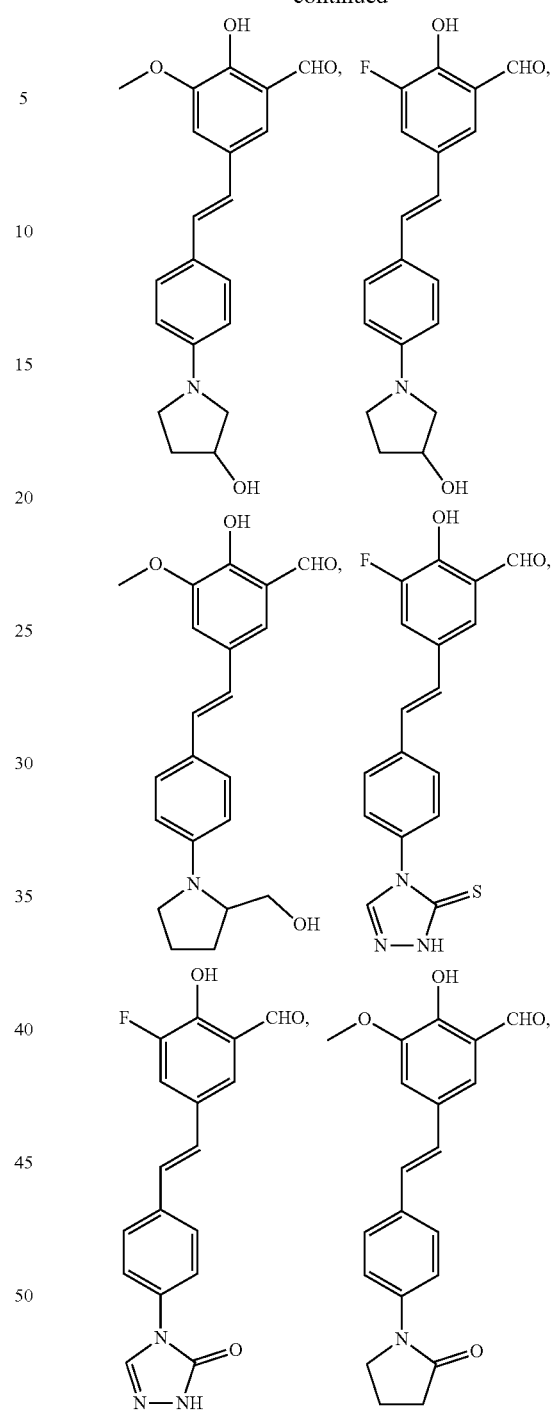

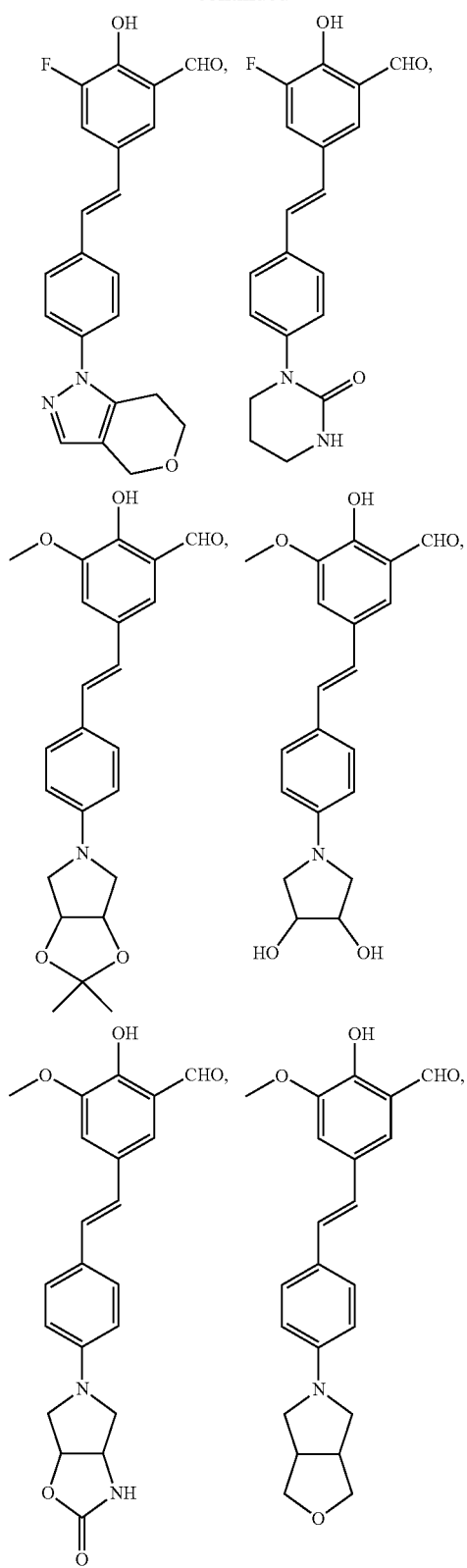
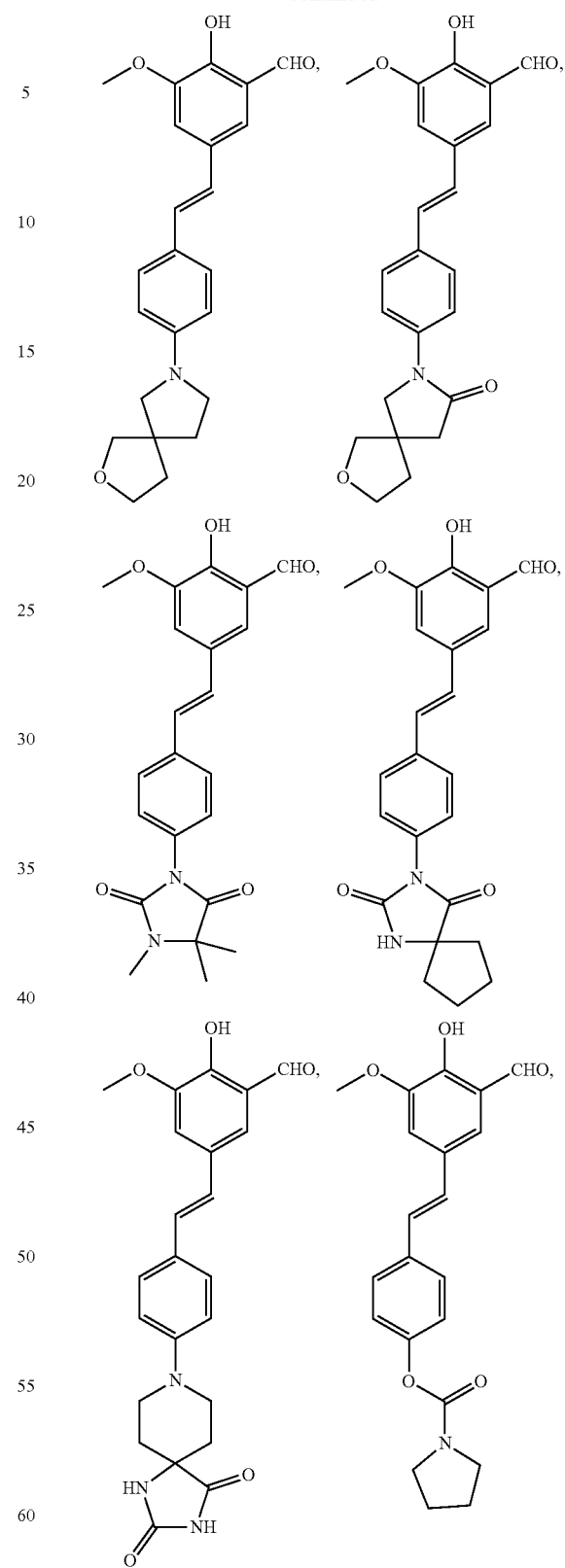

287
-continued
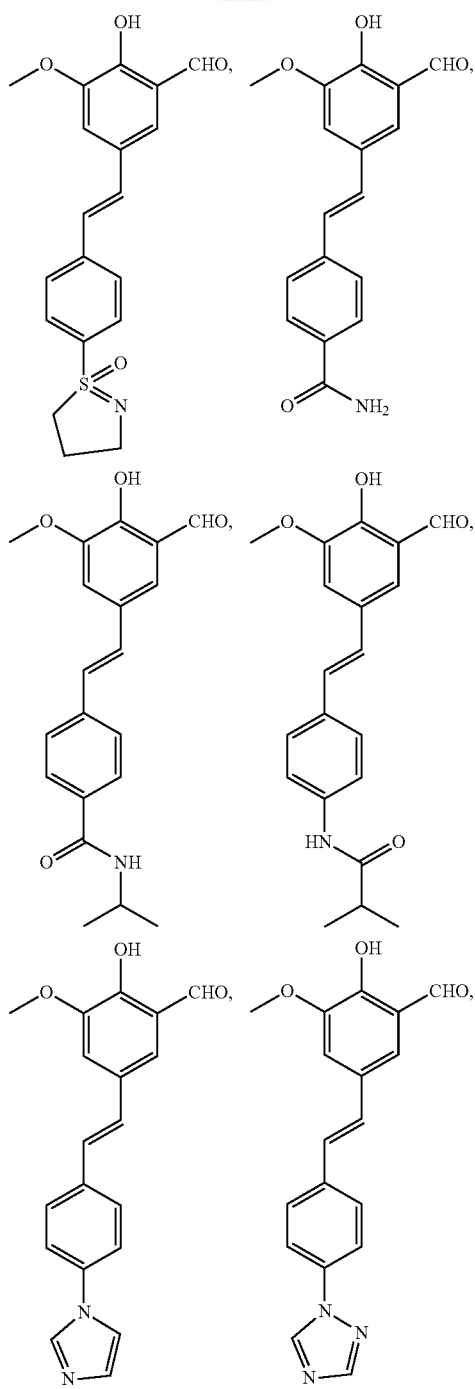
288
-continued
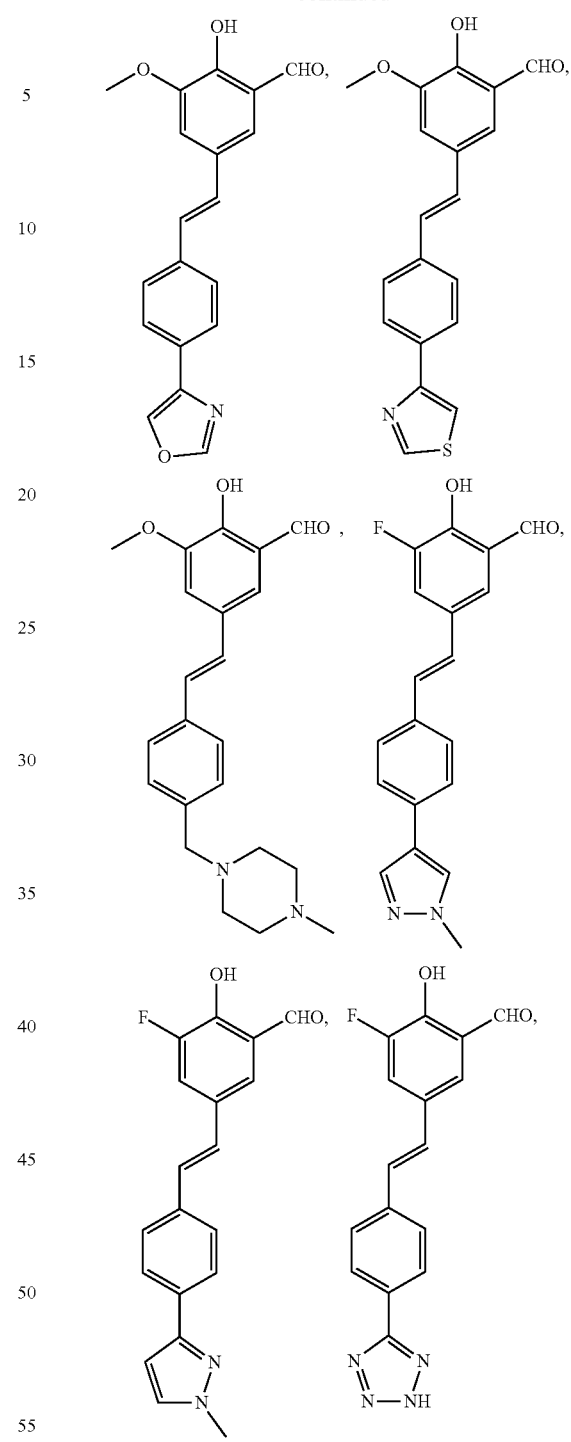

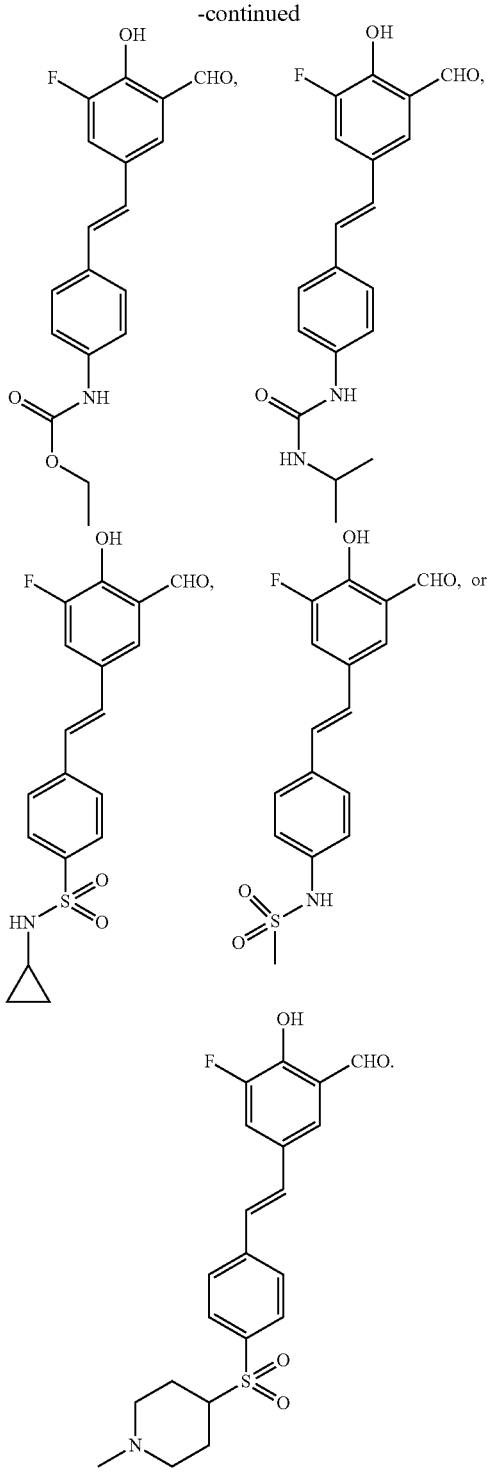

11. A pharmaceutical composition comprising at least one compound according to claim 1, or a tautomer thereof, or a pharmaceutically acceptable salt of any of the foregoing, optionally further comprising a pharmaceutically acceptable excipient.

12. A method of treating a disease or condition associated with TLR2 heterodimerization, comprising administering to a subject in need of such treatment an effective amount of at least one compound according to claim 1, or a tautomer thereof, or a pharmaceutically acceptable salt of any of the foregoing.

13. The method of claim 12, wherein the disease or condition is selected from the group consisting of: Alzheimer's disease, Parkinson's disease, fronto-temporal dementia, dementia with Lewy bodies (Lewy body disease), Parkinson's disease with dementia, multiple system atrophy, amyotrophic lateral sclerosis, Huntington's disease, Progressive Supranuclear Palsy (PSP), Niemann-Pick disease type C, inflammatory diseases, asthma, chronic obstructive pulmonary disease (COPD), chronic peptic ulcers, irritable bowel disease, tuberculosis, rheumatoid arthritis, osteoarthritis, chronic sinusitis, hepatitis, hepatitis B, hepatitis C, gout, lupus, pleurisy, eczema, gastritis, psoriasis, psoriatic arthritis, vasculitis, laryngitis, allergic reactions, multiple sclerosis, Crohn's disease, traumatic brain injury, CIDP (chronic inflammatory demyelinating polyneuropathy), stroke, ischemic heart disease, atopic dermatitis, acne vulgaris, rosacea, non-alcoholic fatty liver disease, non-alcoholic steatohepatisis, corneal wounds, corneal disorders, corneal HSV, Stargardt disease (Juvenile macular degeneration), age-related macular degeneration, sepsis, diabetic wounds, herpes simplex virus, and anti-fungal, anti-bacterial, antiviral and anti-tumor diseases or conditions.

14. A method of interfering with the heterodimerization of TLR2 in a cell, or modulating, preventing, slowing, reversing, or inhibiting TLR2 heterodimerization in a cell, comprising contacting the cell with an effective amount of at least one compound according to claim 1, or a tautomer thereof, or a pharmaceutically acceptable salt of any of the foregoing, wherein the contacting is in vitro, ex vivo, or in vivo.

15. The compound of claim 1, or a tautomer thereof, or a pharmaceutically acceptable salt of any of the foregoing, wherein $G_5$ is $CH(X_3-R^{6c})$ or $C(X_3-R^{6c})$; $X_3$ is absent; m is 1-6; $R^{6c}$ is —OH, —$NR^pR^q$, aryl, heterocyclyl, heteroaryl, —$C_1$-$C_6$alkyl-heterocyclyl, —OC(O)-heterocyclyl, —S(O)$_2NR^{w1}R^{w2}$, —S(O)$_2R^y$, or —$NR^{z1}S(O)_2R^{z2}$.

16. The compound of claim 1, or a tautomer thereof, or a pharmaceutically acceptable salt of any of the foregoing, wherein $R^{6a}$, $R^{6b}$, $R^{6c}$, and $R^{6d}$ are each independently —OH, —$NR^pR^q$, aryl, heterocyclyl, heteroaryl, —$C_1$-$C_6$alkyl-heterocyclyl, —OC(O)-heterocyclyl, —S(O)$_2NR^{w1}R^{w2}$, —S(O)$_2R^y$, or —$NR^{z1}S(O)_2R^{z2}$.

* * * * *